US012459999B2

(12) United States Patent
Moore et al.

(10) Patent No.: US 12,459,999 B2
(45) **Date of Patent: *Nov. 4, 2025**

(54) MATRIX METALLOPROTEASE-CLEAVABLE AND SERINE PROTEASE-CLEAVABLE SUBSTRATES AND METHODS OF USE THEREOF

(71) Applicant: CytomX Therapeutics, Inc., South San Francisco, CA (US)

(72) Inventors: Stephen James Moore, Danville, CA (US); Margaret Thy Luu Nguyen, San Francisco, CA (US); Daniel Robert Hostetter, Palo Alto, CA (US); Olga Vasiljeva, Cupertino, CA (US); Jason Gary Sagert, San Mateo, CA (US); Jonathan Alexander Terrett, Cupertino, CA (US); James William West, Bend, OR (US)

(73) Assignee: CYTOMX THERAPEUTICS, INC., South San Francisco, CA (US)

( * ) Notice: Subject to any disclaimer, the term of this patent is extended or adjusted under 35 U.S.C. 154(b) by 329 days.

This patent is subject to a terminal disclaimer.

(21) Appl. No.: 18/062,619

(22) Filed: Dec. 7, 2022

(65) Prior Publication Data

US 2023/0212283 A1 Jul. 6, 2023

Related U.S. Application Data

(62) Division of application No. 17/360,809, filed on Jun. 28, 2021, now Pat. No. 11,548,944, which is a division of application No. 15/002,131, filed on Jan. 20, 2016, now Pat. No. 11,046,759.

(60) Provisional application No. 62/278,713, filed on Jan. 14, 2016, provisional application No. 62/277,771, filed on Jan. 12, 2016, provisional application No. 62/258,015, filed on Nov. 20, 2015, provisional application No. 62/105,490, filed on Jan. 20, 2015.

(51) Int. Cl.

| | |
|---|---|
| ***C07K 14/00*** | (2006.01) |
| ***A61K 38/05*** | (2006.01) |
| ***A61K 47/68*** | (2017.01) |
| ***A61K 49/00*** | (2006.01) |
| ***C07K 7/08*** | (2006.01) |
| ***C07K 16/28*** | (2006.01) |
| ***C07K 16/40*** | (2006.01) |
| *A61K 39/00* | (2006.01) |

(52) U.S. Cl.

CPC .............. *C07K 16/28* (2013.01); *A61K 38/05* (2013.01); *A61K 47/6849* (2017.08); *A61K 47/6851* (2017.08); *A61K 49/0058* (2013.01); *C07K 7/08* (2013.01); *C07K 14/00* (2013.01); *C07K 16/2863* (2013.01); *C07K 16/2896* (2013.01); *C07K 16/40* (2013.01); *A61K 2039/505* (2013.01); *A61K 2039/507* (2013.01); *C07K 2317/51* (2013.01); *C07K 2317/515* (2013.01); *C07K 2317/92* (2013.01); *C07K 2319/50* (2013.01); *C07K 2319/74* (2013.01)

(58) Field of Classification Search

CPC .... C07K 16/28; C07K 16/2863; C07K 16/40; C07K 2317/51; C07K 2317/515; C07K 2317/92; C07K 2319/50; A61K 47/6849; A61K 47/6851; A61K 2039/505

See application file for complete search history.

(56) References Cited

U.S. PATENT DOCUMENTS

| | | | |
|---|---|---|---|
| 3,773,919 | A | 11/1973 | Boswell |
| 4,485,045 | A | 11/1984 | Regen |
| 4,522,811 | A | 6/1985 | Eppstein et al. |
| 4,544,545 | A | 10/1985 | Ryan et al. |
| 5,013,556 | A | 5/1991 | Woodle et al. |
| 5,030,719 | A | 7/1991 | Umemeto et al. |
| 5,151,510 | A | 9/1992 | Stec et al. |
| 6,551,795 | B1 | 4/2003 | Rubenfield et al. |

(Continued)

FOREIGN PATENT DOCUMENTS

| | | | |
|---|---|---|---|
| BR | 112017001579 | A2 | 11/2017 |
| EP | 1 523 503 | B1 | 4/2009 |

(Continued)

OTHER PUBLICATIONS

Baldrick P. "Pharmaceutical excipient development: the need for preclinical guidance." Regul. Toxicol Pharmacol. (2000) 32(2):210-218.

(Continued)

*Primary Examiner* — Hong Sang

(74) *Attorney, Agent, or Firm* — Rothwell, Figg, Ernst & Manbeck, P.C.

(57) ABSTRACT

The invention relates generally to polypeptides that include at least a first cleavable moiety (CM1) that is a substrate for at least one matrix metalloprotease (MMP) and at least a second cleavable moiety (CM2) that is a substrate for at least one serine protease (SP), to activatable antibodies and other larger molecules that include these polypeptides that include at least a CM1 that is a substrate for at least one MMP protease and at least a CM2 that is a substrate for at least one SP protease, and to methods of making and using these polypeptides that include at least a CM1 that is a substrate for at least one MMP protease and at least a CM2 that is a substrate for at least one SP protease in a variety of therapeutic, diagnostic and prophylactic indications.

8 Claims, 12 Drawing Sheets

Specification includes a Sequence Listing.

(56) References Cited

U.S. PATENT DOCUMENTS

| | | | | |
|---|---|---|---|---|
| 6,558,728 | B1 | 5/2003 | Poulsen et al. | |
| 7,276,497 | B2 | 10/2007 | Chari et al. | |
| 7,439,319 | B2 | 10/2008 | Smith et al. | |
| 7,442,159 | B1 | 10/2008 | Riechmann et al. | |
| 7,465,790 | B2 | 12/2008 | Waldmann et al. | |
| 7,666,817 | B2 | 2/2010 | Daugherty et al. | |
| 7,935,785 | B2 | 5/2011 | Smith et al. | |
| 8,513,390 | B2 | 8/2013 | Stagliano et al. | |
| 8,518,404 | B2 | 8/2013 | Daugherty et al. | |
| 8,524,220 | B1 | 9/2013 | Bermudes | |
| 8,529,898 | B2 | 9/2013 | Daugherty et al. | |
| 8,541,203 | B2 | 9/2013 | Daugherty et al. | |
| 8,563,269 | B2 | 10/2013 | Stagliano et al. | |
| 8,809,504 | B2 | 8/2014 | Lauermann | |
| 9,120,853 | B2 | 9/2015 | Lowman et al. | |
| 9,127,053 | B2 | 9/2015 | West et al. | |
| 9,169,321 | B2 | 10/2015 | Daugherty et al. | |
| 9,309,510 | B2 | 4/2016 | La Porte et al. | |
| 9,453,078 | B2 | 9/2016 | Stagliano et al. | |
| 9,562,073 | B2 | 2/2017 | Moore et al. | |
| 10,059,762 | B2 | 8/2018 | Stagliano et al. | |
| 10,077,300 | B2 | 9/2018 | Daugherty et al. | |
| 10,118,961 | B2 | 11/2018 | Stagliano et al. | |
| 10,138,272 | B2 | 11/2018 | Moore et al. | |
| 10,179,817 | B2 * | 1/2019 | Sagert | C07K 16/30 |
| 10,233,244 | B2 * | 3/2019 | Sagert | A61K 47/68033 |
| 10,336,824 | B2 | 7/2019 | West et al. | |
| 10,513,558 | B2 * | 12/2019 | Tipton | C07K 16/3053 |
| 10,669,337 | B2 | 6/2020 | Irving et al. | |
| 10,669,339 | B2 | 6/2020 | West et al. | |
| 10,745,481 | B2 * | 8/2020 | West | A61K 47/6849 |
| 10,875,913 | B2 | 12/2020 | Stagliano et al. | |
| 11,028,126 | B2 | 6/2021 | Moore et al. | |
| 11,267,896 | B2 * | 3/2022 | Sagert | A61K 49/0058 |
| 11,753,466 | B2 * | 9/2023 | West | A61K 47/6891 424/134.1 |
| 2003/0219402 | A1 | 11/2003 | Rutter | |
| 2004/0109855 | A1 | 6/2004 | Waldmann et al. | |
| 2004/0123343 | A1 | 6/2004 | La Rosa et al. | |
| 2005/0208602 | A1 | 9/2005 | Rosen et al. | |
| 2007/0218074 | A1 | 9/2007 | Man | |
| 2008/0166375 | A1 | 7/2008 | Leppla et al. | |
| 2009/0304719 | A1 | 12/2009 | Daugherty et al. | |
| 2010/0041588 | A1 | 2/2010 | Keay et al. | |
| 2010/0189651 | A1 | 7/2010 | Stagliano et al. | |
| 2010/0221212 | A1 | 9/2010 | Stagliano | |
| 2011/0214205 | A1 | 9/2011 | Dietrich et al. | |
| 2011/0280908 | A1 | 11/2011 | Leppla et al. | |
| 2011/0287517 | A1 | 11/2011 | Steward et al. | |
| 2012/0149061 | A1 | 6/2012 | Stagliano et al. | |
| 2012/0207756 | A1 | 8/2012 | Stagliano et al. | |
| 2012/0237512 | A1 | 9/2012 | Daugherty et al. | |
| 2012/0237977 | A1 | 9/2012 | Daugherty et al. | |
| 2012/0244154 | A1 | 9/2012 | Daugherty et al. | |
| 2012/0321626 | A1 | 12/2012 | Zhou et al. | |
| 2013/0078201 | A1 | 3/2013 | Daly et al. | |
| 2013/0150558 | A1 | 6/2013 | Williams et al. | |
| 2013/0266568 | A1 | 10/2013 | Brinkmann et al. | |
| 2013/0309230 | A1 | 11/2013 | Stagliano et al. | |
| 2014/0010810 | A1 | 1/2014 | West et al. | |
| 2014/0023664 | A1 | 1/2014 | Lowman et al. | |
| 2014/0024810 | A1 | 1/2014 | Stagliano et al. | |
| 2014/0045195 | A1 | 2/2014 | Daugherty et al. | |
| 2014/0255313 | A1 | 9/2014 | Vasiljeva et al. | |
| 2014/0363430 | A1 | 12/2014 | West et al. | |
| 2015/0005477 | A1 | 1/2015 | Lowman et al. | |
| 2015/0087810 | A1 | 3/2015 | Moore et al. | |
| 2016/0122425 | A1 | 5/2016 | Daugherty et al. | |
| 2016/0194399 | A1 | 7/2016 | Irving | |
| 2016/0228546 | A1 | 8/2016 | Stagliano et al. | |
| 2016/0311903 | A1 | 10/2016 | West et al. | |
| 2016/0355587 | A1 | 12/2016 | West et al. | |
| 2016/0355592 | A1 | 12/2016 | Sagert et al. | |
| 2016/0355599 | A1 | 12/2016 | Sagert | |
| 2017/0044259 | A1 | 2/2017 | Tipton et al. | |
| 2017/0081397 | A1 | 3/2017 | Stagliano et al. | |
| 2017/0204139 | A1 | 7/2017 | Moore et al. | |
| 2018/0303952 | A1 | 10/2018 | Sagert et al. | |
| 2019/0016814 | A1 | 1/2019 | Humphrey et al. | |
| 2019/0119370 | A1 | 4/2019 | Stagliano et al. | |
| 2019/0135864 | A1 | 5/2019 | Moore et al. | |
| 2019/0211089 | A1 | 7/2019 | Daugherty et al. | |
| 2019/0359714 | A1 | 11/2019 | Tipton et al. | |
| 2019/0382493 | A1 | 12/2019 | West et al. | |
| 2021/0284721 | A1 | 9/2021 | Stagliano et al. | |

FOREIGN PATENT DOCUMENTS

| | | | | |
|---|---|---|---|---|
| EP | 1 324 771 | B1 | 6/2011 | |
| JP | 2010-536370 | A | 12/2010 | |
| JP | 2012-506408 | A | 3/2012 | |
| JP | 2012-514982 | A | 7/2012 | |
| TW | 200635946 | | 10/2006 | |
| WO | 1994011026 | A2 | 5/1994 | |
| WO | WO 1999/15563 | A1 | 4/1999 | |
| WO | WO 2001/57182 | A2 | 8/2001 | |
| WO | WO 2001/91798 | A2 | 12/2001 | |
| WO | WO 2002/12475 | A2 | 2/2002 | |
| WO | WO 2002/30460 | A2 | 4/2002 | |
| WO | 2002038796 | A3 | 5/2002 | |
| WO | WO 2003/004681 | | 1/2003 | |
| WO | WO 2003/038083 | A1 | 5/2003 | |
| WO | WO 2003/068934 | | 8/2003 | |
| WO | WO 2004/009638 | A1 | 1/2004 | |
| WO | WO 2006/110599 | A2 | 10/2006 | |
| WO | WO 2007/047995 | | 4/2007 | |
| WO | WO 2007/105027 | A1 | 9/2007 | |
| WO | WO 2008/052187 | A1 | 5/2008 | |
| WO | WO 2008/083312 | | 7/2008 | |
| WO | WO 2008/149143 | | 12/2008 | |
| WO | WO 2008/149147 | | 12/2008 | |
| WO | WO 2008/149148 | | 12/2008 | |
| WO | WO 2008/149149 | | 12/2008 | |
| WO | WO 2008/149150 | | 12/2008 | |
| WO | WO 2009/025846 | A2 | 2/2009 | |
| WO | 2010046628 | A1 | 4/2010 | |
| WO | WO 2010/081173 | A2 | 7/2010 | |
| WO | WO 2010/088691 | A2 | 8/2010 | |
| WO | WO 2010/091122 | | 8/2010 | |
| WO | WO 2010/096838 | A2 | 8/2010 | |
| WO | WO 2010/129609 | A2 | 11/2010 | |
| WO | WO 2011/028698 | A2 | 3/2011 | |
| WO | WO 2011/151426 | | 12/2011 | |
| WO | WO 2011/161260 | | 12/2011 | |
| WO | 2012156919 | A1 | 11/2012 | |
| WO | WO 2012/158818 | | 11/2012 | |
| WO | WO 2013/003649 | | 1/2013 | |
| WO | WO 2013/163631 | A2 | 10/2013 | |
| WO | WO 2013/192546 | A2 | 12/2013 | |
| WO | WO 2013/192550 | A2 | 12/2013 | |
| WO | WO 2014/026136 | A2 | 2/2014 | |
| WO | 2014052462 | A2 | 4/2014 | |
| WO | WO 2014/107599 | A2 | 7/2014 | |
| WO | WO 2014/176284 | A1 | 10/2014 | |
| WO | WO 2014/193973 | A2 | 12/2014 | |
| WO | WO 2014/197612 | | 12/2014 | |
| WO | 2015048329 | A2 | 4/2015 | |
| WO | 2015116933 | A2 | 8/2015 | |
| WO | 2016014974 | A2 | 1/2016 | |
| WO | 2016118629 | A1 | 7/2016 | |
| WO | WO-2016149201 | A2 * | 9/2016 | A61K 39/3955 |
| WO | WO 2016/179335 | | 10/2016 | |
| WO | 2016179257 | A2 | 11/2016 | |
| WO | WO 2016/210447 | | 12/2016 | |
| WO | WO 2020/077267 | | 4/2020 | |
| WO | 2020118109 | A2 | 6/2020 | |

OTHER PUBLICATIONS

Bowie et al., "A method to identify protein sequences that fold into a known three-dimensional structure", Science (1991) 253(5016):164-170.

(56) References Cited

OTHER PUBLICATIONS

Charman WN, "Lipids, lipophilic drugs, and oral drug delivery-some emerging concepts." J. Pharm. Sci. (2000) 89(8):967-978.
Chen et al, "Selective Antibody Activation Through Protease-Activated Pro-Antibodies that Mask Binding Sites with Inhibitory Domains", Scientific Reports, (2017) 7(1): 11587 (1-12).
Chothia & Lesk, "Canonical Structures for the Hypervariable Regions of Immunoglobulins", J. Mol. Biol. (1987) 196:901-917.
Chothia et al., "Conformations of immunoglobulin hypervariable regions", Nature (1989) 342:877-883.
Database EMBL, Accession No. OVF07168 (Jun. 15, 2017) "Clavispora lusitaniae hypothetical protein" Durrens et al. [online]; XP055665684, Retrieved from Internet on Feb. 23, 2021 (2 pages): https://www.ebi.ac.uk/ena/browser/ api/embl/OVF07168.1?lineLimit=1000.
Database UNIPROTKB, Accession No. A0A0D8BN56 (Jun. 17, 2020) "Uncharacterized protein from Frankia torreyi", Oshone et al. [online]; UniProt Consortium, www.uniprot.org; Retrieved from Internet on Feb. 23, 2021 (1 page): https://www.uniprot.org/uniprot/A0A0D8BN56.txt.
Database UNIPROTKB, Accession No. T0RF53 (Oct. 13, 2013), "Uncharacterized protein from Saprolegnia diclina", Russ et al [online]; UniProt Consortium, www.uniprot.org; Retrieved from Internet: https://www.uniprot.org/uniprot/T0RF53.txt (Feb. 23, 2021); 1 page.
Davies et al., "Antibody-antigen complexes", Annual Rev. Biochem. (1990) 59:439-473.
Eppstein et al., "Biological activity of liposome-encapsulated murine interferon gamma is mediated by a cell membrane receptor", Proc. Natl. Acad. Sci. USA, (1985) 82(11):3688-3692.
Hwang et al., "Hepatic uptake and degradation of unilamellar sphingomyelin/cholesterol liposomes: a kinetic study", Proc. Natl Acad. Sci. USA (1980) 77(7):4030-4034.
Jansen et al., "Immunotoxins: hybrid molecules combining high specificity and potent cytotoxicity", Immunological Reviews (1982) 62:185-216.
Killen and Lindstrom, "Specific killing of lymphocytes that cause experimental autoimmune myasthenia gravis by ricin toxin-acetylcholine receptor conjugates", J. Immunol. (1984) 133(5):2549-2553.
Kukreja at al., "The High Throughput Multiplexed Peptide-Centric Profiling Illustrates Both the Substrate Cleavage Redundancy and Specificity in the MMP Family", Chem. Biol., (2015) 22(8):1122-1133.
LaPlanche et al., "Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric O-ethyl phosphorothioates", Nucl. Acids Res. (1986) 14(22):9081-9093.
Malmqvist M., "Biospecific interaction analysis using biosensor technology", Nature (1993) 361(6408):186-187.
Marasco et al., "Design, intracellular expression, and activity of a human anti-human immunodeficiency virus type 1 gp120 single-chain antibody", Proc. Natl. Acad. Sci. USA (1993) 90(16):7889-7893.
Martin et al., "Irreversible coupling of immunoglobulin fragments to preformed vesicles. An improved method for liposome targeting", J. Biol. Chem. (1982) 257(1):286-288.
Mitra and Lawton, "Reagents for the crosslinking of proteins by equilibrium transfer alkylation", J. Amer. Chem. Soc. (1979) 101(11):3097-3110.
Powell et al. "Compendium of excipients for parenteral formulations" PDA J Pharm Sci Technol. (1998) 52(5):238-311.
Ramakrishnan et al., "Comparison of the Selective Cytotoxic Effects of Immunotoxins Containing Ricin A Chain or Pokeweed Antiviral Protein and Anti-Thy 1.1 Monoclonal Antibodies", Cancer Res. (1984) 44:201-208.
Scheraga, H.A., "Predicting Three-Dimensional Structures of Oligopeptides" Rev. Computational Chem., (vol. 3, K. B. Lipkowitz and D.B. Boyd (Eds.), John Wiley & Sons, Inc., Hoboken, NJ, (1992)).
Stec et al., "Automated solid-phase synthesis, separation, and stereochemistry of phosphorothioate analogs of pligodeoxyribonucleotides", J. Am. Chem. Soc. (1984) 106(20):6077-6079.
Stein et al., "Physicochemical properties of phosphorothioate oligodeoxynucleotides", Nucl. Acids Res. (1988) 16(8):3209-3221.
Thornton et al., "Prediction of progress at last", Nature (1991) 354:105-106.
Takeuchi et al., "Cellular Localization of Membrane-type Serine Protease 1 and Identification of Protease-activated Receptor-2 and Single-chain Urokinase-type Plasminogen Activator as Substrates", J. Biol. Chem. (2000) 275(34):26333-26342.
Uhlmann and Peyman, "Antisense Oligonucleotides: A New Therapeutic Principle", Chemical Reviews (1990) 90(4):543-584.
Vitetta et al., "Redesigning nature's poisons to create anti-tumor reagents", Science (1987) 238(4830): 1098-1104.
Wang W., "Lyophilization and development of solid protein pharmaceuticals", Int. J. Pharm. (2000) 203(1-2):1-60.
Zon et al., "Phosphorothioate oligonucleotides: chemistry, purification, analysis, scale-up and future directions", Anticancer Drug Des. (1991) 6(6):539-568.
Office Action issued on Jan. 24, 2022 in U.S. Appl. No. 17/360,754, 18 pages.
Office Action issued on Jan. 7, 2022 in U.S. Appl. No. 17/360,855, 30 pages.
Paul, Fundamental Immunology, 3rd Edition, 1993, pp. 292-295.
Rudikoff et al., "Single amino acid substitution altering antigen-binding specificity", Proc. Natl. Acad. Sci. USA, 1982, 79(6):1979-1983.
Colman, "Effects of Amino Acid Sequence changes on antibody-Antigen Interactions", Research in Immunology, 1994, 145:33-36.
Bendig, "Humanization of rodent Monoclonal antibodies by CDR Grafting", Methods: A Companion to Methods in Enzymology, 1995; 8:83-93.
Khantasup et al., "Design and Generation of Humanized Single-chain Fv Derived from Mouse Hybridoma for Potential Targeting Application", Monoclonal Antibodies in Immunodiagnosis and Immunotherapy, 2015, 34(6): 404-417.
Murphy et al., "Enhancing recombinant antibody performance by optimally engineering its format", Journal of Immunological Methods, vol. 463, p. 127-133, 2018.
Harris JL et al. "Rapid and general profiling of protease specificity by using combinatorial fluoreogenic substrate libraries." PNAS vol. 97(14):7754-59 (2000).
Prudova A, auf dem Keller U, Butler GS, Overall CM. Multiplex N-terminome analysis of MMP-2 and MMP-9 substrate degradomes by iTRAQ-TAILS quantitative proteomics. Mol Cell Proteomics. May 2010;9(5):894-911. doi: 10.1074/mcp.M000050-MCP201. Epub Mar. 20, 2010.
Ratnikov et al., "Basis for substrate recognition and distinction by matrix metalloproteinases." Proc. Natl. Acad. Sci., vol. 111(4): E4148-55 (2014).
Takeuchi T et al. "Cellular Location of Membrane-type Serine Protease 1 and Identification of Protease-activated Receptor-2 and Single-chain Urokinase-type Plasminogen Activator as Substrates." J Biol Chem vol. 275(34): 26333-26342 (2000).
ADC Review, "Maytansine" [online]. Retrieved from: http://adcreview.com/adc-university/adcs-101/cytotoxic-agents/maytansine/, on Mar. 17, 2016, 4 pages.
BLAST search of SEQ ID No. 362 from U.S. Pat. No. 9,562,073 (retrieved from http://blast.ncbi.nlm.nih.gov/Blast.cgi on Mar. 17, 2016, 8 pages).
BLAST search of SEQ ID No. 363 from U.S. Pat. No. 9,562,073 (retrieved from http://blast.ncbi.nlm.nih.gov/Blast.cgi on Mar. 17, 2016, 7 pages).
BLAST search of SEQ ID No. 364 from U.S. Pat. No. 9,562,073 (retrieved from http://blast.ncbi.nlm.nih.gov/Blast.cgi on Mar. 17, 2016, 8 pages).
Casadaban et al., "Analysis of gene control signals by DNA fusion and cloning in *Escherichia coli*" J Mol Biol, 138(2):179-207 (1980).

(56) References Cited

OTHER PUBLICATIONS

Donaldson, J.M. et al., "Design and development of masked therapeutic antibodies to limit off-target effects: application to anti-EGFR antibodies", Cancer Biology & Therapy, vol. 8, No. 22, 2009, p. 2147-2152.
GenBank Accession No. ADA97619, "Sequence 28102 from U.S. Pat. No. 6,551,795" Rubenfield, 2009, 1 page.
GenBank Accession No. AEL07912.1, "conserved hypothetical protein [Xanthomonas campestris pv.raphani 756C]" [retrieved on Dec. 28, 2017]. Retrieved from internet: https://www.ncbi.nlm.nih.gov/protein/AEL07912, 1 page.
GenBank Accession No. AF099373, "protein ITFG3 [Callothinchus milii]" 2013, 1 page.
GenBank Accession No. AKP45152, "wall-associated receptor-like kinase 2 [*Zea mays*]" [online]. Retrieved on Jul. 25, 2018 from the Internet: <https://www.ncbi.nlm.nih.gov/protein/Akp45152>, 2 pages.
GenBank Accession No. YP 005352726.1, "petG gene product (chloroplast [Ginko biloba]" [online]. [retrieved on Dec. 28, 2017]. Retrieved from the Internet:< https://www.ncbi.nlm.nih.gov/protein/YP_005352726. 1>, 1 page.
Geneseq Accession No. AAB46481, "B. brevis tyrocidin synthetase activating domain 9" [online] First entry Apr. 9, 2001, revised Sep. 11, 2003, 2 pages.
GenPept Accession No. YP_008873205 "Hypothetical protein [Pseudomonas phage PPpW-3]" Kawato et al.; submitted Dec. 9, 2013, 1 page.
Gerspach et al. "Restoration of membrane TNF-like activity by cell surface targeting and matrix metalloproteinase-mediated processing of a TNF prodrug" Cell Death and Differentiation, 2006.13:273-284.
Henikoff, S et al. (1992) "Amino acid substitution matrices from protein blocks" *Proc Natl Acad Sci U S A*, 89:10915-10919.
Jabaiah, A. and P.S. Daugherty, "Directed evolution of protease beacons that enable sensitive detection of endogenous MTI-MMP activity in tumor cell lines" *Chem Biol*, Mar. 25, 2011;18(3):392-401.
Ke, S-H. et al. "Distinguishing the specificities of closely related proteases" J Biol Chem, Jun. 26, 1997; vol. 272, No. 26, pp. 16603-16609.
Ke, S-H. et al., "Optimal subsite occupancy and design of a selective inhibitor of urokinase", J Biol Chem, Aug. 15, 1997; vol. 272, No. 33, pp. 20456-20462.
Kridel, S.J. et al. "Substrate hydrolysis by matrix metalloproteinase-9" J Biol Chem, Jun. 8, 2001; vol. 276, No. 23, pp. 20572-20578. Epub Mar. 14, 2001.
Liu, S. et al. "Intermolecular complementation achieves high-specificity tumor targeting by anthrax toxin", Nature Biotechnology, vol. 23, No. 6, p. 725-730 (2005).
Lopez-Otin, C. et al. "Protease degradomics: a new challenge for proteomics", Nature Reviews: Molecular Cell Biology, vol. 3, p. 509-519, (2002).
Rothberg, J.M. et al. "An integrated semiconductor device enabling non-optical genome sequencing" Nature. Jul. 20, 2011:475(7356):348-352.
Turk. B.E. et al. "Determination of protease cleavage site motifs using mixture-based oriented peptide libraries" Nat Biotechnol, Jul. 2001; 19(7):661-667.
Uniprot Accession No. B8J087, "Uncharacterized protein" Mar. 3, 2009, 2 pages.
Uniprot Accession No. Q9ZZR8, "Cytochrome b" May 1, 1999, 2 pages.
UniprotKB Accession No. BIFZS3 (BIFZS3_9BURK), "Major facilitator superfamily MFS_I" [online]. Retrieved from the Internet on Jul. 25, 2018 from: <https://www.ncbi.nlm.nih.gov/protein/Akp45152>, 4 pages.
Venkatesh, B. et al. (2014) "Elephant shark genome provides unique insights into gnathostome evolution", Nature, vol. 505, No. 7482, pp. 174-179.
Villacres, E. et al. (1993) "Cloning, Chromosomal Mapping, and Expression of Human Fetal Brain Type I Adenylyl Cyclase" Genomics, vol. 16, No. 2, 1993, p. 473-478.
Waterhouse, A.M. et al. (2009) "Jalview Version 2—a multiple sequence alignment editor and analysis workbench" Bioinformatics, 25(9):1189-1191.
EMBL Database (Jan. 2, 2014) "*Callorhinchus milii* (elephant shark) protein ITFG3" ID AFO99373, 2 pages.
Lebeau et al. (2013) "Imaging a functional tumorigenic biomarker in the transformed epithelium", Proc. Natl. Acad. Sci. USA, 110(1):93-98.
List et al. (2005) "Deregulated matriptase causes ras-independent multistage carcinogenesis and promotes ras-mediated malignant transformation" Genes & Develop., 19:1934-1950.
Vasiljeva et al. (2019) "The Multifaceted Roles of Tumor-Associated Proteases and Harnessing Their Activity for Prodrug Activation", Biol. Chem. [online]. Retrieved from: https://doi.org/10.1515/hsz-2018-0451 (Received Dec. 1, 2018; Accepted Mar. 18, 2019).
Kopylov, A. et al. (2007) "Methods of quantitative proteomics" *Biomed Chem*, 53(6):613-643. Russian; English abstract on p. 643.
"Derivative (chemistry)", Wikipedia, a free online encyclopedia, accessed Sep. 11, 2017, 1 page. Downloaded from: https://en.wikipedia.org/w/index.php?title=Derivative (chemistry)&oldid=779855519.
Jeong K. et al. "Recombinant antibodies: Engineering and production in yeast and bacterial hosts", Biotechnology Journal (2011), vol. 6, p. 16-27.
"Maytansinoid", Wikipedia, a free online encyclopedia, accessed Sep. 11, 2017, 2 pages. Downloaded from: https://en.wikipedia.org/w/index.php?title=Maytansinoid&oldid=732417913.
Kridel et al., "A Unique Substrate Binding Mode Discriminates Membrane Type-I Matrix Metalloproteinase from Other Matrix Metalloproteinases", J. Biol. Chem. (2002) 277(26): 23788-23793.
Portolano et al., Journal of Immunology, 1993, 150(3): 1993, 880-887.
GENPEPT Accession No. POC9K2, "RecName: Full=Protein MGF 110-14L; Flags: Precursor" May 5, 2009; Database DDBJ/EMBL/Genbank [ online]. Retrieved from the Internet: <https://www.ncbi.nlm.nih.gov/protein/229544532?sat=12&satkey=1040226>; retrieved on Sep. 28, 2018, 3 pages.
Nangia-Makker P., et al. (Dec. 15, 2007) "Galectin-3 cleavage: a novel surrogate marker for matrix metalloproteinase activity in growing breast cancers" Cancer Res, 67(24 ): 11760-11768. NIH Public Access Author Manuscript; available in PMC Apr. 2, 2013 [online]. Retrieved from the Internet: https://www.ncbi.nlm.nih.gov/pmc/articles/PMC36I3979; 17 pages.
Zhao T. et al. (May 21, 2010) "A novel strategy to tag matrix metalloproteinasespositive cells for in vivo imaging of invasive and metastatic activity of tumor cells" J Control Release, 144(1):109-114. doi: 10.1016/j.jcomel.2010.01.023. Epub Jan. 21, 2010; abstract.
Irving, "Probodies Empower a New Generation of Antibody Immunotherapies," presented at Keystone Symposia on Molecular and Cellular Biology, Feb. 2015.
Gerspach et al., "Target-selective activation of a TNF prodrug by urokinase-type plasminogen activator (uPA) mediated proteolytic processing at the cell surface." Cancer Immunol Immunother, vol. 55: 1590-1600 (2006).
Tateno, H. et al. (Jul. 24, 1998) "Isolation and Characterization ofRharnnose-binding Lectins from Eggs of Steelhead Trout (*Oncorhynchus mykiss*) Homologous to Low Density Lipoprotein Receptor Superfamily" J Biol Chem, vol. 273, No. 30, pp. 19190-19197.
U.S. Office Action issued on Feb. 3, 2022 in U.S. Appl. No. 17/360,809, 28 pages.
Russian Office Action issued on Dec. 21, 2022 in RU Application No. 2020106752, 20 pages.
Japanese Office Action issued on Sep. 20, 2022 in JP Application No. 2021-016630, 7 pages.
De Groot, N., "AsnC family protein from Sedimentitalea nanhaiensis", XP093016536, (Apr. 12, 2017), Retrieved from the Internet on Jan. 23, 2023: URL:https://rest.uniprot.org/unisave/AOA1I7CZR5?format=txt&versions=3.

(56) References Cited

OTHER PUBLICATIONS

GenBank: EMG45877.1, Yu et al., Mar. 6, 2013, pp. 1-2, (www.ncbi.nlm.gov/protein/ ).
GenBank: EJK72392.1, Lommer et al., Jul. 25, 2012, pp. 1-3 (www.ncbi.nlm.gov/protein/).
Juliano et al., "Differences in substrate specificities between cysteine protease CPB isoforms of Leishmania mexicana are mediated by a few amino acid changes", Eur. J. Biochem. (2004) 271(18):3704-3714.
Liu et al., "Targeting of Tumor Cells by Cell Surface Urokinase Plasminogen Activator dependent Anthrax Toxin", J. Biol. Chem. (2001) 276(21):17976-17984.
Neitzel, James J., "Enzyme Catalysis: The Serine Proteases", Nature Ed. (2010) 3(9):21.
"Uncharacterized protein from Saprolegnia parasitica", ID: A0A0678QW3_SAPPC, Uniprot: https://rest.uniprot.org/unisave/A0A067BQW3?fom1at=txt&versions=1; Sep. 3, 2014.
Yarilin, "The Fundamentals of Immunology," Moscow: Meditsina, 1999, pp. 171-174 (4 pages), ISBN 5-225-02755-5.
Yarmolinskaya et al., "Matrix Metalloproteinases and Inhibitors: Classification, Mechanism of Action", J. Obstetrics and Women's Diseases (2012) 61(1):113-125.

* cited by examiner

H292 Efficacy Study

IVIG

Cetuximab

2001

2003

2005

SEQUENCE LISTING

```
Sequence total quantity: 562
SEQ ID NO: 1            moltype = AA  length = 13
FEATURE                 Location/Qualifiers
REGION                  1..13
                        note = chemically synthesized
source                  1..13
                        mol_type = protein
                        organism = synthetic construct
SEQUENCE: 1
ISSGLLSGRS DNH                                                     13

SEQ ID NO: 2            moltype = AA  length = 22
FEATURE                 Location/Qualifiers
REGION                  1..22
                        note = chemically synthesized
source                  1..22
                        mol_type = protein
                        organism = synthetic construct
SEQUENCE: 2
ISSGLLSSGG SGGSLSGRSD NH                                           22

SEQ ID NO: 3            moltype = AA  length = 22
FEATURE                 Location/Qualifiers
REGION                  1..22
                        note = chemically synthesized
source                  1..22
                        mol_type = protein
                        organism = synthetic construct
SEQUENCE: 3
AVGLLAPPGG TSTSGRSANP RG                                           22

SEQ ID NO: 4            moltype = AA  length = 22
FEATURE                 Location/Qualifiers
REGION                  1..22
                        note = chemically synthesized
source                  1..22
                        mol_type = protein
                        organism = synthetic construct
SEQUENCE: 4
TSTSGRSANP RGGGAVGLLA PP                                           22

SEQ ID NO: 5            moltype = AA  length = 24
FEATURE                 Location/Qualifiers
REGION                  1..24
                        note = chemically synthesized
source                  1..24
                        mol_type = protein
                        organism = synthetic construct
SEQUENCE: 5
```

```
VHMPLGFLGP GGTSTSGRSA NPRG                                              24

SEQ ID NO: 6            moltype = AA  length = 24
FEATURE                 Location/Qualifiers
REGION                  1..24
                        note = chemically synthesized
source                  1..24
                        mol_type = protein
                        organism = synthetic construct
SEQUENCE: 6
TSTSGRSANP RGGGVHMPLG FLGP                                              24

SEQ ID NO: 7            moltype = AA  length = 18
FEATURE                 Location/Qualifiers
REGION                  1..18
                        note = chemically synthesized
source                  1..18
                        mol_type = protein
                        organism = synthetic construct
SEQUENCE: 7
AVGLLAPPGG LSGRSDNH                                                     18

SEQ ID NO: 8            moltype = AA  length = 18
FEATURE                 Location/Qualifiers
REGION                  1..18
                        note = chemically synthesized
source                  1..18
                        mol_type = protein
                        organism = synthetic construct
SEQUENCE: 8
LSGRSDNHGG AVGLLAPP                                                     18

SEQ ID NO: 9            moltype = AA  length = 20
FEATURE                 Location/Qualifiers
REGION                  1..20
                        note = chemically synthesized
source                  1..20
                        mol_type = protein
                        organism = synthetic construct
SEQUENCE: 9
VHMPLGFLGP GGLSGRSDNH                                                   20

SEQ ID NO: 10           moltype = AA  length = 20
FEATURE                 Location/Qualifiers
REGION                  1..20
                        note = chemically synthesized
source                  1..20
                        mol_type = protein
                        organism = synthetic construct
SEQUENCE: 10
LSGRSDNHGG VHMPLGFLGP                                                   20

SEQ ID NO: 11           moltype = AA  length = 22
FEATURE                 Location/Qualifiers
REGION                  1..22
                        note = chemically synthesized
source                  1..22
                        mol_type = protein
                        organism = synthetic construct
SEQUENCE: 11
LSGRSDNHGG SGGSISSGLL SS                                                22

SEQ ID NO: 12           moltype = AA  length = 22
FEATURE                 Location/Qualifiers
REGION                  1..22
                        note = chemically synthesized
source                  1..22
                        mol_type = protein
                        organism = synthetic construct
SEQUENCE: 12
LSGRSGNHGG SGGSISSGLL SS                                                22

SEQ ID NO: 13           moltype = AA  length = 22
FEATURE                 Location/Qualifiers
REGION                  1..22
                        note = chemically synthesized
source                  1..22
                        mol_type = protein
                        organism = synthetic construct
```

```
SEQUENCE: 13
ISSGLLSSGG SGGSLSGRSG NH                                            22

SEQ ID NO: 14          moltype = AA  length = 22
FEATURE                Location/Qualifiers
REGION                 1..22
                       note = chemically synthesized
source                 1..22
                       mol_type = protein
                       organism = synthetic construct
SEQUENCE: 14
LSGRSDNHGG SGGSQNQALR MA                                            22

SEQ ID NO: 15          moltype = AA  length = 22
FEATURE                Location/Qualifiers
REGION                 1..22
                       note = chemically synthesized
source                 1..22
                       mol_type = protein
                       organism = synthetic construct
SEQUENCE: 15
QNQALRMAGG SGGSLSGRSD NH                                            22

SEQ ID NO: 16          moltype = AA  length = 22
FEATURE                Location/Qualifiers
REGION                 1..22
                       note = chemically synthesized
source                 1..22
                       mol_type = protein
                       organism = synthetic construct
SEQUENCE: 16
LSGRSGNHGG SGGSQNQALR MA                                            22

SEQ ID NO: 17          moltype = AA  length = 22
FEATURE                Location/Qualifiers
REGION                 1..22
                       note = chemically synthesized
source                 1..22
                       mol_type = protein
                       organism = synthetic construct
SEQUENCE: 17
QNQALRMAGG SGGSLSGRSG NH                                            22

SEQ ID NO: 18          moltype = AA  length = 8
FEATURE                Location/Qualifiers
REGION                 1..8
                       note = chemically synthesized
source                 1..8
                       mol_type = protein
                       organism = synthetic construct
SEQUENCE: 18
LSGRSDNH                                                            8

SEQ ID NO: 19          moltype = AA  length = 8
FEATURE                Location/Qualifiers
REGION                 1..8
                       note = chemically synthesized
source                 1..8
                       mol_type = protein
                       organism = synthetic construct
SEQUENCE: 19
LSGRSGNH                                                            8

SEQ ID NO: 20          moltype = AA  length = 8
FEATURE                Location/Qualifiers
REGION                 1..8
                       note = chemically synthesized
source                 1..8
                       mol_type = protein
                       organism = synthetic construct
SEQUENCE: 20
ISSGLLSS                                                            8

SEQ ID NO: 21          moltype = AA  length = 8
FEATURE                Location/Qualifiers
REGION                 1..8
                       note = chemically synthesized
source                 1..8
                       mol_type = protein
```

```
                         organism = synthetic construct
SEQUENCE: 21
QNQALRMA                                                          8

SEQ ID NO: 22            moltype = AA  length = 13
FEATURE                  Location/Qualifiers
REGION                   1..13
                         note = chemically synthesized
source                   1..13
                         mol_type = protein
                         organism = synthetic construct
SEQUENCE: 22
ISSGLLSGRS GNH                                                    13

SEQ ID NO: 23            moltype = DNA  length = 24
FEATURE                  Location/Qualifiers
misc_feature             1..24
                         note = chemically synthesized
source                   1..24
                         mol_type = other DNA
                         organism = synthetic construct
SEQUENCE: 23
ttaagcgggc ggtcggacaa ccac                                        24

SEQ ID NO: 24            moltype = DNA  length = 24
FEATURE                  Location/Qualifiers
misc_feature             1..24
                         note = chemically synthesized
source                   1..24
                         mol_type = other DNA
                         organism = synthetic construct
SEQUENCE: 24
cttagcgggc ggagcggcaa ccac                                        24

SEQ ID NO: 25            moltype = DNA  length = 24
FEATURE                  Location/Qualifiers
misc_feature             1..24
                         note = chemically synthesized
source                   1..24
                         mol_type = other DNA
                         organism = synthetic construct
SEQUENCE: 25
atctcctccg ggctactgag ttct                                        24

SEQ ID NO: 26            moltype = DNA  length = 24
FEATURE                  Location/Qualifiers
misc_feature             1..24
                         note = chemically synthesized
source                   1..24
                         mol_type = other DNA
                         organism = synthetic construct
SEQUENCE: 26
cagaaccagg cgctcagaat ggca                                        24

SEQ ID NO: 27            moltype = DNA  length = 39
FEATURE                  Location/Qualifiers
misc_feature             1..39
                         note = chemically synthesized
source                   1..39
                         mol_type = other DNA
                         organism = synthetic construct
SEQUENCE: 27
atatcatccg gcctccttag cggccgttcc gacaatcac                        39

SEQ ID NO: 28            moltype = DNA  length = 39
FEATURE                  Location/Qualifiers
misc_feature             1..39
                         note = chemically synthesized
source                   1..39
                         mol_type = other DNA
                         organism = synthetic construct
SEQUENCE: 28
ataagttctg ggctcctgtc gggccggagt ggaaatcac                        39

SEQ ID NO: 29            moltype = DNA  length = 66
FEATURE                  Location/Qualifiers
misc_feature             1..66
                         note = chemically synthesized
source                   1..66
```

-continued

```
                         mol_type = other DNA
                         organism = synthetic construct
SEQUENCE: 29
ctgagcgggc ggtccgataa tcatggtggt tcaggaggga gtatttcttc cggcttactg  60
agtagc                                                             66

SEQ ID NO: 30            moltype = DNA  length = 66
FEATURE                  Location/Qualifiers
misc_feature             1..66
                         note = chemically synthesized
source                   1..66
                         mol_type = other DNA
                         organism = synthetic construct
SEQUENCE: 30
atctcctctg ggttgctttc ttcaggaggt tcaggggga gcctgagcgg acgctccgac  60
aaccat                                                             66

SEQ ID NO: 31            moltype = DNA  length = 66
FEATURE                  Location/Qualifiers
misc_feature             1..66
                         note = chemically synthesized
source                   1..66
                         mol_type = other DNA
                         organism = synthetic construct
SEQUENCE: 31
ctctcaggaa gatccggaaa tcatgggggg tctgggggga gtatctcatc aggtctgctg  60
agcagc                                                             66

SEQ ID NO: 32            moltype = DNA  length = 66
FEATURE                  Location/Qualifiers
misc_feature             1..66
                         note = chemically synthesized
source                   1..66
                         mol_type = other DNA
                         organism = synthetic construct
SEQUENCE: 32
atctcaagtg ggctgttaag ttccggcggc agtggagggt ccctaagcgg ccgcagcggg  60
aatcac                                                             66

SEQ ID NO: 33            moltype = DNA  length = 66
FEATURE                  Location/Qualifiers
misc_feature             1..66
                         note = chemically synthesized
source                   1..66
                         mol_type = other DNA
                         organism = synthetic construct
SEQUENCE: 33
ctctctggcc gctccgataa tcatggtgga tccggtggct ctcagaacca ggcactacgg  60
atggca                                                             66

SEQ ID NO: 34            moltype = DNA  length = 66
FEATURE                  Location/Qualifiers
misc_feature             1..66
                         note = chemically synthesized
source                   1..66
                         mol_type = other DNA
                         organism = synthetic construct
SEQUENCE: 34
cagaaccagg cgctcaggat ggcagggggg agtggcggaa gcctttctgg tcgatccgat  60
aatcac                                                             66

SEQ ID NO: 35            moltype = DNA  length = 66
FEATURE                  Location/Qualifiers
misc_feature             1..66
                         note = chemically synthesized
source                   1..66
                         mol_type = other DNA
                         organism = synthetic construct
SEQUENCE: 35
cttagcggac gctctggcaa ccacggagga tctggaggaa gtcagaacca ggccttgcgc  60
atggcc                                                             66

SEQ ID NO: 36            moltype = DNA  length = 66
FEATURE                  Location/Qualifiers
misc_feature             1..66
                         note = chemically synthesized
source                   1..66
                         mol_type = other DNA
                         organism = synthetic construct
```

```
SEQUENCE: 36
caaaaccagg ctctgcgcat ggctgggggg tctggtggga gcctgagcgg gcggtcagga  60
aaccac                                                             66

SEQ ID NO: 37          moltype = DNA  length = 37
FEATURE                Location/Qualifiers
misc_feature           1..37
                       note = chemically synthesized
source                 1..37
                       mol_type = other DNA
                       organism = synthetic construct
SEQUENCE: 37
gtgcagccac cgtacgtttg atttccacct tggtccc                            37

SEQ ID NO: 38          moltype = DNA  length = 97
FEATURE                Location/Qualifiers
misc_feature           1..97
                       note = chemically synthesized
source                 1..97
                       mol_type = other DNA
                       organism = synthetic construct
SEQUENCE: 38
cagggggct cgagcggcgg ctctatctct tccggactgc tgtccggcag atccgacaat  60
cacggcggag gctctgacat ccagatgacc cagtctc                            97

SEQ ID NO: 39          moltype = DNA  length = 124
FEATURE                Location/Qualifiers
misc_feature           1..124
                       note = chemically synthesized
source                 1..124
                       mol_type = other DNA
                       organism = synthetic construct
SEQUENCE: 39
caggggggct cgagcggcgg ctctatctct tctggcctgc tgtctagcgg cggctccggc  60
ggatctctgt ctggcagatc tgacaaccac ggcggaggct ccgacatcca gatgacccag  120
tctc                                                               124

SEQ ID NO: 40          moltype = DNA  length = 121
FEATURE                Location/Qualifiers
misc_feature           1..121
                       note = chemically synthesized
source                 1..121
                       mol_type = other DNA
                       organism = synthetic construct
SEQUENCE: 40
caggggggct cgagcggagg atctgctgtg ggactgctgg ctcctcctgg cggcacatct  60
acctctggca gatccgccaa ccctcggggc ggaggatctg acatccagat gacccagtct  120
c                                                                  121

SEQ ID NO: 41          moltype = DNA  length = 121
FEATURE                Location/Qualifiers
misc_feature           1..121
                       note = chemically synthesized
source                 1..121
                       mol_type = other DNA
                       organism = synthetic construct
SEQUENCE: 41
caggggggct cgagcggcgg ctccacatct acctctggca gatccgccaa ccccagaggt  60
ggcggagctg tgggactgct ggctccacca ggcggatctg acatccagat gacccagtct  120
c                                                                  121

SEQ ID NO: 42          moltype = DNA  length = 127
FEATURE                Location/Qualifiers
misc_feature           1..127
                       note = chemically synthesized
source                 1..127
                       mol_type = other DNA
                       organism = synthetic construct
SEQUENCE: 42
caggggggct cgagcggcgg ctctgtgcat atgcccctgg gctttctggg ccctggcggc  60
acatctacct ctggcagatc cgccaaccct cggggcggag gatctgacat ccagatgacc  120
cagtctc                                                            127

SEQ ID NO: 43          moltype = DNA  length = 127
FEATURE                Location/Qualifiers
misc_feature           1..127
                       note = chemically synthesized
source                 1..127
                       mol_type = other DNA
```

```
                         organism = synthetic construct
SEQUENCE: 43
caggggggct cgagcggcgg ctccacatct acctctggca gatccgccaa ccccagaggc  60
ggcggagtgc atatgcctct gggctttctg ggacctggcg gctctgacat ccagatgacc  120
cagtctc                                                            127

SEQ ID NO: 44            moltype = DNA  length = 109
FEATURE                  Location/Qualifiers
misc_feature             1..109
                         note = chemically synthesized
source                   1..109
                         mol_type = other DNA
                         organism = synthetic construct
SEQUENCE: 44
caggggggct cgagcggagg atctgctgtg ggactgctgg ctcctcctgg tggcctgtct  60
ggcagatctg ataaccacgg cggctccgac atccagatga cccagtctc              109

SEQ ID NO: 45            moltype = DNA  length = 112
FEATURE                  Location/Qualifiers
misc_feature             1..112
                         note = chemically synthesized
source                   1..112
                         mol_type = other DNA
                         organism = synthetic construct
SEQUENCE: 45
caggggggct cgagcggagg ctctggcctg tctggcagat ccgataacca tggcggcgct  60
gtgggactgc tggctcctcc tggtggatct gacatccaga tgacccagtc tc          112

SEQ ID NO: 46            moltype = DNA  length = 115
FEATURE                  Location/Qualifiers
misc_feature             1..115
                         note = chemically synthesized
source                   1..115
                         mol_type = other DNA
                         organism = synthetic construct
SEQUENCE: 46
caggggggct cgagcggcgg ctctgtgcat atgcccctgg gctttctggg acctggcggc  60
ctgtctggca gatccgataa tcacggcggc tccgacatcc agatgaccca gtctc       115

SEQ ID NO: 47            moltype = DNA  length = 118
FEATURE                  Location/Qualifiers
misc_feature             1..118
                         note = chemically synthesized
source                   1..118
                         mol_type = other DNA
                         organism = synthetic construct
SEQUENCE: 47
caggggggct cgagcggagg ctctggcctg tctggcagat ctgataacca cggcggcgtg  60
cacatgcccc tgggctttct gggacctggc ggatctgaca tccagatgac ccagtctc    118

SEQ ID NO: 48            moltype = DNA  length = 774
FEATURE                  Location/Qualifiers
misc_feature             1..774
                         note = chemically synthesized
source                   1..774
                         mol_type = other DNA
                         organism = synthetic construct
SEQUENCE: 48
caaggccagt ctggccagtg caatatttgg ctcgtaggtg gtgattgcag ggctggcag  60
gggggctcga gcggcggctc tatctcttcc ggactgctgt ccggcagatc cgacaatcac  120
ggcggaggct ctgacatcca gatgacccag tctccatcct ccctgtctgc atctgtagga  180
gacagagtca ccatcacttg ccgggcaagt cagagcatta gcagctattt aaattggtat  240
cagcagaaac cagggaaagc ccctaagctc ctgatctatg cggcatccag tttgcaaagt  300
ggggtcccat caaggttcag tggcagtgga tctgggacag atttcactct caccatcagc  360
agtctgcaac ctgaagattt tgcaacttac tactgtcaac agacggttgt ggcgcctccg  420
ttattcggcc aagggaccaa ggtggaaatc aaacgtacgg tggctgcacc atctgtcttc  480
atcttcccgc catctgatga gcagttgaaa tctggaactg cctctgttgt gtgcctgctg  540
aataacttct atcccagaga ggccaaagta cagtggaagg tggataacgc cctccaatcg  600
ggtaactccc aggagagtgt cacagagcag gacagcaagg acagcaccta cagcctcagc  660
agcaccctga cgctgagcaa agcagactac gagaaacaca aagtctacgc ctgcgaagtc  720
acccatcagg gcctgagctc gcccgtcaca aagagcttca acaggggaga gtgt        774

SEQ ID NO: 49            moltype = AA  length = 258
FEATURE                  Location/Qualifiers
REGION                   1..258
                         note = chemically synthesized
source                   1..258
                         mol_type = protein
                         organism = synthetic construct
```

```
SEQUENCE: 49
QGQSGQCNIW LVGGDCRGWQ GGSSGGSISS GLLSGRSDNH GGGSDIQMTQ SPSSLSASVG  60
DRVTITCRAS QSISSYLNWY QQKPGKAPKL LIYAASSLQS GVPSRFSGSG SGTDFTLTIS  120
SLQPEDFATY YCQQTVVAPP LFGQGTKVEI KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                               258

SEQ ID NO: 50          moltype = DNA  length = 801
FEATURE                Location/Qualifiers
misc_feature           1..801
                       note = chemically synthesized
source                 1..801
                       mol_type = other DNA
                       organism = synthetic construct
SEQUENCE: 50
caaggccagt ctggccagtg caatatttgg ctcgtaggtg gtgattgcag ggctggcag  60
gggggctcga gcggcggctc tatctcttct ggcctgctgt ctagcggcgg ctccggcgga  120
tctctgtctg gcagatctga caaccacggc ggaggctccg acatccagat gacccagtct  180
ccatcctccc tgtctgcatc tgtaggagac agagtcacca tcacttgccg ggcaagtcag  240
agcattagca gctatttaaa ttggtatcag cagaaaccag ggaaagcccc taagctcctg  300
atctatgcgg catccagttt gcaaagtggg gtcccatcaa ggttcagtgg cagtggatct  360
gggacagatt tcactctcac catcagcagt ctgcaacctg aagattttgc aacttactac  420
tgtcaacaga cggttgtggc gcctccgtta ttcggccaag ggaccaaggt ggaaatcaaa  480
cgtacggtgg ctgcaccatc tgtcttcatc ttcccgccat ctgatgagca gttgaaatct  540
ggaactgcct ctgttgtgtg cctgctgaat aacttctatc ccagagaggc caaagtacag  600
tggaaggtgg ataacgccct ccaatcgggt aactcccagg agagtgtcac agagcaggac  660
agcaaggaca gcacctacag cctcagcagc accctgacgc tgagcaaagc agactacgag  720
aaacacaaag tctacgcctg cgaagtcacc catcagggcc tgagctcgcc cgtcacaaag  780
agcttcaaca ggggagagtg t                                           801

SEQ ID NO: 51          moltype = AA  length = 267
FEATURE                Location/Qualifiers
REGION                 1..267
                       note = chemically synthesized
source                 1..267
                       mol_type = protein
                       organism = synthetic construct
SEQUENCE: 51
QGQSGQCNIW LVGGDCRGWQ GGSSGGSISS GLLSSGGSGG SLSGRSDNHG GGSDIQMTQS  60
PSSLSASVGD RVTITCRASQ SISSYLNWYQ QKPGKAPKLL IYAASSLQSG VPSRFSGSGS  120
GTDFTLTISS LQPEDFATYY CQQTVVAPPL FGQGTKVEIK RTVAAPSVFI FPPSDEQLKS  180
GTASVVCLLN NFYPREAKVQ WKVDNALQSG NSQESVTEQD SKDSTYSLSS TLTLSKADYE  240
KHKVYACEVT HQGLSSPVTK SFNRGEC                                     267

SEQ ID NO: 52          moltype = DNA  length = 798
FEATURE                Location/Qualifiers
misc_feature           1..798
                       note = chemically synthesized
source                 1..798
                       mol_type = other DNA
                       organism = synthetic construct
SEQUENCE: 52
caaggccagt ctggccagtg caatatttgg ctcgtaggtg gtgattgcag ggctggcag  60
gggggctcga gcggaggatc tgctgtggga ctgctggctc ctcctggcgg cacatctacc  120
tctggcagat ccgccaaccc tcggggcgga ggatctgaca tccagatgac ccagtctcca  180
tcctccctgt ctgcatctgt aggagacaga gtcaccatca cttgccgggc aagtcagagc  240
attagcagct atttaaattg gtatcagcag aaaccaggga aagcccctaa gctcctgatc  300
tatgcggcat ccagtttgca aagtggggtc ccatcaaggt tcagtggcag tggatctggg  360
acagatttca ctctcaccat cagcagtctg caacctgaag attttgcaac ttactactgt  420
caacagacgg ttgtggcgcc tccgttattc ggccaaggga ccaaggtgga aatcaaacgt  480
acggtggctg caccatctgt cttcatcttc ccgccatctg atgagcagtt gaaatctgga  540
actgcctctg ttgtgtgcct gctgaataac ttctatccca gagaggccaa agtacagtgg  600
aaggtggata acgccctcca atcgggtaac tcccaggaga gtgtcacaga gcaggacagc  660
aaggacagca cctacagcct cagcagcacc ctgacgctga gcaaagcaga ctacgagaaa  720
cacaaagtct acgcctgcga agtcacccat cagggcctga gctcgcccgt cacaaagagc  780
ttcaacaggg gagagtgt                                               798

SEQ ID NO: 53          moltype = AA  length = 266
FEATURE                Location/Qualifiers
REGION                 1..266
                       note = chemically synthesized
source                 1..266
                       mol_type = protein
                       organism = synthetic construct
SEQUENCE: 53
QGQSGQCNIW LVGGDCRGWQ GGSSGGSAVG LLAPPGGTST SGRSANPRGG GSDIQMTQSP  60
SSLSASVGDR VTITCRASQS ISSYLNWYQQ KPGKAPKLLI YAASSLQSGV PSRFSGSGSG  120
TDFTLTISSL QPEDFATYYC QQTVVAPPLF GQGTKVEIKR TVAAPSVFIF PPSDEQLKSG  180
TASVVCLLNN FYPREAKVQW KVDNALQSGN SQESVTEQDS KDSTYSLSST LTLSKADYEK  240
```

```
HKVYACEVTH QGLSSPVTKS FNRGEC                                        266

SEQ ID NO: 54          moltype = DNA  length = 798
FEATURE                Location/Qualifiers
misc_feature           1..798
                       note = chemically synthesized
source                 1..798
                       mol_type = other DNA
                       organism = synthetic construct
SEQUENCE: 54
caaggccagt ctggccagtg caatatttgg ctcgtaggtg gtgattgcag gggctggcag  60
gggggctcga gcggcggctc cacatctacc tctggcagat ccgccaaccc cagaggtggc  120
ggagctgtgg gactgctggc tccaccaggc ggatctgaca tccagatgac ccagtctcca  180
tcctccctgt ctgcatctgt aggagacaga gtcaccatca cttgccgggc aagtcagagc  240
attagcagct atttaaattg gtatcagcag aaaccaggga aagcccctaa gctcctgatc  300
tatgcggcat ccagtttgca aagtggggtc ccatcaaggt tcagtggcag tggatctggg  360
acagatttca ctctcaccat cagcagtctg caacctgaag attttgcaac ttactactgt  420
caacagacgg ttgtggcgcc tccgttattc ggccaaggga ccaaggtgga aatcaaacgt  480
acggtggctg caccatctgt cttcatcttc ccgccatctg atgagcagtt gaaatctgga  540
actgcctctg ttgtgtgcct gctgaataac ttctatccca gagaggccaa agtacagtgg  600
aaggtggata acgccctcca atcgggtaac tcccaggaga gtgtcacaga gcaggacagc  660
aaggacagca cctacagcct cagcagcacc ctgacgctga gcaaagcaga ctacgagaaa  720
cacaaagtct acgcctgcga agtcacccat cagggcctga gctcgcccgt cacaaagagc  780
ttcaacaggg gagagtgt                                                798

SEQ ID NO: 55          moltype = AA  length = 266
FEATURE                Location/Qualifiers
REGION                 1..266
                       note = chemically synthesized
source                 1..266
                       mol_type = protein
                       organism = synthetic construct
SEQUENCE: 55
QGQSGQCNIW LVGGDCRGWQ GGSSGGSTST SGRSANPRGG GAVGLLAPPG GSDIQMTQSP  60
SSLSASVGDR VTITCRASQS ISSYLNWYQQ KPGKAPKLLI YAASSLQSGV PSRFSGSGSG  120
TDFTLTISSL QPEDFATYYC QQTVVAPPLF GQGTKVEIKR TVAAPSVFIF PPSDEQLKSG  180
TASVVCLLNN FYPREAKVQW KVDNALQSGN SQESVTEQDS KDSTYSLSST LTLSKADYEK  240
HKVYACEVTH QGLSSPVTKS FNRGEC                                        266

SEQ ID NO: 56          moltype = DNA  length = 804
FEATURE                Location/Qualifiers
misc_feature           1..804
                       note = chemically synthesized
source                 1..804
                       mol_type = other DNA
                       organism = synthetic construct
SEQUENCE: 56
caaggccagt ctggccagtg caatatttgg ctcgtaggtg gtgattgcag gggctggcag  60
gggggctcga gcggcggctc tgtgcatatg cccctgggct ttctgggccc tggcggcaca  120
tctacctctg gcagatccgc caaccctcgg ggcggaggat ctgacatcca gatgacccag  180
tctccatcct ccctgtctgc atctgtagga gacagagtca ccatcacttg ccgggcaagt  240
cagagcatta gcagctattt aaattggtat cagcagaaac cagggaaagc ccctaagctc  300
ctgatctatg cggcatccag tttgcaaagt ggggtcccat caaggttcag tggcagtgga  360
tctgggacag atttcactct caccatcagc agtctgcaac ctgaagattt tgcaacttac  420
tactgtcaac agacggttgt ggcgcctccg ttattcggcc aagggaccaa ggtggaaatc  480
aaacgtacgg tggctgcacc atctgtcttc atcttcccgc catctgatga gcagttgaaa  540
tctggaactg cctctgttgt gtgcctgctg aataacttct atcccagaga ggccaaagta  600
cagtggaagg tggataacgc cctccaatcg ggtaactccc aggagagtgt cacagagcag  660
gacagcaagg acagcaccta cagcctcagc agcaccctga cgctgagcaa agcagactac  720
gagaaacaca aagtctacgc ctgcgaagtc acccatcagg gcctgagctc gcccgtcaca  780
aagagcttca acaggggaga gtgt                                          804

SEQ ID NO: 57          moltype = AA  length = 268
FEATURE                Location/Qualifiers
REGION                 1..268
                       note = chemically synthesized
source                 1..268
                       mol_type = protein
                       organism = synthetic construct
SEQUENCE: 57
QGQSGQCNIW LVGGDCRGWQ GGSSGGSVHM PLGFLGPGGT STSGRSANPR GGGSDIQMTQ  60
SPSSLSASVG DRVTITCRAS QSISSYLNWY QQKPGKAPKL LIYAASSLQS GVPSRFSGSG  120
SGTDFTLTIS SLQPEDFATY YCQQTVVAPP LFGQGTKVEI KRTVAAPSVF IFPPSDEQLK  180
SGTASVVCLL NNFYPREAKV QWKVDNALQS GNSQESVTEQ DSKDSTYSLS STLTLSKADY  240
EKHKVYACEV THQGLSSPVT KSFNRGEC                                      268

SEQ ID NO: 58          moltype = DNA  length = 804
FEATURE                Location/Qualifiers
misc_feature           1..804
```

```
                        note = chemically synthesized
source                  1..804
                        mol_type = other DNA
                        organism = synthetic construct
SEQUENCE: 58
caaggccagt ctggccagtg caatatttgg ctcgtaggtg gtgattgcag gggctggcag  60
gggggctcga gcggcggctc cacatctacc tctggcagat ccgccaaccc cagaggcggc  120
ggagtgcata tgcctctggg ctttctggga cctggcggct ctgacatcca gatgacccag  180
tctccatcct ccctgtctgc atctgtagga gacagagtca ccatcacttg ccgggcaagt  240
cagagcatta gcagctattt aaattggtat cagcagaaac cagggaaagc ccctaagctc  300
ctgatctatg cggcatccag tttgcaaagt ggggtcccat caaggttcag tggcagtgga  360
tctgggacag atttcactct caccatcagc agtctgcaac ctgaagattt tgcaacttac  420
tactgtcaac agacggttgt ggcgcctccg ttattcggcc aagggaccaa ggtggaaatc  480
aaacgtacgg tggctgcacc atctgtcttc atcttcccgc catctgatga gcagttgaaa  540
tctggaactg cctctgttgt gtgcctgctg aataacttct atcccagaga ggccaaagta  600
cagtggaagg tggataacgc cctccaatcg ggtaactccc aggagagtgt cacagagcag  660
gacagcaagg acagcaccta cagcctcagc agcaccctga cgctgagcaa agcagactac  720
gagaaacaca aagtctacgc ctgcgaagtc acccatcagg gcctgagctc gcccgtcaca  780
aagagcttca acaggggaga gtgt                                          804

SEQ ID NO: 59           moltype = AA  length = 268
FEATURE                 Location/Qualifiers
REGION                  1..268
                        note = chemically synthesized
source                  1..268
                        mol_type = protein
                        organism = synthetic construct
SEQUENCE: 59
QGQSGQCNIW LVGGDCRGWQ GGSSGGSTST SGRSANPRGG GVHMPLGFLG PGGSDIQMTQ  60
SPSSLSASVG DRVTITCRAS QSISSYLNWY QQKPGKAPKL LIYAASSLQS GVPSRFSGSG  120
SGTDFTLTIS SLQPEDFATY YCQQTVVAPP LFGQGTKVEI KRTVAAPSVF IFPPSDEQLK  180
SGTASVVCLL NNFYPREAKV QWKVDNALQS GNSQESVTEQ DSKDSTYSLS STLTLSKADY  240
EKHKVYACEV THQGLSSPVT KSFNRGEC                                      268

SEQ ID NO: 60           moltype = DNA  length = 786
FEATURE                 Location/Qualifiers
misc_feature            1..786
                        note = chemically synthesized
source                  1..786
                        mol_type = other DNA
                        organism = synthetic construct
SEQUENCE: 60
caaggccagt ctggccagtg caatatttgg ctcgtaggtg gtgattgcag gggctggcag  60
gggggctcga gcggaggatc tgctgtggga ctgctggctc ctcctggtgg cctgtctggc  120
agatctgata accacggcgg ctccgacatc cagatgaccc agtctccatc ctccctgtct  180
gcatctgtag gagacagagt caccatcact tgccgggcaa gtcagagcat tagcagctat  240
ttaaattggt atcagcagaa accagggaaa gcccctaagc tcctgatcta tgcggcatcc  300
agtttgcaaa gtggggtccc atcaaggttc agtggcagtg gatctgggac agatttcact  360
ctcaccatca gcagtctgca acctgaagat tttgcaactt actactgtca acagacggtt  420
gtggcgcctc cgttattcgg ccaagggacc aaggtggaaa tcaaacgtac ggtggctgca  480
ccatctgtct tcatcttccc gccatctgat gagcagttga aatctggaac tgcctctgtt  540
gtgtgcctgc tgaataactt ctatcccaga gaggccaaag tacagtggaa ggtggataac  600
gccctccaat cgggtaactc ccaggagagt gtcacagagc aggacagcaa ggacagcacc  660
tacagcctca gcagcaccct gacgctgagc aaagcagact acgagaaaca caaagtctac  720
gcctgcgaag tcacccatca gggcctgagc tcgcccgtca caaagagctt caacagggga  780
gagtgt                                                              786

SEQ ID NO: 61           moltype = AA  length = 262
FEATURE                 Location/Qualifiers
REGION                  1..262
                        note = chemically synthesized
source                  1..262
                        mol_type = protein
                        organism = synthetic construct
SEQUENCE: 61
QGQSGQCNIW LVGGDCRGWQ GGSSGGSAVG LLAPPGGLSG RSDNHGGSDI QMTQSPSSLS  60
ASVGDRVTIT CRASQSISSY LNWYQQKPGK APKLLIYAAS SLQSGVPSRF SGSGSGTDFT  120
LTISSLQPED FATYYCQQTV VAPPLFGQGT KVEIKRTVAA PSVFIFPPSD EQLKSGTASV  180
VCLLNNFYPR EAKVQWKVDN ALQSGNSQES VTEQDSKDST YSLSSTLTLS KADYEKHKVY  240
ACEVTHQGLS SPVTKSFNRG EC                                            262

SEQ ID NO: 62           moltype = DNA  length = 789
FEATURE                 Location/Qualifiers
misc_feature            1..789
                        note = chemically synthesized
source                  1..789
                        mol_type = other DNA
                        organism = synthetic construct
SEQUENCE: 62
```

```
caaggccagt ctggccagtg caatatttgg ctcgtaggtg gtgattgcag gggctggcag  60
gggggctcga gcggaggctc tggcctgtct ggcagatccg ataaccatgg cggcgctgtg  120
ggactgctgg ctcctcctgg tggatctgac atccagatga cccagtctcc atcctccctg  180
tctgcatctg taggagacag agtcaccatc acttgccggg caagtcagag cattagcagc  240
tatttaaatt ggtatcagca gaaaccaggg aaagccccta agctcctgat ctatgcggca  300
tccagtttgc aaagtggggt cccatcaagg ttcagtggca gtggatctgg gacagatttc  360
actctcacca tcagcagtct gcaacctgaa gattttgcaa cttactactg tcaacagacg  420
gttgtggcgc ctccgttatt cggccaaggg accaaggtgg aaatcaaacg tacggtggct  480
gcaccatctg tcttcatctt cccgccatct gatgagcagt tgaaatctgg aactgcctct  540
gttgtgtgcc tgctgaataa cttctatccc agagaggcca aagtacagtg gaaggtggat  600
aacgccctcc aatcgggtaa ctcccaggag agtgtcacag agcaggacag caaggacagc  660
acctacagcc tcagcagcac cctgacgctg agcaaagcag actacgagaa acacaaagtc  720
tacgcctgcg aagtcaccca tcagggcctg agctcgcccg tcacaaagag cttcaacagg  780
ggagagtgt                                                         789

SEQ ID NO: 63           moltype = AA  length = 263
FEATURE                 Location/Qualifiers
REGION                  1..263
                        note = chemically synthesized
source                  1..263
                        mol_type = protein
                        organism = synthetic construct
SEQUENCE: 63
QGQSGQCNIW LVGGDCRGWQ GGSSGGSGLS GRSDNHGGAV GLLAPPGGSD IQMTQSPSSL  60
SASVGDRVTI TCRASQSISS YLNWYQQKPG KAPKLLIYAA SSLQSGVPSR FSGSGSGTDF  120
TLTISSLQPE DFATYYCQQT VVAPPLFGQG TKVEIKRTVA APSVFIFPPS DEQLKSGTAS  180
VVCLLNNFYP REAKVQWKVD NALQSGNSQE SVTEQDSKDS TYSLSSTLTL SKADYEKHKV  240
YACEVTHQGL SSPVTKSFNR GEC                                         263

SEQ ID NO: 64           moltype = DNA  length = 792
FEATURE                 Location/Qualifiers
misc_feature            1..792
                        note = chemically synthesized
source                  1..792
                        mol_type = other DNA
                        organism = synthetic construct
SEQUENCE: 64
caaggccagt ctggccagtg caatatttgg ctcgtaggtg gtgattgcag gggctggcag  60
gggggctcga gcggcggctc tgtgcatatg cccctgggct ttctgggacc tggcggcctg  120
tctggcagat ccgataatca cggcggctcc gacatccaga tgacccagtc tccatcctcc  180
ctgtctgcat ctgtaggaga cagagtcacc atcacttgcc gggcaagtca gagcattagc  240
agctatttaa attggtatca gcagaaacca gggaaagccc ctaagctcct gatctatgcg  300
gcatccagtt tgcaaagtgg ggtcccatca aggttcagtg gcagtggatc tgggacagat  360
ttcactctca ccatcagcag tctgcaacct gaagattttg caacttacta ctgtcaacag  420
acggttgtgg cgcctccgtt attcggccaa gggaccaagg tggaaatcaa acgtacggtg  480
gctgcaccat ctgtcttcat cttcccgcca tctgatgagc agttgaaatc tggaactgcc  540
tctgttgtgt gcctgctgaa taacttctat cccagagagg ccaaagtaca gtggaaggtg  600
gataacgccc tccaatcggg taactcccag gagagtgtca cagagcagga cagcaaggac  660
agcacctaca gcctcagcag caccctgacg ctgagcaaag cagactacga gaaacacaaa  720
gtctacgcct gcgaagtcac ccatcagggc ctgagctcgc ccgtcacaaa gagcttcaac  780
aggggagagt gt                                                     792

SEQ ID NO: 65           moltype = AA  length = 264
FEATURE                 Location/Qualifiers
REGION                  1..264
                        note = chemically synthesized
source                  1..264
                        mol_type = protein
                        organism = synthetic construct
SEQUENCE: 65
QGQSGQCNIW LVGGDCRGWQ GGSSGGSVHM PLGFLGPGGL SGRSDNHGGS DIQMTQSPSS  60
LSASVGDRVT ITCRASQSIS SYLNWYQQKP GKAPKLLIYA ASSLQSGVPS RFSGSGSGTD  120
FTLTISSLQP EDFATYYCQQ TVVAPPLFGQ GTKVEIKRTV AAPSVFIFPP SDEQLKSGTA  180
SVVCLLNNFY PREAKVQWKV DNALQSGNSQ ESVTEQDSKD STYSLSSTLT LSKADYEKHK  240
VYACEVTHQG LSSPVTKSFN RGEC                                        264

SEQ ID NO: 66           moltype = DNA  length = 795
FEATURE                 Location/Qualifiers
misc_feature            1..795
                        note = chemically synthesized
source                  1..795
                        mol_type = other DNA
                        organism = synthetic construct
SEQUENCE: 66
caaggccagt ctggccagtg caatatttgg ctcgtaggtg gtgattgcag gggctggcag  60
gggggctcga gcggaggctc tggcctgtct ggcagatctg ataaccacgg cggcgtgcac  120
atgcccctgg gctttctggg acctggcgga tctgacatcc agatgaccca gtctccatcc  180
tccctgtctg catctgtagg agacagagtc accatcactt gccgggcaag tcagagcatt  240
agcagctatt taaattggta tcagcagaaa ccagggaaag cccctaagct cctgatctat  300
```

```
gcggcatcca gtttgcaaag tggggtccca tcaaggttca gtggcagtgg atctgggaca  360
gatttcactc tcaccatcag cagtctgcaa cctgaagatt ttgcaactta ctactgtcaa  420
cagacggttg tggcgcctcc gttattcggc caagggacca aggtggaaat caaacgtacg  480
gtggctgcac catctgtctt catcttcccg ccatctgatg agcagttgaa atctggaact  540
gcctctgttg tgtgcctgct gaataacttc tatcccagag aggccaaagt acagtggaag  600
gtggataacg ccctccaatc gggtaactcc caggagagtg tcacagagca ggacagcaag  660
gacagcacct acagcctcag cagcaccctg acgctgagca aagcagacta cgagaaacac  720
aaagtctacg cctgcgaagt cacccatcag ggcctgagct cgcccgtcac aaagagcttc  780
aacaggggag agtgt                                                   795

SEQ ID NO: 67           moltype = AA  length = 449
FEATURE                 Location/Qualifiers
REGION                  1..449
                        note = chemically synthesized
source                  1..449
                        mol_type = protein
                        organism = synthetic construct
SEQUENCE: 67
EVQLLESGGG LVQPGGSLRL SCAASGFTFS SYAMSWVRQA PGKGLEWVSS IDPEGRQTYY  60
ADSVKGRFTI SRDNSKNTLY LQMNSLRAED TAVYYCAKDI GGRSAFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 68           moltype = AA  length = 1347
FEATURE                 Location/Qualifiers
REGION                  1..1347
                        note = chemically synthesized
source                  1..1347
                        mol_type = protein
                        organism = synthetic construct
SEQUENCE: 68
CAGGTACAGC TGAAACAGTC TGGACCCGGG CTTGTACAGC CTAGTCAGTC ACTGTCTATC  60
ACCTGTACCG TCTCAGGTTT TAGCCTGACA AATTACGGTG TGCATTGGGT ACGCCAGTCT  120
CCCGGTAAGG GGCTGGAGTG GCTCGGCGTG ATCTGGTCCG GGGGGAACAC AGATTATAAT  180
ACTCCTTTCA CATCTAGACT GTCCATCAAC AAAGACAACT CCAAATCGCA GGTTTTTTTC  240
AAGATGAATT CCCTGCAATC ACAGGACACT GCCATCTATT ATTGCGCGAG GGCCCTGACT  300
TATTATGACT ATGAGTTCGC TTATTGGGGC CAGGGGACGC TTGTGACCGT AAGCGCTGCT  360
AGTACCAAGG GCCCCAGTGT GTTCCCCCTT GCCCCCAGCA GTAAGTCCAC CTCAGGTGGC  420
ACAGCTGCCC TTGGGTGCCT TGTGAAGGAT TACTTCCCAG AACCAGTGAC CGTGAGCTGG  480
AATTCCGGAG CCCTTACCAG CGGTGTGCAT ACCTTTCCGG CCGTCCTGCA AAGCAGCGGA  540
CTTTACAGTC TGTCTAGCGT GGTCACCGTG CCCAGCAGCA GCCTGGGTAC ACAGACGTAT  600
ATTTGCAACG TTAATCACAA ACCCTCAAAC ACAAAGGTGG ACAAGAAAGT GGAGCCTAAA  660
TCATGTGATA AGACACATAC ATGCCCTCCC TGCCCTGCAC CGGAGCTCTT AGGTGGACCT  720
TCAGTCTTTT TATTTCCACC TAAACCCAAA GATACACTTA TGATCTCACG GACACCCGAG  780
GTGACCTGCG TTGTCGTGGA TGTCTCACAC GAAGACCCTG AAGTGAAATT CAATTGGTAT  840
GTTGACGGTG TTGAGGTGCA TAACGCAAAG ACCAAGCCAC GCGAGGAGCA GTATAATAGC  900
ACCTATAGGG TAGTCAGCGT ACTGACTGTT CTGCATCAGG ATTGGCTGAA CGGTAAAGAG  960
TACAAATGCA AGGTCTCAAA CAAGGCTCTC CCTGCCCCGA TCGAGAAGAC AATTTCTAAG  1020
GCCAAAGGGC AGCCCCGGGA ACCACAAGTC TATACCCTGC CACCCAGTCG GGATGAACTA  1080
ACAAAAAATC AGGTGTCTCT AACCTGCCTG GTGAAGGGAT TTTACCCTTC CGATATAGCT  1140
GTGGAGTGGG AGTCTAATGG CCAACCAGAG AATAATTACA AGACTACCCC CCCCGTTCTT  1200
GACAGTGATG GCTCGTTCTT CTTATACTCA AAATTAACAG TCGACAAATC CCGATGGCAA  1260
CAGGGCAATG TGTTTAGCTG TAGCGTGATG CATGAAGCCC TGCACAACCA TTACACACAG  1320
AAGTCTCTGT CCTTGTCACC TGGCAAG                                      1347

SEQ ID NO: 69           moltype = AA  length = 447
FEATURE                 Location/Qualifiers
REGION                  1..447
                        note = chemically synthesized
source                  1..447
                        mol_type = protein
                        organism = synthetic construct
SEQUENCE: 69
QVQLKQSGPG LVQPSQSLSI TCTVSGFSLT NYGVHWVRQS PGKGLEWLGV IWSGGNTDYN  60
TPFTSRLSIN KDNSKSQVFF KSLQSQDTAI YYCARALTYY DYEFAYWGQG TLVTVSAAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGK                                      447

SEQ ID NO: 70           moltype = DNA  length = 645
FEATURE                 Location/Qualifiers
misc_feature            1..645
```

```
                          note = chemically synthesized
source                    1..645
                          mol_type = other DNA
                          organism = synthetic construct
SEQUENCE: 70
acccaaatcc tcctgaccca gtcccctgtt atcctttctg tgtcgcccgg ggagcgcgtt  60
agctttagct gccgcgccag tcagtcaatc ggaacaaaca tccattggta ccagcagcgt  120
acgaacggca gtccaaggct gctgatcaaa tacgcaagtg aatctatatc ggggattccg  180
tctcggttca gcggatccgg aagcgggact gactttacgc tctccataaa tagcgtcgaa  240
agtgaggaca ttgcagacta ttactgtcag cagaataaca actggccgac cacatttggg  300
gccggaacca agttggaact gaagcgcact gtggcagctc ctagtgtttt tattttcccc  360
ccttctgacg agcaactgaa aagtggtaca gcttcagtag tttgtttgct caataatttc  420
tacccacggg aagcaaaggt gcagtggaaa gtcgacaacg cattacagag cggcaactct  480
caagaaagcg tgacggagca ggatagcaag gactcaacat attccttgtc ttccactctc  540
actctgtcaa aggctgatta tgagaagcat aaggtgtatg cgtgcgaagt gacacaccag  600
ggattatcaa gcccagtgac caagtccttt aaccgtggcg aatgc                  645

SEQ ID NO: 71             moltype = AA  length = 8
FEATURE                   Location/Qualifiers
REGION                    1..8
                          note = chemically synthesized
source                    1..8
                          mol_type = protein
                          organism = synthetic construct
SEQUENCE: 71
LSGRSDNI                                                           8

SEQ ID NO: 72             moltype = DNA  length = 783
FEATURE                   Location/Qualifiers
misc_feature              1..783
                          note = chemically synthesized
source                    1..783
                          mol_type = other DNA
                          organism = synthetic construct
SEQUENCE: 72
cagggccaga gcggccaatg catctccccc cgcggttgtc ccgacgggcc gtacgtgatg  60
tacggcagct ccggcggcag tgggggtagc ggtgggtccg ggctgagtgg ccggtccgac  120
aatcacggga gctcgggaac acagattctg ctgacgcaat ctcccgtgat cctctcggtc  180
tcacccggcg aacgggtctc gttcagctgc agagcgtccc aatcaatcgg gaccaatatt  240
cactggtacc agcaaaggac taatgggtct ccccggctgc tgataaaata cgcctccgag  300
tctatctcgg gcatcccatc ccgatttagt ggtagcggaa gcggcactga tttcaccttg  360
tctattaaca gcgtagaatc tgaggacatt gcagactatt actgtcagca gaataacaat  420
tggcctacaa ctttcggcgc cgggaccaaa ctagagttaa agcgtactgt ggctgccccc  480
agcgttttta tttttccgcc cagcgacgaa cagctgaagt caggcacagc ctctgtggtg  540
tgtctcctga ataacttcta ccccagagag gccaaagttc agtggaaagt ggacaatgcc  600
ttgcagtccg gaaacagtca agagtccgtg accgagcagg acagtaagga tagcacgtat  660
agcctctcta gtactttaac actgtccaag gccgactacg agaagcacaa ggtgtacgca  720
tgcgaagtga cccatcaggg gctttcctcc cccgtcacca agtctttcaa tcgcggggag  780
tgt                                                                783

SEQ ID NO: 73             moltype = AA  length = 261
FEATURE                   Location/Qualifiers
REGION                    1..261
                          note = chemically synthesized
source                    1..261
                          mol_type = protein
                          organism = synthetic construct
SEQUENCE: 73
QGQSGQCISP RGCPDGPYVM YGSSGGSGGS GGSGLSGRSD NHGSSGTQIL LTQSPVILSV  60
SPGERVSFSC RASQSIGTNI HWYQQRTNGS PRLLIKYASE SISGIPSRFS GSGSGTDFTL  120
SINSVESEDI ADYYCQQNNN WPTTFGAGTK LELKRTVAAP SVFIFPPSDE QLKSGTASVV  180
CLLNNFYPRE AKVQWKVDNA LQSGNSQESV TEQDSKDSTY SLSSTLTLSK ADYEKHKVYA  240
CEVTHQGLSS PVTKSFNRGE C                                            261

SEQ ID NO: 74             moltype = DNA  length = 783
FEATURE                   Location/Qualifiers
misc_feature              1..783
                          note = chemically synthesized
source                    1..783
                          mol_type = other DNA
                          organism = synthetic construct
SEQUENCE: 74
caaggtcagt ccggacagtg tatttcccct agaggttgcc ctgacgggcc gtatgtcatg  60
tacggtagtt ctggcggtag tggcggatct ggcggcagtg ggctgagcgg acgtagcggg  120
aatcacggct catccgggac gcagatactg ctgacccagt cccccgtgat cctgtccgtg  180
tcaccgggcg aaagggtcag tttctcttgc cgagcatcac agtccatagg tacgaatatc  240
cattggtacc agcagcggac caatgggagc ccaagactgc tcattaagta cgcatctgag  300
agtatctcag gcattccaag caggttttcc ggcagtggga gcggcactga cttcaccctc  360
agcattaaca gcgtggaaag cgaagacatt gcagattact actgccaaca gaacaataac  420
```

-continued

```
tggcctacta cattcggggc aggaactaag ttggagctca aacgtaccgt cgctgctcct  480
agcgtattta ttttccctcc tagcgatgaa cagttgaaat ctggtaccgc tagtgttgtg  540
tgcttactga acaactttta tccccgggag gccaaggtac aatggaaggt ggacaatgcc  600
ctccaatcag ggaacagcca ggagtctgtt accgagcagg actccaagga cagcacctac  660
agcctgagct ctacccttac attgagcaag gctgattatg agaagcataa ggtctacgct  720
tgtgaggtga cccatcaggg gctcagcagc ccggtgacaa aaagctttaa ccggggggaa  780
tgc                                                               783

SEQ ID NO: 75          moltype = AA  length = 261
FEATURE                Location/Qualifiers
REGION                 1..261
                       note = chemically synthesized
source                 1..261
                       mol_type = protein
                       organism = synthetic construct
SEQUENCE: 75
QGQSGQCISP RGCPDGPYVM YGSSGGSGGS GGSGLSGRSG NHGSSGTQIL LTQSPVILSV  60
SPGERVSFSC RASQSIGTNI HWYQQRTNGS PRLLIKYASE SISGIPSRFS GSGSGTDFTL  120
SINSVESEDI ADYYCQQNNN WPTTFGAGTK LELKRTVAAP SVFIFPPSDE QLKSGTASVV  180
CLLNNFYPRE AKVQWKVDNA LQSGNSQESV TEQDSKDSTY SLSSTLTLSK ADYEKHKVYA  240
CEVTHQGLSS PVTKSFNRGE C                                           261

SEQ ID NO: 76          moltype = DNA  length = 783
FEATURE                Location/Qualifiers
misc_feature           1..783
                       note = chemically synthesized
source                 1..783
                       mol_type = other DNA
                       organism = synthetic construct
SEQUENCE: 76
caggggcagt ctgggcagtg tattagcccc agggggtgcc ccgacgggcc ttacgtgatg  60
tatggcagct ccggtggcag cggaggctct ggcgggagtg ggatcagttc cggcctgctg  120
agctccgggt caagcgggac ccagatcttg ctcacccaat caccagtgat cctaagcgtg  180
agccctggcg aacgggtcag cttctcttgc cgggcatctc agagtattgg cactaacata  240
cactggtacc agcagcgaac caatgggtcc ccccgccttc taatcaaata tgctagcgaa  300
tccatttcag gaattcctag ccgatttagc ggcagcggat caggcactga cttcactctg  360
tcaatcaact cagttgaaag cgaggacatt gcagactact attgccagca gaataataat  420
tggcccacta catttggagc tggaacaaaa ttggagctta agaggacagt ggctgcgcct  480
agtgtattta tctttccccc ctctgacgaa cagttgaaat cgggaaccgc atccgtcgtc  540
tgtttactga acaacttcta tcccagagag gccaaagtgc agtggaaagt ggataatgct  600
ttgcagtctg gcaacagcca ggaaagcgtg acggagcagg actcaaagga tagtacatac  660
tccctgtcct ccaccctgac tctgagtaag gccgactacg agaagcacaa ggtctacgcc  720
tgcgaagtga cgcaccaagg gctatcgagc ccggtcacca agtctttcaa tcgtggagaa  780
tgc                                                               783

SEQ ID NO: 77          moltype = AA  length = 261
FEATURE                Location/Qualifiers
REGION                 1..261
                       note = chemically synthesized
source                 1..261
                       mol_type = protein
                       organism = synthetic construct
SEQUENCE: 77
QGQSGQCISP RGCPDGPYVM YGSSGGSGGS GGSGISSGLL SSGSSGTQIL LTQSPVILSV  60
SPGERVSFSC RASQSIGTNI HWYQQRTNGS PRLLIKYASE SISGIPSRFS GSGSGTDFTL  120
SINSVESEDI ADYYCQQNNN WPTTFGAGTK LELKRTVAAP SVFIFPPSDE QLKSGTASVV  180
CLLNNFYPRE AKVQWKVDNA LQSGNSQESV TEQDSKDSTY SLSSTLTLSK ADYEKHKVYA  240
CEVTHQGLSS PVTKSFNRGE C                                           261

SEQ ID NO: 78          moltype = DNA  length = 783
FEATURE                Location/Qualifiers
misc_feature           1..783
                       note = chemically synthesized
source                 1..783
                       mol_type = other DNA
                       organism = synthetic construct
SEQUENCE: 78
caggggcaat caggacaatg catcagccct aggggctgcc cagacggccc atatgtgatg  60
tacggtagct ctgggggctc aggaggcagc gggggaagcg gacaaaacca ggccttacga  120
atggctggca gctctggcac ccagatattg ctgacgcaga gtccagttat ccttagtgtc  180
agccctggtg aacgggtttc atttagttgc cgtgcctccc agtctattgg aacgaacatt  240
cattggtacc agcaaaggac caacggttca cccaggttgc ttatcaagta tgcttcagag  300
tcaatctccg ggattccctc aaggttttca ggctctggct caggtaccga ttttacgctg  360
agcatcaact ccgtggagag tgaggacatt gctgattatt actgtcagca gaataacaat  420
tggccgacaa ctttcggcgc cggcacaaag ctggaactta agcgtactgt ggctgcgcca  480
tctgtcttca tttttccgcc ctcggacgag cagttgaagt cagggaccgc ctctgtcgtg  540
tgccttctca ataacttcta tcccagagag gctaaagtcc agtggaaagt tgataatgca  600
cttcagagcg ggaatagcca ggagagcgtg acggaacagg actctaagga ctccacctat  660
tctctctcat ccacccttac tctctctaaa gccgactacg aaaagcataa ggtttatgct  720
```

```
tgcgaagtca ctcatcaagg gctatctagt ccggtcacta aaagcttcaa cagaggtgaa  780
tgt                                                                783

SEQ ID NO: 79          moltype = AA  length = 261
FEATURE                Location/Qualifiers
REGION                 1..261
                       note = chemically synthesized
source                 1..261
                       mol_type = protein
                       organism = synthetic construct
SEQUENCE: 79
QGQSGQCISP RGCPDGPYVM YGSSGGSGGS GGSGQNQALR MAGSSGTQIL LTQSPVILSV  60
SPGERVSFSC RASQSIGTNI HWYQQRTNGS PRLLIKYASE SISGIPSRFS GSGSGTDFTL  120
SINSVESEDI ADYYCQQNNN WPTTFGAGTK LELKRTVAAP SVFIFPPSDE QLKSGTASVV  180
CLLNNFYPRE AKVQWKVDNA LQSGNSQESV TEQDSKDSTY SLSSTLTLSK ADYEKHKVYA  240
CEVTHQGLSS PVTKSFNRGE C                                            261

SEQ ID NO: 80          moltype = DNA  length = 798
FEATURE                Location/Qualifiers
misc_feature           1..798
                       note = chemically synthesized
source                 1..798
                       mol_type = other DNA
                       organism = synthetic construct
SEQUENCE: 80
caaggccagt ctggacaatg tatcagcccc cgtggctgtc cagacggtcc ttacgttatg  60
tatggatcta gcgggggctc tggagggtct ggcggctctg gaatctctag tggacttctc  120
tccggaagaa gcgataatca tggatccagc gggacacaaa tcctgttgac acagtcccca  180
gtgatcctgt cagtctcgcc cggagaaagg gtgtctttct cttgtagggc tagtcagtct  240
atcggaacta acatccattg gtaccagcag cggacaaatg ggagcccgag gcttctgatc  300
aagtatgctt cagagagtat aagcggcatc ccctcaagat ttagtggcag cgggtccggg  360
acagatttca ccttgtcaat caattctgtc gaatccgaag acattgcaga ctactattgc  420
cagcaaaaca acaactggcc caccactttc ggtgctggaa ccaaactcga gctgaaacgc  480
actgtggcag ctccttcagt gttcatcttc ccacctagcg acgagcagtt gaaatcgggg  540
acagcctcag tggtgtgtct actgaacaac ttttaccccc gggaagccaa agtgcagtgg  600
aaggtcgaca atgcgctgca atcagggaac agtcaggagt cagttacaga gcaggactct  660
aaggacagta catattcttt gagttccacc ttgacattaa gcaaggcaga ctacgagaaa  720
cacaaggtgt acgcatgtga agttacacac cagggccttt cctccccagt tacgaaaagc  780
ttcaacagag gcgaatgc                                                798

SEQ ID NO: 81          moltype = AA  length = 266
FEATURE                Location/Qualifiers
REGION                 1..266
                       note = chemically synthesized
source                 1..266
                       mol_type = protein
                       organism = synthetic construct
SEQUENCE: 81
QGQSGQCISP RGCPDGPYVM YGSSGGSGGS GGSGISSGLL SGRSDNHGSS GTQILLTQSP  60
VILSVSPGER VSFSCRASQS IGTNIHWYQQ RTNGSPRLLI KYASESISGI PSRFSGSGSG  120
TDFTLSINSV ESEDIADYYC QQNNNWPTTF GAGTKLELKR TVAAPSVFIF PPSDEQLKSG  180
TASVVCLLNN FYPREAKVQW KVDNALQSGN SQESVTEQDS KDSTYSLSST LTLSKADYEK  240
HKVYACEVTH QGLSSPVTKS FNRGEC                                       266

SEQ ID NO: 82          moltype = DNA  length = 798
FEATURE                Location/Qualifiers
misc_feature           1..798
                       note = chemically synthesized
source                 1..798
                       mol_type = other DNA
                       organism = synthetic construct
SEQUENCE: 82
caaggtcaga gtggccaatg catatcgccc agaggatgtc ctgacggacc ctacgtgatg  60
tacgggagtt ctgggggag tggaggctct ggcgggtcag ggattagttc cggcctcttg  120
tctggacgct ccggaaatca cggatcatct gggacccaga tcctcctgac ccagtctccc  180
gtcattctgt ctgtttctcc aggcgagcgg gtttcattta gctgtagggc cagtcagagc  240
attggcacca acatccattg gtaccagcag agaactaatg gcagtcccag actgctcatt  300
aaatatgcaa gcgaatcaat ttccgggatt ccttctcgct tctcgggatc tggatctggc  360
accgacttca cgctgtccat caacagcgtg gagagtgagg acatcgccga ttactactgc  420
cagcagaaca acaactggcc aacaactttt ggcgccggga ccaagcttga gttaaagaga  480
accgtagctg caccctctgt tttcattttc ccaccctcag acgagcagct taagtcagga  540
actgccagtg tggtgtgcct gctgaacaac ttctacccga gagaggctaa agtccagtgg  600
aaggtagaca atgcccttca gtctggcaac tctcaggaga gtgtcacaga gcaggattct  660
aaggactcca cgtacagtct gagttccacc ctcaccctca gtaaggcaga ctacgagaag  720
cacaaagtct acgcatgtga ggttactcac cagggctca gctctcccgt gacgaagtca  780
tttaacagag gtgagtgc                                                798

SEQ ID NO: 83          moltype = AA  length = 266
FEATURE                Location/Qualifiers
```

```
REGION                 1..266
                       note = chemically synthesized
source                 1..266
                       mol_type = protein
                       organism = synthetic construct
SEQUENCE: 83
QGQSGQCISP RGCPDGPYVM YGSSGGSGGS GGSGISSGLL SGRSGNHGSS GTQILLTQSP  60
VILSVSPGER VSFSCRASQS IGTNIHWYQQ RTNGSPRLLI KYASESISGI PSRFSGSGSG  120
TDFTLSINSV ESEDIADYYC QQNNNWPTTF GAGTKLELKR TVAAPSVFIF PPSDEQLKSG  180
TASVVCLLNN FYPREAKVQW KVDNALQSGN SQESVTEQDS KDSTYSLSST LTLSKADYEK  240
HKVYACEVTH QGLSSPVTKS FNRGEC                                      266

SEQ ID NO: 84          moltype = DNA  length = 825
FEATURE                Location/Qualifiers
misc_feature           1..825
                       note = chemically synthesized
source                 1..825
                       mol_type = other DNA
                       organism = synthetic construct
SEQUENCE: 84
cagggacagt cgggacagtg catttctccg agaggctgcc ctgacggccc atacgtaatg  60
tacggatcat ccggtggcag tggagggtcc gggggatccg gtctaagcgg cagaagtgat  120
aatcatggag gctctggcgg gagcatcagc tccggattgc tttccagcgg aagttctggc  180
actcaaattc tgctgacaca aagccctgtg atcttgtcag tctcacctgg cgagcgggtg  240
agcttttcat gccgggcttc ccagagcatc ggtacaaata ttcactggta tcagcagaga  300
accaatggca gtccgcggtt gctgattaag tatgcgagcg agagcatatc aggcatacca  360
agcagattta gcgggagtgg ctctgggacc gattttacac tcagtataaa ttcagtggag  420
agcgaggata tagccgacta ctactgccag caaaacaata actggcccac caccttcggc  480
gcagggacca agcttgaact gaagcgtaca gttgccgccc caagcgtatt tattttccct  540
ccaagcgacg aacagctgaa aagcggtacc gcaagcgttg tgtgcctgct gaataacttt  600
tacccaaggg aagctaaggt gcagtggaag gttgacaatg cgctgcagtc aggcaactcc  660
caggaatcgg taacagagca ggactccaag gattcaactt atagtcttag tagtaccctt  720
actctttcca aagctgatta tgaaaaacac aaagtgtatg catgcgaggt gacccaccaa  780
ggactgtcat ctcctgtcac caagtccttc aaccggggag agtgt                 825

SEQ ID NO: 85          moltype = AA  length = 275
FEATURE                Location/Qualifiers
REGION                 1..275
                       note = chemically synthesized
source                 1..275
                       mol_type = protein
                       organism = synthetic construct
SEQUENCE: 85
QGQSGQCISP RGCPDGPYVM YGSSGGSGGS GGSGLSGRSD NHGGSGGSIS SGLLSSGSSG  60
TQILLTQSPV ILSVSPGERV SFSCRASQSI GTNIHWYQQR TNGSPRLLIK YASESISGIP  120
SRFSGSGSGT DFTLSINSVE SEDIADYYCQ QNNNWPTTFG AGTKLELKRT VAAPSVFIFP  180
PSDEQLKSGT ASVVCLLNNF YPREAKVQWK VDNALQSGNS QESVTEQDSK DSTYSLSSTL  240
TLSKADYEKH KVYACEVTHQ GLSSPVTKSF NRGEC                             275

SEQ ID NO: 86          moltype = DNA  length = 825
FEATURE                Location/Qualifiers
misc_feature           1..825
                       note = chemically synthesized
source                 1..825
                       mol_type = other DNA
                       organism = synthetic construct
SEQUENCE: 86
caaggtcaga gcggccagtg cattagtcct cgcggttgcc ctgatggacc atacgtaatg  60
tatggaagct ctggtggatc cgggggctct ggcggatcag gaatctccag cgggctgctc  120
tcatcaggtg gcagcggggg ctcattaagc ggccgaagtg acaatcacgg ctcgtccggt  180
acacagattc tgctcactca gtcacccgtt atactgtctg tgtcgcctgg agagcgtgtc  240
agcttttcat gtagagcctc gcagtcaata ggcacgaata tacactggta ccagcagaga  300
actaatggaa gcccaaggtt gctcatcaaa tacgcatctg agtcgattag cggcattccg  360
tccaggttta gtggcagtgg aagcggcacc gatttcactt tgtctattaa ctctgtggaa  420
agcgaggaca tcgccgatta ttattgtcag cagaataaca attggcccac caccttcggt  480
gccggtacta agctggagct gaaacgtaca gttgccgctc cctctgtgtt tattttccct  540
ccctcggatg agcaactcaa atcagggaca gcgagtgtcg tatgtctcct gaacaatttt  600
tacccacgtg aagctaaagt tcagtggaag gtggacaacg ctctgcagtc cggcaacagt  660
caggaaagcg taactgaaca ggactcaaag gatagcactt actccttgag cagcactctc  720
actctttcca aggctgatta tgagaagcac aaggtgtacg cgtgtgaagt cacccatcag  780
ggactgtcaa gtccggtgac taaatcattt aacaggggcg aatgc                 825

SEQ ID NO: 87          moltype = AA  length = 275
FEATURE                Location/Qualifiers
REGION                 1..275
                       note = chemically synthesized
source                 1..275
                       mol_type = protein
                       organism = synthetic construct
```

-continued

```
SEQUENCE: 87
QGQSGQCISP RGCPDGPYVM YGSSGGSGGS GGSGISSGLL SSGGSGGSLS GRSDNHGSSG  60
TQILLTQSPV ILSVSPGERV SFSCRASQSI GTNIHWYQQR TNGSPRLLIK YASESISGIP  120
SRFSGSGSGT DFTLSINSVE SEDIADYYCQ QNNNWPTTFG AGTKLELKRT VAAPSVFIFP  180
PSDEQLKSGT ASVVCLLNNF YPREAKVQWK VDNALQSGNS QESVTEQDSK DSTYSLSSTL  240
TLSKADYEKH KVYACEVTHQ GLSSPVTKSF NRGEC                            275

SEQ ID NO: 88          moltype = DNA  length = 825
FEATURE                Location/Qualifiers
misc_feature           1..825
                       note = chemically synthesized
source                 1..825
                       mol_type = other DNA
                       organism = synthetic construct
SEQUENCE: 88
cagggccaga gtgggcagtg tatttcccct cgcggatgtc ccgacggtcc atacgtaatg  60
tatgggtcaa gcgggggatc aggaggaagt ggaggctccg gactcagcgg tcgctccggc  120
aatcacgggg ggtctggcgg atcaataagt tcgggcctcc tgagctccgg ttcatctggc  180
actcagatcc tgctcacgca gtcgccggta atactgagtg tctcaccagg cgagcgtgtc  240
agcttcagct gtcgcgcctc acagtcaatc ggcacaaata tccattggta ccagcaaagg  300
accaatggca gccctaggct gctgataaaa tacgcatccg agtcaatttc agggattcca  360
tcgagattct cgggcagcgg aagtgggacc gactttactc tctccatcaa cagcgtcgag  420
tcggaggaca tcgcggacta ctactgccag cagaataaca attggccaac aacattcggc  480
gcaggaacaa agctagagct caagaggaca gtggctgcac ccagtgtatt catcttccca  540
cctagcgacg agcaactgaa gagcgggacg gcttccgtcg tttgtctatt aaataatttc  600
tatccccgtg aggctaaagt tcagtggaag gttgataatg cgttgcagtc cggcaactcc  660
caggaatccg tcacagagca ggattctaag gattcaacct atagcttaag ctctacactt  720
acgctttcta aagccgatta tgaaaaacac aaggtgtacg cttgtgaggt tacccaccag  780
ggcctgagca gccccgtgac caagtcgttc aaccggggcg agtgt                 825

SEQ ID NO: 89          moltype = AA  length = 275
FEATURE                Location/Qualifiers
REGION                 1..275
                       note = chemically synthesized
source                 1..275
                       mol_type = protein
                       organism = synthetic construct
SEQUENCE: 89
QGQSGQCISP RGCPDGPYVM YGSSGGSGGS GGSGLSGRSG NHGGSGGSIS SGLLSSGSSG  60
TQILLTQSPV ILSVSPGERV SFSCRASQSI GTNIHWYQQR TNGSPRLLIK YASESISGIP  120
SRFSGSGSGT DFTLSINSVE SEDIADYYCQ QNNNWPTTFG AGTKLELKRT VAAPSVFIFP  180
PSDEQLKSGT ASVVCLLNNF YPREAKVQWK VDNALQSGNS QESVTEQDSK DSTYSLSSTL  240
TLSKADYEKH KVYACEVTHQ GLSSPVTKSF NRGEC                            275

SEQ ID NO: 90          moltype = DNA  length = 825
FEATURE                Location/Qualifiers
misc_feature           1..825
                       note = chemically synthesized
source                 1..825
                       mol_type = other DNA
                       organism = synthetic construct
SEQUENCE: 90
caaggacaga gcggacagtg tatctcacct cgcggctgcc ccgacggccc ttacgtcatg  60
tacggctcct cgggtgggtc cgggggaagt ggcgggtctg gcattagttc agggctctta  120
tcttccggcg gaagcggggg atctctttcc gggcggagtg gcaatcacgg cagtagcgga  180
actcagatcc tactcactca gtcaccagtg atcctgtctg tcagtccagg ggagagagtg  240
tctttcagtt gtagagcttc ccagtctatt gggacaaaca ttcactggta tcaacagcga  300
actaatggat cgccaagact cctgattaaa tatgcttctg agagcatctc tggaattcca  360
tcaagattct cagggagtgg tagcggcacc gattttacgt tatcgatcaa ttccgttgag  420
agcgaagata tcgcggacta ttactgtcag cagaacaata actggcctac aacgttcggg  480
gcagggacga aattggagct gaagcggacc gtcgccgcgc caagcgtgtt catcttcccc  540
cctagcgacg agcaattgaa aagcggcacc gcaagtgtgg tttgcctgct gaacaacttt  600
tatcctcgcg aggcgaaagt gcagtggaaa gtcgacaatg cactccagtc agggaacagc  660
caagagtccg ttactgaaca agactctaaa gatagtactt atagcttatc cagcacactg  720
acgctcagta aggccgatta tgaaaaacat aaggtgtatg cgtgtgaggt tacccatcaa  780
ggattgtcat cacccgtcac caaatccttt aacagaggag aatgt                 825

SEQ ID NO: 91          moltype = AA  length = 275
FEATURE                Location/Qualifiers
REGION                 1..275
                       note = chemically synthesized
source                 1..275
                       mol_type = protein
                       organism = synthetic construct
SEQUENCE: 91
QGQSGQCISP RGCPDGPYVM YGSSGGSGGS GGSGISSGLL SSGGSGGSLS GRSGNHGSSG  60
TQILLTQSPV ILSVSPGERV SFSCRASQSI GTNIHWYQQR TNGSPRLLIK YASESISGIP  120
SRFSGSGSGT DFTLSINSVE SEDIADYYCQ QNNNWPTTFG AGTKLELKRT VAAPSVFIFP  180
PSDEQLKSGT ASVVCLLNNF YPREAKVQWK VDNALQSGNS QESVTEQDSK DSTYSLSSTL  240
```

-continued

```
TLSKADYEKH KVYACEVTHQ GLSSPVTKSF NRGEC                    275

SEQ ID NO: 92          moltype = DNA  length = 825
FEATURE                Location/Qualifiers
misc_feature           1..825
                       note = chemically synthesized
source                 1..825
                       mol_type = other DNA
                       organism = synthetic construct
SEQUENCE: 92
cagggtcaaa gtggacagtg tatctcgccc cgcggctgcc cagacggccc atatgtgatg  60
tatggttctt ccggtggatc cggcggatca ggtgggtctg gcctctcagg tcgttccgac  120
aaccacggcg gctcaggtgg gtctcagaat caggcactgc ggatggccgg atcttctggc  180
acccagatat tgctcacaca gtcaccagtt attctgtccg tatctccagg agaacgggta  240
tctttctctt gtagggcaag ccagtccatc ggaacaaaca tccattggta ccagcagcgg  300
accaatggca gtccacggct tctgatcaag tatgctagtg aaagcattag cgggattcca  360
agccgatttt ctgggtcggg tagtggaacc gacttcaccc tgagcattaa ctctgtcgaa  420
tccgaagata ttgctgacta ttactgtcag cagaacaaca attggccgac tacgtttggc  480
gccggaacca aattagaact taagagaacc gtggccgctc cctctgtctt catttcccg  540
ccttccgacg aacagctgaa gagcggaact gcctccgtgg tgtgcctgtt gaataacttt  600
tatccaaggg aagcaaaggt gcagtggaaa gtggacaatg ctctgcagtc tggcaatagc  660
caggagtccg tgactgaaca ggacagtaaa gactcaacct actcactgag cagtactctc  720
acattatcca aagccgatta tgaaaagcat aaggtttatg catgcgaggt tacccaccag  780
ggactgagct cccccgtgac caaaagcttc aataggggtg agtgc                 825

SEQ ID NO: 93          moltype = AA  length = 275
FEATURE                Location/Qualifiers
REGION                 1..275
                       note = chemically synthesized
source                 1..275
                       mol_type = protein
                       organism = synthetic construct
SEQUENCE: 93
QGQSGQCISP RGCPDGPYVM YGSSGGSGGS GGSGLSGRSD NHGGSGGSQN QALRMAGSSG  60
TQILLTQSPV ILSVSPGERV SFSCRASQSI GTNIHWYQQR TNGSPRLLIK YASESISGIP  120
SRFSGSGSGT DFTLSINSVE SEDIADYYCQ QNNNWPTTFG AGTKLELKRT VAAPSVFIFP  180
PSDEQLKSGT ASVVCLLNNF YPREAKVQWK VDNALQSGNS QESVTEQDSK DSTYSLSSTL  240
TLSKADYEKH KVYACEVTHQ GLSSPVTKSF NRGEC                    275

SEQ ID NO: 94          moltype = DNA  length = 825
FEATURE                Location/Qualifiers
misc_feature           1..825
                       note = chemically synthesized
source                 1..825
                       mol_type = other DNA
                       organism = synthetic construct
SEQUENCE: 94
caggggcagt ccggacaatg catcagcccc cgaggctgcc ctgatggccc ctacgtgatg  60
tacgggtcca gcggtggcag cgggggctca ggggggagcg ggcagaatca ggccctgaga  120
atggcgggtg gatccggggg gtccctttct ggcaggtccg ataaccacgg ttctagtgga  180
acacagattt tgctgacaca aagtcccgtc atcctctctg tgtctcccgg tgagcgggtc  240
agtttttcct gccgagcgtc ccagagcatc gggacaaata tccattggta ccagcagaga  300
acgaacggct ctcctagact gctcatcaag tacgcctcgg aaagtatttc cggcattccc  360
tcccgtttca gcggctccgg aagtggtaca gattttaccc tgagtattaa ttccgtcgaa  420
tctgaggaca tagccgacta ctattgccaa cagaataaca attggccaac aacttttggc  480
gccgggacta agctggagct gaaacggacc gtcgcagcac caagtgtttt catcttccca  540
ccaagtgacg agcagctgaa atccggaaca gcgagcgtgg tgtgcctact caataacttc  600
tatccacgcg aagccaaggt gcagtggaaa gtggacaacg ctctgcagtc cggcaatagc  660
caggaaagcg tgacagagca agattctaag gacagtacgt attcactgtc cagtacgctc  720
accttaagca aggctgacta cgaaaaacac aaggtctacg cctgtgaggt cacacatcag  780
ggcctctcca gtccggttac aaaaagtttc aatcgcgggg aatgt                 825

SEQ ID NO: 95          moltype = AA  length = 275
FEATURE                Location/Qualifiers
REGION                 1..275
                       note = chemically synthesized
source                 1..275
                       mol_type = protein
                       organism = synthetic construct
SEQUENCE: 95
QGQSGQCISP RGCPDGPYVM YGSSGGSGGS GGSGQNQALR MAGGSGGSLS GRSDNHGSSG  60
TQILLTQSPV ILSVSPGERV SFSCRASQSI GTNIHWYQQR TNGSPRLLIK YASESISGIP  120
SRFSGSGSGT DFTLSINSVE SEDIADYYCQ QNNNWPTTFG AGTKLELKRT VAAPSVFIFP  180
PSDEQLKSGT ASVVCLLNNF YPREAKVQWK VDNALQSGNS QESVTEQDSK DSTYSLSSTL  240
TLSKADYEKH KVYACEVTHQ GLSSPVTKSF NRGEC                    275

SEQ ID NO: 96          moltype = DNA  length = 825
FEATURE                Location/Qualifiers
misc_feature           1..825
```

```
                        note = chemically synthesized
source                  1..825
                        mol_type = other DNA
                        organism = synthetic construct
SEQUENCE: 96
caaggccaat ccggtcagtg catcagtccc agaggctgcc ctgacgggcc ctacgtgatg  60
tatggtagct cagggggctc cggcggctcc ggcggaagcg gacttagcgg ccgtagcggc  120
aaccatgggg gttctggagg atcccagaat caggctctgc gcatggctgg aagcagcggt  180
acccagatcc tgctcaccca atcacccgtc atcttgtctg tgagtcctgg cgaaagggtg  240
tcgttctctt gtcgcgcgtc ccagtccatt gggaccaaca ttcattggta ccagcagagg  300
actaacggga gcccccgcct gctgatcaaa tacgccagtg aatctatctc tggaatccca  360
tcacgatttt cagggtccgg tagtgggacc gacttcactt tgagtattaa cagtgtggaa  420
tccgaggaca tagccgacta ttactgtcag cagaacaata actggccaac aacctttggc  480
gccgggacaa agttagagct taagcggact gttgcagccc cctccgtttt tatcttcccg  540
cccagtgatg aacagctgaa aagcggtacc gcctccgtag tgtgccttct caataatttt  600
taccccagag aagctaaagt acagtggaaa gtcgacaacg ccctccagag cggcaacagt  660
caggagtccg tcaccgagca ggattctaaa gactcaacat atagcctttc gtccacccta  720
acactttcaa aagcagacta tgaaaaacat aaggtgtatg cctgcgaggt cacacaccag  780
gggctcagct ctccagttac taagtcattc aaccgcggag agtgt                  825

SEQ ID NO: 97           moltype = AA  length = 275
FEATURE                 Location/Qualifiers
REGION                  1..275
                        note = chemically synthesized
source                  1..275
                        mol_type = protein
                        organism = synthetic construct
SEQUENCE: 97
QGQSGQCISP RGCPDGPYVM YGSSGGSGGS GGSGLSGRSG NHGGSGGSQN QALRMAGSSG  60
TQILLTQSPV ILSVSPGERV SFSCRASQSI GTNIHWYQQR TNGSPRLLIK YASESISGIP  120
SRFSGSGSGT DFTLSINSVE SEDIADYYCQ QNNNWPTTFG AGTKLELKRT VAAPSVFIFP  180
PSDEQLKSGT ASVVCLLNNF YPREAKVQWK VDNALQSGNS QESVTEQDSK DSTYSLSSTL  240
TLSKADYEKH KVYACEVTHQ GLSSPVTKSF NRGEC                             275

SEQ ID NO: 98           moltype = DNA  length = 825
FEATURE                 Location/Qualifiers
misc_feature            1..825
                        note = chemically synthesized
source                  1..825
                        mol_type = other DNA
                        organism = synthetic construct
SEQUENCE: 98
cagggccaat caggtcagtg cattagcccc cgagggtgtc ccgatgggcc ctacgtaatg  60
tacggatcat cgggcggatc tgggggctcc ggtggctctg gtcagaatca agctctgcgc  120
atggccggag gtagcggtgg aagcctgagc ggccgaagtg gaaaccacgg ctcctctggc  180
actcagattc ttctcacgca gtcgcccgtg atcttgtccg tgagcccagg cgagcgggtg  240
agcttctctt gccgggccag ccaaagtata ggtacaaata ttcactggta ccaacagcga  300
accaacgggt cgcctaggtt gctcataaag tacgcatccg agagtataag cggcatacca  360
tctaggttct caggtagcgg cagcgggacc gattttaccc tcagcattaa ttcggttgaa  420
tctgaagata tcgccgatta ttattgtcag cagaataaca attggcctac tactttcggc  480
gccggaacaa agctggaact taagcgcaca gtggccgctc cttctgtctt tatcttccct  540
ccatctgacg agcaattaaa gagtgggaca gcctcggtgg tgtgtttgct caataacttc  600
tatccaaggg aggcaaaggt gcagtggaag gtcgataacg ctctccagag tgggaattcc  660
caggagtccg tgaccgagca ggattctaaa gatagcacat actcactgtc ttccaccctg  720
accctgtcca aggcagacta cgagaagcac aaagtttacg cctgtgaagt gacacaccag  780
ggcctcagct ctcctgtcac aaagagtttt aatcggggcg agtgt                  825

SEQ ID NO: 99           moltype = AA  length = 275
FEATURE                 Location/Qualifiers
REGION                  1..275
                        note = chemically synthesized
source                  1..275
                        mol_type = protein
                        organism = synthetic construct
SEQUENCE: 99
QGQSGQCISP RGCPDGPYVM YGSSGGSGGS GGSGQNQALR MAGGSGGSLS GRSGNHGSSG  60
TQILLTQSPV ILSVSPGERV SFSCRASQSI GTNIHWYQQR TNGSPRLLIK YASESISGIP  120
SRFSGSGSGT DFTLSINSVE SEDIADYYCQ QNNNWPTTFG AGTKLELKRT VAAPSVFIFP  180
PSDEQLKSGT ASVVCLLNNF YPREAKVQWK VDNALQSGNS QESVTEQDSK DSTYSLSSTL  240
TLSKADYEKH KVYACEVTHQ GLSSPVTKSF NRGEC                             275

SEQ ID NO: 100          moltype = AA  length = 449
FEATURE                 Location/Qualifiers
REGION                  1..449
                        note = chemically synthesized
source                  1..449
                        mol_type = protein
                        organism = synthetic construct
SEQUENCE: 100
```

-continued

```
QVQLQESGPG LVRPSQTLSL TCTVSGYSIT SDHAWSWVRQ PPGRGLEWIG YISYSGITTY  60
NPSLKSRVTI SRDNSKNTLY LQMNSLRAED TAVYYCARSL ARTTAMDYWG QGSLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                  449

SEQ ID NO: 101         moltype = AA  length = 214
FEATURE                Location/Qualifiers
REGION                 1..214
                       note = chemically synthesized
source                 1..214
                       mol_type = protein
                       organism = synthetic construct
SEQUENCE: 101
DIQMTQSPSS LSASVGDRVT ITCRASQDIS SYLNWYQQKP GKAPKLLIYY TSRLHSGVPS  60
RFSGSGSGTD FTFTISSLQP EDIATYYCQQ GNTLPYTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 102         moltype = AA  length = 15
FEATURE                Location/Qualifiers
REGION                 1..15
                       note = chemically synthesized
source                 1..15
                       mol_type = protein
                       organism = synthetic construct
SEQUENCE: 102
YGSCSWNYVH IFMDC                                                  15

SEQ ID NO: 103         moltype = AA  length = 16
FEATURE                Location/Qualifiers
REGION                 1..16
                       note = chemically synthesized
source                 1..16
                       mol_type = protein
                       organism = synthetic construct
SEQUENCE: 103
QGDFDIPFPA HWVPIT                                                 16

SEQ ID NO: 104         moltype = AA  length = 18
FEATURE                Location/Qualifiers
REGION                 1..18
                       note = chemically synthesized
source                 1..18
                       mol_type = protein
                       organism = synthetic construct
SEQUENCE: 104
MGVPAGCVWN YAHIFMDC                                               18

SEQ ID NO: 105         moltype = AA  length = 21
FEATURE                Location/Qualifiers
REGION                 1..21
                       note = chemically synthesized
source                 1..21
                       mol_type = protein
                       organism = synthetic construct
SEQUENCE: 105
QGQSGQYGSC SWNYVHIFMD C                                           21

SEQ ID NO: 106         moltype = AA  length = 21
FEATURE                Location/Qualifiers
REGION                 1..21
                       note = chemically synthesized
source                 1..21
                       mol_type = protein
                       organism = synthetic construct
SEQUENCE: 106
QGQSGQGDFD IPFPAHWVPI T                                           21

SEQ ID NO: 107         moltype = AA  length = 24
FEATURE                Location/Qualifiers
REGION                 1..24
                       note = chemically synthesized
source                 1..24
                       mol_type = protein
                       organism = synthetic construct
```

-continued

```
SEQUENCE: 107
QGQSGQMGVP AGCVWNYAHI FMDC                                  24

SEQ ID NO: 108          moltype = AA  length = 449
FEATURE                 Location/Qualifiers
REGION                  1..449
                        note = chemically synthesized
source                  1..449
                        mol_type = protein
                        organism = synthetic construct
SEQUENCE: 108
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                             449

SEQ ID NO: 109          moltype = AA  length = 449
FEATURE                 Location/Qualifiers
REGION                  1..449
                        note = chemically synthesized
source                  1..449
                        mol_type = protein
                        organism = synthetic construct
SEQUENCE: 109
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSNDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                             449

SEQ ID NO: 110          moltype = AA  length = 449
FEATURE                 Location/Qualifiers
REGION                  1..449
                        note = chemically synthesized
source                  1..449
                        mol_type = protein
                        organism = synthetic construct
SEQUENCE: 110
QVQLKQSGPG LVQPSQSLSI TCTVSGFSLT NYGVHWVRQS PGKGLEWLGV IWSGGNTDYN  60
TPFTSRLSIN KDNSKSQVFF KMNSLQSQDT AIYYCARALT YYDYEFAYWG QGTLVTVSAA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYAS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                             449

SEQ ID NO: 111          moltype = AA  length = 214
FEATURE                 Location/Qualifiers
REGION                  1..214
                        note = chemically synthesized
source                  1..214
                        mol_type = protein
                        organism = synthetic construct
SEQUENCE: 111
QILLTQSPVI LSVSPGERVS FSCRASQSIG TNIHWYQQRT NGSPRLLIKY ASESISGIPS  60
RFSGSGSGTD FTLSINSVES EDIADYYCQQ NNNWPTTFGA GTKLELKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                       214

SEQ ID NO: 112          moltype = AA  length = 108
FEATURE                 Location/Qualifiers
REGION                  1..108
                        note = chemically synthesized
source                  1..108
                        mol_type = protein
                        organism = synthetic construct
SEQUENCE: 112
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR         108

SEQ ID NO: 113          moltype = AA  length = 119
```

```
FEATURE                Location/Qualifiers
REGION                 1..119
                       note = chemically synthesized
source                 1..119
                       mol_type = protein
                       organism = synthetic construct
SEQUENCE: 113
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKDI GGRSAFDYWG QGTLVTVSS   119

SEQ ID NO: 114         moltype = AA  length = 108
FEATURE                Location/Qualifiers
REGION                 1..108
                       note = chemically synthesized
source                 1..108
                       mol_type = protein
                       organism = synthetic construct
SEQUENCE: 114
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR              108

SEQ ID NO: 115         moltype = AA  length = 119
FEATURE                Location/Qualifiers
REGION                 1..119
                       note = chemically synthesized
source                 1..119
                       mol_type = protein
                       organism = synthetic construct
SEQUENCE: 115
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PYHGQFDYWG QGTLVTVSS   119

SEQ ID NO: 116         moltype = AA  length = 108
FEATURE                Location/Qualifiers
REGION                 1..108
                       note = chemically synthesized
source                 1..108
                       mol_type = protein
                       organism = synthetic construct
SEQUENCE: 116
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR              108

SEQ ID NO: 117         moltype = AA  length = 119
FEATURE                Location/Qualifiers
REGION                 1..119
                       note = chemically synthesized
source                 1..119
                       mol_type = protein
                       organism = synthetic construct
SEQUENCE: 117
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PFFGQFDYWG QGTLVTVSS   119

SEQ ID NO: 118         moltype = AA  length = 108
FEATURE                Location/Qualifiers
REGION                 1..108
                       note = chemically synthesized
source                 1..108
                       mol_type = protein
                       organism = synthetic construct
SEQUENCE: 118
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR              108

SEQ ID NO: 119         moltype = AA  length = 119
FEATURE                Location/Qualifiers
REGION                 1..119
                       note = chemically synthesized
source                 1..119
                       mol_type = protein
                       organism = synthetic construct
SEQUENCE: 119
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKHI GRTNPFDYWG QGTLVTVSS   119

SEQ ID NO: 120         moltype = AA  length = 108
FEATURE                Location/Qualifiers
REGION                 1..108
```

```
                         note = chemically synthesized
source                   1..108
                         mol_type = protein
                         organism = synthetic construct
SEQUENCE: 120
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 121           moltype = AA  length = 116
FEATURE                  Location/Qualifiers
REGION                   1..116
                         note = chemically synthesized
source                   1..116
                         mol_type = protein
                         organism = synthetic construct
SEQUENCE: 121
EVQLLESGGG LVQPGGSLRL SCAASGFTFS SYAMSWVRQA PGKGLEWVSS IEQMGWQTEY  60
ADSVKGRFTI SRDNSKNTLY LQMNSLRAED TAVYYCAKSA AAFDYWGQGT LVTVSS      116

SEQ ID NO: 122           moltype = AA  length = 108
FEATURE                  Location/Qualifiers
REGION                   1..108
                         note = chemically synthesized
source                   1..108
                         mol_type = protein
                         organism = synthetic construct
SEQUENCE: 122
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 123           moltype = AA  length = 119
FEATURE                  Location/Qualifiers
REGION                   1..119
                         note = chemically synthesized
source                   1..119
                         mol_type = protein
                         organism = synthetic construct
SEQUENCE: 123
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PYYGQFDYWG QGTLVTVSS   119

SEQ ID NO: 124           moltype = AA  length = 108
FEATURE                  Location/Qualifiers
REGION                   1..108
                         note = chemically synthesized
source                   1..108
                         mol_type = protein
                         organism = synthetic construct
SEQUENCE: 124
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 125           moltype = AA  length = 119
FEATURE                  Location/Qualifiers
REGION                   1..119
                         note = chemically synthesized
source                   1..119
                         mol_type = protein
                         organism = synthetic construct
SEQUENCE: 125
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PFFGQFDYWG QGTLVTVSS   119

SEQ ID NO: 126           moltype = AA  length = 108
FEATURE                  Location/Qualifiers
REGION                   1..108
                         note = chemically synthesized
source                   1..108
                         mol_type = protein
                         organism = synthetic construct
SEQUENCE: 126
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 127           moltype = AA  length = 119
FEATURE                  Location/Qualifiers
REGION                   1..119
                         note = chemically synthesized
source                   1..119
```

```
                        mol_type = protein
                        organism = synthetic construct
SEQUENCE: 127
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKDI GGRSAFDYWG QGTLVTVSS   119

SEQ ID NO: 128          moltype = AA  length = 108
FEATURE                 Location/Qualifiers
REGION                  1..108
                        note = chemically synthesized
source                  1..108
                        mol_type = protein
                        organism = synthetic construct
SEQUENCE: 128
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 129          moltype = AA  length = 116
FEATURE                 Location/Qualifiers
REGION                  1..116
                        note = chemically synthesized
source                  1..116
                        mol_type = protein
                        organism = synthetic construct
SEQUENCE: 129
EVQLLESGGG LVQPGGSLRL SCAASGFTFS SYAMSWVRQA PGKGLEWVSS IEEMGWQTLY  60
ADSVKGRFTI SRDNSKNTLY LQMNSLRAED TAVYYCAKSA AAFDYWGQGT LVTVSS      116

SEQ ID NO: 130          moltype = AA  length = 108
FEATURE                 Location/Qualifiers
REGION                  1..108
                        note = chemically synthesized
source                  1..108
                        mol_type = protein
                        organism = synthetic construct
SEQUENCE: 130
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 131          moltype = AA  length = 119
FEATURE                 Location/Qualifiers
REGION                  1..119
                        note = chemically synthesized
source                  1..119
                        mol_type = protein
                        organism = synthetic construct
SEQUENCE: 131
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKDI GGRSAFDYWG QGTLVTVSS   119

SEQ ID NO: 132          moltype = AA  length = 108
FEATURE                 Location/Qualifiers
REGION                  1..108
                        note = chemically synthesized
source                  1..108
                        mol_type = protein
                        organism = synthetic construct
SEQUENCE: 132
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 133          moltype = AA  length = 119
FEATURE                 Location/Qualifiers
REGION                  1..119
                        note = chemically synthesized
source                  1..119
                        mol_type = protein
                        organism = synthetic construct
SEQUENCE: 133
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PFYGQFDYWG QGTLVTVSS   119

SEQ ID NO: 134          moltype = AA  length = 108
FEATURE                 Location/Qualifiers
REGION                  1..108
                        note = chemically synthesized
source                  1..108
                        mol_type = protein
                        organism = synthetic construct
```

```
SEQUENCE: 134
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 135         moltype = AA  length = 119
FEATURE                Location/Qualifiers
REGION                 1..119
                       note = chemically synthesized
source                 1..119
                       mol_type = protein
                       organism = synthetic construct
SEQUENCE: 135
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PFFGQFDYWG QGTLVTVSS   119

SEQ ID NO: 136         moltype = AA  length = 108
FEATURE                Location/Qualifiers
REGION                 1..108
                       note = chemically synthesized
source                 1..108
                       mol_type = protein
                       organism = synthetic construct
SEQUENCE: 136
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 137         moltype = AA  length = 115
FEATURE                Location/Qualifiers
REGION                 1..115
                       note = chemically synthesized
source                 1..115
                       mol_type = protein
                       organism = synthetic construct
SEQUENCE: 137
EVQLLESGGG LVQPGGSLRL SCAASGFTFS SYAMSWVRQA PGKGLEWVSS IEEMGWQTLY  60
ADSVKGRFTI SRDNSKNTLY LQMNSLRAED TAVYYAKSAA AFDYWGQGTL VTVSS       115

SEQ ID NO: 138         moltype = AA  length = 108
FEATURE                Location/Qualifiers
REGION                 1..108
                       note = chemically synthesized
source                 1..108
                       mol_type = protein
                       organism = synthetic construct
SEQUENCE: 138
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 139         moltype = AA  length = 119
FEATURE                Location/Qualifiers
REGION                 1..119
                       note = chemically synthesized
source                 1..119
                       mol_type = protein
                       organism = synthetic construct
SEQUENCE: 139
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKDI GGRSAFDYWG QGTLVTVSS   119

SEQ ID NO: 140         moltype = AA  length = 108
FEATURE                Location/Qualifiers
REGION                 1..108
                       note = chemically synthesized
source                 1..108
                       mol_type = protein
                       organism = synthetic construct
SEQUENCE: 140
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 141         moltype = AA  length = 116
FEATURE                Location/Qualifiers
REGION                 1..116
                       note = chemically synthesized
source                 1..116
                       mol_type = protein
                       organism = synthetic construct
SEQUENCE: 141
EVQLLESGGG LVQPGGSLRL SCAASGFTFS SYAMSWVRQA PGKGLEWVSS IDPEGWQTYY  60
```

-continued

```
ADSVKGRFTI SRDNSKNTLY LQMNSLRAED TAVYYCAKSA AAFDYWGQGT LVTVSS      116

SEQ ID NO: 142          moltype = AA  length = 108
FEATURE                 Location/Qualifiers
REGION                  1..108
                        note = chemically synthesized
source                  1..108
                        mol_type = protein
                        organism = synthetic construct
SEQUENCE: 142
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 143          moltype = AA  length = 119
FEATURE                 Location/Qualifiers
REGION                  1..119
                        note = chemically synthesized
source                  1..119
                        mol_type = protein
                        organism = synthetic construct
SEQUENCE: 143
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PHNGQFDYWG QGTLVTVSS   119

SEQ ID NO: 144          moltype = AA  length = 108
FEATURE                 Location/Qualifiers
REGION                  1..108
                        note = chemically synthesized
source                  1..108
                        mol_type = protein
                        organism = synthetic construct
SEQUENCE: 144
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 145          moltype = AA  length = 116
FEATURE                 Location/Qualifiers
REGION                  1..116
                        note = chemically synthesized
source                  1..116
                        mol_type = protein
                        organism = synthetic construct
SEQUENCE: 145
EVQLLESGGG LVQPGGSLRL SCAASGFTFS SYAMSWVRQA PGKGLEWVSS IEQMGWQTEY  60
ADSVKGRFTI SRDNSKNTLY LQMNSLRAED TAVYYCAKSA AAFDYWGQGT LVTVSS      116

SEQ ID NO: 146          moltype = AA  length = 108
FEATURE                 Location/Qualifiers
REGION                  1..108
                        note = chemically synthesized
source                  1..108
                        mol_type = protein
                        organism = synthetic construct
SEQUENCE: 146
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108

SEQ ID NO: 147          moltype = AA  length = 119
FEATURE                 Location/Qualifiers
REGION                  1..119
                        note = chemically synthesized
source                  1..119
                        mol_type = protein
                        organism = synthetic construct
SEQUENCE: 147
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKSP PFFGQFDYWG QGTLVTVSS   119

SEQ ID NO: 148          moltype = AA  length = 108
FEATURE                 Location/Qualifiers
REGION                  1..108
                        note = chemically synthesized
source                  1..108
                        mol_type = protein
                        organism = synthetic construct
SEQUENCE: 148
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SVVAPLTFGQ GTKVEIKR               108
```

```
SEQ ID NO: 149         moltype = AA  length = 116
FEATURE                Location/Qualifiers
REGION                 1..116
                       note = chemically synthesized
source                 1..116
                       mol_type = protein
                       organism = synthetic construct
SEQUENCE: 149
EVQLLESGGG LVQPGGSLRL SCAASGFTFS SYAMSWVRQA PGKGLEWVSS IDEMGWQTEY  60
ADSVKGRFTI SRDNSKNTLY LQMNSLRAED TAVYYCAKSA AAFDYWGQGT LVTVSS      116

SEQ ID NO: 150         moltype = AA  length = 108
FEATURE                Location/Qualifiers
REGION                 1..108
                       note = chemically synthesized
source                 1..108
                       mol_type = protein
                       organism = synthetic construct
SEQUENCE: 150
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ TLDAPPQFGQ GTKVEIKR               108

SEQ ID NO: 151         moltype = AA  length = 119
FEATURE                Location/Qualifiers
REGION                 1..119
                       note = chemically synthesized
source                 1..119
                       mol_type = protein
                       organism = synthetic construct
SEQUENCE: 151
EVQLLESGGG LVQPGGSLRL SCAASGFTFS SYAMSWVRQA PGKGLEWVSS IEQMGWQTYY  60
ADSVKGRFTI SRDNSKNTLY LQMNSLRAED TAVYYCAKDI GGRSAFDYWG QGTLVTVSS   119

SEQ ID NO: 152         moltype = AA  length = 108
FEATURE                Location/Qualifiers
REGION                 1..108
                       note = chemically synthesized
source                 1..108
                       mol_type = protein
                       organism = synthetic construct
SEQUENCE: 152
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ TVVAPPLFGQ GTKVEIKR               108

SEQ ID NO: 153         moltype = AA  length = 119
FEATURE                Location/Qualifiers
REGION                 1..119
                       note = chemically synthesized
source                 1..119
                       mol_type = protein
                       organism = synthetic construct
SEQUENCE: 153
EVQLLESGGG LVQPGGSLRL SCAASGFTFS SYAMSWVRQA PGKGLEWVSS IDPEGRQTYY  60
ADSVKGRFTI SRDNSKNTLY LQMNSLRAED TAVYYCAKDI GGRSAFDYWG QGTLVTVSS   119

SEQ ID NO: 154         moltype = AA  length = 108
FEATURE                Location/Qualifiers
REGION                 1..108
                       note = chemically synthesized
source                 1..108
                       mol_type = protein
                       organism = synthetic construct
SEQUENCE: 154
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SLVAPLTFGQ GTKVEIKR               108

SEQ ID NO: 155         moltype = AA  length = 116
FEATURE                Location/Qualifiers
REGION                 1..116
                       note = chemically synthesized
source                 1..116
                       mol_type = protein
                       organism = synthetic construct
SEQUENCE: 155
EVQLLESGGG LVQPGGSLRL SCAASGFTFS SYAMSWVRQA PGKGLEWVSS IEEMGWQTKY  60
ADSVKGRFTI SRDNSKNTLY LQMNSLRAED TAVYYCAKSA AAFDYWGQGT LVTVSS      116

SEQ ID NO: 156         moltype = AA  length = 108
FEATURE                Location/Qualifiers
```

```
REGION                  1..108
                        note = chemically synthesized
source                  1..108
                        mol_type = protein
                        organism = synthetic construct
SEQUENCE: 156
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ ALDAPLMFGQ GTKVEIKR              108

SEQ ID NO: 157          moltype = AA  length = 119
FEATURE                 Location/Qualifiers
REGION                  1..119
                        note = chemically synthesized
source                  1..119
                        mol_type = protein
                        organism = synthetic construct
SEQUENCE: 157
EVQLLESGGG LVQPGGSLRL SCAASGFTFS SYAMSWVRQA PGKGLEWVSS IEPMGQLTEY  60
ADSVKGRFTI SRDNSKNTLY LQMNSLRAED TAVYYCAKDI GGRSAFDYWG QGTLVTVSS   119

SEQ ID NO: 158          moltype = AA  length = 108
FEATURE                 Location/Qualifiers
REGION                  1..108
                        note = chemically synthesized
source                  1..108
                        mol_type = protein
                        organism = synthetic construct
SEQUENCE: 158
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ ALVAPLTFGQ GTKVEIKR              108

SEQ ID NO: 159          moltype = AA  length = 116
FEATURE                 Location/Qualifiers
REGION                  1..116
                        note = chemically synthesized
source                  1..116
                        mol_type = protein
                        organism = synthetic construct
SEQUENCE: 159
EVQLLESGGG LVQPGGSLRL SCAASGFTFS SYAMSWVRQA PGKGLEWVSS IDEMGWQTYY  60
ADSVKGRFTI SRDNSKNTLY LQMNSLRAED TAVYYCAKSA AAFDYWGQGT LVTVSS      116

SEQ ID NO: 160          moltype = AA  length = 108
FEATURE                 Location/Qualifiers
REGION                  1..108
                        note = chemically synthesized
source                  1..108
                        mol_type = protein
                        organism = synthetic construct
SEQUENCE: 160
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ ALVAPLTFGQ GTKVEIKR              108

SEQ ID NO: 161          moltype = AA  length = 116
FEATURE                 Location/Qualifiers
REGION                  1..116
                        note = chemically synthesized
source                  1..116
                        mol_type = protein
                        organism = synthetic construct
SEQUENCE: 161
EVQLLESGGG LVQPGGSLRL SCAASGFTFS SYAMSWVRQA PGKGLEWVSS IDEMGWQTYY  60
ADSVKGRFTI SRDNSKNTLY LQMNSLRAED TAVYYCAKSA AAFDYWGQGT LVTVSS      116

SEQ ID NO: 162          moltype = AA  length = 214
FEATURE                 Location/Qualifiers
REGION                  1..214
                        note = chemically synthesized
source                  1..214
                        mol_type = protein
                        organism = synthetic construct
SEQUENCE: 162
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ TVVAPPLFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 163          moltype = AA  length = 449
FEATURE                 Location/Qualifiers
```

```
REGION                  1..449
                        note = chemically synthesized
source                  1..449
                        mol_type = protein
                        organism = synthetic construct
SEQUENCE: 163
EVHLLESGGG LVQPGGSLRL SCAASGFTFS SYAMSWVRQA PGKGLEWVSS IDPEGRQTYY  60
ADSVKGRFTI SRDNSKNTLY LQMNSLRAED TAVYYCAKDI GGRSAFDYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 164          moltype = AA  length = 214
FEATURE                 Location/Qualifiers
REGION                  1..214
                        note = chemically synthesized
VARIANT                 182
                        note = X is any amino acid
source                  1..214
                        mol_type = protein
                        organism = synthetic construct
SEQUENCE: 164
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ TVVAPPLFGQ GTKVEIKRTV AAPSVFIFPP  120
SDEQLKSGTA SVVCLLNNFY PREAKVQWKV DNALQSGNSQ ESVTEQDSKD STYSLSSTLT  180
LXKADYEKHK VYACEVTHQG LSSPVTKSFN RGEC                              214

SEQ ID NO: 165          moltype = AA  length = 6
FEATURE                 Location/Qualifiers
REGION                  1..6
                        note = chemically synthesized
source                  1..6
                        mol_type = protein
                        organism = synthetic construct
SEQUENCE: 165
CISPRG                                                             6

SEQ ID NO: 166          moltype = AA  length = 7
FEATURE                 Location/Qualifiers
REGION                  1..7
                        note = chemically synthesized
source                  1..7
                        mol_type = protein
                        organism = synthetic construct
SEQUENCE: 166
CISPRGC                                                            7

SEQ ID NO: 167          moltype = AA  length = 8
FEATURE                 Location/Qualifiers
REGION                  1..8
                        note = chemically synthesized
source                  1..8
                        mol_type = protein
                        organism = synthetic construct
SEQUENCE: 167
CISPRGCG                                                           8

SEQ ID NO: 168          moltype = AA  length = 15
FEATURE                 Location/Qualifiers
REGION                  1..15
                        note = chemically synthesized
source                  1..15
                        mol_type = protein
                        organism = synthetic construct
SEQUENCE: 168
CISPRGCPDG PYVMY                                                   15

SEQ ID NO: 169          moltype = AA  length = 14
FEATURE                 Location/Qualifiers
REGION                  1..14
                        note = chemically synthesized
source                  1..14
                        mol_type = protein
                        organism = synthetic construct
SEQUENCE: 169
CISPRGCPDG PYVM                                                    14
```

```
SEQ ID NO: 170          moltype = AA  length = 15
FEATURE                 Location/Qualifiers
REGION                  1..15
                        note = chemically synthesized
source                  1..15
                        mol_type = protein
                        organism = synthetic construct
SEQUENCE: 170
CISPRGCEPG TYVPT                                                   15

SEQ ID NO: 171          moltype = AA  length = 15
FEATURE                 Location/Qualifiers
REGION                  1..15
                        note = chemically synthesized
source                  1..15
                        mol_type = protein
                        organism = synthetic construct
SEQUENCE: 171
CISPRGCPGQ IWHPP                                                   15

SEQ ID NO: 172          moltype = AA  length = 15
FEATURE                 Location/Qualifiers
REGION                  1..15
                        note = chemically synthesized
source                  1..15
                        mol_type = protein
                        organism = synthetic construct
SEQUENCE: 172
GSHCLIPINM GAPSC                                                   15

SEQ ID NO: 173          moltype = AA  length = 32
FEATURE                 Location/Qualifiers
REGION                  1..32
                        note = chemically synthesized
source                  1..32
                        mol_type = protein
                        organism = synthetic construct
SEQUENCE: 173
CISPRGCGGS SASQSGQGSH CLIPINMGAP SC                                32

SEQ ID NO: 174          moltype = AA  length = 19
FEATURE                 Location/Qualifiers
REGION                  1..19
                        note = chemically synthesized
source                  1..19
                        mol_type = protein
                        organism = synthetic construct
SEQUENCE: 174
CNHHYFYTCG CISPRGCPG                                               19

SEQ ID NO: 175          moltype = AA  length = 19
FEATURE                 Location/Qualifiers
REGION                  1..19
                        note = chemically synthesized
source                  1..19
                        mol_type = protein
                        organism = synthetic construct
SEQUENCE: 175
ADHVFWGSYG CISPRGCPG                                               19

SEQ ID NO: 176          moltype = AA  length = 19
FEATURE                 Location/Qualifiers
REGION                  1..19
                        note = chemically synthesized
source                  1..19
                        mol_type = protein
                        organism = synthetic construct
SEQUENCE: 176
CHHVYWGHCG CISPRGCPG                                               19

SEQ ID NO: 177          moltype = AA  length = 19
FEATURE                 Location/Qualifiers
REGION                  1..19
                        note = chemically synthesized
source                  1..19
                        mol_type = protein
                        organism = synthetic construct
SEQUENCE: 177
```

-continued

```
CPHFTTTSCG CISPRGCPG                                           19

SEQ ID NO: 178          moltype = AA  length = 19
FEATURE                 Location/Qualifiers
REGION                  1..19
                        note = chemically synthesized
source                  1..19
                        mol_type = protein
                        organism = synthetic construct
SEQUENCE: 178
CNHHYHYYCG CISPRGCPG                                           19

SEQ ID NO: 179          moltype = AA  length = 19
FEATURE                 Location/Qualifiers
REGION                  1..19
                        note = chemically synthesized
source                  1..19
                        mol_type = protein
                        organism = synthetic construct
SEQUENCE: 179
CPHVSFGSCG CISPRGCPG                                           19

SEQ ID NO: 180          moltype = AA  length = 19
FEATURE                 Location/Qualifiers
REGION                  1..19
                        note = chemically synthesized
source                  1..19
                        mol_type = protein
                        organism = synthetic construct
SEQUENCE: 180
CPYYTLSYCG CISPRGCPG                                           19

SEQ ID NO: 181          moltype = AA  length = 19
FEATURE                 Location/Qualifiers
REGION                  1..19
                        note = chemically synthesized
source                  1..19
                        mol_type = protein
                        organism = synthetic construct
SEQUENCE: 181
CNHVYFGTCG CISPRGCPG                                           19

SEQ ID NO: 182          moltype = AA  length = 19
FEATURE                 Location/Qualifiers
REGION                  1..19
                        note = chemically synthesized
source                  1..19
                        mol_type = protein
                        organism = synthetic construct
SEQUENCE: 182
CNHFTLTTCG CISPRGCPG                                           19

SEQ ID NO: 183          moltype = AA  length = 19
FEATURE                 Location/Qualifiers
REGION                  1..19
                        note = chemically synthesized
source                  1..19
                        mol_type = protein
                        organism = synthetic construct
SEQUENCE: 183
CHHFTLTTCG CISPRGCPG                                           19

SEQ ID NO: 184          moltype = AA  length = 18
FEATURE                 Location/Qualifiers
REGION                  1..18
                        note = chemically synthesized
source                  1..18
                        mol_type = protein
                        organism = synthetic construct
SEQUENCE: 184
YNPCATPMCC ISPRGCPG                                            18

SEQ ID NO: 185          moltype = AA  length = 18
FEATURE                 Location/Qualifiers
REGION                  1..18
                        note = chemically synthesized
source                  1..18
                        mol_type = protein
                        organism = synthetic construct
```

```
SEQUENCE: 185
CNHHYFYTCG CISPRGCG                                                18

SEQ ID NO: 186          moltype = AA  length = 18
FEATURE                 Location/Qualifiers
REGION                  1..18
                        note = chemically synthesized
source                  1..18
                        mol_type = protein
                        organism = synthetic construct
SEQUENCE: 186
CNHHYHYYCG CISPRGCG                                                18

SEQ ID NO: 187          moltype = AA  length = 18
FEATURE                 Location/Qualifiers
REGION                  1..18
                        note = chemically synthesized
source                  1..18
                        mol_type = protein
                        organism = synthetic construct
SEQUENCE: 187
CNHVYFGTCG CISPRGCG                                                18

SEQ ID NO: 188          moltype = AA  length = 18
FEATURE                 Location/Qualifiers
REGION                  1..18
                        note = chemically synthesized
source                  1..18
                        mol_type = protein
                        organism = synthetic construct
SEQUENCE: 188
CHHVYWGHCG CISPRGCG                                                18

SEQ ID NO: 189          moltype = AA  length = 18
FEATURE                 Location/Qualifiers
REGION                  1..18
                        note = chemically synthesized
source                  1..18
                        mol_type = protein
                        organism = synthetic construct
SEQUENCE: 189
CPHFTTTSCG CISPRGCG                                                18

SEQ ID NO: 190          moltype = AA  length = 18
FEATURE                 Location/Qualifiers
REGION                  1..18
                        note = chemically synthesized
source                  1..18
                        mol_type = protein
                        organism = synthetic construct
SEQUENCE: 190
CNHFTLTTCG CISPRGCG                                                18

SEQ ID NO: 191          moltype = AA  length = 18
FEATURE                 Location/Qualifiers
REGION                  1..18
                        note = chemically synthesized
source                  1..18
                        mol_type = protein
                        organism = synthetic construct
SEQUENCE: 191
CHHFTLTTCG CISPRGCG                                                18

SEQ ID NO: 192          moltype = AA  length = 18
FEATURE                 Location/Qualifiers
REGION                  1..18
                        note = chemically synthesized
source                  1..18
                        mol_type = protein
                        organism = synthetic construct
SEQUENCE: 192
CPYYTLSYCG CISPRGCG                                                18

SEQ ID NO: 193          moltype = AA  length = 18
FEATURE                 Location/Qualifiers
REGION                  1..18
                        note = chemically synthesized
source                  1..18
                        mol_type = protein
```

```
                        organism = synthetic construct
SEQUENCE: 193
CPHVSFGSCG CISPRGCG                                                   18

SEQ ID NO: 194          moltype = AA  length = 18
FEATURE                 Location/Qualifiers
REGION                  1..18
                        note = chemically synthesized
source                  1..18
                        mol_type = protein
                        organism = synthetic construct
SEQUENCE: 194
ADHVFWGSYG CISPRGCG                                                   18

SEQ ID NO: 195          moltype = AA  length = 17
FEATURE                 Location/Qualifiers
REGION                  1..17
                        note = chemically synthesized
source                  1..17
                        mol_type = protein
                        organism = synthetic construct
SEQUENCE: 195
YNPCATPMCC ISPRGCG                                                    17

SEQ ID NO: 196          moltype = AA  length = 18
FEATURE                 Location/Qualifiers
REGION                  1..18
                        note = chemically synthesized
source                  1..18
                        mol_type = protein
                        organism = synthetic construct
SEQUENCE: 196
CHHVYWGHCG CISPRGCG                                                   18

SEQ ID NO: 197          moltype = AA  length = 18
FEATURE                 Location/Qualifiers
REGION                  1..18
                        note = chemically synthesized
VARIANT                 2
                        note = X is N or P
VARIANT                 4
                        note = X is H, V, or F
VARIANT                 5
                        note = X is Y or T
VARIANT                 6
                        note = X is F, W, T, or L
VARIANT                 7
                        note = X is Y, G, T, or S
VARIANT                 8
                        note = X is T, S, Y, or H
source                  1..18
                        mol_type = protein
                        organism = synthetic construct
SEQUENCE: 197
CXHXXXXXCG CISPRGCG                                                   18

SEQ ID NO: 198          moltype = AA  length = 15
FEATURE                 Location/Qualifiers
REGION                  1..15
                        note = chemically synthesized
source                  1..15
                        mol_type = protein
                        organism = synthetic construct
SEQUENCE: 198
CISPRGCGQP IPSVK                                                      15

SEQ ID NO: 199          moltype = AA  length = 15
FEATURE                 Location/Qualifiers
REGION                  1..15
                        note = chemically synthesized
source                  1..15
                        mol_type = protein
                        organism = synthetic construct
SEQUENCE: 199
CISPRGCTQP YHVSR                                                      15

SEQ ID NO: 200          moltype = AA  length = 15
FEATURE                 Location/Qualifiers
REGION                  1..15
```

```
                        note = chemically synthesized
source                  1..15
                        mol_type = protein
                        organism = synthetic construct
SEQUENCE: 200
CISPRGCNAV SGLGS                                                    15

SEQ ID NO: 201          moltype = AA  length = 21
FEATURE                 Location/Qualifiers
REGION                  1..21
                        note = chemically synthesized
source                  1..21
                        mol_type = protein
                        organism = synthetic construct
SEQUENCE: 201
QGQSGQCNIW LVGGDCRGWQ G                                             21

SEQ ID NO: 202          moltype = AA  length = 26
FEATURE                 Location/Qualifiers
REGION                  1..26
                        note = chemically synthesized
source                  1..26
                        mol_type = protein
                        organism = synthetic construct
SEQUENCE: 202
QGQSGQGQQQ WCNIWINGGD CRGWNG                                        26

SEQ ID NO: 203          moltype = AA  length = 15
FEATURE                 Location/Qualifiers
REGION                  1..15
                        note = chemically synthesized
source                  1..15
                        mol_type = protein
                        organism = synthetic construct
SEQUENCE: 203
PWCMQRQDFL RCPQP                                                    15

SEQ ID NO: 204          moltype = AA  length = 15
FEATURE                 Location/Qualifiers
REGION                  1..15
                        note = chemically synthesized
source                  1..15
                        mol_type = protein
                        organism = synthetic construct
SEQUENCE: 204
QLGLPAYMCT FECLR                                                    15

SEQ ID NO: 205          moltype = AA  length = 15
FEATURE                 Location/Qualifiers
REGION                  1..15
                        note = chemically synthesized
source                  1..15
                        mol_type = protein
                        organism = synthetic construct
SEQUENCE: 205
CNLWVSGGDC GGLQG                                                    15

SEQ ID NO: 206          moltype = AA  length = 15
FEATURE                 Location/Qualifiers
REGION                  1..15
                        note = chemically synthesized
source                  1..15
                        mol_type = protein
                        organism = synthetic construct
SEQUENCE: 206
SCSLWTSGSC LPHSP                                                    15

SEQ ID NO: 207          moltype = AA  length = 15
FEATURE                 Location/Qualifiers
REGION                  1..15
                        note = chemically synthesized
source                  1..15
                        mol_type = protein
                        organism = synthetic construct
SEQUENCE: 207
YCLQLPHYMQ AMCGR                                                    15

SEQ ID NO: 208          moltype = AA  length = 15
FEATURE                 Location/Qualifiers
```

```
REGION                 1..15
                       note = chemically synthesized
source                 1..15
                       mol_type = protein
                       organism = synthetic construct
SEQUENCE: 208
CFLYSCTDVS YWNNT                                                      15

SEQ ID NO: 209         moltype = AA  length = 15
FEATURE                Location/Qualifiers
REGION                 1..15
                       note = chemically synthesized
source                 1..15
                       mol_type = protein
                       organism = synthetic construct
SEQUENCE: 209
PWCMQRQDYL RCPQP                                                      15

SEQ ID NO: 210         moltype = AA  length = 15
FEATURE                Location/Qualifiers
REGION                 1..15
                       note = chemically synthesized
source                 1..15
                       mol_type = protein
                       organism = synthetic construct
SEQUENCE: 210
CNLWISGGDC RGLAG                                                      15

SEQ ID NO: 211         moltype = AA  length = 15
FEATURE                Location/Qualifiers
REGION                 1..15
                       note = chemically synthesized
source                 1..15
                       mol_type = protein
                       organism = synthetic construct
SEQUENCE: 211
CNLWVSGGDC RGVQG                                                      15

SEQ ID NO: 212         moltype = AA  length = 15
FEATURE                Location/Qualifiers
REGION                 1..15
                       note = chemically synthesized
source                 1..15
                       mol_type = protein
                       organism = synthetic construct
SEQUENCE: 212
CNLWVSGGDC RGLRG                                                      15

SEQ ID NO: 213         moltype = AA  length = 15
FEATURE                Location/Qualifiers
REGION                 1..15
                       note = chemically synthesized
source                 1..15
                       mol_type = protein
                       organism = synthetic construct
SEQUENCE: 213
CNLWISGGDC RGLPG                                                      15

SEQ ID NO: 214         moltype = AA  length = 15
FEATURE                Location/Qualifiers
REGION                 1..15
                       note = chemically synthesized
source                 1..15
                       mol_type = protein
                       organism = synthetic construct
SEQUENCE: 214
CNLWVSGGDC RDAPW                                                      15

SEQ ID NO: 215         moltype = AA  length = 15
FEATURE                Location/Qualifiers
REGION                 1..15
                       note = chemically synthesized
source                 1..15
                       mol_type = protein
                       organism = synthetic construct
SEQUENCE: 215
CNLWVSGGDC RDLLG                                                      15

SEQ ID NO: 216         moltype = AA  length = 15
```

```
FEATURE                Location/Qualifiers
REGION                 1..15
                       note = chemically synthesized
source                 1..15
                       mol_type = protein
                       organism = synthetic construct
SEQUENCE: 216
CNLWVSGGDC RGLQG                                                15

SEQ ID NO: 217         moltype = AA  length = 15
FEATURE                Location/Qualifiers
REGION                 1..15
                       note = chemically synthesized
source                 1..15
                       mol_type = protein
                       organism = synthetic construct
SEQUENCE: 217
CNLWLHGGDC RGWQG                                                15

SEQ ID NO: 218         moltype = AA  length = 15
FEATURE                Location/Qualifiers
REGION                 1..15
                       note = chemically synthesized
source                 1..15
                       mol_type = protein
                       organism = synthetic construct
SEQUENCE: 218
CNIWLVGGDC RGWQG                                                15

SEQ ID NO: 219         moltype = AA  length = 15
FEATURE                Location/Qualifiers
REGION                 1..15
                       note = chemically synthesized
source                 1..15
                       mol_type = protein
                       organism = synthetic construct
SEQUENCE: 219
CTTWFCGGDC GVMRG                                                15

SEQ ID NO: 220         moltype = AA  length = 15
FEATURE                Location/Qualifiers
REGION                 1..15
                       note = chemically synthesized
source                 1..15
                       mol_type = protein
                       organism = synthetic construct
SEQUENCE: 220
CNIWGPSVDC GALLG                                                15

SEQ ID NO: 221         moltype = AA  length = 15
FEATURE                Location/Qualifiers
REGION                 1..15
                       note = chemically synthesized
source                 1..15
                       mol_type = protein
                       organism = synthetic construct
SEQUENCE: 221
CNIWVNGGDC RSFEG                                                15

SEQ ID NO: 222         moltype = AA  length = 15
FEATURE                Location/Qualifiers
REGION                 1..15
                       note = chemically synthesized
source                 1..15
                       mol_type = protein
                       organism = synthetic construct
SEQUENCE: 222
YCLNLPRYMQ DMCWA                                                15

SEQ ID NO: 223         moltype = AA  length = 15
FEATURE                Location/Qualifiers
REGION                 1..15
                       note = chemically synthesized
source                 1..15
                       mol_type = protein
                       organism = synthetic construct
SEQUENCE: 223
YCLALPHYMQ ADCAR                                                15
```

```
SEQ ID NO: 224          moltype = AA  length = 15
FEATURE                 Location/Qualifiers
REGION                  1..15
                        note = chemically synthesized
source                  1..15
                        mol_type = protein
                        organism = synthetic construct
SEQUENCE: 224
CFLYSCGDVS YWGSA                                                    15

SEQ ID NO: 225          moltype = AA  length = 15
FEATURE                 Location/Qualifiers
REGION                  1..15
                        note = chemically synthesized
source                  1..15
                        mol_type = protein
                        organism = synthetic construct
SEQUENCE: 225
CYLYSCTDSA FWNNR                                                    15

SEQ ID NO: 226          moltype = AA  length = 15
FEATURE                 Location/Qualifiers
REGION                  1..15
                        note = chemically synthesized
source                  1..15
                        mol_type = protein
                        organism = synthetic construct
SEQUENCE: 226
CYLYSCNDVS YWSNT                                                    15

SEQ ID NO: 227          moltype = AA  length = 12
FEATURE                 Location/Qualifiers
REGION                  1..12
                        note = chemically synthesized
source                  1..12
                        mol_type = protein
                        organism = synthetic construct
SEQUENCE: 227
CFLYSCTDVS YW                                                       12

SEQ ID NO: 228          moltype = AA  length = 15
FEATURE                 Location/Qualifiers
REGION                  1..15
                        note = chemically synthesized
source                  1..15
                        mol_type = protein
                        organism = synthetic construct
SEQUENCE: 228
CFLYSCTDVA YWNSA                                                    15

SEQ ID NO: 229          moltype = AA  length = 15
FEATURE                 Location/Qualifiers
REGION                  1..15
                        note = chemically synthesized
source                  1..15
                        mol_type = protein
                        organism = synthetic construct
SEQUENCE: 229
CFLYSCTDVS YWGDT                                                    15

SEQ ID NO: 230          moltype = AA  length = 15
FEATURE                 Location/Qualifiers
REGION                  1..15
                        note = chemically synthesized
source                  1..15
                        mol_type = protein
                        organism = synthetic construct
SEQUENCE: 230
CFLYSCTDVS YWGNS                                                    15

SEQ ID NO: 231          moltype = AA  length = 15
FEATURE                 Location/Qualifiers
REGION                  1..15
                        note = chemically synthesized
source                  1..15
                        mol_type = protein
                        organism = synthetic construct
SEQUENCE: 231
CFLYSCTDVA YWNNT                                                    15
```

```
SEQ ID NO: 232          moltype = AA  length = 18
FEATURE                 Location/Qualifiers
REGION                  1..18
                        note = chemically synthesized
source                  1..18
                        mol_type = protein
                        organism = synthetic construct
SEQUENCE: 232
CFLYSCGDVS YWGNPGLS                                                18

SEQ ID NO: 233          moltype = AA  length = 15
FEATURE                 Location/Qualifiers
REGION                  1..15
                        note = chemically synthesized
source                  1..15
                        mol_type = protein
                        organism = synthetic construct
SEQUENCE: 233
CFLYSCTDVA YWSGL                                                   15

SEQ ID NO: 234          moltype = AA  length = 15
FEATURE                 Location/Qualifiers
REGION                  1..15
                        note = chemically synthesized
source                  1..15
                        mol_type = protein
                        organism = synthetic construct
SEQUENCE: 234
CYLYSCTDGS YWNST                                                   15

SEQ ID NO: 235          moltype = AA  length = 15
FEATURE                 Location/Qualifiers
REGION                  1..15
                        note = chemically synthesized
source                  1..15
                        mol_type = protein
                        organism = synthetic construct
SEQUENCE: 235
CFLYSCSDVS YWGNI                                                   15

SEQ ID NO: 236          moltype = AA  length = 12
FEATURE                 Location/Qualifiers
REGION                  1..12
                        note = chemically synthesized
source                  1..12
                        mol_type = protein
                        organism = synthetic construct
SEQUENCE: 236
CFLYSCTDVA YW                                                      12

SEQ ID NO: 237          moltype = AA  length = 15
FEATURE                 Location/Qualifiers
REGION                  1..15
                        note = chemically synthesized
source                  1..15
                        mol_type = protein
                        organism = synthetic construct
SEQUENCE: 237
CFLYSCTDVS YWGST                                                   15

SEQ ID NO: 238          moltype = AA  length = 15
FEATURE                 Location/Qualifiers
REGION                  1..15
                        note = chemically synthesized
source                  1..15
                        mol_type = protein
                        organism = synthetic construct
SEQUENCE: 238
CFLYSCTDVA YWGDT                                                   15

SEQ ID NO: 239          moltype = AA  length = 20
FEATURE                 Location/Qualifiers
REGION                  1..20
                        note = chemically synthesized
source                  1..20
                        mol_type = protein
                        organism = synthetic construct
SEQUENCE: 239
```

```
GCNIWLNGGD CRGWVDPLQG                                         20

SEQ ID NO: 240         moltype = AA  length = 20
FEATURE                Location/Qualifiers
REGION                 1..20
                       note = chemically synthesized
source                 1..20
                       mol_type = protein
                       organism = synthetic construct
SEQUENCE: 240
GCNIWLVGGD CRGWIGDTNG                                         20

SEQ ID NO: 241         moltype = AA  length = 20
FEATURE                Location/Qualifiers
REGION                 1..20
                       note = chemically synthesized
source                 1..20
                       mol_type = protein
                       organism = synthetic construct
SEQUENCE: 241
GCNIWLVGGD CRGWIEDSNG                                         20

SEQ ID NO: 242         moltype = AA  length = 20
FEATURE                Location/Qualifiers
REGION                 1..20
                       note = chemically synthesized
source                 1..20
                       mol_type = protein
                       organism = synthetic construct
SEQUENCE: 242
GCNIWANGGD CRGWIDNIDG                                         20

SEQ ID NO: 243         moltype = AA  length = 20
FEATURE                Location/Qualifiers
REGION                 1..20
                       note = chemically synthesized
source                 1..20
                       mol_type = protein
                       organism = synthetic construct
SEQUENCE: 243
GCNIWLVGGD CRGWLGEAVG                                         20

SEQ ID NO: 244         moltype = AA  length = 20
FEATURE                Location/Qualifiers
REGION                 1..20
                       note = chemically synthesized
source                 1..20
                       mol_type = protein
                       organism = synthetic construct
SEQUENCE: 244
GCNIWLVGGD CRGWLEEAVG                                         20

SEQ ID NO: 245         moltype = AA  length = 20
FEATURE                Location/Qualifiers
REGION                 1..20
                       note = chemically synthesized
source                 1..20
                       mol_type = protein
                       organism = synthetic construct
SEQUENCE: 245
GGPALCNIWL NGGDCRGWSG                                         20

SEQ ID NO: 246         moltype = AA  length = 20
FEATURE                Location/Qualifiers
REGION                 1..20
                       note = chemically synthesized
source                 1..20
                       mol_type = protein
                       organism = synthetic construct
SEQUENCE: 246
GAPVFCNIWL NGGDCRGWMG                                         20

SEQ ID NO: 247         moltype = AA  length = 20
FEATURE                Location/Qualifiers
REGION                 1..20
                       note = chemically synthesized
source                 1..20
                       mol_type = protein
                       organism = synthetic construct
```

```
SEQUENCE: 247
GQQQWCNIWI NGGDCRGWNG                                                20

SEQ ID NO: 248          moltype = AA  length = 20
FEATURE                 Location/Qualifiers
REGION                  1..20
                        note = chemically synthesized
source                  1..20
                        mol_type = protein
                        organism = synthetic construct
SEQUENCE: 248
GKSEFCNIWL NGGDCRGWIG                                                20

SEQ ID NO: 249          moltype = AA  length = 20
FEATURE                 Location/Qualifiers
REGION                  1..20
                        note = chemically synthesized
source                  1..20
                        mol_type = protein
                        organism = synthetic construct
SEQUENCE: 249
GTPGGCNIWA NGGDCRGWEG                                                20

SEQ ID NO: 250          moltype = AA  length = 20
FEATURE                 Location/Qualifiers
REGION                  1..20
                        note = chemically synthesized
source                  1..20
                        mol_type = protein
                        organism = synthetic construct
SEQUENCE: 250
GASQYCNLWI NGGDCRGWRG                                                20

SEQ ID NO: 251          moltype = AA  length = 18
FEATURE                 Location/Qualifiers
REGION                  1..18
                        note = chemically synthesized
source                  1..18
                        mol_type = protein
                        organism = synthetic construct
SEQUENCE: 251
GCNIWLVGGD CRPWVEGG                                                  18

SEQ ID NO: 252          moltype = AA  length = 18
FEATURE                 Location/Qualifiers
REGION                  1..18
                        note = chemically synthesized
source                  1..18
                        mol_type = protein
                        organism = synthetic construct
SEQUENCE: 252
GCNIWAVGGD CRPFVDGG                                                  18

SEQ ID NO: 253          moltype = AA  length = 18
FEATURE                 Location/Qualifiers
REGION                  1..18
                        note = chemically synthesized
source                  1..18
                        mol_type = protein
                        organism = synthetic construct
SEQUENCE: 253
GCNIWLNGGD CRAWVDTG                                                  18

SEQ ID NO: 254          moltype = AA  length = 18
FEATURE                 Location/Qualifiers
REGION                  1..18
                        note = chemically synthesized
source                  1..18
                        mol_type = protein
                        organism = synthetic construct
SEQUENCE: 254
GCNIWIVGGD CRPFINDG                                                  18

SEQ ID NO: 255          moltype = AA  length = 18
FEATURE                 Location/Qualifiers
REGION                  1..18
                        note = chemically synthesized
source                  1..18
                        mol_type = protein
```

```
                        organism = synthetic construct
SEQUENCE: 255
GCNIWLNGGD CRPVVFGG                                                   18

SEQ ID NO: 256          moltype = AA  length = 18
FEATURE                 Location/Qualifiers
REGION                  1..18
                        note = chemically synthesized
source                  1..18
                        mol_type = protein
                        organism = synthetic construct
SEQUENCE: 256
GCNIWLSGGD CRMFMNEG                                                   18

SEQ ID NO: 257          moltype = AA  length = 18
FEATURE                 Location/Qualifiers
REGION                  1..18
                        note = chemically synthesized
source                  1..18
                        mol_type = protein
                        organism = synthetic construct
SEQUENCE: 257
GCNIWVNGGD CRSFVYSG                                                   18

SEQ ID NO: 258          moltype = AA  length = 18
FEATURE                 Location/Qualifiers
REGION                  1..18
                        note = chemically synthesized
source                  1..18
                        mol_type = protein
                        organism = synthetic construct
SEQUENCE: 258
GCNIWLNGGD CRGWEASG                                                   18

SEQ ID NO: 259          moltype = AA  length = 18
FEATURE                 Location/Qualifiers
REGION                  1..18
                        note = chemically synthesized
source                  1..18
                        mol_type = protein
                        organism = synthetic construct
SEQUENCE: 259
GCNIWAHGGD CRGFIEPG                                                   18

SEQ ID NO: 260          moltype = AA  length = 18
FEATURE                 Location/Qualifiers
REGION                  1..18
                        note = chemically synthesized
source                  1..18
                        mol_type = protein
                        organism = synthetic construct
SEQUENCE: 260
GCNIWLNGGD CRTFVASG                                                   18

SEQ ID NO: 261          moltype = AA  length = 18
FEATURE                 Location/Qualifiers
REGION                  1..18
                        note = chemically synthesized
source                  1..18
                        mol_type = protein
                        organism = synthetic construct
SEQUENCE: 261
GCNIWAHGGD CRGFIEPG                                                   18

SEQ ID NO: 262          moltype = AA  length = 18
FEATURE                 Location/Qualifiers
REGION                  1..18
                        note = chemically synthesized
source                  1..18
                        mol_type = protein
                        organism = synthetic construct
SEQUENCE: 262
GFLENCNIWL NGGDCRTG                                                   18

SEQ ID NO: 263          moltype = AA  length = 18
FEATURE                 Location/Qualifiers
REGION                  1..18
                        note = chemically synthesized
source                  1..18
```

```
                        mol_type = protein
                        organism = synthetic construct
SEQUENCE: 263
GIYENCNIWL NGGDCRMG                                                  18

SEQ ID NO: 264          moltype = AA  length = 18
FEATURE                 Location/Qualifiers
REGION                  1..18
                        note = chemically synthesized
source                  1..18
                        mol_type = protein
                        organism = synthetic construct
SEQUENCE: 264
GIPDNCNIWI NGGDCRYG                                                  18

SEQ ID NO: 265          moltype = AA  length = 21
FEATURE                 Location/Qualifiers
REGION                  1..21
                        note = chemically synthesized
source                  1..21
                        mol_type = protein
                        organism = synthetic construct
SEQUENCE: 265
QGQSGQYGSC SWNYVHIFMD C                                              21

SEQ ID NO: 266          moltype = AA  length = 21
FEATURE                 Location/Qualifiers
REGION                  1..21
                        note = chemically synthesized
source                  1..21
                        mol_type = protein
                        organism = synthetic construct
SEQUENCE: 266
QGQSGQGDFD IPFPAHWVPI T                                              21

SEQ ID NO: 267          moltype = AA  length = 24
FEATURE                 Location/Qualifiers
REGION                  1..24
                        note = chemically synthesized
source                  1..24
                        mol_type = protein
                        organism = synthetic construct
SEQUENCE: 267
QGQSGQMGVP AGCVWNYAHI FMDC                                           24

SEQ ID NO: 268          moltype = AA  length = 15
FEATURE                 Location/Qualifiers
REGION                  1..15
                        note = chemically synthesized
source                  1..15
                        mol_type = protein
                        organism = synthetic construct
SEQUENCE: 268
YRSCNWNYVS IFLDC                                                     15

SEQ ID NO: 269          moltype = AA  length = 16
FEATURE                 Location/Qualifiers
REGION                  1..16
                        note = chemically synthesized
source                  1..16
                        mol_type = protein
                        organism = synthetic construct
SEQUENCE: 269
PGAFDIPFPA HWVPNT                                                    16

SEQ ID NO: 270          moltype = AA  length = 15
FEATURE                 Location/Qualifiers
REGION                  1..15
                        note = chemically synthesized
source                  1..15
                        mol_type = protein
                        organism = synthetic construct
SEQUENCE: 270
ESSCVWNYVH IYMDC                                                     15

SEQ ID NO: 271          moltype = AA  length = 15
FEATURE                 Location/Qualifiers
REGION                  1..15
                        note = chemically synthesized
```

```
source                  1..15
                        mol_type = protein
                        organism = synthetic construct
SEQUENCE: 271
YPGCKWNYDR IFLDC                                                      15

SEQ ID NO: 272          moltype = AA  length = 15
FEATURE                 Location/Qualifiers
REGION                  1..15
                        note = chemically synthesized
source                  1..15
                        mol_type = protein
                        organism = synthetic construct
SEQUENCE: 272
YRTCSWNYVG IFLDC                                                      15

SEQ ID NO: 273          moltype = AA  length = 15
FEATURE                 Location/Qualifiers
REGION                  1..15
                        note = chemically synthesized
source                  1..15
                        mol_type = protein
                        organism = synthetic construct
SEQUENCE: 273
YGSCSWNYVH IFMDC                                                      15

SEQ ID NO: 274          moltype = AA  length = 15
FEATURE                 Location/Qualifiers
REGION                  1..15
                        note = chemically synthesized
source                  1..15
                        mol_type = protein
                        organism = synthetic construct
SEQUENCE: 274
YGSCSWNYVH IFLDC                                                      15

SEQ ID NO: 275          moltype = AA  length = 15
FEATURE                 Location/Qualifiers
REGION                  1..15
                        note = chemically synthesized
source                  1..15
                        mol_type = protein
                        organism = synthetic construct
SEQUENCE: 275
YGSCNWNYVH IFLDC                                                      15

SEQ ID NO: 276          moltype = AA  length = 15
FEATURE                 Location/Qualifiers
REGION                  1..15
                        note = chemically synthesized
source                  1..15
                        mol_type = protein
                        organism = synthetic construct
SEQUENCE: 276
YTSCNWNYVH IFMDC                                                      15

SEQ ID NO: 277          moltype = AA  length = 15
FEATURE                 Location/Qualifiers
REGION                  1..15
                        note = chemically synthesized
source                  1..15
                        mol_type = protein
                        organism = synthetic construct
SEQUENCE: 277
YPGCKWNYDR IFLDC                                                      15

SEQ ID NO: 278          moltype = AA  length = 15
FEATURE                 Location/Qualifiers
REGION                  1..15
                        note = chemically synthesized
source                  1..15
                        mol_type = protein
                        organism = synthetic construct
SEQUENCE: 278
WRSCNWNYAH IFLDC                                                      15

SEQ ID NO: 279          moltype = AA  length = 15
FEATURE                 Location/Qualifiers
REGION                  1..15
```

```
                        note = chemically synthesized
source                  1..15
                        mol_type = protein
                        organism = synthetic construct
SEQUENCE: 279
WSNCHWNYVH IFLDC                                                15

SEQ ID NO: 280          moltype = AA  length = 15
FEATURE                 Location/Qualifiers
REGION                  1..15
                        note = chemically synthesized
source                  1..15
                        mol_type = protein
                        organism = synthetic construct
SEQUENCE: 280
DRSCTWNYVR ISYDC                                                15

SEQ ID NO: 281          moltype = AA  length = 15
FEATURE                 Location/Qualifiers
REGION                  1..15
                        note = chemically synthesized
source                  1..15
                        mol_type = protein
                        organism = synthetic construct
SEQUENCE: 281
SGSCKWDYVH IFLDC                                                15

SEQ ID NO: 282          moltype = AA  length = 15
FEATURE                 Location/Qualifiers
REGION                  1..15
                        note = chemically synthesized
source                  1..15
                        mol_type = protein
                        organism = synthetic construct
SEQUENCE: 282
SRSCIWNYAH IHLDC                                                15

SEQ ID NO: 283          moltype = AA  length = 15
FEATURE                 Location/Qualifiers
REGION                  1..15
                        note = chemically synthesized
source                  1..15
                        mol_type = protein
                        organism = synthetic construct
SEQUENCE: 283
SMSCYWQYER IFLDC                                                15

SEQ ID NO: 284          moltype = AA  length = 15
FEATURE                 Location/Qualifiers
REGION                  1..15
                        note = chemically synthesized
source                  1..15
                        mol_type = protein
                        organism = synthetic construct
SEQUENCE: 284
YRSCNWNYVS IFLDC                                                15

SEQ ID NO: 285          moltype = AA  length = 15
FEATURE                 Location/Qualifiers
REGION                  1..15
                        note = chemically synthesized
source                  1..15
                        mol_type = protein
                        organism = synthetic construct
SEQUENCE: 285
SGSCKWDYVH IFLDC                                                15

SEQ ID NO: 286          moltype = AA  length = 15
FEATURE                 Location/Qualifiers
REGION                  1..15
                        note = chemically synthesized
source                  1..15
                        mol_type = protein
                        organism = synthetic construct
SEQUENCE: 286
YKSCHWDYVH IFLDC                                                15

SEQ ID NO: 287          moltype = AA  length = 15
FEATURE                 Location/Qualifiers
```

```
REGION                  1..15
                        note = chemically synthesized
source                  1..15
                        mol_type = protein
                        organism = synthetic construct
SEQUENCE: 287
YGSCTWNYVH IFMEC                                                            15

SEQ ID NO: 288          moltype = AA  length = 15
FEATURE                 Location/Qualifiers
REGION                  1..15
                        note = chemically synthesized
source                  1..15
                        mol_type = protein
                        organism = synthetic construct
SEQUENCE: 288
FSSCNWNYVH IFLDC                                                            15

SEQ ID NO: 289          moltype = AA  length = 15
FEATURE                 Location/Qualifiers
REGION                  1..15
                        note = chemically synthesized
source                  1..15
                        mol_type = protein
                        organism = synthetic construct
SEQUENCE: 289
WRSCNWNYAH IFLDC                                                            15

SEQ ID NO: 290          moltype = AA  length = 15
FEATURE                 Location/Qualifiers
REGION                  1..15
                        note = chemically synthesized
source                  1..15
                        mol_type = protein
                        organism = synthetic construct
SEQUENCE: 290
YGSCQWNYVH IFLDC                                                            15

SEQ ID NO: 291          moltype = AA  length = 15
FEATURE                 Location/Qualifiers
REGION                  1..15
                        note = chemically synthesized
source                  1..15
                        mol_type = protein
                        organism = synthetic construct
SEQUENCE: 291
YRSCNWNYVH IFLDC                                                            15

SEQ ID NO: 292          moltype = AA  length = 15
FEATURE                 Location/Qualifiers
REGION                  1..15
                        note = chemically synthesized
source                  1..15
                        mol_type = protein
                        organism = synthetic construct
SEQUENCE: 292
NMSCHWDYVH IFLDC                                                            15

SEQ ID NO: 293          moltype = AA  length = 15
FEATURE                 Location/Qualifiers
REGION                  1..15
                        note = chemically synthesized
source                  1..15
                        mol_type = protein
                        organism = synthetic construct
SEQUENCE: 293
FGPCTWNYAR ISWDC                                                            15

SEQ ID NO: 294          moltype = AA  length = 15
FEATURE                 Location/Qualifiers
REGION                  1..15
                        note = chemically synthesized
VARIANT                 1..13
                        note = X is any amino acid
SITE                    5
                        note = MISC_FEATURE - X is any amino acid
SITE                    7
                        note = MISC_FEATURE - X is any amino acid
SITE                    13
```

```
                        note = MISC_FEATURE - X is any amino acid
source                  1..15
                        mol_type = protein
                        organism = synthetic construct
SEQUENCE: 294
XXSCXWXYVH IFXDC                                                     15

SEQ ID NO: 295          moltype = AA  length = 18
FEATURE                 Location/Qualifiers
REGION                  1..18
                        note = chemically synthesized
source                  1..18
                        mol_type = protein
                        organism = synthetic construct
SEQUENCE: 295
MGVPAGCVWN YAHIFMDC                                                  18

SEQ ID NO: 296          moltype = AA  length = 18
FEATURE                 Location/Qualifiers
REGION                  1..18
                        note = chemically synthesized
source                  1..18
                        mol_type = protein
                        organism = synthetic construct
SEQUENCE: 296
RDTGGQCRWD YVHIFMDC                                                  18

SEQ ID NO: 297          moltype = AA  length = 18
FEATURE                 Location/Qualifiers
REGION                  1..18
                        note = chemically synthesized
source                  1..18
                        mol_type = protein
                        organism = synthetic construct
SEQUENCE: 297
AGVPAGCTWN YVHIFMEC                                                  18

SEQ ID NO: 298          moltype = AA  length = 18
FEATURE                 Location/Qualifiers
REGION                  1..18
                        note = chemically synthesized
source                  1..18
                        mol_type = protein
                        organism = synthetic construct
SEQUENCE: 298
VGVPNGCVWN YAHIFMEC                                                  18

SEQ ID NO: 299          moltype = AA  length = 18
FEATURE                 Location/Qualifiers
REGION                  1..18
                        note = chemically synthesized
source                  1..18
                        mol_type = protein
                        organism = synthetic construct
SEQUENCE: 299
DGGPAGCSWN YVHIFMEC                                                  18

SEQ ID NO: 300          moltype = AA  length = 18
FEATURE                 Location/Qualifiers
REGION                  1..18
                        note = chemically synthesized
source                  1..18
                        mol_type = protein
                        organism = synthetic construct
SEQUENCE: 300
AVGPAGCWWN YVHIFMEC                                                  18

SEQ ID NO: 301          moltype = AA  length = 18
FEATURE                 Location/Qualifiers
REGION                  1..18
                        note = chemically synthesized
source                  1..18
                        mol_type = protein
                        organism = synthetic construct
SEQUENCE: 301
CTWNYVHIFM DCGEGEGP                                                  18

SEQ ID NO: 302          moltype = AA  length = 18
FEATURE                 Location/Qualifiers
```

```
REGION                  1..18
                        note = chemically synthesized
source                  1..18
                        mol_type = protein
                        organism = synthetic construct
SEQUENCE: 302
GGVPEGCTWN YAHIFMEC                                                    18

SEQ ID NO: 303          moltype = AA  length = 18
FEATURE                 Location/Qualifiers
REGION                  1..18
                        note = chemically synthesized
source                  1..18
                        mol_type = protein
                        organism = synthetic construct
SEQUENCE: 303
AEVPAGCWWN YVHIFMEC                                                    18

SEQ ID NO: 304          moltype = AA  length = 18
FEATURE                 Location/Qualifiers
REGION                  1..18
                        note = chemically synthesized
source                  1..18
                        mol_type = protein
                        organism = synthetic construct
SEQUENCE: 304
AGVPAGCTWN YVHIFMEC                                                    18

SEQ ID NO: 305          moltype = AA  length = 18
FEATURE                 Location/Qualifiers
REGION                  1..18
                        note = chemically synthesized
source                  1..18
                        mol_type = protein
                        organism = synthetic construct
SEQUENCE: 305
SGASGGCKWN YVHIFMDC                                                    18

SEQ ID NO: 306          moltype = AA  length = 18
FEATURE                 Location/Qualifiers
REGION                  1..18
                        note = chemically synthesized
source                  1..18
                        mol_type = protein
                        organism = synthetic construct
SEQUENCE: 306
TPGCRWNYVH IFMECEAL                                                    18

SEQ ID NO: 307          moltype = AA  length = 18
FEATURE                 Location/Qualifiers
REGION                  1..18
                        note = chemically synthesized
source                  1..18
                        mol_type = protein
                        organism = synthetic construct
SEQUENCE: 307
VGVPNGCVWN YAHIFMEC                                                    18

SEQ ID NO: 308          moltype = AA  length = 16
FEATURE                 Location/Qualifiers
REGION                  1..16
                        note = chemically synthesized
source                  1..16
                        mol_type = protein
                        organism = synthetic construct
SEQUENCE: 308
PGAFDIPFPA HWVPNT                                                      16

SEQ ID NO: 309          moltype = AA  length = 16
FEATURE                 Location/Qualifiers
REGION                  1..16
                        note = chemically synthesized
source                  1..16
                        mol_type = protein
                        organism = synthetic construct
SEQUENCE: 309
RGACDIPFPA HWIPNT                                                      16

SEQ ID NO: 310          moltype = AA  length = 16
```

```
FEATURE                Location/Qualifiers
REGION                 1..16
                       note = chemically synthesized
source                 1..16
                       mol_type = protein
                       organism = synthetic construct
SEQUENCE: 310
QGDFDIPFPA HWVPIT                                                        16

SEQ ID NO: 311         moltype = AA  length = 16
FEATURE                Location/Qualifiers
REGION                 1..16
                       note = chemically synthesized
VARIANT                1
                       note = X is any amino acid
source                 1..16
                       mol_type = protein
                       organism = synthetic construct
SEQUENCE: 311
XGAFDIPFPA HWVPNT                                                        16

SEQ ID NO: 312         moltype = AA  length = 19
FEATURE                Location/Qualifiers
REGION                 1..19
                       note = chemically synthesized
source                 1..19
                       mol_type = protein
                       organism = synthetic construct
SEQUENCE: 312
RGDGNDSDIP FPAHWVPRT                                                     19

SEQ ID NO: 313         moltype = AA  length = 19
FEATURE                Location/Qualifiers
REGION                 1..19
                       note = chemically synthesized
source                 1..19
                       mol_type = protein
                       organism = synthetic construct
SEQUENCE: 313
SGVGRDRDIP FPAHWVPRT                                                     19

SEQ ID NO: 314         moltype = AA  length = 19
FEATURE                Location/Qualifiers
REGION                 1..19
                       note = chemically synthesized
source                 1..19
                       mol_type = protein
                       organism = synthetic construct
SEQUENCE: 314
WAGGNDCDIP FPAHWIPNT                                                     19

SEQ ID NO: 315         moltype = AA  length = 19
FEATURE                Location/Qualifiers
REGION                 1..19
                       note = chemically synthesized
source                 1..19
                       mol_type = protein
                       organism = synthetic construct
SEQUENCE: 315
WGDGMDVDIP FPAHWVPVT                                                     19

SEQ ID NO: 316         moltype = AA  length = 19
FEATURE                Location/Qualifiers
REGION                 1..19
                       note = chemically synthesized
source                 1..19
                       mol_type = protein
                       organism = synthetic construct
SEQUENCE: 316
AGSGNDSDIP FPAHWVPRT                                                     19

SEQ ID NO: 317         moltype = AA  length = 19
FEATURE                Location/Qualifiers
REGION                 1..19
                       note = chemically synthesized
source                 1..19
                       mol_type = protein
                       organism = synthetic construct
SEQUENCE: 317
```

```
ESRSGYADIP FPAHWVPRT                                         19

SEQ ID NO: 318          moltype = AA  length = 19
FEATURE                 Location/Qualifiers
REGION                  1..19
                        note = chemically synthesized
source                  1..19
                        mol_type = protein
                        organism = synthetic construct
SEQUENCE: 318
RECGRCGDIP FPAHWVPRT                                         19

SEQ ID NO: 319          moltype = AA  length = 8
FEATURE                 Location/Qualifiers
REGION                  1..8
                        note = chemically synthesized
source                  1..8
                        mol_type = protein
                        organism = synthetic construct
SEQUENCE: 319
PRFKIIGG                                                     8

SEQ ID NO: 320          moltype = AA  length = 8
FEATURE                 Location/Qualifiers
REGION                  1..8
                        note = chemically synthesized
source                  1..8
                        mol_type = protein
                        organism = synthetic construct
SEQUENCE: 320
PRFRIIGG                                                     8

SEQ ID NO: 321          moltype = AA  length = 9
FEATURE                 Location/Qualifiers
REGION                  1..9
                        note = chemically synthesized
source                  1..9
                        mol_type = protein
                        organism = synthetic construct
SEQUENCE: 321
SSRHRRALD                                                    9

SEQ ID NO: 322          moltype = AA  length = 14
FEATURE                 Location/Qualifiers
REGION                  1..14
                        note = chemically synthesized
source                  1..14
                        mol_type = protein
                        organism = synthetic construct
SEQUENCE: 322
RKSSIIIRMR DVVL                                              14

SEQ ID NO: 323          moltype = AA  length = 15
FEATURE                 Location/Qualifiers
REGION                  1..15
                        note = chemically synthesized
source                  1..15
                        mol_type = protein
                        organism = synthetic construct
SEQUENCE: 323
SSSFDKGKYK KGDDA                                             15

SEQ ID NO: 324          moltype = AA  length = 15
FEATURE                 Location/Qualifiers
REGION                  1..15
                        note = chemically synthesized
source                  1..15
                        mol_type = protein
                        organism = synthetic construct
SEQUENCE: 324
SSSFDKGKYK RGDDA                                             15

SEQ ID NO: 325          moltype = AA  length = 4
FEATURE                 Location/Qualifiers
REGION                  1..4
                        note = chemically synthesized
source                  1..4
                        mol_type = protein
                        organism = synthetic construct
```

```
SEQUENCE: 325
IEGR                                                                4

SEQ ID NO: 326          moltype = AA  length = 4
FEATURE                 Location/Qualifiers
REGION                  1..4
                        note = chemically synthesized
source                  1..4
                        mol_type = protein
                        organism = synthetic construct
SEQUENCE: 326
IDGR                                                                4

SEQ ID NO: 327          moltype = AA  length = 7
FEATURE                 Location/Qualifiers
REGION                  1..7
                        note = chemically synthesized
source                  1..7
                        mol_type = protein
                        organism = synthetic construct
SEQUENCE: 327
GGSIDGR                                                             7

SEQ ID NO: 328          moltype = AA  length = 6
FEATURE                 Location/Qualifiers
REGION                  1..6
                        note = chemically synthesized
source                  1..6
                        mol_type = protein
                        organism = synthetic construct
SEQUENCE: 328
PLGLWA                                                              6

SEQ ID NO: 329          moltype = AA  length = 8
FEATURE                 Location/Qualifiers
REGION                  1..8
                        note = chemically synthesized
source                  1..8
                        mol_type = protein
                        organism = synthetic construct
SEQUENCE: 329
GPQGIAGQ                                                            8

SEQ ID NO: 330          moltype = AA  length = 8
FEATURE                 Location/Qualifiers
REGION                  1..8
                        note = chemically synthesized
source                  1..8
                        mol_type = protein
                        organism = synthetic construct
SEQUENCE: 330
GPQGLLGA                                                            8

SEQ ID NO: 331          moltype = AA  length = 5
FEATURE                 Location/Qualifiers
REGION                  1..5
                        note = chemically synthesized
source                  1..5
                        mol_type = protein
                        organism = synthetic construct
SEQUENCE: 331
GIAGQ                                                               5

SEQ ID NO: 332          moltype = AA  length = 8
FEATURE                 Location/Qualifiers
REGION                  1..8
                        note = chemically synthesized
source                  1..8
                        mol_type = protein
                        organism = synthetic construct
SEQUENCE: 332
GPLGIAGI                                                            8

SEQ ID NO: 333          moltype = AA  length = 8
FEATURE                 Location/Qualifiers
REGION                  1..8
                        note = chemically synthesized
source                  1..8
                        mol_type = protein
```

```
                        organism = synthetic construct
SEQUENCE: 333
GPEGLRVG                                                                  8

SEQ ID NO: 334          moltype = AA  length = 8
FEATURE                 Location/Qualifiers
REGION                  1..8
                        note = chemically synthesized
source                  1..8
                        mol_type = protein
                        organism = synthetic construct
SEQUENCE: 334
YGAGLGVV                                                                  8

SEQ ID NO: 335          moltype = AA  length = 8
FEATURE                 Location/Qualifiers
REGION                  1..8
                        note = chemically synthesized
source                  1..8
                        mol_type = protein
                        organism = synthetic construct
SEQUENCE: 335
AGLGVVER                                                                  8

SEQ ID NO: 336          moltype = AA  length = 8
FEATURE                 Location/Qualifiers
REGION                  1..8
                        note = chemically synthesized
source                  1..8
                        mol_type = protein
                        organism = synthetic construct
SEQUENCE: 336
AGLGISST                                                                  8

SEQ ID NO: 337          moltype = AA  length = 8
FEATURE                 Location/Qualifiers
REGION                  1..8
                        note = chemically synthesized
source                  1..8
                        mol_type = protein
                        organism = synthetic construct
SEQUENCE: 337
EPQALAMS                                                                  8

SEQ ID NO: 338          moltype = AA  length = 8
FEATURE                 Location/Qualifiers
REGION                  1..8
                        note = chemically synthesized
source                  1..8
                        mol_type = protein
                        organism = synthetic construct
SEQUENCE: 338
QALAMSAI                                                                  8

SEQ ID NO: 339          moltype = AA  length = 8
FEATURE                 Location/Qualifiers
REGION                  1..8
                        note = chemically synthesized
source                  1..8
                        mol_type = protein
                        organism = synthetic construct
SEQUENCE: 339
AAYHLVSQ                                                                  8

SEQ ID NO: 340          moltype = AA  length = 8
FEATURE                 Location/Qualifiers
REGION                  1..8
                        note = chemically synthesized
source                  1..8
                        mol_type = protein
                        organism = synthetic construct
SEQUENCE: 340
MDAFLESS                                                                  8

SEQ ID NO: 341          moltype = AA  length = 8
FEATURE                 Location/Qualifiers
REGION                  1..8
                        note = chemically synthesized
source                  1..8
```

```
                        mol_type = protein
                        organism = synthetic construct
SEQUENCE: 341
ESLPVVAV                                                8

SEQ ID NO: 342          moltype = AA  length = 8
FEATURE                 Location/Qualifiers
REGION                  1..8
                        note = chemically synthesized
source                  1..8
                        mol_type = protein
                        organism = synthetic construct
SEQUENCE: 342
SAPAVESE                                                8

SEQ ID NO: 343          moltype = AA  length = 8
FEATURE                 Location/Qualifiers
REGION                  1..8
                        note = chemically synthesized
source                  1..8
                        mol_type = protein
                        organism = synthetic construct
SEQUENCE: 343
DVAQFVLT                                                8

SEQ ID NO: 344          moltype = AA  length = 8
FEATURE                 Location/Qualifiers
REGION                  1..8
                        note = chemically synthesized
source                  1..8
                        mol_type = protein
                        organism = synthetic construct
SEQUENCE: 344
VAQFVLTE                                                8

SEQ ID NO: 345          moltype = AA  length = 8
FEATURE                 Location/Qualifiers
REGION                  1..8
                        note = chemically synthesized
source                  1..8
                        mol_type = protein
                        organism = synthetic construct
SEQUENCE: 345
AQFVLTEG                                                8

SEQ ID NO: 346          moltype = AA  length = 8
FEATURE                 Location/Qualifiers
REGION                  1..8
                        note = chemically synthesized
source                  1..8
                        mol_type = protein
                        organism = synthetic construct
SEQUENCE: 346
PVQPIGPQ                                                8

SEQ ID NO: 347          moltype = AA  length = 273
FEATURE                 Location/Qualifiers
REGION                  1..273
                        note = chemically synthesized
source                  1..273
                        mol_type = protein
                        organism = synthetic construct
SEQUENCE: 347
GGGSGGGGSG SGGGSGGGGS GGGEIVLTQS PGTLSLSPGE RATLSCRASQ SVSSSYLAWY  60
QQKPGQAPRL LIYGASSRAT GIPDRFSGSG SGTDFTLTIS RLEPEDFAVY YCQQYGSSPL  120
TFGGGTKVEI KRSGGSTITS YNVYYTKLSS SGTQVQLVQT GGGVVQPGRS LRLSCAASGS  180
TFSSYAMSWV RQAPGKGLEW VSAISGSGGS TYYADSVKGR FTISRDNSKN TLYLQMNSLR  240
AEDTAVYYCA TNSLYWYFDL WGRGTLVTVS SAS                             273

SEQ ID NO: 348          moltype =   length =
SEQUENCE: 348
000

SEQ ID NO: 349          moltype = AA  length = 264
FEATURE                 Location/Qualifiers
REGION                  1..264
                        note = chemically synthesized
source                  1..264
                        mol_type = protein
```

```
                       organism = synthetic construct
SEQUENCE: 349
GGGSGGGGSG SGGGSGGGGS GGGQVQLQQS GAELARPGAS VKMSCKASGY TFTRYTMHWV  60
KQRPGQGLEW IGYINPSRGY TNYNQKFKDK ATLTTDKSSS TAYMQLSSLT SEDSAVYYCA  120
RYYDDHYCLD YWGQGTTLTV SSGGGGSGGG GSGGGGSQIV LTQSPAIMSA SPGEKVTMTC  180
SASSSVSYMN WYQQKSGTSP KRWIYDTSKL ASGVPAHFRG SGSGTSYSLT ISGMEAEDAA  240
TYYCQQWSSN PFTFGSGTKL EINR                                         264

SEQ ID NO: 350         moltype = AA  length = 6
FEATURE                Location/Qualifiers
REGION                 1..6
                       note = chemically synthesized
source                 1..6
                       mol_type = protein
                       organism = synthetic construct
SEQUENCE: 350
GGSGGS                                                             6

SEQ ID NO: 351         moltype = AA  length = 8
FEATURE                Location/Qualifiers
REGION                 1..8
                       note = chemically synthesized
source                 1..8
                       mol_type = protein
                       organism = synthetic construct
SEQUENCE: 351
AQNLLGMV                                                           8

SEQ ID NO: 352         moltype = AA  length = 8
FEATURE                Location/Qualifiers
REGION                 1..8
                       note = chemically synthesized
source                 1..8
                       mol_type = protein
                       organism = synthetic construct
SEQUENCE: 352
STFPFGMF                                                           8

SEQ ID NO: 353         moltype = AA  length = 8
FEATURE                Location/Qualifiers
REGION                 1..8
                       note = chemically synthesized
source                 1..8
                       mol_type = protein
                       organism = synthetic construct
SEQUENCE: 353
PVGYTSSL                                                           8

SEQ ID NO: 354         moltype = AA  length = 8
FEATURE                Location/Qualifiers
REGION                 1..8
                       note = chemically synthesized
source                 1..8
                       mol_type = protein
                       organism = synthetic construct
SEQUENCE: 354
DWLYWPGI                                                           8

SEQ ID NO: 355         moltype = AA  length = 8
FEATURE                Location/Qualifiers
REGION                 1..8
                       note = chemically synthesized
source                 1..8
                       mol_type = protein
                       organism = synthetic construct
SEQUENCE: 355
MIAPVAYR                                                           8

SEQ ID NO: 356         moltype = AA  length = 8
FEATURE                Location/Qualifiers
REGION                 1..8
                       note = chemically synthesized
source                 1..8
                       mol_type = protein
                       organism = synthetic construct
SEQUENCE: 356
RPSPMWAY                                                           8

SEQ ID NO: 357         moltype = AA  length = 8
```

```
FEATURE                 Location/Qualifiers
REGION                  1..8
                        note = chemically synthesized
source                  1..8
                        mol_type = protein
                        organism = synthetic construct
SEQUENCE: 357
WATPRPMR                                                                  8

SEQ ID NO: 358          moltype = AA  length = 8
FEATURE                 Location/Qualifiers
REGION                  1..8
                        note = chemically synthesized
source                  1..8
                        mol_type = protein
                        organism = synthetic construct
SEQUENCE: 358
FRLLDWQW                                                                  8

SEQ ID NO: 359          moltype = AA  length = 8
FEATURE                 Location/Qualifiers
REGION                  1..8
                        note = chemically synthesized
source                  1..8
                        mol_type = protein
                        organism = synthetic construct
SEQUENCE: 359
LKAAPRWA                                                                  8

SEQ ID NO: 360          moltype = AA  length = 8
FEATURE                 Location/Qualifiers
REGION                  1..8
                        note = chemically synthesized
source                  1..8
                        mol_type = protein
                        organism = synthetic construct
SEQUENCE: 360
GPSHLVLT                                                                  8

SEQ ID NO: 361          moltype = AA  length = 8
FEATURE                 Location/Qualifiers
REGION                  1..8
                        note = chemically synthesized
source                  1..8
                        mol_type = protein
                        organism = synthetic construct
SEQUENCE: 361
LPGGLSPW                                                                  8

SEQ ID NO: 362          moltype = AA  length = 8
FEATURE                 Location/Qualifiers
REGION                  1..8
                        note = chemically synthesized
source                  1..8
                        mol_type = protein
                        organism = synthetic construct
SEQUENCE: 362
MGLFSEAG                                                                  8

SEQ ID NO: 363          moltype = AA  length = 8
FEATURE                 Location/Qualifiers
REGION                  1..8
                        note = chemically synthesized
source                  1..8
                        mol_type = protein
                        organism = synthetic construct
SEQUENCE: 363
SPLPLRVP                                                                  8

SEQ ID NO: 364          moltype = AA  length = 8
FEATURE                 Location/Qualifiers
REGION                  1..8
                        note = chemically synthesized
source                  1..8
                        mol_type = protein
                        organism = synthetic construct
SEQUENCE: 364
RMHLRSLG                                                                  8
```

```
SEQ ID NO: 365          moltype = AA  length = 8
FEATURE                 Location/Qualifiers
REGION                  1..8
                        note = chemically synthesized
source                  1..8
                        mol_type = protein
                        organism = synthetic construct
SEQUENCE: 365
LAAPLGLL                                                                  8

SEQ ID NO: 366          moltype = AA  length = 8
FEATURE                 Location/Qualifiers
REGION                  1..8
                        note = chemically synthesized
source                  1..8
                        mol_type = protein
                        organism = synthetic construct
SEQUENCE: 366
AVGLLAPP                                                                  8

SEQ ID NO: 367          moltype = AA  length = 8
FEATURE                 Location/Qualifiers
REGION                  1..8
                        note = chemically synthesized
source                  1..8
                        mol_type = protein
                        organism = synthetic construct
SEQUENCE: 367
LLAPSHRA                                                                  8

SEQ ID NO: 368          moltype = AA  length = 8
FEATURE                 Location/Qualifiers
REGION                  1..8
                        note = chemically synthesized
source                  1..8
                        mol_type = protein
                        organism = synthetic construct
SEQUENCE: 368
PAGLWLDP                                                                  8

SEQ ID NO: 369          moltype = AA  length = 7
FEATURE                 Location/Qualifiers
REGION                  1..7
                        note = chemically synthesized
source                  1..7
                        mol_type = protein
                        organism = synthetic construct
SEQUENCE: 369
ISSGLSS                                                                   7

SEQ ID NO: 370          moltype = AA  length = 8
FEATURE                 Location/Qualifiers
REGION                  1..8
                        note = chemically synthesized
source                  1..8
                        mol_type = protein
                        organism = synthetic construct
SEQUENCE: 370
TGRGPSWV                                                                  8

SEQ ID NO: 371          moltype = AA  length = 8
FEATURE                 Location/Qualifiers
REGION                  1..8
                        note = chemically synthesized
source                  1..8
                        mol_type = protein
                        organism = synthetic construct
SEQUENCE: 371
SARGPSRW                                                                  8

SEQ ID NO: 372          moltype = AA  length = 8
FEATURE                 Location/Qualifiers
REGION                  1..8
                        note = chemically synthesized
source                  1..8
                        mol_type = protein
                        organism = synthetic construct
SEQUENCE: 372
TARGPSFK                                                                  8
```

```
SEQ ID NO: 373          moltype = AA  length = 8
FEATURE                 Location/Qualifiers
REGION                  1..8
                        note = chemically synthesized
source                  1..8
                        mol_type = protein
                        organism = synthetic construct
SEQUENCE: 373
GGWHTGRN                                                            8

SEQ ID NO: 374          moltype = AA  length = 8
FEATURE                 Location/Qualifiers
REGION                  1..8
                        note = chemically synthesized
source                  1..8
                        mol_type = protein
                        organism = synthetic construct
SEQUENCE: 374
HTGRSGAL                                                            8

SEQ ID NO: 375          moltype = AA  length = 8
FEATURE                 Location/Qualifiers
REGION                  1..8
                        note = chemically synthesized
source                  1..8
                        mol_type = protein
                        organism = synthetic construct
SEQUENCE: 375
PLTGRSGG                                                            8

SEQ ID NO: 376          moltype = AA  length = 8
FEATURE                 Location/Qualifiers
REGION                  1..8
                        note = chemically synthesized
source                  1..8
                        mol_type = protein
                        organism = synthetic construct
SEQUENCE: 376
AARGPAIH                                                            8

SEQ ID NO: 377          moltype = AA  length = 8
FEATURE                 Location/Qualifiers
REGION                  1..8
                        note = chemically synthesized
source                  1..8
                        mol_type = protein
                        organism = synthetic construct
SEQUENCE: 377
RGPAFNPM                                                            8

SEQ ID NO: 378          moltype = AA  length = 8
FEATURE                 Location/Qualifiers
REGION                  1..8
                        note = chemically synthesized
source                  1..8
                        mol_type = protein
                        organism = synthetic construct
SEQUENCE: 378
SSRGPAYL                                                            8

SEQ ID NO: 379          moltype = AA  length = 8
FEATURE                 Location/Qualifiers
REGION                  1..8
                        note = chemically synthesized
source                  1..8
                        mol_type = protein
                        organism = synthetic construct
SEQUENCE: 379
RGPATPIM                                                            8

SEQ ID NO: 380          moltype = AA  length = 4
FEATURE                 Location/Qualifiers
REGION                  1..4
                        note = chemically synthesized
source                  1..4
                        mol_type = protein
                        organism = synthetic construct
SEQUENCE: 380
```

```
RGPA                                                        4

SEQ ID NO: 381          moltype = AA  length = 5
FEATURE                 Location/Qualifiers
REGION                  1..5
                        note = chemically synthesized
source                  1..5
                        mol_type = protein
                        organism = synthetic construct
SEQUENCE: 381
GSGGS                                                       5

SEQ ID NO: 382          moltype = AA  length = 4
FEATURE                 Location/Qualifiers
REGION                  1..4
                        note = chemically synthesized
source                  1..4
                        mol_type = protein
                        organism = synthetic construct
SEQUENCE: 382
GGGS                                                        4

SEQ ID NO: 383          moltype = AA  length = 4
FEATURE                 Location/Qualifiers
REGION                  1..4
                        note = chemically synthesized
source                  1..4
                        mol_type = protein
                        organism = synthetic construct
SEQUENCE: 383
GGSG                                                        4

SEQ ID NO: 384          moltype = AA  length = 5
FEATURE                 Location/Qualifiers
REGION                  1..5
                        note = chemically synthesized
source                  1..5
                        mol_type = protein
                        organism = synthetic construct
SEQUENCE: 384
GGSGG                                                       5

SEQ ID NO: 385          moltype = AA  length = 5
FEATURE                 Location/Qualifiers
REGION                  1..5
                        note = chemically synthesized
source                  1..5
                        mol_type = protein
                        organism = synthetic construct
SEQUENCE: 385
GSGSG                                                       5

SEQ ID NO: 386          moltype = AA  length = 5
FEATURE                 Location/Qualifiers
REGION                  1..5
                        note = chemically synthesized
source                  1..5
                        mol_type = protein
                        organism = synthetic construct
SEQUENCE: 386
GSGGG                                                       5

SEQ ID NO: 387          moltype = AA  length = 5
FEATURE                 Location/Qualifiers
REGION                  1..5
                        note = chemically synthesized
source                  1..5
                        mol_type = protein
                        organism = synthetic construct
SEQUENCE: 387
GGGSG                                                       5

SEQ ID NO: 388          moltype = AA  length = 5
FEATURE                 Location/Qualifiers
REGION                  1..5
                        note = chemically synthesized
source                  1..5
                        mol_type = protein
                        organism = synthetic construct
```

```
SEQUENCE: 388
GSSSG                                                               5

SEQ ID NO: 389          moltype = AA  length = 13
FEATURE                 Location/Qualifiers
REGION                  1..13
                        note = chemically synthesized
source                  1..13
                        mol_type = protein
                        organism = synthetic construct
SEQUENCE: 389
GSSGGSGGSG GSG                                                      13

SEQ ID NO: 390          moltype = AA  length = 11
FEATURE                 Location/Qualifiers
REGION                  1..11
                        note = chemically synthesized
source                  1..11
                        mol_type = protein
                        organism = synthetic construct
SEQUENCE: 390
GSSGGSGGSG G                                                        11

SEQ ID NO: 391          moltype = AA  length = 12
FEATURE                 Location/Qualifiers
REGION                  1..12
                        note = chemically synthesized
source                  1..12
                        mol_type = protein
                        organism = synthetic construct
SEQUENCE: 391
GSSGGSGGSG GS                                                       12

SEQ ID NO: 392          moltype = AA  length = 16
FEATURE                 Location/Qualifiers
REGION                  1..16
                        note = chemically synthesized
source                  1..16
                        mol_type = protein
                        organism = synthetic construct
SEQUENCE: 392
GSSGGSGGSG GSGGGS                                                   16

SEQ ID NO: 393          moltype = AA  length = 10
FEATURE                 Location/Qualifiers
REGION                  1..10
                        note = chemically synthesized
source                  1..10
                        mol_type = protein
                        organism = synthetic construct
SEQUENCE: 393
GSSGGSGGSG                                                          10

SEQ ID NO: 394          moltype = AA  length = 11
FEATURE                 Location/Qualifiers
REGION                  1..11
                        note = chemically synthesized
source                  1..11
                        mol_type = protein
                        organism = synthetic construct
SEQUENCE: 394
GSSGGSGGSG S                                                        11

SEQ ID NO: 395          moltype = AA  length = 4
FEATURE                 Location/Qualifiers
REGION                  1..4
                        note = chemically synthesized
source                  1..4
                        mol_type = protein
                        organism = synthetic construct
SEQUENCE: 395
GGGS                                                                4

SEQ ID NO: 396          moltype = AA  length = 5
FEATURE                 Location/Qualifiers
REGION                  1..5
                        note = chemically synthesized
source                  1..5
                        mol_type = protein
```

```
                         organism = synthetic construct
SEQUENCE: 396
GSSGT                                                                    5

SEQ ID NO: 397           moltype = AA  length = 4
FEATURE                  Location/Qualifiers
REGION                   1..4
                         note = chemically synthesized
source                   1..4
                         mol_type = protein
                         organism = synthetic construct
SEQUENCE: 397
GSSG                                                                     4

SEQ ID NO: 398           moltype = AA  length = 5
FEATURE                  Location/Qualifiers
REGION                   1..5
                         note = chemically synthesized
source                   1..5
                         mol_type = protein
                         organism = synthetic construct
SEQUENCE: 398
SYAMS                                                                    5

SEQ ID NO: 399           moltype = AA  length = 17
FEATURE                  Location/Qualifiers
REGION                   1..17
                         note = chemically synthesized
source                   1..17
                         mol_type = protein
                         organism = synthetic construct
SEQUENCE: 399
SIDPEGRQTY YADSVKG                                                       17

SEQ ID NO: 400           moltype = AA  length = 10
FEATURE                  Location/Qualifiers
REGION                   1..10
                         note = chemically synthesized
source                   1..10
                         mol_type = protein
                         organism = synthetic construct
SEQUENCE: 400
DIGGRSAFDY                                                               10

SEQ ID NO: 401           moltype = AA  length = 9
FEATURE                  Location/Qualifiers
REGION                   1..9
                         note = chemically synthesized
source                   1..9
                         mol_type = protein
                         organism = synthetic construct
SEQUENCE: 401
RASQSISSY                                                                9

SEQ ID NO: 402           moltype = AA  length = 7
FEATURE                  Location/Qualifiers
REGION                   1..7
                         note = chemically synthesized
source                   1..7
                         mol_type = protein
                         organism = synthetic construct
SEQUENCE: 402
AASSLQS                                                                  7

SEQ ID NO: 403           moltype = AA  length = 9
FEATURE                  Location/Qualifiers
REGION                   1..9
                         note = chemically synthesized
source                   1..9
                         mol_type = protein
                         organism = synthetic construct
SEQUENCE: 403
QQTVVAPPL                                                                9

SEQ ID NO: 404           moltype = AA  length = 5
FEATURE                  Location/Qualifiers
REGION                   1..5
                         note = chemically synthesized
source                   1..5
```

```
                        mol_type = protein
                        organism = synthetic construct
SEQUENCE: 404
NYGVH                                                          5

SEQ ID NO: 405          moltype = AA  length = 16
FEATURE                 Location/Qualifiers
REGION                  1..16
                        note = chemically synthesized
source                  1..16
                        mol_type = protein
                        organism = synthetic construct
SEQUENCE: 405
VIWSGGNTDY NTPFTS                                              16

SEQ ID NO: 406          moltype = AA  length = 11
FEATURE                 Location/Qualifiers
REGION                  1..11
                        note = chemically synthesized
source                  1..11
                        mol_type = protein
                        organism = synthetic construct
SEQUENCE: 406
ALTYYDYEFA Y                                                   11

SEQ ID NO: 407          moltype = AA  length = 11
FEATURE                 Location/Qualifiers
REGION                  1..11
                        note = chemically synthesized
source                  1..11
                        mol_type = protein
                        organism = synthetic construct
SEQUENCE: 407
RASQSIGTNI H                                                   11

SEQ ID NO: 408          moltype = AA  length = 8
FEATURE                 Location/Qualifiers
REGION                  1..8
                        note = chemically synthesized
source                  1..8
                        mol_type = protein
                        organism = synthetic construct
SEQUENCE: 408
KYASESIS                                                       8

SEQ ID NO: 409          moltype = AA  length = 9
FEATURE                 Location/Qualifiers
REGION                  1..9
                        note = chemically synthesized
source                  1..9
                        mol_type = protein
                        organism = synthetic construct
SEQUENCE: 409
QQNNNWPTT                                                      9

SEQ ID NO: 410          moltype = AA  length = 6
FEATURE                 Location/Qualifiers
REGION                  1..6
                        note = chemically synthesized
source                  1..6
                        mol_type = protein
                        organism = synthetic construct
SEQUENCE: 410
QGQSGQ                                                         6

SEQ ID NO: 411          moltype = AA  length = 10
FEATURE                 Location/Qualifiers
REGION                  1..10
                        note = chemically synthesized
source                  1..10
                        mol_type = protein
                        organism = synthetic construct
SEQUENCE: 411
VHMPLGFLGP                                                     10

SEQ ID NO: 412          moltype = AA  length = 8
FEATURE                 Location/Qualifiers
REGION                  1..8
                        note = chemically synthesized
```

```
source                  1..8
                        mol_type = protein
                        organism = synthetic construct
SEQUENCE: 412
LSGRSGNH                                                                    8

SEQ ID NO: 413          moltype = AA  length = 12
FEATURE                 Location/Qualifiers
REGION                  1..12
                        note = chemically synthesized
source                  1..12
                        mol_type = protein
                        organism = synthetic construct
SEQUENCE: 413
TSTSGRSANP RG                                                               12

SEQ ID NO: 414          moltype = AA  length = 8
FEATURE                 Location/Qualifiers
REGION                  1..8
                        note = chemically synthesized
source                  1..8
                        mol_type = protein
                        organism = synthetic construct
SEQUENCE: 414
TSGRSANP                                                                    8

SEQ ID NO: 415          moltype = AA  length = 8
FEATURE                 Location/Qualifiers
REGION                  1..8
                        note = chemically synthesized
source                  1..8
                        mol_type = protein
                        organism = synthetic construct
SEQUENCE: 415
VAGRSMRP                                                                    8

SEQ ID NO: 416          moltype = AA  length = 5
FEATURE                 Location/Qualifiers
REGION                  1..5
                        note = chemically synthesized
source                  1..5
                        mol_type = protein
                        organism = synthetic construct
SEQUENCE: 416
GQSGQ                                                                       5

SEQ ID NO: 417          moltype = AA  length = 4
FEATURE                 Location/Qualifiers
REGION                  1..4
                        note = chemically synthesized
source                  1..4
                        mol_type = protein
                        organism = synthetic construct
SEQUENCE: 417
QSGQ                                                                        4

SEQ ID NO: 418          moltype =   length =
SEQUENCE: 418
000

SEQ ID NO: 419          moltype = DNA  length = 756
FEATURE                 Location/Qualifiers
misc_feature            1..756
                        note = chemically synthesized
source                  1..756
                        mol_type = other DNA
                        organism = synthetic construct
SEQUENCE: 419
tgcaatattt ggctcgtagg tggtgattgc aggggctggc agggggggctc gagcggcggc  60
tctatctctt ccggactgct gtcggcaga tccgacaatc acggcggagg ctctgacatc  120
cagatgaccc agtctccatc ctccctgtct gcatctgtag gagacagagt caccatcact  180
tgccgggcaa gtcagagcat tagcagctat ttaaattggt atcagcagaa accagggaaa  240
gcccctaagc tcctgatcta tgcggcatcc agtttgcaaa gtggggtccc atcaaggttc  300
agtggcagtg gatctgggac agatttcact ctcaccatca gcagtctgca acctgaagat  360
tttgcaactt actactgtca acagacggtt gtggcgcctc cgttattcgg ccaagggacc  420
aaggtggaaa tcaaacgtac ggtggctgca ccatctgtct tcatcttccc gccatctgat  480
gagcagttga aatctggaac tgcctctgtt gtgtgcctgc tgaataactt ctatcccaga  540
gaggccaaag tacagtggaa ggtggataac gccctccaat cgggtaactc ccaggagagt  600
gtcacagagc aggacagcaa ggacagcacc tacagcctca gcagcaccct gacgctgagc  660
```

```
aaagcagact acgagaaaca caaagtctac gcctgcgaag tcacccatca gggcctgagc  720
tcgcccgtca caaagagctt caacagggga gagtgt                            756

SEQ ID NO: 420         moltype = AA  length = 252
FEATURE                Location/Qualifiers
REGION                 1..252
                       note = chemically synthesized
source                 1..252
                       mol_type = protein
                       organism = synthetic construct
SEQUENCE: 420
CNIWLVGGDC RGWQGGSSGG SISSGLLSGR SDNHGGGSDI QMTQSPSSLS ASVGDRVTIT  60
CRASQSISSY LNWYQQKPGK APKLLIYAAS SLQSGVPSRF SGSGSGTDFT LTISSLQPED  120
FATYYCQQTV VAPPLFGQGT KVEIKRTVAA PSVFIFPPSD EQLKSGTASV VCLLNNFYPR  180
EAKVQWKVDN ALQSGNSQES VTEQDSKDST YSLSSTLTLS KADYEKHKVY ACEVTHQGLS  240
SPVTKSFNRG EC                                                      252

SEQ ID NO: 421         moltype = DNA  length = 783
FEATURE                Location/Qualifiers
misc_feature           1..783
                       note = chemically synthesized
source                 1..783
                       mol_type = other DNA
                       organism = synthetic construct
SEQUENCE: 421
tgcaatattt ggctcgtagg tggtgattgc aggggctggc agggggggctc gagcggcggc  60
tctatctctt ctggcctgct gtctagcggc ggctccggcg gatctctgtc tggcagatct  120
gacaaccacg gcggaggctc cgacatccag atgacccagt ctccatcctc cctgtctgca  180
tctgtaggag acagagtcac catcacttgc cgggcaagtc agagcattag cagctattta  240
aattggtatc agcagaaacc agggaaagcc cctaagctcc tgatctatgc ggcatccagt  300
ttgcaaagtg gggtcccatc aaggttcagt ggcagtggat ctgggacaga tttcactctc  360
accatcagca gtctgcaacc tgaagatttt gcaacttact actgtcaaca gacggttgtg  420
gcgcctccgt tattcggcca agggaccaag gtggaaatca aacgtacggt ggctgcacca  480
tctgtcttca tcttcccgcc atctgatgag cagttgaaat ctggaactgc ctctgttgtg  540
tgcctgctga ataacttcta tcccagagag gccaaagtac agtggaaggt ggataacgcc  600
ctccaatcgg gtaactccca ggagagtgtc acagagcagg acagcaagga cagcacctac  660
agcctcagca gcaccctgac gctgagcaaa gcagactacg agaaacacaa agtctacgcc  720
tgcgaagtca cccatcaggg cctgagctcg cccgtcacaa agagcttcaa caggggagag  780
tgt                                                                783

SEQ ID NO: 422         moltype = AA  length = 261
FEATURE                Location/Qualifiers
REGION                 1..261
                       note = chemically synthesized
source                 1..261
                       mol_type = protein
                       organism = synthetic construct
SEQUENCE: 422
CNIWLVGGDC RGWQGGSSGG SISSGLLSSG GSGGSLSGRS DNHGGGSDIQ MTQSPSSLSA  60
SVGDRVTITC RASQSISSYL NWYQQKPGKA PKLLIYAASS LQSGVPSRFS GSGSGTDFTL  120
TISSLQPEDF ATYYCQQTVV APPLFGQGTK VEIKRTVAAP SVFIFPPSDE QLKSGTASVV  180
CLLNNFYPRE AKVQWKVDNA LQSGNSQESV TEQDSKDSTY SLSSTLTLSK ADYEKHKVYA  240
CEVTHQGLSS PVTKSFNRGE C                                            261

SEQ ID NO: 423         moltype = DNA  length = 780
FEATURE                Location/Qualifiers
misc_feature           1..780
                       note = chemically synthesized
source                 1..780
                       mol_type = other DNA
                       organism = synthetic construct
SEQUENCE: 423
tgcaatattt ggctcgtagg tggtgattgc aggggctggc agggggggctc gagcggagga  60
tctgctgtgg gactgctggc tcctcctggc ggcacatcta cctctggcag atccgccaac  120
cctcggggcg gaggatctga catccagatg acccagtctc catcctccct gtctgcatct  180
gtaggagaca gagtcaccat cacttgccgg gcaagtcaga gcattagcag ctatttaaat  240
tggtatcagc agaaaccagg gaaagcccct aagctcctga tctatgcggc atccagtttg  300
caaagtgggg tcccatcaag gttcagtggc agtggatctg ggacagattt cactctcacc  360
atcagcagtc tgcaacctga agattttgca acttactact gtcaacagac ggttgtggcg  420
cctccgttat tcggccaagg gaccaaggtg gaaatcaaac gtacggtggc tgcaccatct  480
gtcttcatct tcccgccatc tgatgagcag ttgaaatctg gaactgcctc tgttgtgtgc  540
ctgctgaata acttctatcc cagagaggcc aaagtacagt ggaaggtgga taacgccctc  600
caatcgggta actcccagga gagtgtcaca gagcaggaca gcaaggacag cacctacagc  660
ctcagcagca ccctgacgct gagcaaagca gactacgaga aacacaaagt ctacgcctgc  720
gaagtcaccc atcagggcct gagctcgccc gtcacaaaga gcttcaacag gggagagtgt  780

SEQ ID NO: 424         moltype = AA  length = 260
FEATURE                Location/Qualifiers
REGION                 1..260
```

```
                         note = chemically synthesized
source                   1..260
                         mol_type = protein
                         organism = synthetic construct
SEQUENCE: 424
CNIWLVGGDC RGWQGGSSGG SAVGLLAPPG GTSTSGRSAN PRGGGSDIQM TQSPSSLSAS  60
VGDRVTITCR ASQSISSYLN WYQQKPGKAP KLLIYAASSL QSGVPSRFSG SGSGTDFTLT  120
ISSLQPEDFA TYYCQQTVVA PPLFGQGTKV EIKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260

SEQ ID NO: 425           moltype = DNA  length = 780
FEATURE                  Location/Qualifiers
misc_feature             1..780
                         note = chemically synthesized
source                   1..780
                         mol_type = other DNA
                         organism = synthetic construct
SEQUENCE: 425
tgcaatattt ggctcgtagg tggtgattgc aggggctggc agggggctc gagcggcggc  60
tccacatcta cctctggcag atccgccaac cccagaggtg gcggagctgt gggactgctg  120
gctccaccag gcggatctga catccagatg acccagtctc catcctccct gtctgcatct  180
gtaggagaca gagtcaccat cacttgccgg gcaagtcaga gcattagcag ctatttaaat  240
tggtatcagc agaaaccagg gaaagcccct aagctcctga tctatgcggc atccagtttg  300
caaagtgggg tcccatcaag gttcagtggc agtggatctg ggacagattt cactctcacc  360
atcagcagtc tgcaacctga agattttgca acttactact gtcaacagac ggttgtggcg  420
cctccgttat tcggccaagg gaccaaggtg gaaatcaaac gtacggtggc tgcaccatct  480
gtcttcatct tcccgccatc tgatgagcag ttgaaatctg gaactgcctc tgttgtgtgc  540
ctgctgaata acttctatcc cagagaggcc aaagtacagt ggaaggtgga taacgccctc  600
caatcgggta actcccagga gagtgtcaca gagcaggaca gcaaggacag cacctacagc  660
ctcagcagca ccctgacgct gagcaaagca gactacgaga aacacaaagt ctacgcctgc  720
gaagtcaccc atcagggcct gagctcgccc gtcacaaaga gcttcaacag gggagagtgt  780

SEQ ID NO: 426           moltype = AA  length = 260
FEATURE                  Location/Qualifiers
REGION                   1..260
                         note = chemically synthesized
source                   1..260
                         mol_type = protein
                         organism = synthetic construct
SEQUENCE: 426
CNIWLVGGDC RGWQGGSSGG STSTSGRSAN PRGGGAVGLL APPGGSDIQM TQSPSSLSAS  60
VGDRVTITCR ASQSISSYLN WYQQKPGKAP KLLIYAASSL QSGVPSRFSG SGSGTDFTLT  120
ISSLQPEDFA TYYCQQTVVA PPLFGQGTKV EIKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260

SEQ ID NO: 427           moltype = DNA  length = 786
FEATURE                  Location/Qualifiers
misc_feature             1..786
                         note = chemically synthesized
source                   1..786
                         mol_type = other DNA
                         organism = synthetic construct
SEQUENCE: 427
tgcaatattt ggctcgtagg tggtgattgc aggggctggc agggggctc gagcggcggc  60
tctgtgcata tgcccctggg ctttctgggc cctggcggca catctacctc tggcagatcc  120
gccaaccctc ggggcggagg atctgacatc cagatgaccc agtctccatc ctccctgtct  180
gcatctgtag gagacagagt caccatcact tgccgggcaa gtcagagcat tagcagctat  240
ttaaattggt atcagcagaa accagggaaa gcccctaagc tcctgatcta tgcggcatcc  300
agtttgcaaa gtggggtccc atcaaggttc agtggcagtg gatctgggac agatttcact  360
ctcaccatca gcagtctgca acctgaagat tttgcaactt actactgtca acagacggtt  420
gtggcgcctc cgttattcgg ccaagggacc aaggtggaaa tcaaacgtac ggtggctgca  480
ccatctgtct tcatcttccc gccatctgat gagcagttga aatctggaac tgcctctgtt  540
gtgtgcctgc tgaataactt ctatcccaga gaggccaaag tacagtggaa ggtggataac  600
gccctccaat cgggtaactc ccaggagagt gtcacagagc aggacagcaa ggacagcacc  660
tacagcctca gcagcaccct gacgctgagc aaagcagact acgagaaaca caaagtctac  720
gcctgcgaag tcacccatca gggcctgagc tcgcccgtca caaagagctt caacagggga  780
gagtgt                                                             786

SEQ ID NO: 428           moltype = AA  length = 262
FEATURE                  Location/Qualifiers
REGION                   1..262
                         note = chemically synthesized
source                   1..262
                         mol_type = protein
                         organism = synthetic construct
SEQUENCE: 428
CNIWLVGGDC RGWQGGSSGG SVHMPLGFLG PGGTSTSGRS ANPRGGGSDI QMTQSPSSLS  60
```

```
ASVGDRVTIT CRASQSISSY LNWYQQKPGK APKLLIYAAS SLQSGVPSRF SGSGSGTDFT  120
LTISSLQPED FATYYCQQTV VAPPLFGQGT KVEIKRTVAA PSVFIFPPSD EQLKSGTASV  180
VCLLNNFYPR EAKVQWKVDN ALQSGNSQES VTEQDSKDST YSLSSTLTLS KADYEKHKVY  240
ACEVTHQGLS SPVTKSFNRG EC                                           262

SEQ ID NO: 429         moltype = DNA  length = 786
FEATURE                Location/Qualifiers
misc_feature           1..786
                       note = chemically synthesized
source                 1..786
                       mol_type = other DNA
                       organism = synthetic construct
SEQUENCE: 429
tgcaatattt ggctcgtagg tggtgattgc aggggctggc agggggggctc gagcggcggc  60
tccacatcta cctctggcag atccgccaac cccagaggcg gcggagtgca tatgcctctg  120
ggctttctgg gacctggcgg ctctgacatc cagatgaccc agtctccatc ctccctgtct  180
gcatctgtag gagacagagt caccatcact tgccgggcaa gtcagagcat tagcagctat  240
ttaaattggt atcagcagaa accagggaaa gcccctaagc tcctgatcta tgcggcatcc  300
agtttgcaaa gtggggtccc atcaaggttc agtggcagtg gatctgggac agatttcact  360
ctcaccatca gcagtctgca acctgaagat tttgcaactt actactgtca acagacggtt  420
gtggcgcctc cgttattcgg ccaagggacc aaggtggaaa tcaaacgtac ggtggctgca  480
ccatctgtct tcatcttccc gccatctgat gagcagttga aatctggaac tgcctctgtt  540
gtgtgcctgc tgaataactt ctatcccaga gaggccaaag tacagtggaa ggtggataac  600
gccctccaat cgggtaactc ccaggagagt gtcacagagc aggacagcaa ggacagcacc  660
tacagcctca gcagcaccct gacgctgagc aaagcagact acgagaaaca caaagtctac  720
gcctgcgaag tcacccatca gggcctgagc tcgcccgtca caaagagctt caacagggga  780
gagtgt                                                             786

SEQ ID NO: 430         moltype = AA  length = 262
FEATURE                Location/Qualifiers
REGION                 1..262
                       note = chemically synthesized
source                 1..262
                       mol_type = protein
                       organism = synthetic construct
SEQUENCE: 430
CNIWLVGGDC RGWQGGSSGG STSTSGRSAN PRGGGVHMPL GFLGPGGSDI QMTQSPSSLS  60
ASVGDRVTIT CRASQSISSY LNWYQQKPGK APKLLIYAAS SLQSGVPSRF SGSGSGTDFT  120
LTISSLQPED FATYYCQQTV VAPPLFGQGT KVEIKRTVAA PSVFIFPPSD EQLKSGTASV  180
VCLLNNFYPR EAKVQWKVDN ALQSGNSQES VTEQDSKDST YSLSSTLTLS KADYEKHKVY  240
ACEVTHQGLS SPVTKSFNRG EC                                           262

SEQ ID NO: 431         moltype = DNA  length = 768
FEATURE                Location/Qualifiers
misc_feature           1..768
                       note = chemically synthesized
source                 1..768
                       mol_type = other DNA
                       organism = synthetic construct
SEQUENCE: 431
tgcaatattt ggctcgtagg tggtgattgc aggggctggc agggggggctc gagcggagga  60
tctgctgtgg gactgctggc tcctcctggt ggcctgtctg gcagatctga taaccacggc  120
ggctccgaca tccagatgac ccagtctcca tcctccctgt ctgcatctgt aggagacaga  180
gtcaccatca cttgccgggc aagtcagagc attagcagct atttaaattg gtatcagcag  240
aaaccaggga aagcccctaa gctcctgatc tatgcggcat ccagtttgca aagtggggtc  300
ccatcaaggt tcagtggcag tggatctggg acagatttca ctctcaccat cagcagtctg  360
caacctgaag attttgcaac ttactactgt caacagacgg ttgtggcgcc tccgttattc  420
ggccaaggga ccaaggtgga aatcaaacgt acggtggctg caccatctgt cttcatcttc  480
ccgccatctg atgagcagtt gaaatctgga actgcctctg ttgtgtgcct gctgaataac  540
ttctatccca gagaggccaa agtacagtgg aaggtggata acgccctcca atcgggtaac  600
tcccaggaga gtgtcacaga gcaggacagc aaggacagca cctacagcct cagcagcacc  660
ctgacgctga gcaaagcaga ctacgagaaa cacaaagtct acgcctgcga agtcacccat  720
cagggcctga gctcgcccgt cacaaagagc ttcaacaggg gagagtgt               768

SEQ ID NO: 432         moltype = AA  length = 256
FEATURE                Location/Qualifiers
REGION                 1..256
                       note = chemically synthesized
source                 1..256
                       mol_type = protein
                       organism = synthetic construct
SEQUENCE: 432
CNIWLVGGDC RGWQGGSSGG SAVGLLAPPG GLSGRSDNHG GSDIQMTQSP SSLSASVGDR  60
VTITCRASQS ISSYLNWYQQ KPGKAPKLLI YAASSLQSGV PSRFSGSGSG TDFTLTISSL  120
QPEDFATYYC QQTVVAPPLF GQGTKVEIKR TVAAPSVFIF PPSDEQLKSG TASVVCLLNN  180
FYPREAKVQW KVDNALQSGN SQESVTEQDS KDSTYSLSST LTLSKADYEK HKVYACEVTH  240
QGLSSPVTKS FNRGEC                                                  256

SEQ ID NO: 433         moltype = DNA  length = 771
```

-continued

```
FEATURE                Location/Qualifiers
misc_feature           1..771
                       note = chemically synthesized
source                 1..771
                       mol_type = other DNA
                       organism = synthetic construct
SEQUENCE: 433
tgcaatattt ggctcgtagg tggtgattgc aggggctggc agggggggctc gagcggaggc  60
tctggcctgt ctggcagatc cgataaccat ggcggcgctg tgggactgct ggctcctcct  120
ggtggatctg acatccagat gacccagtct ccatcctccc tgtctgcatc tgtaggagac  180
agagtcacca tcacttgccg ggcaagtcag agcattagca gctatttaaa ttggtatcag  240
cagaaaccag ggaaagcccc taagctcctg atctatgcgg catccagttt gcaaagtggg  300
gtcccatcaa ggttcagtgg cagtggatct gggacagatt tcactctcac catcagcagt  360
ctgcaacctg aagattttgc aacttactac tgtcaacaga cggttgtggc gcctccgtta  420
ttcggccaag ggaccaaggt ggaaatcaaa cgtacggtgg ctgcaccatc tgtcttcatc  480
ttcccgccat ctgatgagca gttgaaatct ggaactgcct ctgttgtgtg cctgctgaat  540
aacttctatc ccagagaggc caaagtacag tggaaggtgg ataacgccct ccaatcgggt  600
aactcccagg agagtgtcac agagcaggac agcaaggaca gcacctacag cctcagcagc  660
accctgacgc tgagcaaagc agactacgag aaacacaaag tctacgcctg cgaagtcacc  720
catcagggcc tgagctcgcc cgtcacaaag agcttcaaca ggggagagtg t           771

SEQ ID NO: 434         moltype = AA  length = 257
FEATURE                Location/Qualifiers
REGION                 1..257
                       note = chemically synthesized
source                 1..257
                       mol_type = protein
                       organism = synthetic construct
SEQUENCE: 434
CNIWLVGGDC RGWQGGSSGG SGLSGRSDNH GGAVGLLAPP GGSDIQMTQS PSSLSASVGD  60
RVTITCRASQ SISSYLNWYQ QKPGKAPKLL IYAASSLQSG VPSRFSGSGS GTDFTLTISS  120
LQPEDFATYY CQQTVVAPPL FGQGTKVEIK RTVAAPSVFI FPPSDEQLKS GTASVVCLLN  180
NFYPREAKVQ WKVDNALQSG NSQESVTEQD SKDSTYSLSS TLTLSKADYE KHKVYACEVT  240
HQGLSSPVTK SFNRGEC                                                 257

SEQ ID NO: 435         moltype = DNA  length = 774
FEATURE                Location/Qualifiers
misc_feature           1..774
                       note = chemically synthesized
source                 1..774
                       mol_type = other DNA
                       organism = synthetic construct
SEQUENCE: 435
tgcaatattt ggctcgtagg tggtgattgc aggggctggc agggggggctc gagcggcggc  60
tctgtgcata tgcccctggg ctttctggga cctggcggcc tgtctggcag atccgataat  120
cacggcggct ccgacatcca gatgacccag tctccatcct ccctgtctgc atctgtagga  180
gacagagtca ccatcacttg ccgggcaagt cagagcatta gcagctattt aaattggtat  240
cagcagaaac cagggaaagc ccctaagctc ctgatctatg cggcatccag tttgcaaagt  300
ggggtcccat caaggttcag tggcagtgga tctgggacag atttcactct caccatcagc  360
agtctgcaac ctgaagattt tgcaacttac tactgtcaac agacggttgt ggcgcctccg  420
ttattcggcc aagggaccaa ggtggaaatc aaacgtacgg tggctgcacc atctgtcttc  480
atcttcccgc catctgatga gcagttgaaa tctggaactg cctctgttgt gtgcctgctg  540
aataacttct atcccagaga ggccaaagta cagtggaagg tggataacgc cctccaatcg  600
ggtaactccc aggagagtgt cacagagcag gacagcaagg acagcaccta cagcctcagc  660
agcaccctga cgctgagcaa agcagactac gagaaacaca aagtctacgc ctgcgaagtc  720
acccatcagg gcctgagctc gcccgtcaca aagagcttca acaggggaga gtgt        774

SEQ ID NO: 436         moltype = AA  length = 258
FEATURE                Location/Qualifiers
REGION                 1..258
                       note = chemically synthesized
source                 1..258
                       mol_type = protein
                       organism = synthetic construct
SEQUENCE: 436
CNIWLVGGDC RGWQGGSSGG SVHMPLGFLG PGGLSGRSDN HGGSDIQMTQ SPSSLSASVG  60
DRVTITCRAS QSISSYLNWY QQKPGKAPKL LIYAASSLQS GVPSRFSGSG SGTDFTLTIS  120
SLQPEDFATY YCQQTVVAPP LFGQGTKVEI KRTVAAPSVF IFPPSDEQLK SGTASVVCLL  180
NNFYPREAKV QWKVDNALQS GNSQESVTEQ DSKDSTYSLS STLTLSKADY EKHKVYACEV  240
THQGLSSPVT KSFNRGEC                                                258

SEQ ID NO: 437         moltype = AA  length = 265
FEATURE                Location/Qualifiers
REGION                 1..265
                       note = chemically synthesized
source                 1..265
                       mol_type = protein
                       organism = synthetic construct
SEQUENCE: 437
```

-continued

```
QGQSGQCNIW LVGGDCRGWQ GGSSGGSGLS GRSDNHGGVH MPLGFLGPGG SDIQMTQSPS  60
SLSASVGDRV TITCRASQSI SSYLNWYQQK PGKAPKLLIY AASSLQSGVP SRFSGSGSGT  120
DFTLTISSLQ PEDFATYYCQ QTVVAPPLFG QGTKVEIKRT VAAPSVFIFP PSDEQLKSGT  180
ASVVCLLNNF YPREAKVQWK VDNALQSGNS QESVTEQDSK DSTYSLSSTL TLSKADYEKH  240
KVYACEVTHQ GLSSPVTKSF NRGEC                                      265

SEQ ID NO: 438         moltype = DNA  length = 777
FEATURE                Location/Qualifiers
misc_feature           1..777
                       note = chemically synthesized
source                 1..777
                       mol_type = other DNA
                       organism = synthetic construct
SEQUENCE: 438
tgcaatattt ggctcgtagg tggtgattgc aggggctggc agggggggctc gagcggaggc  60
tctggcctgt ctggcagatc tgataaccac ggcggcgtgc acatgcccct gggctttctg  120
ggacctggcg gatctgacat ccagatgacc cagtctccat cctccctgtc tgcatctgta  180
ggagacagag tcaccatcac ttgccgggca agtcagagca ttagcagcta tttaaattgg  240
tatcagcaga aaccagggaa agcccctaag ctcctgatct atgcggcatc cagtttgcaa  300
agtggggtcc catcaaggtt cagtggcagt ggatctggga cagatttcac tctcaccatc  360
agcagtctgc aacctgaaga ttttgcaact tactactgtc aacagacggt tgtggcgcct  420
ccgttattcg gccaagggac caaggtggaa atcaaacgta cggtggctgc accatctgtc  480
ttcatcttcc cgccatctga tgagcagttg aaatctggaa ctgcctctgt tgtgtgcctg  540
ctgaataact tctatcccag agaggccaaa gtacagtgga aggtggataa cgccctccaa  600
tcgggtaact cccaggagag tgtcacagag caggacagca aggacagcac ctacagcctc  660
agcagcaccc tgacgctgag caaagcagac tacgagaaac acaaagtcta cgcctgcgaa  720
gtcacccatc agggcctgag ctcgcccgtc acaaagagct tcaacagggg agagtgt     777

SEQ ID NO: 439         moltype = AA  length = 259
FEATURE                Location/Qualifiers
REGION                 1..259
                       note = chemically synthesized
source                 1..259
                       mol_type = protein
                       organism = synthetic construct
SEQUENCE: 439
CNIWLVGGDC RGWQGGSSGG SGLSGRSDNH GGVHMPLGFL GPGGSDIQMT QSPSSLSASV  60
GDRVTITCRA SQSISSYLNW YQQKPGKAPK LLIYAASSLQ SGVPSRFSGS GSGTDFTLTI  120
SSLQPEDFAT YYCQQTVVAP PLFGQGTKVE IKRTVAAPSV FIFPPSDEQL KSGTASVVCL  180
LNNFYPREAK VQWKVDNALQ SGNSQESVTE QDSKDSTYSL SSTLTLSKAD YEKHKVYACE  240
VTHQGLSSPV TKSFNRGEC                                             259

SEQ ID NO: 440         moltype = DNA  length = 765
FEATURE                Location/Qualifiers
misc_feature           1..765
                       note = chemically synthesized
source                 1..765
                       mol_type = other DNA
                       organism = synthetic construct
SEQUENCE: 440
tgcatctccc cccgcggttg tcccgacggg ccgtacgtga tgtacggcag ctccggcggc  60
agtgggggta gcggtgggtc cggggctgagt ggccggtccg acaatcacgg gagctcggga  120
acacagattc tgctgacgca atctcccgtg atcctctcgg tctcacccgg cgaacgggtc  180
tcgttcagct gcagagcgtc ccaatcaatc gggaccaata ttcactggta ccagcaaagg  240
actaatgggt ctccccggct gctgataaaa tacgcctccg agtctatctc gggcatccca  300
tcccgattta gtggtagcgg aagcggcact gatttcacct tgtctattaa cagcgtagaa  360
tctgaggaca ttgcagacta ttactgtcag cagaataaca attggcctac aactttcggc  420
gccgggacca aactagagtt aaagcgtact gtggctgccc ccagcgtttt tatttttccg  480
cccagcgacg aacagctgaa gtcaggcaca gcctctgtgg tgtgtctcct gaataacttc  540
taccccagag aggccaaagt tcagtggaaa gtggacaatg ccttgcagtc cggaaacagt  600
caagagtccg tgaccgagca ggacagtaag gatagcacgt atagcctctc tagtacttta  660
acactgtcca aggccgacta cgagaagcac aaggtgtacg catgcgaagt gacccatcag  720
ggctttcct cccccgtcac caagtctttc aatcgcgggg agtgt                765

SEQ ID NO: 441         moltype = AA  length = 255
FEATURE                Location/Qualifiers
REGION                 1..255
                       note = chemically synthesized
source                 1..255
                       mol_type = protein
                       organism = synthetic construct
SEQUENCE: 441
CISPRGCPDG PYVMYGSSGG SGGSGGSGLS GRSDNHGSSG TQILLTQSPV ILSVSPGERV  60
SFSCRASQSI GTNIHWYQQR TNGSPRLLIK YASESISGIP SRFSGSGSGT DFTLSINSVE  120
SEDIADYYCQ QNNNWPTTFG AGTKLELKRT VAAPSVFIFP PSDEQLKSGT ASVVCLLNNF  180
YPREAKVQWK VDNALQSGNS QESVTEQDSK DSTYSLSSTL TLSKADYEKH KVYACEVTHQ  240
GLSSPVTKSF NRGEC                                                 255

SEQ ID NO: 442         moltype = DNA  length = 765
```

-continued

```
FEATURE               Location/Qualifiers
misc_feature          1..765
                      note = chemically synthesized
source                1..765
                      mol_type = other DNA
                      organism = synthetic construct
SEQUENCE: 442
tgtatttccc ctagaggttg ccctgacggg ccgtatgtca tgtacggtag ttctggcggt  60
agtggcggat ctggcggcag tgggctgagc ggacgtagcg ggaatcacgg ctcatccggg  120
acgcagatac tgctgaccca gtcccccgtg atcctgtccg tgtcaccggg cgaaagggtc  180
agtttctctt gccgagcatc acagtccata ggtacgaata tccattggta ccagcagcgg  240
accaatggga gcccaagact gctcattaag tacgcatctg agagtatctc aggcattcca  300
agcaggtttt ccggcagtgg gagcggcact gacttcaccc tcagcattaa cagcgtggaa  360
agcgaagaca ttgcagatta ctactgccaa cagaacaata actggcctac tacattcggg  420
gcaggaacta agttggagct caaacgtacc gtcgctgctc ctagcgtatt tattttccct  480
cctagcgatg aacagttgaa atctggtacc gctagtgttg tgtgcttact gaacaacttt  540
tatccccggg aggccaaggt acaatggaag gtggacaatg ccctccaatc agggaacagc  600
caggagtctg ttaccgagca ggactccaag gacagcacct acagcctgag ctctaccctt  660
acattgagca aggctgatta tgagaagcat aaggtctacg cttgtgaggt gacccatcag  720
gggctcagca gcccggtgac aaaaagcttt aaccgggggg aatgc                 765

SEQ ID NO: 443        moltype = AA  length = 255
FEATURE               Location/Qualifiers
REGION                1..255
                      note = chemically synthesized
source                1..255
                      mol_type = protein
                      organism = synthetic construct
SEQUENCE: 443
CISPRGCPDG PYVMYGSSGG SGGSGGSGLS GRSGNHGSSG TQILLTQSPV ILSVSPGERV  60
SFSCRASQSI GTNIHWYQQR TNGSPRLLIK YASESISGIP SRFSGSGSGT DFTLSINSVE  120
SEDIADYYCQ QNNNWPTTFG AGTKLELKRT VAAPSVFIFP PSDEQLKSGT ASVVCLLNNF  180
YPREAKVQWK VDNALQSGNS QESVTEQDSK DSTYSLSSTL TLSKADYEKH KVYACEVTHQ  240
GLSSPVTKSF NRGEC                                                  255

SEQ ID NO: 444        moltype = DNA  length = 765
FEATURE               Location/Qualifiers
misc_feature          1..765
                      note = chemically synthesized
source                1..765
                      mol_type = other DNA
                      organism = synthetic construct
SEQUENCE: 444
tgtattagcc ccaggggggtg ccccgacggg ccttacgtga tgtatggcag ctccggtggc  60
agcggaggct ctggcgggag tgggatcagt tccggcctgc tgagctccgg gtcaagcggg  120
acccagatct tgctcaccca atcaccagtg atcctaagcg tgagccctgg cgaacgggtc  180
agcttctctt gccgggcatc tcagagtatt ggcactaaca tacactggta ccagcagcga  240
accaatgggt ccccccgcct tctaatcaaa tatgctagcg aatccatttc aggaattcct  300
agccgattta gcggcagcgg atcaggcact gacttcactc tgtcaatcaa ctcagttgaa  360
agcgaggaca ttgcagacta ctattgccag cagaataata attggcccac tacatttgga  420
gctggaacaa aattggagct taagaggaca gtggctgcgc ctagtgtatt tatctttccc  480
ccctctgacg aacagttgaa atcgggaacc gcatccgtcg tctgtttact gaacaacttc  540
tatcccagag aggccaaagt gcagtggaaa gtggataatg ctttgcagtc tggcaacagc  600
caggaaagcg tgacggagca ggactcaaag gatagtacat actccctgtc ctccaccctg  660
actctgagta aggccgacta cgagaagcac aaggtctacg cctgcgaagt gacgcaccaa  720
gggctatcga gcccggtcac caagtctttc aatcgtggag aatgc                 765

SEQ ID NO: 445        moltype = AA  length = 255
FEATURE               Location/Qualifiers
REGION                1..255
                      note = chemically synthesized
source                1..255
                      mol_type = protein
                      organism = synthetic construct
SEQUENCE: 445
CISPRGCPDG PYVMYGSSGG SGGSGGSGIS SGLLSSGSSG TQILLTQSPV ILSVSPGERV  60
SFSCRASQSI GTNIHWYQQR TNGSPRLLIK YASESISGIP SRFSGSGSGT DFTLSINSVE  120
SEDIADYYCQ QNNNWPTTFG AGTKLELKRT VAAPSVFIFP PSDEQLKSGT ASVVCLLNNF  180
YPREAKVQWK VDNALQSGNS QESVTEQDSK DSTYSLSSTL TLSKADYEKH KVYACEVTHQ  240
GLSSPVTKSF NRGEC                                                  255

SEQ ID NO: 446        moltype = DNA  length = 765
FEATURE               Location/Qualifiers
misc_feature          1..765
                      note = chemically synthesized
source                1..765
                      mol_type = other DNA
                      organism = synthetic construct
SEQUENCE: 446
```

-continued

```
tgcatcagcc ctaggggctg cccagacggc ccatatgtga tgtacggtag ctctgggggc  60
tcaggaggca gcgggggaag cggacaaaac caggccttac gaatggctgg cagctctggc  120
acccagatat tgctgacgca gagtccagtt atccttagtg tcagccctgg tgaacgggtt  180
tcatttagtt gccgtgcctc ccagtctatt ggaacgaaca ttcattggta ccagcaaagg  240
accaacggtt cacccaggtt gcttatcaag tatgcttcag agtcaatctc cgggattccc  300
tcaaggtttt caggctctgg ctcaggtacc gattttacgc tgagcatcaa ctccgtggag  360
agtgaggaca ttgctgatta ttactgtcag cagaataaca attggccgac aactttcggc  420
gccggcacaa agctggaact taagcgtact gtggctgcgc catctgtctt catttttccg  480
ccctcggacg agcagttgaa gtcagggacc gcctctgtcg tgtgccttct caataacttc  540
tatcccagag aggctaaagt ccagtggaaa gttgataatg cacttcagag cgggaatagc  600
caggagagcg tgacggaaca ggactctaag gactccacct attctctctc atccaccctt  660
actctctcta aagccgacta cgaaaagcat aaggtttatg cttgcgaagt cactcatcaa  720
gggctatcta gtccggtcac taaaagcttc aacagaggtg aatgt                 765

SEQ ID NO: 447         moltype = AA  length = 255
FEATURE                Location/Qualifiers
REGION                 1..255
                       note = chemically synthesized
source                 1..255
                       mol_type = protein
                       organism = synthetic construct
SEQUENCE: 447
CISPRGCPDG PYVMYGSSGG SGGSGGSGQN QALRMAGSSG TQILLTQSPV ILSVSPGERV  60
SFSCRASQSI GTNIHWYQQR TNGSPRLLIK YASESISGIP SRFSGSGSGT DFTLSINSVE  120
SEDIADYYCQ QNNNWPTTFG AGTKLELKRT VAAPSVFIFP PSDEQLKSGT ASVVCLLNNF  180
YPREAKVQWK VDNALQSGNS QESVTEQDSK DSTYSLSSTL TLSKADYEKH KVYACEVTHQ  240
GLSSPVTKSF NRGEC                                                  255

SEQ ID NO: 448         moltype = DNA  length = 780
FEATURE                Location/Qualifiers
misc_feature           1..780
                       note = chemically synthesized
source                 1..780
                       mol_type = other DNA
                       organism = synthetic construct
SEQUENCE: 448
tgtatcagcc cccgtggctg tccagacggt ccttacgtta tgtatggatc tagcgggggc  60
tctggagggt ctggcggctc tggaatctct agtggacttc tctccggaag aagcgataat  120
catggatcca gcgggacaca aatcctgttg acacagtccc cagtgatcct gtcagtctcg  180
cccggagaaa gggtgtcttt ctcttgtagg gctagtcagt ctatcggaac taacatccat  240
tggtaccagc agcggacaaa tgggagcccg aggcttctga tcaagtatgc ttcagagagt  300
ataagcggca tcccctcaag atttagtggc agcgggtccg ggacagattt caccttgtca  360
atcaattctg tcgaatccga agacattgca gactactatt gccagcaaaa caacaactgg  420
cccaccactt tcggtgctgg aaccaaactc gagctgaaac gcactgtggc agctccttca  480
gtgttcatct tcccacctag cgacgagcag ttgaaatcgg ggacagcctc agtggtgtgt  540
ctactgaaca acttttaccc ccgggaagcc aaagtgcagt ggaaggtcga caatgcgctg  600
caatcaggga acagtcagga gtcagttaca gagcaggact ctaaggacag tacatattct  660
ttgagttcca ccttgacatt aagcaaggca gactacgaga aacacaaggt gtacgcatgt  720
gaagttacac accagggcct ttcctcccca gttacgaaaa gcttcaacag aggcgaatgc  780

SEQ ID NO: 449         moltype = AA  length = 260
FEATURE                Location/Qualifiers
REGION                 1..260
                       note = chemically synthesized
source                 1..260
                       mol_type = protein
                       organism = synthetic construct
SEQUENCE: 449
CISPRGCPDG PYVMYGSSGG SGGSGGSGIS SGLLSGRSDN HGSSGTQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                             260

SEQ ID NO: 450         moltype = DNA  length = 780
FEATURE                Location/Qualifiers
misc_feature           1..780
                       note = chemically synthesized
source                 1..780
                       mol_type = other DNA
                       organism = synthetic construct
SEQUENCE: 450
tgcatatcgc ccagaggatg tcctgacgga ccctacgtga tgtacgggag ttctgggggg  60
agtggaggct ctggcgggtc agggattagt tccggcctct tgtctggacg ctccggaaat  120
cacggatcat ctgggaccca gatcctcctg acccagtctc ccgtcattct gtctgtttct  180
ccaggcgagc gggtttcatt tagctgtagg gccagtcaga gcattggcac caacatccat  240
tggtaccagc agagaactaa tggcagtccc agactgctca ttaaatatgc aagcgaatca  300
atttccggga ttccttctcg cttctcggga tctggatctg gcaccgactt cacgctgtcc  360
atcaacagcg tggagagtga ggacatcgcc gattactact gccagcagaa caacaactgg  420
```

```
ccaacaactt ttggcgccgg gaccaagctt gagttaaaga gaaccgtagc tgcaccctct  480
gttttcattt tcccaccctc agacgagcag cttaagtcag gaactgccag tgtggtgtgc  540
ctgctgaaca acttctaccc gagagaggct aaagtccagt ggaaggtaga caatgccctt  600
cagtctggca actctcagga gagtgtcaca gagcaggatt ctaaggactc cacgtacagt  660
ctgagttcca ccctcaccct cagtaaggca gactacgaga agcacaaagt ctacgcatgt  720
gaggttactc accaggggct cagctctccc gtgacgaagt catttaacag aggtgagtgc  780

SEQ ID NO: 451          moltype = AA  length = 260
FEATURE                 Location/Qualifiers
REGION                  1..260
                        note = chemically synthesized
source                  1..260
                        mol_type = protein
                        organism = synthetic construct
SEQUENCE: 451
CISPRGCPDG PYVMYGSSGG SGGSGGSGIS SGLLSGRSGN HGSSGTQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                             260

SEQ ID NO: 452          moltype = DNA  length = 807
FEATURE                 Location/Qualifiers
misc_feature            1..807
                        note = chemically synthesized
source                  1..807
                        mol_type = other DNA
                        organism = synthetic construct
SEQUENCE: 452
tgcatttctc cgagaggctg ccctgacggc ccatacgtaa tgtacggatc atccggtggc  60
agtggagggt ccgggggatc cggtctaagc ggcagaagtg ataatcatgg aggctctggc  120
gggagcatca gctccggatt gctttccagc ggaagttctg gcactcaaat tctgctgaca  180
caaagccctg tgatcttgtc agtctcacct ggcgagcggg tgagcttttc atgccgggct  240
tcccagagca tcggtacaaa tattcactgg tatcagcaga gaaccaatgg cagtccgcgg  300
ttgctgatta agtatgcgag cgagagcata tcaggcatac caagcagatt tagcgggagt  360
ggctctggga ccgattttac actcagtata aattcagtgg agagcgagga tatagccgac  420
tactactgcc agcaaaacaa taactggccc accaccttcg gcgcagggac caagcttgaa  480
ctgaagcgta cagttgccgc cccaagcgta tttattttcc ctccaagcga cgaacagctg  540
aaaagcggta ccgcaagcgt tgtgtgcctg ctgaataact tttacccaag ggaagctaag  600
gtgcagtgga aggttgacaa tgcgctgcag tcaggcaact cccaggaatc ggtaacagag  660
caggactcca aggattcaac ttatagtctt agtagtaccc ttactctttc caaagctgat  720
tatgaaaaac acaaagtgta tgcatgcgag gtgacccacc aaggactgtc atctcctgtc  780
accaagtcct tcaaccgggg agagtgt                                     807

SEQ ID NO: 453          moltype = AA  length = 269
FEATURE                 Location/Qualifiers
REGION                  1..269
                        note = chemically synthesized
source                  1..269
                        mol_type = protein
                        organism = synthetic construct
SEQUENCE: 453
CISPRGCPDG PYVMYGSSGG SGGSGGSGLS GRSDNHGGSG GSISSGLLSS GSSGTQILLT  60
QSPVILSVSP GERVSFSCRA SQSIGTNIHW YQQRTNGSPR LLIKYASESI SGIPSRFSGS  120
GSGTDFTLSI NSVESEDIAD YYCQQNNNWP TTFGAGTKLE LKRTVAAPSV FIFPPSDEQL  180
KSGTASVVCL LNNFYPREAK VQWKVDNALQ SGNSQESVTE QDSKDSTYSL SSTLTLSKAD  240
YEKHKVYACE VTHQGLSSPV TKSFNRGEC                                   269

SEQ ID NO: 454          moltype = DNA  length = 807
FEATURE                 Location/Qualifiers
misc_feature            1..807
                        note = chemically synthesized
source                  1..807
                        mol_type = other DNA
                        organism = synthetic construct
SEQUENCE: 454
tgcattagtc ctcgcggttg ccctgatgga ccatacgtaa tgtatggaag ctctggtgga  60
tccgggggct ctggcggatc aggaatctcc agcgggctgc tctcatcagg tggcagcggg  120
ggctcattaa gcggccgaag tgacaatcac ggctcgtccg gtacacagat tctgctcact  180
cagtcacccg ttatactgtc tgtgtcgcct ggagagcgtg tcagcttttc atgtagagcc  240
tcgcagtcaa taggcacgaa tatacactgg taccagcaga gaactaatgg aagcccaagg  300
ttgctcatca aatacgcatc tgagtcgatt agcggcattc cgtccaggtt tagtggcagt  360
ggaagcggca ccgatttcac tttgtctatt aactctgtgg aaagcgagga catcgccgat  420
tattattgtc agcagaataa caattggccc accaccttcg gtgccggtac taagctggag  480
ctgaaacgta cagttgccgc tccctctgtg tttattttcc ctccctcgga tgagcaactc  540
aaatcaggga cagcgagtgt cgtatgtctc ctgaacaatt tttacccacg tgaagctaaa  600
gttcagtgga aggtggacaa cgctctgcag tccggcaaca gtcaggaaag cgtaactgaa  660
caggactcaa aggatagcac ttactccttg agcagcactc tcactctttc caaggctgat  720
tatgagaagc acaaggtgta cgcgtgtgaa gtcacccatc agggactgtc aagtccggtg  780
```

```
actaaatcat ttaacagggg cgaatgc                                        807

SEQ ID NO: 455          moltype = AA  length = 269
FEATURE                 Location/Qualifiers
REGION                  1..269
                        note = chemically synthesized
source                  1..269
                        mol_type = protein
                        organism = synthetic construct
SEQUENCE: 455
CISPRGCPDG PYVMYGSSGG SGGSGGSGIS SGLLSSGGSG GSLSGRSDNH GSSGTQILLT  60
QSPVILSVSP GERVSFSCRA SQSIGTNIHW YQQRTNGSPR LLIKYASESI SGIPSRFSGS  120
GSGTDFTLSI NSVESEDIAD YYCQQNNNWP TTFGAGTKLE LKRTVAAPSV FIFPPSDEQL  180
KSGTASVVCL LNNFYPREAK VQWKVDNALQ SGNSQESVTE QDSKDSTYSL SSTLTLSKAD  240
YEKHKVYACE VTHQGLSSPV TKSFNRGEC                                      269

SEQ ID NO: 456          moltype = DNA  length = 807
FEATURE                 Location/Qualifiers
misc_feature            1..807
                        note = chemically synthesized
source                  1..807
                        mol_type = other DNA
                        organism = synthetic construct
SEQUENCE: 456
tgtatttccc ctcgcggatg tcccgacggt ccatacgtaa tgtatgggtc aagcggggga  60
tcaggaggaa gtggaggctc cggactcagc ggtcgctccg gcaatcacgg ggggtctggc  120
ggatcaataa gttcgggcct cctgagctcc ggttcatctg gcactcagat cctgctcacg  180
cagtcgccgg taatactgag tgtctcacca ggcgagcgtg tcagcttcag ctgtcgcgcc  240
tcacagtcaa tcggcacaaa tatccattgg taccagcaaa ggaccaatgg cagccctagg  300
ctgctgataa aatacgcatc cgagtcaatt tcagggattc catcgagatt ctcgggcagc  360
ggaagtggga ccgactttac tctctccatc aacagcgtcg agtcggagga catcgcggac  420
tactactgcc agcagaataa caattggcca acaacattcg gcgcaggaac aaagctagag  480
ctcaagagga cagtggctgc acccagtgta ttcatcttcc cacctagcga cgagcaactg  540
aagagcggga cggcttccgt cgtttgtcta ttaaataatt tctatccccg tgaggctaaa  600
gttcagtgga aggttgataa tgcgttgcag tccggcaact cccaggaatc cgtcacagag  660
caggattcta aggattcaac ctatagctta agctctacac ttacgctttc taaagccgat  720
tatgaaaaac acaaggtgta cgcttgtgag gttacccacc agggcctgag cagccccgtg  780
accaagtcgt tcaaccgggg cgagtgt                                        807

SEQ ID NO: 457          moltype = AA  length = 269
FEATURE                 Location/Qualifiers
REGION                  1..269
                        note = chemically synthesized
source                  1..269
                        mol_type = protein
                        organism = synthetic construct
SEQUENCE: 457
CISPRGCPDG PYVMYGSSGG SGGSGGSGLS GRSGNHGGSG GSISSGLLSS GSSGTQILLT  60
QSPVILSVSP GERVSFSCRA SQSIGTNIHW YQQRTNGSPR LLIKYASESI SGIPSRFSGS  120
GSGTDFTLSI NSVESEDIAD YYCQQNNNWP TTFGAGTKLE LKRTVAAPSV FIFPPSDEQL  180
KSGTASVVCL LNNFYPREAK VQWKVDNALQ SGNSQESVTE QDSKDSTYSL SSTLTLSKAD  240
YEKHKVYACE VTHQGLSSPV TKSFNRGEC                                      269

SEQ ID NO: 458          moltype = DNA  length = 807
FEATURE                 Location/Qualifiers
misc_feature            1..807
                        note = chemically synthesized
source                  1..807
                        mol_type = other DNA
                        organism = synthetic construct
SEQUENCE: 458
tgtatctcac ctcgcggctg ccccgacggc ccttacgtca tgtacggctc ctcgggtggg  60
tccgggggaa gtggcgggtc tggcattagt tcagggctct tatcttccgg cggaagcggg  120
ggatctcttt ccgggcggag tggcaatcac ggcagtagcg gaactcagat cctactcact  180
cagtcaccag tgatcctgtc tgtcagtcca ggggagagag tgtctttcag ttgtagagct  240
tcccagtcta ttgggacaaa cattcactgg tatcaacagc gaactaatgg atcgccaaga  300
ctcctgatta aatatgcttc tgagagcatc tctggaattc catcaagatt ctcagggagt  360
ggtagcggca ccgattttac gttatcgatc aattccgttg agagcgaaga tatcgcggac  420
tattactgtc agcagaacaa taactggcct acaacgttcg gggcagggac gaaattggag  480
ctgaagcgga ccgtcgccgc gccaagcgtg ttcatcttcc cccctagcga cgagcaattg  540
aaaagcggca ccgcaagtgt ggtttgcctg ctgaacaact tttatcctcg cgaggcgaaa  600
gtgcagtgga aagtcgacaa tgcactccag tcagggaaca gccaagagtc cgttactgaa  660
caagactcta aagatagtac ttatagctta tccagcacac tgacgctcag taaggccgat  720
tatgaaaaac ataaggtgta tgcgtgtgag gttacccatc aaggattgtc atcacccgtc  780
accaaatcct ttaacagagg agaatgt                                        807

SEQ ID NO: 459          moltype = AA  length = 269
FEATURE                 Location/Qualifiers
REGION                  1..269
```

```
                         note = chemically synthesized
source                   1..269
                         mol_type = protein
                         organism = synthetic construct
SEQUENCE: 459
CISPRGCPDG PYVMYGSSGG SGGSGGSGIS SGLLSSGGSG GSLSGRSGNH GSSGTQILLT  60
QSPVILSVSP GERVSFSCRA SQSIGTNIHW YQQRTNGSPR LLIKYASESI SGIPSRFSGS  120
GSGTDFTLSI NSVESEDIAD YYCQQNNNWP TTFGAGTKLE LKRTVAAPSV FIFPPSDEQL  180
KSGTASVVCL LNNFYPREAK VQWKVDNALQ SGNSQESVTE QDSKDSTYSL SSTLTLSKAD  240
YEKHKVYACE VTHQGLSSPV TKSFNRGEC                                   269

SEQ ID NO: 460           moltype = DNA  length = 807
FEATURE                  Location/Qualifiers
misc_feature             1..807
                         note = chemically synthesized
source                   1..807
                         mol_type = other DNA
                         organism = synthetic construct
SEQUENCE: 460
tgtatctcgc cccgcggctg cccagacggc ccatatgtga tgtatggttc ttccggtgga  60
tccggcggat caggtgggtc tggcctctca ggtcgttccg acaaccacgg cggctcaggt  120
gggtctcaga atcaggcact gcggatggcc ggatcttctg gcacccagat attgctcaca  180
cagtcaccag ttattctgtc cgtatctcca ggagaacggg tatctttctc ttgtagggca  240
agccagtcca tcggaacaaa catccattgg taccagcagc ggaccaatgg cagtccacgg  300
cttctgatca agtatgctag tgaaagcatt agcgggattc caagccgatt ttctgggtcg  360
ggtagtggaa ccgacttcac cctgagcatt aactctgtcg aatccgaaga tattgctgac  420
tattactgtc agcagaacaa caattggccg actacgtttg gcgccggaac caaattagaa  480
cttaagagaa ccgtggccgc tccctctgtc ttcattttcc cgccttccga cgaacagctg  540
aagagcggaa ctgcctccgt ggtgtgcctg ttgaataact tttatccaag ggaagcaaag  600
gtgcagtgga aagtggacaa tgctctgcag tctggcaata gccaggagtc cgtgactgaa  660
caggacagta aagactcaac ctactcactg agcagtactc tcacattatc caaagccgat  720
tatgaaaagc ataaggttta tgcatgcgag gttacccacc agggactgag ctcccccgtg  780
accaaaagct tcaatagggg tgagtgc                                     807

SEQ ID NO: 461           moltype = AA  length = 269
FEATURE                  Location/Qualifiers
REGION                   1..269
                         note = chemically synthesized
source                   1..269
                         mol_type = protein
                         organism = synthetic construct
SEQUENCE: 461
CISPRGCPDG PYVMYGSSGG SGGSGGSGLS GRSDNHGGSG GSQNQALRMA GSSGTQILLT  60
QSPVILSVSP GERVSFSCRA SQSIGTNIHW YQQRTNGSPR LLIKYASESI SGIPSRFSGS  120
GSGTDFTLSI NSVESEDIAD YYCQQNNNWP TTFGAGTKLE LKRTVAAPSV FIFPPSDEQL  180
KSGTASVVCL LNNFYPREAK VQWKVDNALQ SGNSQESVTE QDSKDSTYSL SSTLTLSKAD  240
YEKHKVYACE VTHQGLSSPV TKSFNRGEC                                   269

SEQ ID NO: 462           moltype = DNA  length = 807
FEATURE                  Location/Qualifiers
misc_feature             1..807
                         note = chemically synthesized
source                   1..807
                         mol_type = other DNA
                         organism = synthetic construct
SEQUENCE: 462
tgcatcagcc cccgaggctg ccctgatggc cctacgtga tgtacgggtc cagcggtggc  60
agcgggggct cagggggag cgggcagaat caggccctga gaatggcggg tggatccggg  120
gggtcccttt ctggcaggtc cgataaccac ggttctagtg gaacacagat tttgctgaca  180
caaagtcccg tcatcctctc tgtgtctccc ggtgagcggg tcagtttttc ctgccgagcg  240
tcccagagca tcgggacaaa tatccattgg taccagcaga gaacgaacgg ctctcctaga  300
ctgctcatca agtacgcctc ggaaagtatt tccggcattc cctcccgttt cagcggctcc  360
ggaagtggta cagattttac cctgagtatt aattccgtcg aatctgagga catagccgac  420
tactattgcc aacagaataa caattggcca acaacttttg gcgccgggac taagctggag  480
ctgaaacgga ccgtcgcagc accaagtgtt ttcatcttcc caccaagtga cgagcagctg  540
aaatccggaa cagcgagcgt ggtgtgccta ctcaataact tctatccacg cgaagccaag  600
gtgcagtgga aagtggacaa cgctctgcag tccggcaata gccaggaaag cgtgacagag  660
caagattcta aggacagtac gtattcactg tccagtacgc tcaccttaag caaggctgac  720
tacgaaaaac acaaggtcta cgcctgtgag gtcacacatc agggcctctc cagtccggtt  780
acaaaaagtt tcaatcgcgg ggaatgt                                     807

SEQ ID NO: 463           moltype = AA  length = 269
FEATURE                  Location/Qualifiers
REGION                   1..269
                         note = chemically synthesized
source                   1..269
                         mol_type = protein
                         organism = synthetic construct
SEQUENCE: 463
```

```
CISPRGCPDG PYVMYGSSGG SGGSGGSGQN QALRMAGGSG GSLSGRSDNH GSSGTQILLT  60
QSPVILSVSP GERVSFSCRA SQSIGTNIHW YQQRTNGSPR LLIKYASESI SGIPSRFSGS  120
GSGTDFTLSI NSVESEDIAD YYCQQNNNWP TTFGAGTKLE LKRTVAAPSV FIFPPSDEQL  180
KSGTASVVCL LNNFYPREAK VQWKVDNALQ SGNSQESVTE QDSKDSTYSL SSTLTLSKAD  240
YEKHKVYACE VTHQGLSSPV TKSFNRGEC                                    269

SEQ ID NO: 464          moltype = DNA  length = 807
FEATURE                 Location/Qualifiers
misc_feature            1..807
                        note = chemically synthesized
source                  1..807
                        mol_type = other DNA
                        organism = synthetic construct
SEQUENCE: 464
tgcatcagtc ccagaggctg ccctgacggg ccctacgtga tgtatggtag ctcagggggc  60
tccggcggct ccggcggaag cggacttagc ggccgtagcg gcaaccatgg gggttctgga  120
ggatcccaga atcaggctct gcgcatggct ggaagcagcg gtacccagat cctgctcacc  180
caatcacccg tcatcttgtc tgtgagtcct ggcgaaaggg tgtcgttctc ttgtcgcgcg  240
tcccagtcca ttgggaccaa cattcattgg taccagcaga ggactaacgg gagccccccgc  300
ctgctgatca aatacgccag tgaatctatc tctggaatcc catcacgatt ttcagggtcc  360
ggtagtggga ccgacttcac tttgagtatt aacagtgtgg aatccgagga catagccgac  420
tattactgtc agcagaacaa taactggcca acaacctttg gcgccgggac aaagttagag  480
cttaagcgga ctgttgcagc cccctccgtt tttatcttcc cgcccagtga tgaacagctg  540
aaaagcggta ccgcctccgt agtgtgcctt ctcaataatt tttaccccag agaagctaaa  600
gtacagtgga aagtcgacaa cgccctccag agcggcaaca gtcaggagtc cgtcaccgag  660
caggattcta aagactcaac atatagcctt tcgtccaccc taacactttc aaaagcagac  720
tatgaaaaac ataaggtgta tgcctgcgag gtcacacacc aggggctcag ctctccagtt  780
actaagtcat tcaaccgcgg agagtgt                                      807

SEQ ID NO: 465          moltype = AA  length = 269
FEATURE                 Location/Qualifiers
REGION                  1..269
                        note = chemically synthesized
source                  1..269
                        mol_type = protein
                        organism = synthetic construct
SEQUENCE: 465
CISPRGCPDG PYVMYGSSGG SGGSGGSGLS GRSGNHGGSG GSQNQALRMA GSSGTQILLT  60
QSPVILSVSP GERVSFSCRA SQSIGTNIHW YQQRTNGSPR LLIKYASESI SGIPSRFSGS  120
GSGTDFTLSI NSVESEDIAD YYCQQNNNWP TTFGAGTKLE LKRTVAAPSV FIFPPSDEQL  180
KSGTASVVCL LNNFYPREAK VQWKVDNALQ SGNSQESVTE QDSKDSTYSL SSTLTLSKAD  240
YEKHKVYACE VTHQGLSSPV TKSFNRGEC                                    269

SEQ ID NO: 466          moltype = DNA  length = 807
FEATURE                 Location/Qualifiers
misc_feature            1..807
                        note = chemically synthesized
source                  1..807
                        mol_type = other DNA
                        organism = synthetic construct
SEQUENCE: 466
tgcattagcc cccgagggtg tcccgatggg ccctacgtaa tgtacggatc atcgggcgga  60
tctgggggct ccggtggctc tggtcagaat caagctctgc gcatggccgg aggtagcggt  120
ggaagcctga gcggccgaag tggaaaccac ggctcctctg gcactcagat tcttctcacg  180
cagtcgcccg tgatcttgtc cgtgagccca ggcgagcggg tgagcttctc ttgccgggcc  240
agccaaagta taggtacaaa tattcactgg taccaacagc gaaccaacgg gtcgcctagg  300
ttgctcataa agtacgcatc cgagagtata agcggcatac catctaggtt ctcaggtagc  360
ggcagcggga ccgattttac cctcagcatt aattcggttg aatctgaaga tatcgccgat  420
tattattgtc agcagaataa caattggcct actactttcg gcgccggaac aaagctggaa  480
cttaagcgca cagtggccgc tccttctgtc tttatcttcc ctccatctga cgagcaatta  540
aagagtggga cagcctcggt ggtgtgtttg ctcaataact tctatccaag ggaggcaaag  600
gtgcagtgga aggtcgataa cgctctccag agtgggaatt cccaggagtc cgtgaccgag  660
caggattcta aagatagcac atactcactg tcttccaccc tgaccctgtc caaggcagac  720
tacgagaagc acaaagttta cgcctgtgaa gtgacacacc agggcctcag ctctcctgtc  780
acaaagagtt ttaatcgggg cgagtgt                                      807

SEQ ID NO: 467          moltype = AA  length = 269
FEATURE                 Location/Qualifiers
REGION                  1..269
                        note = chemically synthesized
source                  1..269
                        mol_type = protein
                        organism = synthetic construct
SEQUENCE: 467
CISPRGCPDG PYVMYGSSGG SGGSGGSGQN QALRMAGGSG GSLSGRSGNH GSSGTQILLT  60
QSPVILSVSP GERVSFSCRA SQSIGTNIHW YQQRTNGSPR LLIKYASESI SGIPSRFSGS  120
GSGTDFTLSI NSVESEDIAD YYCQQNNNWP TTFGAGTKLE LKRTVAAPSV FIFPPSDEQL  180
KSGTASVVCL LNNFYPREAK VQWKVDNALQ SGNSQESVTE QDSKDSTYSL SSTLTLSKAD  240
YEKHKVYACE VTHQGLSSPV TKSFNRGEC                                    269
```

```
SEQ ID NO: 468          moltype = AA  length = 9
FEATURE                 Location/Qualifiers
REGION                  1..9
                        note = chemically synthesized
source                  1..9
                        mol_type = protein
                        organism = synthetic construct
SEQUENCE: 468
SGRSANPRG                                                          9

SEQ ID NO: 469          moltype = AA  length = 15
FEATURE                 Location/Qualifiers
REGION                  1..15
                        note = chemically synthesized
source                  1..15
                        mol_type = protein
                        organism = synthetic construct
SEQUENCE: 469
ISSGLLSGRS ANPRG                                                   15

SEQ ID NO: 470          moltype = AA  length = 18
FEATURE                 Location/Qualifiers
REGION                  1..18
                        note = chemically synthesized
source                  1..18
                        mol_type = protein
                        organism = synthetic construct
SEQUENCE: 470
AVGLLAPPTS GRSANPRG                                                18

SEQ ID NO: 471          moltype = AA  length = 17
FEATURE                 Location/Qualifiers
REGION                  1..17
                        note = chemically synthesized
source                  1..17
                        mol_type = protein
                        organism = synthetic construct
SEQUENCE: 471
AVGLLAPPSG RSANPRG                                                 17

SEQ ID NO: 472          moltype = AA  length = 262
FEATURE                 Location/Qualifiers
REGION                  1..262
                        note = chemically synthesized
source                  1..262
                        mol_type = protein
                        organism = synthetic construct
SEQUENCE: 472
CISPRGCPDG PYVMYGSSGG SGGSGGSGIS SGLLSGRSAN PRGGSSGTQI LLTQSPVILS  60
VSPGERVSFS CRASQSIGTN IHWYQQRTNG SPRLLIKYAS ESISGIPSRF SGSGSGTDFT  120
LSINSVESED IADYYCQQNN NWPTTFGAGT KLELKRTVAA PSVFIFPPSD EQLKSGTASV  180
VCLLNNFYPR EAKVQWKVDN ALQSGNSQES VTEQDSKDST YSLSSTLTLS KADYEKHKVY  240
ACEVTHQGLS SPVTKSFNRG EC                                           262

SEQ ID NO: 473          moltype = AA  length = 268
FEATURE                 Location/Qualifiers
REGION                  1..268
                        note = chemically synthesized
source                  1..268
                        mol_type = protein
                        organism = synthetic construct
SEQUENCE: 473
QGQSGQCISP RGCPDGPYVM YGSSGGSGGS GGSGISSGLL SGRSANPRGG SSGTQILLTQ  60
SPVILSVSPG ERVSFSCRAS QSIGTNIHWY QQRTNGSPRL LIKYASESIS GIPSRFSGSG  120
SGTDFTLSIN SVESEDIADY YCQQNNNWPT TFGAGTKLEL KRTVAAPSVF IFPPSDEQLK  180
SGTASVVCLL NNFYPREAKV QWKVDNALQS GNSQESVTEQ DSKDSTYSLS STLTLSKADY  240
EKHKVYACEV THQGLSSPVT KSFNRGEC                                     268

SEQ ID NO: 474          moltype = AA  length = 264
FEATURE                 Location/Qualifiers
REGION                  1..264
                        note = chemically synthesized
source                  1..264
                        mol_type = protein
                        organism = synthetic construct
SEQUENCE: 474
CISPRGCPDG PYVMYGSSGG SGGSGGSGAV GLLAPPSGRS ANPRGGSSGT QILLTQSPVI  60
LSVSPGERVS FSCRASQSIG TNIHWYQQRT NGSPRLLIKY ASESISGIPS RFSGSGSGTD  120
```

```
FTLSINSVES EDIADYYCQQ NNNWPTTFGA GTKLELKRTV AAPSVFIFPP SDEQLKSGTA  180
SVVCLLNNFY PREAKVQWKV DNALQSGNSQ ESVTEQDSKD STYSLSSTLT LSKADYEKHK  240
VYACEVTHQG LSSPVTKSFN RGEC                                         264

SEQ ID NO: 475         moltype = AA  length = 270
FEATURE                Location/Qualifiers
REGION                 1..270
                       note = chemically synthesized
source                 1..270
                       mol_type = protein
                       organism = synthetic construct
SEQUENCE: 475
QGQSGQCISP RGCPDGPYVM YGSSGGSGGS GGSGAVGLLA PPSGRSANPR GGSSGTQILL  60
TQSPVILSVS PGERVSFSCR ASQSIGTNIH WYQQRTNGSP RLLIKYASES ISGIPSRFSG  120
SGSGTDFTLS INSVESEDIA DYYCQQNNNW PTTFGAGTKL ELKRTVAAPS VFIFPPSDEQ  180
LKSGTASVVC LLNNFYPREA KVQWKVDNAL QSGNSQESVT EQDSKDSTYS LSSTLTLSKA  240
DYEKHKVYAC EVTHQGLSSP VTKSFNRGEC                                   270

SEQ ID NO: 476         moltype = AA  length = 259
FEATURE                Location/Qualifiers
REGION                 1..259
                       note = chemically synthesized
source                 1..259
                       mol_type = protein
                       organism = synthetic construct
SEQUENCE: 476
QGQSGQCNIW LVGGDCRGWQ GGSSGGSISS GLLSGRSANP RGGGSDIQMT QSPSSLSASV  60
GDRVTITCRA SQSISSYLNW YQQKPGKAPK LLIYAASSLQ SGVPSRFSGS GSGTDFTLTI  120
SSLQPEDFAT YYCQQTVVAP PLFGQGTKVE IKRTVAAPSV FIFPPSDEQL KSGTASVVCL  180
LNNFYPREAK VQWKVDNALQ SGNSQESVTE QDSKDSTYSL SSTLTLSKAD YEKHKVYACE  240
VTHQGLSSPV TKSFNRGEC                                               259

SEQ ID NO: 477         moltype = AA  length = 253
FEATURE                Location/Qualifiers
REGION                 1..253
                       note = chemically synthesized
source                 1..253
                       mol_type = protein
                       organism = synthetic construct
SEQUENCE: 477
CNIWLVGGDC RGWQGGSSGG SISSGLLSGR SANPRGGGSD IQMTQSPSSL SASVGDRVTI  60
TCRASQSISS YLNWYQQKPG KAPKLLIYAA SSLQSGVPSR FSGSGSGTDF TLTISSLQPE  120
DFATYYCQQT VVAPPLFGQG TKVEIKRTVA APSVFIFPPS DEQLKSGTAS VVCLLNNFYP  180
REAKVQWKVD NALQSGNSQE SVTEQDSKDS TYSLSSTLTL SKADYEKHKV YACEVTHQGL  240
SSPVTKSFNR GEC                                                     253

SEQ ID NO: 478         moltype = AA  length = 261
FEATURE                Location/Qualifiers
REGION                 1..261
                       note = chemically synthesized
source                 1..261
                       mol_type = protein
                       organism = synthetic construct
SEQUENCE: 478
QGQSGQCNIW LVGGDCRGWQ GGSSGGSAVG LLAPPSGRSA NPRGGGSDIQ MTQSPSSLSA  60
SVGDRVTITC RASQSISSYL NWYQQKPGKA PKLLIYAASS LQSGVPSRFS GSGSGTDFTL  120
TISSLQPEDF ATYYCQQTVV APPLFGQGTK VEIKRTVAAP SVFIFPPSDE QLKSGTASVV  180
CLLNNFYPRE AKVQWKVDNA LQSGNSQESV TEQDSKDSTY SLSSTLTLSK ADYEKHKVYA  240
CEVTHQGLSS PVTKSFNRGE C                                            261

SEQ ID NO: 479         moltype = AA  length = 255
FEATURE                Location/Qualifiers
REGION                 1..255
                       note = chemically synthesized
source                 1..255
                       mol_type = protein
                       organism = synthetic construct
SEQUENCE: 479
CNIWLVGGDC RGWQGGSSGG SAVGLLAPPS GRSANPRGGG SDIQMTQSPS SLSASVGDRV  60
TITCRASQSI SSYLNWYQQK PGKAPKLLIY AASSLQSGVP SRFSGSGSGT DFTLTISSLQ  120
PEDFATYYCQ QTVVAPPLFG QGTKVEIKRT VAAPSVFIFP PSDEQLKSGT ASVVCLLNNF  180
YPREAKVQWK VDNALQSGNS QESVTEQDSK DSTYSLSSTL TLSKADYEKH KVYACEVTHQ  240
GLSSPVTKSF NRGEC                                                   255

SEQ ID NO: 480         moltype = AA  length = 5
FEATURE                Location/Qualifiers
REGION                 1..5
                       note = chemically synthesized
source                 1..5
```

```
                        mol_type = protein
                        organism = synthetic construct
SEQUENCE: 480
ISSGL                                                                   5

SEQ ID NO: 481          moltype = AA  length = 7
FEATURE                 Location/Qualifiers
REGION                  1..7
                        note = chemically synthesized
source                  1..7
                        mol_type = protein
                        organism = synthetic construct
SEQUENCE: 481
ISSGLLS                                                                 7

SEQ ID NO: 482          moltype = AA  length = 6
FEATURE                 Location/Qualifiers
REGION                  1..6
                        note = chemically synthesized
source                  1..6
                        mol_type = protein
                        organism = synthetic construct
SEQUENCE: 482
ISSGLL                                                                  6

SEQ ID NO: 483          moltype = AA  length = 13
FEATURE                 Location/Qualifiers
REGION                  1..13
                        note = chemically synthesized
source                  1..13
                        mol_type = protein
                        organism = synthetic construct
SEQUENCE: 483
ISSGLLSGRS DDH                                                          13

SEQ ID NO: 484          moltype = AA  length = 13
FEATURE                 Location/Qualifiers
REGION                  1..13
                        note = chemically synthesized
source                  1..13
                        mol_type = protein
                        organism = synthetic construct
SEQUENCE: 484
ISSGLLSGRS DIH                                                          13

SEQ ID NO: 485          moltype = AA  length = 13
FEATURE                 Location/Qualifiers
REGION                  1..13
                        note = chemically synthesized
source                  1..13
                        mol_type = protein
                        organism = synthetic construct
SEQUENCE: 485
ISSGLLSGRS DQH                                                          13

SEQ ID NO: 486          moltype = AA  length = 13
FEATURE                 Location/Qualifiers
REGION                  1..13
                        note = chemically synthesized
source                  1..13
                        mol_type = protein
                        organism = synthetic construct
SEQUENCE: 486
ISSGLLSGRS DTH                                                          13

SEQ ID NO: 487          moltype = AA  length = 13
FEATURE                 Location/Qualifiers
REGION                  1..13
                        note = chemically synthesized
source                  1..13
                        mol_type = protein
                        organism = synthetic construct
SEQUENCE: 487
ISSGLLSGRS DYH                                                          13

SEQ ID NO: 488          moltype = AA  length = 13
FEATURE                 Location/Qualifiers
REGION                  1..13
                        note = chemically synthesized
```

```
source                  1..13
                        mol_type = protein
                        organism = synthetic construct
SEQUENCE: 488
ISSGLLSGRS DNP                                                      13

SEQ ID NO: 489          moltype = AA  length = 13
FEATURE                 Location/Qualifiers
REGION                  1..13
                        note = chemically synthesized
source                  1..13
                        mol_type = protein
                        organism = synthetic construct
SEQUENCE: 489
ISSGLLSGRS ANP                                                      13

SEQ ID NO: 490          moltype = AA  length = 13
FEATURE                 Location/Qualifiers
REGION                  1..13
                        note = chemically synthesized
source                  1..13
                        mol_type = protein
                        organism = synthetic construct
SEQUENCE: 490
ISSGLLSGRS ANI                                                      13

SEQ ID NO: 491          moltype = DNA  length = 39
FEATURE                 Location/Qualifiers
misc_feature            1..39
                        note = chemically synthesized
source                  1..39
                        mol_type = other DNA
                        organism = synthetic construct
SEQUENCE: 491
atatcgagtg gattgctgtc tggcagatct gacgatcac                          39

SEQ ID NO: 492          moltype = DNA  length = 39
FEATURE                 Location/Qualifiers
misc_feature            1..39
                        note = chemically synthesized
source                  1..39
                        mol_type = other DNA
                        organism = synthetic construct
SEQUENCE: 492
atatcgagtg gattgctgtc tggcagatct gacatacac                          39

SEQ ID NO: 493          moltype = DNA  length = 39
FEATURE                 Location/Qualifiers
misc_feature            1..39
                        note = chemically synthesized
source                  1..39
                        mol_type = other DNA
                        organism = synthetic construct
SEQUENCE: 493
atatcgagtg gattgctgtc tggcagatct gaccaacac                          39

SEQ ID NO: 494          moltype = DNA  length = 39
FEATURE                 Location/Qualifiers
misc_feature            1..39
                        note = chemically synthesized
source                  1..39
                        mol_type = other DNA
                        organism = synthetic construct
SEQUENCE: 494
atatcgagtg gattgctgtc tggcagatct gacactcac                          39

SEQ ID NO: 495          moltype = DNA  length = 39
FEATURE                 Location/Qualifiers
misc_feature            1..39
                        note = chemically synthesized
source                  1..39
                        mol_type = other DNA
                        organism = synthetic construct
SEQUENCE: 495
atatcgagtg gattgctgtc tggcagatct gactatcac                          39

SEQ ID NO: 496          moltype = DNA  length = 39
FEATURE                 Location/Qualifiers
misc_feature            1..39
```

```
                        note = chemically synthesized
source                  1..39
                        mol_type = other DNA
                        organism = synthetic construct
SEQUENCE: 496
attagctcag gccttcttag cggccgcagc gacaatccc                     39

SEQ ID NO: 497          moltype = DNA  length = 39
FEATURE                 Location/Qualifiers
misc_feature            1..39
                        note = chemically synthesized
source                  1..39
                        mol_type = other DNA
                        organism = synthetic construct
SEQUENCE: 497
atatcgagtg gattgctgtc tggcagatct gctaatccc                     39

SEQ ID NO: 498          moltype = DNA  length = 39
FEATURE                 Location/Qualifiers
misc_feature            1..39
                        note = chemically synthesized
source                  1..39
                        mol_type = other DNA
                        organism = synthetic construct
SEQUENCE: 498
atatcgagtg gattgctgtc tggcagatct gctaatata                     39

SEQ ID NO: 499          moltype = AA  length = 260
FEATURE                 Location/Qualifiers
REGION                  1..260
                        note = chemically synthesized
source                  1..260
                        mol_type = protein
                        organism = synthetic construct
SEQUENCE: 499
CISPRGCPDG PYVMYGSSGG SGGSGGSGIS SGLLSGRSDD HGSSGTQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260

SEQ ID NO: 500          moltype = AA  length = 260
FEATURE                 Location/Qualifiers
REGION                  1..260
                        note = chemically synthesized
source                  1..260
                        mol_type = protein
                        organism = synthetic construct
SEQUENCE: 500
CISPRGCPDG PYVMYGSSGG SGGSGGSGIS SGLLSGRSDI HGSSGTQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260

SEQ ID NO: 501          moltype = AA  length = 260
FEATURE                 Location/Qualifiers
REGION                  1..260
                        note = chemically synthesized
source                  1..260
                        mol_type = protein
                        organism = synthetic construct
SEQUENCE: 501
CISPRGCPDG PYVMYGSSGG SGGSGGSGIS SGLLSGRSDQ HGSSGTQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260

SEQ ID NO: 502          moltype = AA  length = 260
FEATURE                 Location/Qualifiers
REGION                  1..260
                        note = chemically synthesized
source                  1..260
                        mol_type = protein
                        organism = synthetic construct
SEQUENCE: 502
CISPRGCPDG PYVMYGSSGG SGGSGGSGIS SGLLSGRSDT HGSSGTQILL TQSPVILSVS  60
PGERVSFSCR ASQSIGTNIH WYQQRTNGSP RLLIKYASES ISGIPSRFSG SGSGTDFTLS  120
```

-continued

```
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260

SEQ ID NO: 503         moltype = AA  length = 260
FEATURE                Location/Qualifiers
REGION                 1..260
                       note = chemically synthesized
source                 1..260
                       mol_type = protein
                       organism = synthetic construct
SEQUENCE: 503
CISPRGCPDG PYVMYGSSGG SGGSGGSGIS SGLLSGRSDY HGSSGTQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260

SEQ ID NO: 504         moltype = AA  length = 260
FEATURE                Location/Qualifiers
REGION                 1..260
                       note = chemically synthesized
source                 1..260
                       mol_type = protein
                       organism = synthetic construct
SEQUENCE: 504
CISPRGCPDG PYVMYGSSGG SGGSGGSGIS SGLLSGRSDN PGSSGTQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260

SEQ ID NO: 505         moltype = AA  length = 260
FEATURE                Location/Qualifiers
REGION                 1..260
                       note = chemically synthesized
source                 1..260
                       mol_type = protein
                       organism = synthetic construct
SEQUENCE: 505
CISPRGCPDG PYVMYGSSGG SGGSGGSGIS SGLLSGRSAN PGSSGTQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260

SEQ ID NO: 506         moltype = AA  length = 260
FEATURE                Location/Qualifiers
REGION                 1..260
                       note = chemically synthesized
source                 1..260
                       mol_type = protein
                       organism = synthetic construct
SEQUENCE: 506
CISPRGCPDG PYVMYGSSGG SGGSGGSGIS SGLLSGRSAN IGSSGTQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                              260

SEQ ID NO: 507         moltype = AA  length = 252
FEATURE                Location/Qualifiers
REGION                 1..252
                       note = chemically synthesized
source                 1..252
                       mol_type = protein
                       organism = synthetic construct
SEQUENCE: 507
CNIWLVGGDC RGWQGGSSGG SISSGLLSGR SDDHGGGSDI QMTQSPSSLS ASVGDRVTIT  60
CRASQSISSY LNWYQQKPGK APKLLIYAAS SLQSGVPSRF SGSGSGTDFT LTISSLQPED  120
FATYYCQQTV VAPPLFGQGT KVEIKRTVAA PSVFIFPPSD EQLKSGTASV VCLLNNFYPR  180
EAKVQWKVDN ALQSGNSQES VTEQDSKDST YSLSSTLTLS KADYEKHKVY ACEVTHQGLS  240
SPVTKSFNRG EC                                                      252

SEQ ID NO: 508         moltype = AA  length = 252
FEATURE                Location/Qualifiers
REGION                 1..252
                       note = chemically synthesized
source                 1..252
```

```
                        mol_type = protein
                        organism = synthetic construct
SEQUENCE: 508
CNIWLVGGDC RGWQGGSSGG SISSGLLSGR SDIHGGGSDI QMTQSPSSLS ASVGDRVTIT  60
CRASQSISSY LNWYQQKPGK APKLLIYAAS SLQSGVPSRF SGSGSGTDFT LTISSLQPED  120
FATYYCQQTV VAPPLFGQGT KVEIKRTVAA PSVFIFPPSD EQLKSGTASV VCLLNNFYPR  180
EAKVQWKVDN ALQSGNSQES VTEQDSKDST YSLSSTLTLS KADYEKHKVY ACEVTHQGLS  240
SPVTKSFNRG EC                                                      252

SEQ ID NO: 509          moltype = AA  length = 252
FEATURE                 Location/Qualifiers
REGION                  1..252
                        note = chemically synthesized
source                  1..252
                        mol_type = protein
                        organism = synthetic construct
SEQUENCE: 509
CNIWLVGGDC RGWQGGSSGG SISSGLLSGR SDQHGGGSDI QMTQSPSSLS ASVGDRVTIT  60
CRASQSISSY LNWYQQKPGK APKLLIYAAS SLQSGVPSRF SGSGSGTDFT LTISSLQPED  120
FATYYCQQTV VAPPLFGQGT KVEIKRTVAA PSVFIFPPSD EQLKSGTASV VCLLNNFYPR  180
EAKVQWKVDN ALQSGNSQES VTEQDSKDST YSLSSTLTLS KADYEKHKVY ACEVTHQGLS  240
SPVTKSFNRG EC                                                      252

SEQ ID NO: 510          moltype = AA  length = 252
FEATURE                 Location/Qualifiers
REGION                  1..252
                        note = chemically synthesized
source                  1..252
                        mol_type = protein
                        organism = synthetic construct
SEQUENCE: 510
CNIWLVGGDC RGWQGGSSGG SISSGLLSGR SDTHGGGSDI QMTQSPSSLS ASVGDRVTIT  60
CRASQSISSY LNWYQQKPGK APKLLIYAAS SLQSGVPSRF SGSGSGTDFT LTISSLQPED  120
FATYYCQQTV VAPPLFGQGT KVEIKRTVAA PSVFIFPPSD EQLKSGTASV VCLLNNFYPR  180
EAKVQWKVDN ALQSGNSQES VTEQDSKDST YSLSSTLTLS KADYEKHKVY ACEVTHQGLS  240
SPVTKSFNRG EC                                                      252

SEQ ID NO: 511          moltype = AA  length = 252
FEATURE                 Location/Qualifiers
REGION                  1..252
                        note = chemically synthesized
source                  1..252
                        mol_type = protein
                        organism = synthetic construct
SEQUENCE: 511
CNIWLVGGDC RGWQGGSSGG SISSGLLSGR SDYHGGGSDI QMTQSPSSLS ASVGDRVTIT  60
CRASQSISSY LNWYQQKPGK APKLLIYAAS SLQSGVPSRF SGSGSGTDFT LTISSLQPED  120
FATYYCQQTV VAPPLFGQGT KVEIKRTVAA PSVFIFPPSD EQLKSGTASV VCLLNNFYPR  180
EAKVQWKVDN ALQSGNSQES VTEQDSKDST YSLSSTLTLS KADYEKHKVY ACEVTHQGLS  240
SPVTKSFNRG EC                                                      252

SEQ ID NO: 512          moltype = AA  length = 252
FEATURE                 Location/Qualifiers
REGION                  1..252
                        note = chemically synthesized
source                  1..252
                        mol_type = protein
                        organism = synthetic construct
SEQUENCE: 512
CNIWLVGGDC RGWQGGSSGG SISSGLLSGR SDNPGGGSDI QMTQSPSSLS ASVGDRVTIT  60
CRASQSISSY LNWYQQKPGK APKLLIYAAS SLQSGVPSRF SGSGSGTDFT LTISSLQPED  120
FATYYCQQTV VAPPLFGQGT KVEIKRTVAA PSVFIFPPSD EQLKSGTASV VCLLNNFYPR  180
EAKVQWKVDN ALQSGNSQES VTEQDSKDST YSLSSTLTLS KADYEKHKVY ACEVTHQGLS  240
SPVTKSFNRG EC                                                      252

SEQ ID NO: 513          moltype = AA  length = 252
FEATURE                 Location/Qualifiers
REGION                  1..252
                        note = chemically synthesized
source                  1..252
                        mol_type = protein
                        organism = synthetic construct
SEQUENCE: 513
CNIWLVGGDC RGWQGGSSGG SISSGLLSGR SANPGGGSDI QMTQSPSSLS ASVGDRVTIT  60
CRASQSISSY LNWYQQKPGK APKLLIYAAS SLQSGVPSRF SGSGSGTDFT LTISSLQPED  120
FATYYCQQTV VAPPLFGQGT KVEIKRTVAA PSVFIFPPSD EQLKSGTASV VCLLNNFYPR  180
EAKVQWKVDN ALQSGNSQES VTEQDSKDST YSLSSTLTLS KADYEKHKVY ACEVTHQGLS  240
SPVTKSFNRG EC                                                      252
```

```
SEQ ID NO: 514          moltype = AA  length = 252
FEATURE                 Location/Qualifiers
REGION                  1..252
                        note = chemically synthesized
source                  1..252
                        mol_type = protein
                        organism = synthetic construct
SEQUENCE: 514
CNIWLVGGDC RGWQGGSSGG SISSGLLSGR SANIGGGSDI QMTQSPSSLS ASVGDRVTIT  60
CRASQSISSY LNWYQQKPGK APKLLIYAAS SLQSGVPSRF SGSGSGTDFT LTISSLQPED  120
FATYYCQQTV VAPPLFGQGT KVEIKRTVAA PSVFIFPPSD EQLKSGTASV VCLLNNFYPR  180
EAKVQWKVDN ALQSGNSQES VTEQDSKDST YSLSSTLTLS KADYEKHKVY ACEVTHQGLS  240
SPVTKSFNRG EC                                                      252

SEQ ID NO: 515          moltype = AA  length = 18
FEATURE                 Location/Qualifiers
REGION                  1..18
                        note = chemically synthesized
source                  1..18
                        mol_type = protein
                        organism = synthetic construct
SEQUENCE: 515
AVGLLAPPGG LSGRSDDH                                                18

SEQ ID NO: 516          moltype = AA  length = 18
FEATURE                 Location/Qualifiers
REGION                  1..18
                        note = chemically synthesized
source                  1..18
                        mol_type = protein
                        organism = synthetic construct
SEQUENCE: 516
AVGLLAPPGG LSGRSDIH                                                18

SEQ ID NO: 517          moltype = AA  length = 18
FEATURE                 Location/Qualifiers
REGION                  1..18
                        note = chemically synthesized
source                  1..18
                        mol_type = protein
                        organism = synthetic construct
SEQUENCE: 517
AVGLLAPPGG LSGRSDQH                                                18

SEQ ID NO: 518          moltype = AA  length = 18
FEATURE                 Location/Qualifiers
REGION                  1..18
                        note = chemically synthesized
source                  1..18
                        mol_type = protein
                        organism = synthetic construct
SEQUENCE: 518
AVGLLAPPGG LSGRSDTH                                                18

SEQ ID NO: 519          moltype = AA  length = 18
FEATURE                 Location/Qualifiers
REGION                  1..18
                        note = chemically synthesized
source                  1..18
                        mol_type = protein
                        organism = synthetic construct
SEQUENCE: 519
AVGLLAPPGG LSGRSDYH                                                18

SEQ ID NO: 520          moltype = AA  length = 18
FEATURE                 Location/Qualifiers
REGION                  1..18
                        note = chemically synthesized
source                  1..18
                        mol_type = protein
                        organism = synthetic construct
SEQUENCE: 520
AVGLLAPPGG LSGRSDNP                                                18

SEQ ID NO: 521          moltype = AA  length = 18
FEATURE                 Location/Qualifiers
REGION                  1..18
                        note = chemically synthesized
source                  1..18
```

```
                        mol_type = protein
                        organism = synthetic construct
SEQUENCE: 521
AVGLLAPPGG LSGRSANP                                                18

SEQ ID NO: 522          moltype = AA  length = 18
FEATURE                 Location/Qualifiers
REGION                  1..18
                        note = chemically synthesized
source                  1..18
                        mol_type = protein
                        organism = synthetic construct
SEQUENCE: 522
AVGLLAPPGG LSGRSANI                                                18

SEQ ID NO: 523          moltype = DNA  length = 54
FEATURE                 Location/Qualifiers
misc_feature            1..54
                        note = chemically synthesized
source                  1..54
                        mol_type = other DNA
                        organism = synthetic construct
SEQUENCE: 523
gctgtgggac tgctggctcc tcctggtggc ctgtctggca gatctgacga tcac        54

SEQ ID NO: 524          moltype = DNA  length = 54
FEATURE                 Location/Qualifiers
misc_feature            1..54
                        note = chemically synthesized
source                  1..54
                        mol_type = other DNA
                        organism = synthetic construct
SEQUENCE: 524
gctgtgggac tgctggctcc tcctggtggc ctgtctggca gatctgacat acac        54

SEQ ID NO: 525          moltype = DNA  length = 54
FEATURE                 Location/Qualifiers
misc_feature            1..54
                        note = chemically synthesized
source                  1..54
                        mol_type = other DNA
                        organism = synthetic construct
SEQUENCE: 525
gctgtgggac tgctggctcc tcctggtggc ctgtctggca gatctgacca acac        54

SEQ ID NO: 526          moltype = DNA  length = 54
FEATURE                 Location/Qualifiers
misc_feature            1..54
                        note = chemically synthesized
source                  1..54
                        mol_type = other DNA
                        organism = synthetic construct
SEQUENCE: 526
gctgtgggac tgctggctcc tcctggtggc ctgtctggca gatctgacac tcac        54

SEQ ID NO: 527          moltype = DNA  length = 54
FEATURE                 Location/Qualifiers
misc_feature            1..54
                        note = chemically synthesized
source                  1..54
                        mol_type = other DNA
                        organism = synthetic construct
SEQUENCE: 527
gctgtgggac tgctggctcc tcctggtggc ctgtctggca gatctgacta tcac        54

SEQ ID NO: 528          moltype = DNA  length = 54
FEATURE                 Location/Qualifiers
misc_feature            1..54
                        note = chemically synthesized
source                  1..54
                        mol_type = other DNA
                        organism = synthetic construct
SEQUENCE: 528
gctgtgggac tgctggctcc tcctggtggc ctgtctggca gatctgacaa tccc        54

SEQ ID NO: 529          moltype = DNA  length = 54
FEATURE                 Location/Qualifiers
misc_feature            1..54
                        note = chemically synthesized
```

```
source                  1..54
                        mol_type = other DNA
                        organism = synthetic construct
SEQUENCE: 529
gctgtgggac tgctggctcc tcctggtggc ctgtctggca gatctgctaa tccc        54

SEQ ID NO: 530          moltype = DNA  length = 54
FEATURE                 Location/Qualifiers
misc_feature            1..54
                        note = chemically synthesized
source                  1..54
                        mol_type = other DNA
                        organism = synthetic construct
SEQUENCE: 530
gctgtgggac tgctggctcc tcctggtggc ctgtctggca gatctgctaa tata        54

SEQ ID NO: 531          moltype = AA  length = 265
FEATURE                 Location/Qualifiers
REGION                  1..265
                        note = chemically synthesized
source                  1..265
                        mol_type = protein
                        organism = synthetic construct
SEQUENCE: 531
CISPRGCPDG PYVMYGSSGG SGGSGGSGAV GLLAPPGGLS GRSDDHGSSG TQILLTQSPV  60
ILSVSPGERV SFSCRASQSI GTNIHWYQQR TNGSPRLLIK YASESISGIP SRFSGSGSGT  120
DFTLSINSVE SEDIADYYCQ QNNNWPTTFG AGTKLELKRT VAAPSVFIFP PSDEQLKSGT  180
ASVVCLLNNF YPREAKVQWK VDNALQSGNS QESVTEQDSK DSTYSLSSTL TLSKADYEKH  240
KVYACEVTHQ GLSSPVTKSF NRGEC                                        265

SEQ ID NO: 532          moltype = AA  length = 265
FEATURE                 Location/Qualifiers
REGION                  1..265
                        note = chemically synthesized
source                  1..265
                        mol_type = protein
                        organism = synthetic construct
SEQUENCE: 532
CISPRGCPDG PYVMYGSSGG SGGSGGSGAV GLLAPPGGLS GRSDIHGSSG TQILLTQSPV  60
ILSVSPGERV SFSCRASQSI GTNIHWYQQR TNGSPRLLIK YASESISGIP SRFSGSGSGT  120
DFTLSINSVE SEDIADYYCQ QNNNWPTTFG AGTKLELKRT VAAPSVFIFP PSDEQLKSGT  180
ASVVCLLNNF YPREAKVQWK VDNALQSGNS QESVTEQDSK DSTYSLSSTL TLSKADYEKH  240
KVYACEVTHQ GLSSPVTKSF NRGEC                                        265

SEQ ID NO: 533          moltype = AA  length = 265
FEATURE                 Location/Qualifiers
REGION                  1..265
                        note = chemically synthesized
source                  1..265
                        mol_type = protein
                        organism = synthetic construct
SEQUENCE: 533
CISPRGCPDG PYVMYGSSGG SGGSGGSGAV GLLAPPGGLS GRSDQHGSSG TQILLTQSPV  60
ILSVSPGERV SFSCRASQSI GTNIHWYQQR TNGSPRLLIK YASESISGIP SRFSGSGSGT  120
DFTLSINSVE SEDIADYYCQ QNNNWPTTFG AGTKLELKRT VAAPSVFIFP PSDEQLKSGT  180
ASVVCLLNNF YPREAKVQWK VDNALQSGNS QESVTEQDSK DSTYSLSSTL TLSKADYEKH  240
KVYACEVTHQ GLSSPVTKSF NRGEC                                        265

SEQ ID NO: 534          moltype = AA  length = 265
FEATURE                 Location/Qualifiers
REGION                  1..265
                        note = chemically synthesized
source                  1..265
                        mol_type = protein
                        organism = synthetic construct
SEQUENCE: 534
CISPRGCPDG PYVMYGSSGG SGGSGGSGAV GLLAPPGGLS GRSDTHGSSG TQILLTQSPV  60
ILSVSPGERV SFSCRASQSI GTNIHWYQQR TNGSPRLLIK YASESISGIP SRFSGSGSGT  120
DFTLSINSVE SEDIADYYCQ QNNNWPTTFG AGTKLELKRT VAAPSVFIFP PSDEQLKSGT  180
ASVVCLLNNF YPREAKVQWK VDNALQSGNS QESVTEQDSK DSTYSLSSTL TLSKADYEKH  240
KVYACEVTHQ GLSSPVTKSF NRGEC                                        265

SEQ ID NO: 535          moltype = AA  length = 265
FEATURE                 Location/Qualifiers
REGION                  1..265
                        note = chemically synthesized
source                  1..265
                        mol_type = protein
                        organism = synthetic construct
```

```
SEQUENCE: 535
CISPRGCPDG PYVMYGSSGG SGGSGGSGAV GLLAPPGGLS GRSDYHGSSG TQILLTQSPV  60
ILSVSPGERV SFSCRASQSI GTNIHWYQQR TNGSPRLLIK YASESISGIP SRFSGSGSGT  120
DFTLSINSVE SEDIADYYCQ QNNNWPTTFG AGTKLELKRT VAAPSVFIFP PSDEQLKSGT  180
ASVVCLLNNF YPREAKVQWK VDNALQSGNS QESVTEQDSK DSTYSLSSTL TLSKADYEKH  240
KVYACEVTHQ GLSSPVTKSF NRGEC                                        265

SEQ ID NO: 536         moltype = AA  length = 265
FEATURE                Location/Qualifiers
REGION                 1..265
                       note = chemically synthesized
source                 1..265
                       mol_type = protein
                       organism = synthetic construct
SEQUENCE: 536
CISPRGCPDG PYVMYGSSGG SGGSGGSGAV GLLAPPGGLS GRSDNPGSSG TQILLTQSPV  60
ILSVSPGERV SFSCRASQSI GTNIHWYQQR TNGSPRLLIK YASESISGIP SRFSGSGSGT  120
DFTLSINSVE SEDIADYYCQ QNNNWPTTFG AGTKLELKRT VAAPSVFIFP PSDEQLKSGT  180
ASVVCLLNNF YPREAKVQWK VDNALQSGNS QESVTEQDSK DSTYSLSSTL TLSKADYEKH  240
KVYACEVTHQ GLSSPVTKSF NRGEC                                        265

SEQ ID NO: 537         moltype = AA  length = 265
FEATURE                Location/Qualifiers
REGION                 1..265
                       note = chemically synthesized
source                 1..265
                       mol_type = protein
                       organism = synthetic construct
SEQUENCE: 537
CISPRGCPDG PYVMYGSSGG SGGSGGSGAV GLLAPPGGLS GRSANPGSSG TQILLTQSPV  60
ILSVSPGERV SFSCRASQSI GTNIHWYQQR TNGSPRLLIK YASESISGIP SRFSGSGSGT  120
DFTLSINSVE SEDIADYYCQ QNNNWPTTFG AGTKLELKRT VAAPSVFIFP PSDEQLKSGT  180
ASVVCLLNNF YPREAKVQWK VDNALQSGNS QESVTEQDSK DSTYSLSSTL TLSKADYEKH  240
KVYACEVTHQ GLSSPVTKSF NRGEC                                        265

SEQ ID NO: 538         moltype = AA  length = 265
FEATURE                Location/Qualifiers
REGION                 1..265
                       note = chemically synthesized
source                 1..265
                       mol_type = protein
                       organism = synthetic construct
SEQUENCE: 538
CISPRGCPDG PYVMYGSSGG SGGSGGSGAV GLLAPPGGLS GRSANIGSSG TQILLTQSPV  60
ILSVSPGERV SFSCRASQSI GTNIHWYQQR TNGSPRLLIK YASESISGIP SRFSGSGSGT  120
DFTLSINSVE SEDIADYYCQ QNNNWPTTFG AGTKLELKRT VAAPSVFIFP PSDEQLKSGT  180
ASVVCLLNNF YPREAKVQWK VDNALQSGNS QESVTEQDSK DSTYSLSSTL TLSKADYEKH  240
KVYACEVTHQ GLSSPVTKSF NRGEC                                        265

SEQ ID NO: 539         moltype = AA  length = 257
FEATURE                Location/Qualifiers
REGION                 1..257
                       note = chemically synthesized
source                 1..257
                       mol_type = protein
                       organism = synthetic construct
SEQUENCE: 539
CNIWLVGGDC RGWQGGSSGG SAVGLLAPPG GLSGRSDDHG GGSDIQMTQS PSSLSASVGD  60
RVTITCRASQ SISSYLNWYQ QKPGKAPKLL IYAASSLQSG VPSRFSGSGS GTDFTLTISS  120
LQPEDFATYY CQQTVVAPPL FGQGTKVEIK RTVAAPSVFI FPPSDEQLKS GTASVVCLLN  180
NFYPREAKVQ WKVDNALQSG NSQESVTEQD SKDSTYSLSS TLTLSKADYE KHKVYACEVT  240
HQGLSSPVTK SFNRGEC                                                 257

SEQ ID NO: 540         moltype = AA  length = 257
FEATURE                Location/Qualifiers
REGION                 1..257
                       note = chemically synthesized
source                 1..257
                       mol_type = protein
                       organism = synthetic construct
SEQUENCE: 540
CNIWLVGGDC RGWQGGSSGG SAVGLLAPPG GLSGRSDIHG GGSDIQMTQS PSSLSASVGD  60
RVTITCRASQ SISSYLNWYQ QKPGKAPKLL IYAASSLQSG VPSRFSGSGS GTDFTLTISS  120
LQPEDFATYY CQQTVVAPPL FGQGTKVEIK RTVAAPSVFI FPPSDEQLKS GTASVVCLLN  180
NFYPREAKVQ WKVDNALQSG NSQESVTEQD SKDSTYSLSS TLTLSKADYE KHKVYACEVT  240
HQGLSSPVTK SFNRGEC                                                 257

SEQ ID NO: 541         moltype = AA  length = 257
FEATURE                Location/Qualifiers
```

```
REGION                 1..257
                       note = chemically synthesized
source                 1..257
                       mol_type = protein
                       organism = synthetic construct
SEQUENCE: 541
CNIWLVGGDC RGWQGGSSGG SAVGLLAPPG GLSGRSDQHG GGSDIQMTQS PSSLSASVGD  60
RVTITCRASQ SISSYLNWYQ QKPGKAPKLL IYAASSLQSG VPSRFSGSGS GTDFTLTISS  120
LQPEDFATYY CQQTVVAPPL FGQGTKVEIK RTVAAPSVFI FPPSDEQLKS GTASVVCLLN  180
NFYPREAKVQ WKVDNALQSG NSQESVTEQD SKDSTYSLSS TLTLSKADYE KHKVYACEVT  240
HQGLSSPVTK SFNRGEC                                                 257

SEQ ID NO: 542         moltype = AA  length = 257
FEATURE                Location/Qualifiers
REGION                 1..257
                       note = chemically synthesized
source                 1..257
                       mol_type = protein
                       organism = synthetic construct
SEQUENCE: 542
CNIWLVGGDC RGWQGGSSGG SAVGLLAPPG GLSGRSDTHG GGSDIQMTQS PSSLSASVGD  60
RVTITCRASQ SISSYLNWYQ QKPGKAPKLL IYAASSLQSG VPSRFSGSGS GTDFTLTISS  120
LQPEDFATYY CQQTVVAPPL FGQGTKVEIK RTVAAPSVFI FPPSDEQLKS GTASVVCLLN  180
NFYPREAKVQ WKVDNALQSG NSQESVTEQD SKDSTYSLSS TLTLSKADYE KHKVYACEVT  240
HQGLSSPVTK SFNRGEC                                                 257

SEQ ID NO: 543         moltype = AA  length = 257
FEATURE                Location/Qualifiers
REGION                 1..257
                       note = chemically synthesized
source                 1..257
                       mol_type = protein
                       organism = synthetic construct
SEQUENCE: 543
CNIWLVGGDC RGWQGGSSGG SAVGLLAPPG GLSGRSDYHG GGSDIQMTQS PSSLSASVGD  60
RVTITCRASQ SISSYLNWYQ QKPGKAPKLL IYAASSLQSG VPSRFSGSGS GTDFTLTISS  120
LQPEDFATYY CQQTVVAPPL FGQGTKVEIK RTVAAPSVFI FPPSDEQLKS GTASVVCLLN  180
NFYPREAKVQ WKVDNALQSG NSQESVTEQD SKDSTYSLSS TLTLSKADYE KHKVYACEVT  240
HQGLSSPVTK SFNRGEC                                                 257

SEQ ID NO: 544         moltype = AA  length = 257
FEATURE                Location/Qualifiers
REGION                 1..257
                       note = chemically synthesized
source                 1..257
                       mol_type = protein
                       organism = synthetic construct
SEQUENCE: 544
CNIWLVGGDC RGWQGGSSGG SAVGLLAPPG GLSGRSDNPG GGSDIQMTQS PSSLSASVGD  60
RVTITCRASQ SISSYLNWYQ QKPGKAPKLL IYAASSLQSG VPSRFSGSGS GTDFTLTISS  120
LQPEDFATYY CQQTVVAPPL FGQGTKVEIK RTVAAPSVFI FPPSDEQLKS GTASVVCLLN  180
NFYPREAKVQ WKVDNALQSG NSQESVTEQD SKDSTYSLSS TLTLSKADYE KHKVYACEVT  240
HQGLSSPVTK SFNRGEC                                                 257

SEQ ID NO: 545         moltype = AA  length = 257
FEATURE                Location/Qualifiers
REGION                 1..257
                       note = chemically synthesized
source                 1..257
                       mol_type = protein
                       organism = synthetic construct
SEQUENCE: 545
CNIWLVGGDC RGWQGGSSGG SAVGLLAPPG GLSGRSANPG GGSDIQMTQS PSSLSASVGD  60
RVTITCRASQ SISSYLNWYQ QKPGKAPKLL IYAASSLQSG VPSRFSGSGS GTDFTLTISS  120
LQPEDFATYY CQQTVVAPPL FGQGTKVEIK RTVAAPSVFI FPPSDEQLKS GTASVVCLLN  180
NFYPREAKVQ WKVDNALQSG NSQESVTEQD SKDSTYSLSS TLTLSKADYE KHKVYACEVT  240
HQGLSSPVTK SFNRGEC                                                 257

SEQ ID NO: 546         moltype = AA  length = 257
FEATURE                Location/Qualifiers
REGION                 1..257
                       note = chemically synthesized
source                 1..257
                       mol_type = protein
                       organism = synthetic construct
SEQUENCE: 546
CNIWLVGGDC RGWQGGSSGG SAVGLLAPPG GLSGRSANIG GGSDIQMTQS PSSLSASVGD  60
RVTITCRASQ SISSYLNWYQ QKPGKAPKLL IYAASSLQSG VPSRFSGSGS GTDFTLTISS  120
LQPEDFATYY CQQTVVAPPL FGQGTKVEIK RTVAAPSVFI FPPSDEQLKS GTASVVCLLN  180
```

```
NFYPREAKVQ WKVDNALQSG NSQESVTEQD SKDSTYSLSS TLTLSKADYE KHKVYACEVT  240
HQGLSSPVTK SFNRGEC                                                 257

SEQ ID NO: 547          moltype = AA  length = 8
FEATURE                 Location/Qualifiers
REGION                  1..8
                        note = chemically synthesized
source                  1..8
                        mol_type = protein
                        organism = synthetic construct
SEQUENCE: 547
LSGRSDDH                                                           8

SEQ ID NO: 548          moltype = AA  length = 8
FEATURE                 Location/Qualifiers
REGION                  1..8
                        note = chemically synthesized
source                  1..8
                        mol_type = protein
                        organism = synthetic construct
SEQUENCE: 548
LSGRSDIH                                                           8

SEQ ID NO: 549          moltype = AA  length = 8
FEATURE                 Location/Qualifiers
REGION                  1..8
                        note = chemically synthesized
source                  1..8
                        mol_type = protein
                        organism = synthetic construct
SEQUENCE: 549
LSGRSDQH                                                           8

SEQ ID NO: 550          moltype = AA  length = 8
FEATURE                 Location/Qualifiers
REGION                  1..8
                        note = chemically synthesized
source                  1..8
                        mol_type = protein
                        organism = synthetic construct
SEQUENCE: 550
LSGRSDTH                                                           8

SEQ ID NO: 551          moltype = AA  length = 8
FEATURE                 Location/Qualifiers
REGION                  1..8
                        note = chemically synthesized
source                  1..8
                        mol_type = protein
                        organism = synthetic construct
SEQUENCE: 551
LSGRSDYH                                                           8

SEQ ID NO: 552          moltype = AA  length = 8
FEATURE                 Location/Qualifiers
REGION                  1..8
                        note = chemically synthesized
source                  1..8
                        mol_type = protein
                        organism = synthetic construct
SEQUENCE: 552
LSGRSDNP                                                           8

SEQ ID NO: 553          moltype = AA  length = 8
FEATURE                 Location/Qualifiers
REGION                  1..8
                        note = chemically synthesized
source                  1..8
                        mol_type = protein
                        organism = synthetic construct
SEQUENCE: 553
LSGRSANP                                                           8

SEQ ID NO: 554          moltype = AA  length = 8
FEATURE                 Location/Qualifiers
REGION                  1..8
                        note = chemically synthesized
source                  1..8
                        mol_type = protein
```

```
                        organism = synthetic construct
SEQUENCE: 554
LSGRSANI                                                            8

SEQ ID NO: 555          moltype = AA  length = 13
FEATURE                 Location/Qualifiers
REGION                  1..13
                        note = chemically synthesized
source                  1..13
                        mol_type = protein
                        organism = synthetic construct
SEQUENCE: 555
ISSGLLSGRS DNI                                                      13

SEQ ID NO: 556          moltype = DNA  length = 39
FEATURE                 Location/Qualifiers
misc_feature            1..39
                        note = chemically synthesized
source                  1..39
                        mol_type = other DNA
                        organism = synthetic construct
SEQUENCE: 556
atatcgagtg gattgctgtc tggcagatct gacaatata                          39

SEQ ID NO: 557          moltype = AA  length = 18
FEATURE                 Location/Qualifiers
REGION                  1..18
                        note = chemically synthesized
source                  1..18
                        mol_type = protein
                        organism = synthetic construct
SEQUENCE: 557
AVGLLAPPGG LSGRSDNI                                                 18

SEQ ID NO: 558          moltype = DNA  length = 54
FEATURE                 Location/Qualifiers
misc_feature            1..54
                        note = chemically synthesized
source                  1..54
                        mol_type = other DNA
                        organism = synthetic construct
SEQUENCE: 558
gctgtgggac tgctggctcc tcctggtggc ctgtctggca gatctgacaa tata        54

SEQ ID NO: 559          moltype = AA  length = 260
FEATURE                 Location/Qualifiers
REGION                  1..260
                        note = chemically synthesized
source                  1..260
                        mol_type = protein
                        organism = synthetic construct
SEQUENCE: 559
CISPRGCPDG PYVMYGSSGG SGGSGGSGIS SGLLSGRSDN IGSSGTQILL TQSPVILSVS  60
PGERVSFSCR ASQSIGTNIH WYQQRTNGSP RLLIKYASES ISGIPSRFSG SGSGTDFTLS  120
INSVESEDIA DYYCQQNNNW PTTFGAGTKL ELKRTVAAPS VFIFPPSDEQ LKSGTASVVC  180
LLNNFYPREA KVQWKVDNAL QSGNSQESVT EQDSKDSTYS LSSTLTLSKA DYEKHKVYAC  240
EVTHQGLSSP VTKSFNRGEC                                               260

SEQ ID NO: 560          moltype = AA  length = 265
FEATURE                 Location/Qualifiers
REGION                  1..265
                        note = chemically synthesized
source                  1..265
                        mol_type = protein
                        organism = synthetic construct
SEQUENCE: 560
CISPRGCPDG PYVMYGSSGG SGGSGGSGAV GLLAPPGGLS GRSDNIGSSG TQILLTQSPV  60
ILSVSPGERV SFSCRASQSI GTNIHWYQQR TNGSPRLLIK YASESISGIP SRFSGSGSGT  120
DFTLSINSVE SEDIADYYCQ QNNNWPTTFG AGTKLELKRT VAAPSVFIFP PSDEQLKSGT  180
ASVVCLLNNF YPREAKVQWK VDNALQSGNS QESVTEQDSK DSTYSLSSTL TLSKADYEKH  240
KVYACEVTHQ GLSSPVTKSF NRGEC                                         265

SEQ ID NO: 561          moltype = AA  length = 252
FEATURE                 Location/Qualifiers
REGION                  1..252
                        note = chemically synthesized
source                  1..252
                        mol_type = protein
                        organism = synthetic construct
```

-continued

```
SEQUENCE: 561
CNIWLVGGDC RGWQGGSSGG SISSGLLSGR SDNIGGGSDI QMTQSPSSLS ASVGDRVTIT  60
CRASQSISSY LNWYQQKPGK APKLLIYAAS SLQSGVPSRF SGSGSGTDFT LTISSLQPED  120
FATYYCQQTV VAPPLFGQGT KVEIKRTVAA PSVFIFPPSD EQLKSGTASV VCLLNNFYPR  180
EAKVQWKVDN ALQSGNSQES VTEQDSKDST YSLSSTLTLS KADYEKHKVY ACEVTHQGLS  240
SPVTKSFNRG EC                                                      252

SEQ ID NO: 562          moltype = AA  length = 257
FEATURE                 Location/Qualifiers
REGION                  1..257
                        note = chemically synthesized
source                  1..257
                        mol_type = protein
                        organism = synthetic construct
SEQUENCE: 562
CNIWLVGGDC RGWQGGSSGG SAVGLLAPPG GLSGRSDNIG GGSDIQMTQS PSSLSASVGD  60
RVTITCRASQ SISSYLNWYQ QKPGKAPKLL IYAASSLQSG VPSRFSGSGS GTDFTLTISS  120
LQPEDFATYY CQQTVVAPPL FGQGTKVEIK RTVAAPSVFI FPPSDEQLKS GTASVVCLLN  180
NFYPREAKVQ WKVDNALQSG NSQESVTEQD SKDSTYSLSS TLTLSKADYE KHKVYACEVT  240
HQGLSSPVTK SFNRGEC                                                 257
```

MATRIX METALLOPROTEASE-CLEAVABLE AND SERINE PROTEASE-CLEAVABLE SUBSTRATES AND METHODS OF USE THEREOF

CROSS-REFERENCE TO RELATED APPLICATIONS

This application is a divisional U.S. Ser. No. 17/360,809, filed Jun. 28, 2021, which is a divisional of U.S. Ser. No. 15/002,131, filed Jan. 20, 2016, now U.S. Pat. No. 11,046, 759, which claims the benefit of U.S. Provisional Application No. 62/105,490, filed Jan. 20, 2015, U.S. Provisional Application No. 62/258,015, filed Nov. 20, 2015, U.S. Provisional Application No. 62/277,771, filed Jan. 12, 2016, and U.S. Provisional Application No. 62/278,713, filed Jan. 14, 2016, the contents of each of which are incorporated herein by reference in their entirety.

INCORPORATION OF SEQUENCE LISTING

The contents of the text file named "CYTX027.XML", which was created on Dec. 5, 2022, and is 782,839 bytes in size, are hereby incorporated by reference in their entirety.

FIELD OF THE INVENTION

The invention relates generally to polypeptides that include at least a first cleavable moiety (CM1) that is a substrate for at least one matrix metalloprotease (MMP) and at least a second cleavable moiety (CM2) that is a substrate for at least one serine protease (SP), to activatable antibodies and other larger molecules that include these polypeptides that include at least a CM1 that is a substrate for at least one MMP protease and a CM2 that is a substrate for at least one SP protease, and to methods of making and using these polypeptides that include at least a CM1 that is a substrate for at least one MMP protease and a CM2 that is a substrate for at least one SP protease in a variety of therapeutic, diagnostic and prophylactic indications.

BACKGROUND OF THE INVENTION

Proteases are enzymes that degrade proteins by cleaving the peptide bonds between amino acid residues. Proteases occur naturally in all organisms and are involved in a variety of physiological reactions from simple degradation to highly regulated pathways. Some proteases are known to break specific peptide bonds based on the presence of a particular amino acid sequence within a protein.

Accordingly, there exists a need to identify new substrates for proteases and to use these substrates in a variety of therapeutic, diagnostic and prophylactic indications.

SUMMARY OF THE INVENTION

The disclosure provides amino acid sequences that include at least a first cleavable moiety (CM1) that is a substrate for at least one matrix metalloprotease (MMP) and at least a second cleavable moiety (CM2) that is a substrate for at least one serine protease (SP). These amino acid sequences are collectively referred to herein as "CM1-CM2 substrates." This term is not intended to convey any requirement regarding the orientation or other structural arrangement of the first cleavable moiety (CM1) that is a substrate for at least one matrix metalloprotease (MMP) and at least a second cleavable moiety (CM2) that is a substrate for at least one serine protease (SP). Thus, the term "CM1-CM2 substrates" encompasses CM1-CM2 substrates having the structural arrangement from N-terminus to C-terminus as follows: CM1-CM2 or CM2-CM1. The term "CM1-CM2 substrates" also encompasses substrates where at least a portion of the CM1 sequence overlaps with at least a portion of the CM2 sequence.

The CM1-CM2 substrates described herein are useful in a variety of therapeutic, diagnostic and prophylactic indications. For example, these CM1-CM2 substrates are useful in activatable antibodies that include antibodies or antigen-binding fragments thereof (AB) that include at least one masking moiety (MM) linked to at least one antigen- or epitope-binding domain of the AB such that coupling of the MM reduces the ability of the AB to bind its target.

In some embodiments, the activatable antibody includes at least a first CM (CM1) and a second CM (CM2). In some embodiments, at least a portion of the CM1 substrate sequence overlaps with at least a portion of the CM2 sequence. In some embodiments, the CM1 substrate sequence and the CM2 substrate sequence share at least one amino acid residue in common. In some embodiments, the CM1 substrate sequence and the CM2 substrate sequence share at least two amino acid residues in common. In some embodiments, the CM1 substrate sequence and the CM2 substrate sequence share at least three amino acid residues in common. In some embodiments, the CM1 substrate sequence and the CM2 substrate sequence share three or more amino acid residues in common.

In some embodiments, CM1 and CM2 are separate polypeptides that are operably linked together.

In some embodiments, CM1 and CM2 are separate polypeptides that are directly linked together, i.e., the N-terminus of one substrate is linked directly to the C-terminus of the other substrate polypeptide. In some embodiments, the N-terminus of the CM1 is linked directly to the C-terminus of the CM2. In some embodiments, the N-terminus of the CM2 is linked directly to the C-terminus of the CM1.

In some embodiments, CM1 and CM2 are separate polypeptides that are operably linked together via at least one linking moiety.

In some embodiments, the first cleavable moiety CM1 and the second cleavable moiety CM2 in the activatable antibody in the uncleaved state have the structural arrangement from N-terminus to C-terminus as follows: MM-CM1-CM2-AB, AB-CM2-CM1-MM, MM-CM2-CM1-AB, or AB-CM1-CM2-MM.

In some embodiments, the activatable antibody includes a linking peptide (LP') between CM1 and CM2. In some embodiments, the activatable antibody includes a linking peptide (LP'') between the masking moiety (MM) and CM1. In some embodiments, the activatable antibody includes a linking peptide (LP''') between CM2 and AB. In some embodiments, the activatable antibody includes a linking peptide (LP'') between the MM and CM1 and a linking peptide (LP') between CM2 and AB. In some embodiments, the activatable antibody includes a linking peptide between the MM and CM1 (LP'') and a linking peptide between CM1 and CM2 (LP'). In some embodiments, the activatable antibody includes a linking peptide (LP') between CM1 and CM2 and a linking peptide (LP''') between CM2 and AB. In some embodiments, the activatable antibody includes a linking peptide (LP'') between the MM and CM1, a linking peptide (LP') between CM1 and CM2, and a linking peptide (LP''') between CM2 and AB.

In some embodiments, the activatable antibody includes a linking peptide (LP') between CM1 and CM2. In some embodiments, the activatable antibody includes a linking peptide (LP") between the AB and CM1. In some embodiments, the activatable antibody includes a linking peptide (LP"') between CM2 and the masking moiety (MM). In some embodiments, the activatable antibody includes a linking peptide (LP") between the AB and CM1 and a linking peptide (LP"') between CM2 and MM. In some embodiments, the activatable antibody includes a linking peptide between the AB and CM1 (LP") and a linking peptide between CM1 and CM2 (LP'). In some embodiments, the activatable antibody includes a linking peptide (LP') between CM1 and CM2 and a linking peptide (LP') between CM2 and MM. In some embodiments, the activatable antibody includes a linking peptide (LP") between the AB and CM1, a linking peptide (LP') between CM1 and CM2, and a linking peptide (LP"') between CM2 and MM.

In some embodiments, LP' is GG. In some embodiments, LP' is GGSGGS (SEQ ID NO: 350).

In some embodiments, CM1 is a substrate for at least one matrix metalloprotease (MMP). Examples of MMPs include MMP1; MMP2; MMP3; MMP1; MMP8; MMP9; MMP10; MMP11; MMP12; MMP13; MMP14; MMP15; MMP16; MMP17; MMP19; MMP20; MMP23; MMP24; MMP26; and MMP27.

In some embodiments, CM1 is a substrate for MMP2, MMP9, MMP14, MMP1, MMP3, MMP13, MMP17, MMP11, and/or MMP19. In some embodiments, CM1 is a substrate for MMP2. In some embodiments, CM1 is a substrate for MMP9. In some embodiments, CM1 is a substrate for MMP14. In some embodiments, CM1 is a substrate for two or more MMPs. In some embodiments, CM1 is a substrate for at least MMP9 and MMP14. In some embodiments, CM1 is a substrate for at least MMP2 and MMP9. In some embodiments, CM1 is a substrate for at least MMP2 and MMP14. In some embodiments, CM1 is a substrate for three or more MMPs. In some embodiments, CM1 is a substrate for at least MMP2, MMP9, and MMP14. In some embodiments, the CM1 comprises two or more substrates for the same MMP. In some embodiments, the CM1 comprises at least two or more MMP2 substrates. In some embodiments, the CM1 comprises at least two or more MMP9 substrates. In some embodiments, the CM1 comprises at least two or more MMP14 substrates.

In some embodiments, CM1 is a substrate for an MMP and includes at least the sequence ISSGLLSS (SEQ ID NO: 20); QNQALRMA (SEQ ID NO: 21); AQNLLGMV (SEQ ID NO: 351); STFPFGMF (SEQ ID NO: 352); PVGYTSSL (SEQ ID NO: 353); DWLYWPGI (SEQ ID NO: 354); MIAPVAYR (SEQ ID NO: 355); RPSPMWAY (SEQ ID NO: 356); WATPRPMR (SEQ ID NO: 357); FRLLDWQW (SEQ ID NO: 358); LKAAPRWA (SEQ ID NO: 359); GPSHLVLT (SEQ ID NO: 360); LPGGLSPW (SEQ ID NO: 361); MGLFSEAG (SEQ ID NO: 362); SPLPLRVP (SEQ ID NO: 363); RMHLRSLG (SEQ ID NO: 364); LAAPLGLL (SEQ ID NO: 365); AVGLLAPP (SEQ ID NO: 366); LLAPSHRA (SEQ ID NO: 367); PAGLWLDP (SEQ ID NO: 368); ISSGLSS (SEQ ID NO: 369); ISSGL (SEQ ID NO: 480); ISSGLLS (SEQ ID NO: 481); ISSGLL (SEQ ID NO: 482); and/or VHMPLGFLGP (SEQ ID NO: 411).

In some embodiments, the CM1 comprises the amino acid sequence ISSGLLSS (SEQ ID NO: 20). In some embodiments, the CM1 comprises the amino acid sequence QNQALRMA (SEQ ID NO: 21). In some embodiments, the CM1 comprises the amino acid sequence AQNLLGMV (SEQ ID NO: 351). In some embodiments, the CM1 comprises the amino acid sequence STFPFGMF (SEQ ID NO: 352). In some embodiments, the CM1 comprises the amino acid sequence PVGYTSSL (SEQ ID NO: 353). In some embodiments, the CM1 comprises the amino acid sequence DWLYWPGI (SEQ ID NO: 354). In some embodiments, the CM1 comprises the amino acid sequence MIAPVAYR (SEQ ID NO: 355). In some embodiments, the CM1 comprises the amino acid sequence RPSPMWAY (SEQ ID NO: 356). In some embodiments, the CM1 comprises the amino acid sequence WATPRPMR (SEQ ID NO: 357). In some embodiments, the CM1 comprises the amino acid sequence FRLLDWQW (SEQ ID NO: 358). In some embodiments, the CM1 comprises the amino acid sequence LKAAPRWA (SEQ ID NO: 359). In some embodiments, the CM1 comprises the amino acid sequence GPSHLVLT (SEQ ID NO: 360). In some embodiments, the CM1 comprises the amino acid sequence LPGGLSPW (SEQ ID NO: 361). In some embodiments, the CM1 comprises the amino acid sequence MGLFSEAG (SEQ ID NO: 362). In some embodiments, the CM1 comprises the amino acid sequence SPLPLRVP (SEQ ID NO: 363). In some embodiments, the CM1 comprises the amino acid sequence RMHLRSLG (SEQ ID NO: 364). In some embodiments, the CM1 comprises the amino acid sequence LAAPLGLL (SEQ ID NO: 365). In some embodiments, the CM1 comprises the amino acid sequence AVGLLAPP (SEQ ID NO: 366). In some embodiments, the CM1 comprises the amino acid sequence LLAPSHRA (SEQ ID NO: 367). In some embodiments, the CM1 comprises the amino acid sequence PAGLWLDP (SEQ ID NO: 368). In some embodiments, the CM1 comprises the amino acid sequence ISSGLSS (SEQ ID NO: 369). In some embodiments, CM1 comprises the amino acid sequence VHMPLGFLGP (SEQ ID NO: 411). In some embodiments, CM1 comprises the amino acid sequence ISSGL (SEQ ID NO: 480). In some embodiments, CM1 comprises the amino acid sequence ISSGLLS (SEQ ID NO: 481). In some embodiments, CM1 comprises the amino acid sequence ISSGLL (SEQ ID NO: 482).

In some embodiments, CM2 is a substrate for at least one serine protease (SP). In some embodiments, the SP is selected from u-type plasminogen activator (uPA, also referred to as urokinase), matriptase (also referred to herein as MT-SP1 or MTSP1), and combinations thereof. Examples of other SP that cleave a CM2 described herein include, by way of non-limiting example, activated protein C; Cathepsin A; Cathepsin G; Chymase; a coagulation factor protease such as, e.g., FVIIa, FIXa, FXa, FXIa, FXIIa; Elastase; Granzyme B; Guanidinobenzoatase; HtrA1; Human Neutrophil Elastase; Lactoferrin; Marapsin; NS3/4A; PACE4; Plasmin; PSA; tPA; Thrombin; Tryptase; a Type II Transmembrane Serine Protease (TTSP) such as, e.g., DESC1, DPP-4, FAP, Hepsin, Matriptase-2, TMPRSS2, TMPRSS3, and/or TMPRSS4.

For example, suitable CM2 are cleaved by at least one serine protease and include the sequence TGRGPSWV (SEQ ID NO: 370); SARGPSRW (SEQ ID NO: 371); TARGPSFK (SEQ ID NO: 372); LSGRSDNH (SEQ ID NO: 18); GGWHTGRN (SEQ ID NO: 373); HTGRSGAL (SEQ ID NO: 374); PLTGRSGG (SEQ ID NO: 375); AARGPAIH (SEQ ID NO: 376); RGPAFNPM (SEQ ID NO: 377); SSRGPAYL (SEQ ID NO: 378); RGPATPIM (SEQ ID NO: 379); RGPA (SEQ ID NO: 380); LSGRSGNH (SEQ ID NO: 412); TSTSGRSANPRG (SEQ ID NO: 413); TSGRSANP (SEQ ID NO: 414); SGRSANPRG (SEQ ID NO: 468); VAGRSMRP (SEQ ID NO: 415); LSGRSDDH (SEQ ID NO: 547); LSGRSDIH (SEQ ID NO: 548); LSGRSDQH (SEQ ID NO: 549); LSGRSDTH (SEQ ID NO: 550); LSGRSDYH (SEQ ID NO: 551); LSGRSDNP (SEQ ID NO: 552); LSGRSANP (SEQ ID NO: 553); LSGRSANI (SEQ ID NO: 554); and/or LSGRSDNI (SEQ ID NO: 71).

In some embodiments, CM2 comprises the amino acid sequence TGRGPSWV (SEQ ID NO: 370). In some embodiments, CM2 comprises the amino acid sequence SARGPSRW (SEQ ID NO: 371). In some embodiments, CM2 comprises the amino acid sequence TARGPSFK (SEQ ID NO: 372). In some embodiments, CM2 comprises the amino acid sequence LSGRSDNH (SEQ ID NO: 18). In some embodiments, CM2 comprises the amino acid sequence GGWHTGRN (SEQ ID NO: 373). In some embodiments, CM2 comprises the amino acid sequence HTGRSGAL (SEQ ID NO: 374). In some embodiments, CM2 comprises the amino acid sequence PLTGRSGG (SEQ ID NO: 375). In some embodiments, CM2 comprises the amino acid sequence AARGPAIH (SEQ ID NO: 376). In some embodiments, CM2 comprises the amino acid sequence RGPAFNPM (SEQ ID NO: 377). In some embodiments, CM2 comprises the amino acid sequence SSRGPAYL (SEQ ID NO: 378). In some embodiments, CM2 comprises the amino acid sequence RGPATPIM (SEQ ID NO: 379). In some embodiments, CM2 comprises the amino acid sequence RGPA (SEQ ID NO: 380). In some embodiments, CM2 comprises the amino acid sequence LSGRSGNH (SEQ ID NO: 412). In some embodiments, CM2 comprises the amino acid sequence TSTSGRSANPRG (SEQ ID NO: 413). In some embodiments, the CM2 comprises the amino acid sequence SGRSANPRG (SEQ ID NO: 468). In some embodiments, CM2 comprises the amino acid sequence TSGRSANP (SEQ ID NO: 414). In some embodiments, CM2 comprises the amino acid sequence VAGRSMRP (SEQ ID NO: 415). In some embodiments, CM2 comprises the amino acid sequence LSGRSDDH (SEQ ID NO: 547). In some embodiments, CM2 comprises the amino acid sequence LSGRSDIH (SEQ ID NO: 548). In some embodiments, CM2 comprises the amino acid sequence LSGRSDQH (SEQ ID NO: 549). In some embodiments, CM2 comprises the amino acid sequence LSGRSDTH (SEQ ID NO: 550). In some embodiments, CM2 comprises the amino acid sequence LSGRSDYH (SEQ ID NO: 551). In some embodiments, CM2 comprises the amino acid sequence LSGRSDNP (SEQ ID NO: 552). In some embodiments, CM2 comprises the amino acid sequence LSGRSANP (SEQ ID NO: 553). In some embodiments, CM2 comprises the amino acid sequence LSGRSANI (SEQ ID NO: 554). In some embodiments, CM2 comprises the amino acid sequence LSGRSDNI (SEQ ID NO: 71).

In some embodiments, the CM1-CM2 substrate includes the sequence ISSGLLSGRSDNH (SEQ ID NO: 1); ISSGLLSSGGSGGSLSGRSDNH (SEQ ID NO: 2); AVGLLAPPGGTSTSGRSANPRG (SEQ ID NO: 3); TSTSGRSANPRGGGAVGLLAPP (SEQ ID NO: 4); VHMPLGFLGPGGTSTSGRSANPRG (SEQ ID NO: 5); TSTSGRSANPRGGGVHMPLGFLGP (SEQ ID NO: 6); AVGLLAPPGGLSGRSDNH (SEQ ID NO: 7); LSGRSDNHGGAVGLLAPP (SEQ ID NO: 8); VHMPLGFLGPGGLSGRSDNH (SEQ ID NO: 9); LSGRSDNHGGVHMPLGFLGP (SEQ ID NO: 10); LSGRSDNHGGSGGSISSGLLSS (SEQ ID NO: 11); LSGRSGNHGGSGGSISSGLLSS (SEQ ID NO: 12); ISSGLLSSGGSGGSLSGRSGNH (SEQ ID NO: 13); LSGRSDNHGGSGGSQNQALRMA (SEQ ID NO: 14); QNQALRMAGGSGGSLSGRSDNH (SEQ ID NO: 15); LSGRSGNHGGSGGSQNQALRMA (SEQ ID NO: 16); QNQALRMAGGSGGSLSGRSGNH (SEQ ID NO: 17); ISSGLLSGRSGNH (SEQ ID NO: 22); ISSGLLSGRSANPRG (SEQ ID NO: 469); AVGLLAPPTSGRSANPRG (SEQ ID NO: 470); AVGLLAPPSGRSANPRG (SEQ ID NO: 471); ISSGLLSGRSDDH (SEQ ID NO: 483); ISSGLLSGRSDIH (SEQ ID NO: 484); ISSGLLSGRSDQH (SEQ ID NO: 485); ISSGLLSGRSDTH (SEQ ID NO: 486); ISSGLLSGRSDYH (SEQ ID NO: 487); ISSGLLSGRSDNP (SEQ ID NO: 488); ISSGLLSGRSANP (SEQ ID NO: 489); ISSGLLSGRSANI (SEQ ID NO: 490); AVGLLAPPGGLSGRSDDH (SEQ ID NO: 515); AVGLLAPPGGLSGRSDIH (SEQ ID NO: 516); AVGLLAPPGGLSGRSDQH (SEQ ID NO: 517); AVGLLAPPGGLSGRSDTH (SEQ ID NO: 518); AVGLLAPPGGLSGRSDYH (SEQ ID NO: 519); AVGLLAPPGGLSGRSDNP (SEQ ID NO: 520); AVGLLAPPGGLSGRSANP (SEQ ID NO: 521); AVGLLAPPGGLSGRSANI (SEQ ID NO: 522); ISSGLLSGRSDNI (SEQ ID NO: 555); and/or AVGLLAPPGGLSGRSDNI (SEQ ID NO: 557).

In some embodiments, the CM1-CM2 substrate includes the sequence ISSGLLSGRSDNH (SEQ ID NO: 1). In some embodiments, the CM1-CM2 substrate includes the sequence ISSGLLSSGGSGGSLSGRSDNH (SEQ ID NO: 2). In some embodiments, the CM1-CM2 substrate includes the sequence AVGLLAPPGGTSTSGRSANPRG (SEQ ID NO: 3).

In some embodiments, the CM1-CM2 substrate includes the sequence TSTSGRSANPRGGGAVGLLAPP (SEQ ID NO: 4). In some embodiments, the CM1-CM2 substrate includes the sequence VHMPLGFLGPGGTSTSGRSANPRG (SEQ ID NO: 5). In some embodiments, the CM1-CM2 substrate includes the sequence TSTSGRSANPRGGGVHMPLGFLGP (SEQ ID NO: 6). In some embodiments, the CM1-CM2 substrate includes the sequence AVGLLAPPGGLSGRSDNH (SEQ ID NO: 7). In some embodiments, the CM1-CM2 substrate includes the sequence LSGRSDNHGGAVGLLAPP (SEQ ID NO: 8). In some embodiments, the CM1-CM2 substrate includes the sequence VHMPLGFLGPGGLSGRSDNH (SEQ ID NO: 9). In some embodiments, the CM1-CM2 substrate includes the sequence LSGRSDNHGGVHMPLGFLGP (SEQ ID NO: 10). In some embodiments, the CM1-CM2 substrate includes the sequence LSGRSDNHGGSGGSISSGLLSS (SEQ ID NO: 11). In some embodiments, the CM1-CM2 substrate includes the sequence LSGRSGNHGGSGGSISSGLLSS (SEQ ID NO: 12). In some embodiments, the CM1-CM2 substrate includes the sequence ISSGLLSSGGSGGSLSGRSGNH (SEQ ID NO: 13). In some embodiments, the CM1-CM2 substrate includes the sequence LSGRSDNHGGSGGSQNQALRMA (SEQ ID NO: 14). In some embodiments, the CM1-CM2 substrate includes the sequence QNQALRMAGGSGGSLSGRSDNH (SEQ ID NO: 15). In some embodiments, the CM1-CM2 substrate includes the sequence LSGRSGNHGGSGGSQNQALRMA (SEQ ID NO: 16). In some embodiments, the CM1-CM2 substrate includes the sequence QNQALRMAGGSGGSLSGRSGNH (SEQ ID NO: 17). In some embodiments, the CM1-CM2 substrate includes the sequence ISSGLLSGRSGNH (SEQ ID NO: 22). In some embodiments, the CM1-CM2 substrate includes the sequence ISSGLLSGRSANPRG (SEQ ID NO: 469). In some embodiments, the CM1-CM2 substrate includes the sequence AVGLLAPPTSGRSANPRG (SEQ ID NO: 470). In some embodiments, the CM1-CM2 substrate includes the sequence AVGLLAPPSGRSANPRG (SEQ ID NO: 471). In some embodiments, the CM1-CM2 substrate includes the sequence ISSGLLSGRSDDH (SEQ ID NO: 483). In some embodiments, the CM1-CM2 substrate includes the sequence ISSGLLSGRSDIH (SEQ ID NO: 484). In some embodiments, the CM1-CM2 substrate includes the sequence ISSGLLSGRSDQH (SEQ ID NO: 485). In some embodiments, the CM1-CM2 substrate includes the sequence. In some embodiments, the CM1-CM2 substrate includes the sequence ISSGLLSGRSDTH (SEQ ID NO: 486). In some embodiments, the CM1-CM2 substrate includes the sequence ISSGLLSGRSDYH (SEQ ID NO: 487). In some embodiments, the CM1-CM2 substrate includes the sequence ISSGLLSGRSDNP (SEQ ID NO: 488). In some embodiments, the CM1-CM2 substrate includes the sequence ISSGLLSGRSANP (SEQ ID NO: 489). In some embodiments, the CM1-CM2 substrate includes the sequence ISSGLLSGRSANI (SEQ ID NO: 490). In some embodiments, the CM1-CM2 substrate includes the sequence AVGLLAPPGGLSGRSDDH (SEQ ID NO: 515). In some embodiments, the CM1-CM2 substrate includes the sequence AVGLLAPPGGLSGRSDIH (SEQ ID NO: 516). In some embodiments, the CM1-CM2 substrate includes the sequence AVGLLAPPGGLSGRSDQH (SEQ ID NO: 517). In some embodiments, the CM1-CM2 substrate includes the sequence AVGLLAPPGGLSGRSDTH (SEQ ID NO: 518). In some embodiments, the CM1-CM2 substrate includes the sequence AVGLLAPPGGLSGRSDYH (SEQ ID NO: 519). In some embodiments, the CM1-CM2 substrate includes the sequence AVGLLAPPGGLSGRSDNP (SEQ ID NO: 520). In some embodiments, the CM1-CM2 substrate includes the sequence AVGLLAPPGGLSGRSANP (SEQ ID NO: 521). In some embodiments, the CM1-CM2 substrate includes the sequence AVGLLAPPGGLSGRSANI (SEQ ID NO: 522). In some embodiments, the CM1-CM2 substrate includes the sequence ISSGLLSGRSDNI (SEQ ID NO: 555). In some embodiments, the CM1-CM2 substrate includes the sequence AVGLLAPPGGLSGRSDNI (SEQ ID NO: 557).

In some embodiments, the activatable antibody in the uncleaved state has the structural arrangement from N-terminus to C-terminus as follows: MM-CM1-CM2-AB, AB-CM2-CM1-MM, MM-CM2-CM1-AB, or AB-CM1-CM2-MM.

In some embodiments, the activatable antibody comprises a first linking peptide (LP1) and a second linking peptide (LP2), and the antibody in the uncleaved state has the structural arrangement from N-terminus to C-terminus as follows: MM1-LP1-CM1-CM2-LP2-AB, AB-LP2-CM2-CM1-LP1-MM, MM1-LP1-CM2-CM1-LP2-AB, or AB-LP2-CM1-CM2-LP1-MM. In some embodiments, each of LP1 and LP2 is a peptide of about 1 to 20 amino acids in length. In some embodiments, the two linking peptides need not be identical to each other.

In some embodiments, the activatable antibody includes a linking peptide (LP') between CM1 and CM2. In some embodiments, the activatable antibody includes a linking peptide (LP") between the masking moiety (MM) and CM1. In some embodiments, the activatable antibody includes a linking peptide (LP"') between CM2 and AB. In some embodiments, the activatable antibody includes a linking peptide (LP") between the MM and CM1 and a linking peptide (LP') between CM2 and AB. In some embodiments, the activatable antibody includes a linking peptide between the MM and CM1 (LP") and a linking peptide between CM1 and CM2 (LP'). In some embodiments, the activatable antibody includes a linking peptide (LP') between CM1 and CM2 and a linking peptide (LP"') between CM2 and AB. In some embodiments, the activatable antibody includes a linking peptide (LP") between the MM and CM1, a linking peptide (LP') between CM1 and CM2, and a linking peptide (LP"') between CM2 and AB.

In some embodiments, the activatable antibody includes a linking peptide (LP') between CM1 and CM2. In some embodiments, the activatable antibody includes a linking peptide (LP") between the AB and CM1. In some embodiments, the activatable antibody includes a linking peptide (LP"') between CM2 and the masking moiety (MM). In some embodiments, the activatable antibody includes a linking peptide (LP") between the AB and CM1 and a linking peptide (LP"') between CM2 and MM. In some embodiments, the activatable antibody includes a linking peptide between the AB and CM1 (LP") and a linking peptide between CM1 and CM2 (LP'). In some embodiments, the activatable antibody includes a linking peptide (LP') between CM1 and CM2 and a linking peptide (LP') between CM2 and MM. In some embodiments, the activatable antibody includes a linking peptide (LP") between the AB and CM1, a linking peptide (LP') between CM1 and CM2, and a linking peptide (LP"') between CM2 and MM.

In some embodiments, LP' is GG. In some embodiments, LP' is GGSGGS (SEQ ID NO: 350).

In some embodiments, at least one of LP1 or LP2 comprises an amino acid sequence selected from the group consisting of $(GS)_n$, $(GGS)_n$, $(GSGGS)_n$ (SEQ ID NO: 381) and $(GGGS)_n$ (SEQ ID NO: 382), where n is an integer of at least one.

In some embodiments, at least one of LP1 or LP2 comprises an amino acid sequence selected from the group consisting of GGSG (SEQ ID NO: 383), GGSGG (SEQ ID NO: 384), GSGSG (SEQ ID NO: 385), GSGGG (SEQ ID NO: 386), GGGSG (SEQ ID NO: 387), and GSSSG (SEQ ID NO: 388).

In some embodiments, LP1 comprises the amino acid sequence GSSGGSGGSGGSG (SEQ ID NO: 389), GSSGGSGGSGG (SEQ ID NO: 390), GSSGGSGGSGGS (SEQ ID NO: 391), GSSGGSGGSGGSGGGS (SEQ ID NO: 392), GSSGGSGGSG (SEQ ID NO: 393), or GSSGGSGGSGS (SEQ ID NO: 394).

In some embodiments, LP2 comprises the amino acid sequence GSS, GGS, GGGS (SEQ ID NO: 395), GSSGT (SEQ ID NO: 396) or GSSG (SEQ ID NO: 397).

In some embodiments, the AB has a dissociation constant of about 100 nM or less for binding to the target.

In some embodiments, the activatable antibody includes an antibody or antigen-binding fragment (AB) thereof that specifically binds a target. In some embodiments, the AB is a full-length antibody. In some embodiments, the AB is an immunologically active fragment. In some embodiments, the AB is an antigen-binding fragment. In some embodiments, the AB is a monoclonal antibody, domain antibody, single chain, Fab fragment, a F(ab')2 fragment, a scFv, a scab, a dAb, a single domain heavy chain antibody, or a single domain light chain antibody. In some embodiments, such an AB is a mouse, other rodent, chimeric, humanized or fully human monoclonal antibody.

In some embodiments, the MMP protease is co-localized with the target in a tissue, and the MMP protease cleaves the CM1 in the antibody when the antibody is exposed to the protease. In some embodiments, the SP protease is co-localized with the target in a tissue, and the SP protease cleaves the CM2 substrate in the antibody when the antibody is exposed to the protease. In some embodiments, the MMP protease and/or the SP protease are co-localized with the target in a tissue, and the MMP protease and/or the SP protease cleave the CM1-CM2 substrate in the antibody when the antibody is exposed to the protease. In some embodiments, the MMP protease and the SP protease are co-localized with the target in a tissue, and at least one of the MMP protease and the SP protease cleave the CM1-CM2 substrate in the antibody when the antibody is exposed to the protease.

In some embodiments, each of the CM1 substrate sequence and the CM2 substrate sequence of the CM1-CM2 substrate is independently a polypeptide of up to 15 amino acids in length.

In some embodiments, the CM1 substrate sequence of the CM1-CM2 substrate is a substrate for at least one MMP and comprises a polypeptide sequence that is not substantially identical to any polypeptide sequence, e.g., any animal polypeptide sequence, that is naturally cleaved by the same MMP protease. In some embodiments, the CM1 substrate sequence of the CM1-CM2 substrate is a substrate for at least one MMP and comprises a polypeptide sequence that is not substantially identical to any mammalian polypeptide sequence that is naturally cleaved by the same MMP protease. In some embodiments, the CM1 substrate sequence of the CM1-CM2 substrate is a substrate for at least one MMP and comprises a polypeptide sequence that is not substantially identical to any human polypeptide sequence that is naturally cleaved by the same MMP protease. In some embodiments, the CM1 substrate sequence of the CM1-CM2 substrate is a substrate for at least one MMP and comprises a polypeptide sequence that is no more than 90% or more identical to any polypeptide sequence, e.g., any animal polypeptide sequence, that is naturally cleaved by the same MMP protease. In some embodiments, the CM1 substrate sequence of the CM1-CM2 substrate is a substrate for at least one MMP and comprises a polypeptide sequence that is no more than 90% or more identical to any mammalian polypeptide sequence that is naturally cleaved by the same MMP protease. In some embodiments, the CM1 substrate sequence of the CM1-CM2 substrate is a substrate for at least one MMP and comprises a polypeptide sequence that is no more than 90% or more identical to any human polypeptide sequence that is naturally cleaved by the same MMP protease.

In some embodiments, the CM2 substrate sequence of the CM1-CM2 substrate is a substrate for at least one SP and comprises a polypeptide sequence that is not substantially identical to any polypeptide sequence, e.g., any animal polypeptide sequence, that is naturally cleaved by the same SP protease. In some embodiments, the CM2 substrate sequence of the CM1-CM2 substrate is a substrate for at least one SP and comprises a polypeptide sequence that is not substantially identical to any mammalian polypeptide sequence that is naturally cleaved by the same SP protease. In some embodiments, the CM2 substrate sequence of the CM1-CM2 substrate is a substrate for at least one SP and comprises a polypeptide sequence that is not substantially identical to any human polypeptide sequence that is naturally cleaved by the same SP protease. In some embodiments, the CM2 substrate sequence of the CM1-CM2 substrate is a substrate for at least one SP and comprises a polypeptide sequence that is no more than 90% or more identical to any polypeptide sequence, e.g., any animal polypeptide sequence, that is naturally cleaved by the same SP protease. In some embodiments, the CM2 substrate sequence of the CM1-CM2 substrate is a substrate for at least one SP and comprises a polypeptide sequence that is no more than 90% or more identical to any mammalian polypeptide sequence that is naturally cleaved by the same SP protease. In some embodiments, the CM2 substrate sequence of the CM1-CM2 substrate is a substrate for at least one SP and comprises a polypeptide sequence that is no more than 90% or more identical to any human polypeptide sequence that is naturally cleaved by the same SP protease.

In some embodiments, the CM1-CM2 substrate comprises an amino acid sequence selected from the group consisting of SEQ ID NOs: 1-17, 22, 469-471, 483-490, 515-522, 555, and 557. In some embodiments, an activatable antibody comprises a CM1-CM2 substrate comprising an amino acid sequence selected from the group consisting of SEQ ID NOs: 1-17, 22, 469-471, 483-490, 515-522, 555, and 557, as well as an antibody or antigen binding fragment thereof (AB) that binds a target and a masking moiety (MM) that reduces the ability of the antigen- or epitope-binding domain of the AB to bind its target.

In some embodiments, an activatable antibody comprises a CM1-CM2 substrate comprising an amino acid sequence selected from the group consisting of SEQ ID NOs: 1-17, 22, 469-471, 483-490, 515-522, 555, and 557, and an anti-Jagged antibody comprising an amino acid sequence of an anti-Jagged antibody disclosed herein. In some embodiments, an activatable antibody comprises a CM1-CM2 substrate comprising an amino acid sequence selected from the group consisting of SEQ ID NOs: 1-17, 22, 469-471, 483-490, 515-522, 555, and 557, and an antibody having a light chain comprising amino acid sequence SEQ ID NO: 162 or SEQ ID NO: 164 and a heavy chain comprising amino acid sequence SEQ ID NO: 67 or SEQ ID NO: 163.

In some embodiments, the CM1-CM2 is included in an activatable antibody having a light chain amino acid sequence selected from the group consisting of SEQ ID NOs: 420, 422, 424, 426, 428, 430, 432, 434, 436, 439, 477, 479, 507-514, 539-546, 561, and 562, and a heavy chain amino acid sequence of SEQ ID NO: 67.

In some embodiments, the CM1-CM2 is included in an activatable antibody having a light chain amino acid sequence selected from the group consisting of SEQ ID NOs: 420, 422, 424, 426, 428, 430, 432, 434, 436, 439, 477, 479, 507-514, 539-546, 561, and 562, and a heavy chain amino acid sequence of SEQ ID NO: 163.

In some embodiments, an activatable antibody comprises a CM1-CM2 substrate comprising an amino acid sequence selected from the group consisting of SEQ ID NOs: 1-17, 22, 469-471, 483-490, 515-522, 555, and 557, and an anti-EGFR antibody comprising an amino acid sequence of an anti-EGFR antibody disclosed herein. In some embodiments, an activatable antibody comprises a CM1-CM2 substrate comprising an amino acid sequence selected from the group consisting of SEQ ID NOs: 1-17, 22, 469-471, 483-490, 515-522, 555, and 557, and an antibody having a light chain comprising amino acid sequence SEQ ID NO: 111 and a heavy chain comprising amino acid sequence SEQ ID NO: 108, SEQ ID NO: 109, or SEQ ID NO: 110.

In some embodiments, the CM1-CM2 is included in an activatable antibody having a light chain amino acid sequence selected from the group consisting of SEQ ID NOs: 449, 451, 453, 455, 457, 459, 461, 463, 465, 467, 472, 474, 499-506, 531-538, 559, and 560, and a heavy chain amino acid sequence of SEQ ID NO: 108.

In some embodiments, the CM1-CM2 is included in an activatable antibody having a light chain amino acid sequence selected from the group consisting of SEQ ID NOs: 449, 451, 453, 455, 457, 459, 461, 463, 465, 467, 472, 474, 499-506, 531-538, 559, and 560, and a heavy chain amino acid sequence of SEQ ID NO: 109.

In some embodiments, the CM1-CM2 is included in an activatable antibody having a light chain amino acid sequence selected from the group consisting of SEQ ID NOs: 449, 451, 453, 455, 457, 459, 461, 463, 465, 467, 472, 474, 499-506, 531-538, 559, and 560, and a heavy chain amino acid sequence of SEQ ID NO: 110.

In some embodiments, the CM1-CM2 substrate is also a substrate for at least one additional protease.

In some embodiments, the at least one additional protease is a different MMP protease than the MMP protease that cleaves the CM1. In some embodiments, the at least one additional protease is an MMP protease selected from the group consisting of MMP1; MMP2; MMP3; MMP1; MMP8; MMP9; MMP10; MMP11; MMP12; MMP13; MMP14; MMP15; MMP16; MMP17; MMP19; MMP20; MMP23; MMP24; MMP26; and MMP27.

In some embodiments, the at least one additional protease is a different SP protease than the SP protease that cleaves CM2. In some embodiments, the at least one additional SP protease is selected from the group consisting of uPA; matriptase; activated protein C; Cathepsin A; Cathepsin G; Chymase; a coagulation factor protease such as, e.g., FVIIa, FIXa, FXa, FXIa, FXIIa; Elastase; Granzyme B; Guanidinobenzoatase; HtrA1; Human Neutrophil Elastase; Lactoferrin; Marapsin; NS3/4A; PACE4; Plasmin; PSA; tPA; Thrombin; Tryptase; a Type II Transmembrane Serine Protease (TTSP) such as, e.g., DESC1, DPP-4, FAP, Hepsin, Matriptase-2, TMPRSS2, TMPRSS3, and TMPRSS4.

In some embodiments, the at least one additional protease is selected from the group consisting of those shown in Table 6.

TABLE 6

| Exemplary Proteases and/or Enzymes |
|---|
| ADAMS, ADAMTS, e.g. |
| ADAM8 |
| ADAM9 |
| ADAM10 |
| ADAM12 |
| ADAM15 |
| ADAM17/TACE |
| ADAMDEC1 |
| ADAMTS1 |
| ADAMTS4 |
| ADAMTS5 |
| Aspartate proteases, e.g., |
| BACE |
| Renin |
| Aspartic cathepsins, e.g., |
| Cathepsin D |
| Cathepsin E |
| Caspases, e.g., |
| Caspase 1 |
| Caspase 2 |
| Caspase 3 |
| Caspase 4 |
| Caspase 5 |
| Caspase 6 |
| Caspase 7 |
| Caspase 8 |
| Caspase 9 |
| Caspase 10 |
| Caspase 14 |
| Cysteine cathepsins, e.g., |
| Cathepsin B |
| Cathepsin C |
| Cathepsin K |
| Cathepsin L |
| Cathepsin S |
| Cathepsin V/L2 |
| Cathepsin X/Z/P |
| Cysteine proteinases, e.g., |
| Cruzipain |
| Legumain |
| Otubain-2 |
| KLKs, e.g., |

TABLE 6-continued

| Exemplary Proteases and/or Enzymes |
|---|
| KLK4 |
| KLK5 |
| KLK6 |
| KLK7 |
| KLK8 |
| KLK10 |
| KLK11 |
| KLK13 |
| KLK14 |
| Metallo proteinases, e.g., |
| Meprin |
| Neprilysin |
| PSMA |
| BMP-1 |

The disclosure also provides an antibody includes at least a first CM1 and a second CM2 and is conjugated to an agent. In some embodiments, the first CM1 and the second CM2 are each polypeptides of no more than 15 amino acids long. In some embodiments, the activatable antibody is a conjugated activatable antibody that, in the uncleaved state has the structural arrangement from N-terminus to C-terminus as follows: MM-CM1-CM2-AB-Agent, Agent-AB-CM2-CM1-MM, MM-CM2-CM1-AB-Agent, or Agent-AB-CM1-CM2-MM. In some embodiments, the activatable antibody is a conjugated activatable antibody that, in the uncleaved state has the structural arrangement from N-terminus to C-terminus as follows: Agent-MM-CM1-CM2-AB, AB-CM2-CM1-MM-Agent, Agent-MM-CM2-CM1-AB, or AB-CM1-CM2-MM-Agent. In some embodiments, the activatable antibody is a conjugated activatable antibody that, in the uncleaved state has the structural arrangement from N-terminus to C-terminus as follows: Agent-MM-CM1-CM2-AB-Agent, Agent-AB-CM2-CM1-MM-Agent, Agent-MM-CM2-CM1-AB-Agent, or Agent-AB-CM1-CM2-MM-Agent.

In some embodiments, the activatable antibody is a conjugated activatable antibody that comprises a masking moiety (MM), a first linking peptide (LP1) and a second linking peptide (LP2), and the antibody in the uncleaved state has the structural arrangement from N-terminus to C-terminus as follows: MM1-LP1-CM1-CM2-LP2-AB-Agent, Agent-AB-LP2-CM2-CM1-LP1-MM, MM1-LP1-CM2-CM1-LP2-AB-Agent, or Agent-AB-LP2-CM1-CM2-LP1-MM. In some embodiments, each of LP1 and LP2 is a peptide of about 1 to 20 amino acids in length. In some embodiments, the two linking peptides need not be identical to each other.

In some embodiments, the activatable antibody is a conjugated activatable antibody that comprises a masking moiety (MM), a first linking peptide (LP1) and a second linking peptide (LP2), and the antibody in the uncleaved state has the structural arrangement from N-terminus to C-terminus as follows: Agent-MM1-LP1-CM1-CM2-LP2-AB, AB-LP2-CM2-CM1-LP1-MM-Agent, Agent-MM1-LP1-CM2-CM1-LP2-AB, or AB-LP2-CM1-CM2-LP1-MM-Agent. In some embodiments, each of LP1 and LP2 is a peptide of about 1 to 20 amino acids in length. In some embodiments, the two linking peptides need not be identical to each other.

In some embodiments, the activatable antibody is a conjugated activatable antibody that comprises a masking moiety (MM), a first linking peptide (LP1) and a second linking peptide (LP2), and the antibody in the uncleaved state has the structural arrangement from N-terminus to C-terminus as follows: Agent-MM1-LP1-CM1-CM2-LP2-AB-Agent, Agent-AB-LP2-CM2-CM1-LP1-MM-Agent, Agent-MM1-

LP1-CM2-CM1-LP2-AB-Agent, or Agent-AB-LP2-CM1-CM2-LP1-MM-Agent. In some embodiments, each of LP1 and LP2 is a peptide of about 1 to 20 amino acids in length. In some embodiments, the two linking peptides need not be identical to each other.

In some embodiments, the conjugated activatable antibody includes a linking peptide (LP') between CM1 and CM2. In some embodiments, the conjugated activatable antibody includes a linking peptide (LP") between the masking moiety (MM) and CM1. In some embodiments, the conjugated activatable antibody includes a linking peptide (LP') between CM2 and AB. In some embodiments, the conjugated activatable antibody includes a linking peptide (LP") between the MM and CM1 and a linking peptide (LP"') between CM2 and AB. In some embodiments, the conjugated activatable antibody includes a linking peptide between the MM and CM1 (LP") and a linking peptide between CM1 and CM2 (LP'). In some embodiments, the conjugated activatable antibody includes a linking peptide (LP') between CM1 and CM2 and a linking peptide (LP"') between CM2 and AB. In some embodiments, the conjugated activatable antibody includes a linking peptide (LP") between the MM and CM1, a linking peptide (LP') between CM1 and CM2, and a linking peptide (LP"') between CM2 and AB.

In some embodiments, the conjugated activatable antibody includes a linking peptide (LP') between CM1 and CM2. In some embodiments, the conjugated activatable antibody includes a linking peptide (LP") between the AB and CM1. In some embodiments, the conjugated activatable antibody includes a linking peptide (LP"') between CM2 and the masking moiety (MM). In some embodiments, the conjugated activatable antibody includes a linking peptide (LP") between the AB and CM1 and a linking peptide (LP"') between CM2 and MM. In some embodiments, the conjugated activatable antibody includes a linking peptide between the AB and CM1 (LP") and a linking peptide between CM1 and CM2 (LP'). In some embodiments, the conjugated activatable antibody includes a linking peptide (LP') between CM1 and CM2 and a linking peptide (LP"') between CM2 and MM. In some embodiments, the conjugated activatable antibody includes a linking peptide (LP") between the AB and CM1, a linking peptide (LP') between CM1 and CM2, and a linking peptide (LP"') between CM2 and MM.

In some embodiments, LP' is GG. In some embodiments, LP' is GGSGGS (SEQ ID NO: 350).

In some embodiments, at least one of LP1 or LP2 comprises an amino acid sequence selected from the group consisting of $(GS)_n$, $(GGS)_n$, $(GSGGS)_n$ (SEQ ID NO: 381) and $(GGGS)_n$ (SEQ ID NO: 382), where n is an integer of at least one.

In some embodiments, at least one of LP1 or LP2 comprises an amino acid sequence selected from the group consisting of GGSG (SEQ ID NO: 383), GGSGG (SEQ ID NO: 384), GSGSG (SEQ ID NO: 385), GSGGG (SEQ ID NO: 386), GGGSG (SEQ ID NO: 387), and GSSSG (SEQ ID NO: 388).

In some embodiments, LP1 comprises the amino acid sequence GSSGGSGGSGGSG (SEQ ID NO: 389), GSSGGSGGSGG (SEQ ID NO: 390), GSSGGSGGSGGS (SEQ ID NO: 391), GSSGGSGGSGGSGGGS (SEQ ID NO: 392), GSSGGSGGSG (SEQ ID NO: 393), or GSSGGSGGSGS (SEQ ID NO: 394).

In some embodiments, LP2 comprises the amino acid sequence GSS, GGS, GGGS (SEQ ID NO: 395), GSSGT (SEQ ID NO: 396) or GSSG (SEQ ID NO: 397).

In some embodiments, the CM1-CM2 substrate is linked or otherwise attached to an antibody. For example, the CM1-CM2 is used to link one or more agents to the antibody or antigen binding fragment thereof (AB) that binds a given target, such that the CM1-CM2 is cleaved when exposed to the MMP and/or the SP, and the agent is released from the AB. Exemplary targets include, but are not limited to the targets shown in Table 1. Exemplary ABs include, but are not limited to, the antibodies shown in Table 2.

In some embodiments, the AB has a dissociation constant of about 100 nM or less for binding to the target.

In some embodiments, the antibody includes an antibody or antigen-binding fragment thereof that specifically binds a target. In some embodiments, the antibody or immunologically active fragment thereof that binds the target is a monoclonal antibody, domain antibody, single chain, Fab fragment, a $F(ab')_2$ fragment, a scFv, a scab, a dAb, a single domain heavy chain antibody, or a single domain light chain antibody. In some embodiments, such an antibody or immunologically active fragment thereof that binds the target is a mouse, other rodent, chimeric, humanized or fully human monoclonal antibody.

In some embodiments, the MM has a dissociation constant for binding to the AB that is no more than the dissociation constant of the AB to the target.

In some embodiments, the MM does not interfere or compete with the AB for binding to the target in a cleaved state.

In some embodiments, the MM is a polypeptide of about 2 to 40 amino acids in length. For example, the MM is a polypeptide of up to about 40 amino acids in length.

In some embodiments, the MM polypeptide sequence is different from that of any natural binding partner of the AB. In some embodiments, the MM polypeptide sequence is no more than 50% identical to any natural binding partner of the AB. In some embodiments, the MM polypeptide sequence is no more than 40%, 30%, 25%, 20%, 15%, or 10% identical to any natural binding partner of the AB.

In some embodiments, the agent conjugated to the AB or the AB of an activatable antibody is a therapeutic agent. In some embodiments, the agent is an antineoplastic agent. In some embodiments, the agent is a toxin or fragment thereof. As used herein, a fragment of a toxin is a fragment that retains toxic activity. In some embodiments, the agent is conjugated to the AB via a cleavable linker. In some embodiments, the agent is conjugated to the AB via a linker that includes at least one CM1-CM2 substrate sequence. In some embodiments, the agent is conjugated to the AB via a noncleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the agent is an anti-inflammatory agent.

In some embodiments, the antibody and/or activatable antibody also includes a detectable moiety. In some embodiments, the detectable moiety is a diagnostic agent.

In some embodiments, the conjugated antibody and/or conjugated activatable antibody includes a detectable label. In some embodiments, the detectable label includes an imaging agent, a contrasting agent, an enzyme, a fluorescent label, a chromophore, a dye, one or more metal ions, or a ligand-based label. In some embodiments, the imaging agent comprises a radioisotope. In some embodiments, the radioisotope is indium or technetium. In some embodiments, the contrasting agent comprises iodine, gadolinium or iron oxide. In some embodiments, the enzyme comprises horseradish peroxidase, alkaline phosphatase, or (3-galactosidase. In some embodiments, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments, the luminescent label comprises an N-methylacrydium derivative. In some embodiments, the label comprises an Alexa Fluor® label, such as Alex Fluor® 680 or Alexa Fluor® 750. In some embodiments, the ligand-based label comprises biotin, avidin, streptavidin or one or more haptens.

In some embodiments, the antibody and/or the AB of the activatable antibody naturally contains one or more disulfide bonds. In some embodiments, the AB can be engineered to include one or more disulfide bonds.

In some embodiments, the antibody and/or conjugated antibody is monospecific. In some embodiments, the antibody and/or conjugated antibody is multispecific, referred to herein as multispecific antibodies and/or conjugated multispecific antibodies. In some embodiments, the multispecific antibody and/or conjugated multispecific antibody is bispecific or trifunctional. In some embodiments, the antibody and/or conjugated antibody is formulated as part of a pro-Bispecific T Cell Engager (pro-BITE) molecule. In some embodiments, the antibody and/or conjugated antibody is formulated as part of a pro-Chimeric Antigen Receptor (pro-CAR) modified T cell or other engineered receptor or other immune effector cell, such as a CAR modified NK cell. In some embodiments, the activatable antibody and/or conjugated activatable antibody is formulated as part of a pro-Chimeric Antigen Receptor (CAR) modified T cell. In some embodiments, the activatable antibody and/or conjugated activatable antibody is formulated as part of a pro-Chimeric Antigen Receptor (CAR) modified NK cell.

In some embodiments, the activatable antibody and/or conjugated activatable antibody is monospecific. In some embodiments, the activatable antibody and/or conjugated activatable antibody is multispecific, referred to herein as multispecific activatable antibodies and/or conjugated multispecific activatable antibodies. As used herein, terms such as "activatable antibody" and all grammatical variations thereof, unless otherwise noted, are intended to encompass, but are not limited to embodiments where the activatable antibody is a multispecific activatable antibody of the disclosure. As used herein, terms such as "conjugated activatable antibody" and all grammatical variations thereof, unless otherwise noted, are intended to encompass, but are not limited to embodiments where the conjugated activatable antibody is a conjugated multispecific activatable antibody of the disclosure. In some embodiments, the multispecific activatable antibody and/or conjugated multispecific activatable antibody is bispecific or trifunctional. In some embodiments, the activatable antibody and/or conjugated activatable antibody is formulated as part of a pro-Bispecific T Cell Engager (pro-BITE) molecule. In some embodiments, the activatable antibody and/or conjugated activatable antibody is formulated as part of a pro-Chimeric Antigen Receptor (pro-CAR) modified T cell or other engineered receptor.

In some embodiments, the antibodies, antibody conjugates, activatable antibodies, conjugated activatable antibodies, multispecific activatable antibodies, and/or conjugated multispecific activatable antibodies described herein are used in conjunction with one or more additional agents or a combination of additional agents. Suitable additional agents include current pharmaceutical and/or surgical therapies for an intended application, such as, for example, cancer. For example, the activatable antibodies, conjugated activatable antibodies, multispecific activatable antibodies, and/or conjugated multispecific activatable antibodies can be used in conjunction with an additional chemotherapeutic or anti-neoplastic agent.

In some embodiments, the activatable antibody is a multispecific activatable antibody. The multispecific activatable antibodies provided herein are multispecific antibodies that recognize two or more different antigens or epitopes and that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a CM1-CM2 substrate that functions as a substrate for at least one MMP protease and at least one SP protease. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 that sequence includes at least the amino acid sequence SYAMS (SEQ ID NO: 398); a VH CD2 sequence that includes at least the amino acid sequence SIDPEGRQTYYADSVKG (SEQ ID NO: 399); a VH CDR3 sequence that includes at least the amino acid sequence DIGGRSAFDY (SEQ ID NO: 400), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes at least the amino acid sequence RASQSISSY (SEQ ID NO: 401); a VL CDR2 sequence that includes at least the amino acid sequence AASSLQS (SEQ ID NO: 402); a VL CDR3 sequence that includes at least the amino acid sequence QQTVVAPPL (SEQ ID NO: 403), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes a sequence that is at least 90%, 91%, 92%, 93%, 94%, 95%, 96%, 97%, 98%, 99% or more identical to the amino acid sequence SYAMS (SEQ ID NO: 398); a VH CD2 sequence that includes a sequence that is at least 90%, 91%, 92%, 93%, 94%, 95%, 96%, 97%, 98%, 99% or more identical to the amino acid sequence SIDPEGRQTYYADSVKG (SEQ ID NO: 399); a VH CDR3 sequence that includes a sequence that is at least 90%, 91%, 92%, 93%, 94%, 95%, 96%, 97%, 98%, 99% or more identical to the amino acid sequence DIGGRSAFDY (SEQ ID NO: 400), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes a sequence that is at least 90%, 91%, 92%, 93%, 94%, 95%, 96%, 97%, 98%, 99% or more identical to the amino acid sequence RASQSISSY (SEQ ID NO: 401); a VL CDR2 sequence that includes a sequence that is at least 90%, 91%, 92%, 93%, 94%, 95%, 96%, 97%, 98%, 99% or more identical to the amino acid sequence AASSLQS (SEQ ID NO: 402); and a VL CDR3 sequence that includes a sequence that is at least 90%, 91%, 92%, 93%, 94%, 95%, 96%, 97%, 98%, 99% or more identical to the amino acid sequence QQTVVAPPL (SEQ ID NO: 403), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes at least the amino acid sequence SYAMS (SEQ ID NO: 398); the VH CD2 sequence includes at least the amino acid sequence SIDPEGRQTYYADSVKG (SEQ ID NO: 399); the VH CDR3 sequence includes at least the amino acid sequence DIGGRSAFDY (SEQ ID NO: 400); the VL CDR1 sequence includes at least the amino acid sequence RASQSISSY (SEQ ID NO: 401); the VL CDR2 sequence includes at least the amino acid sequence AASSLQS (SEQ ID NO: 402); and the VL CDR3 sequence includes at least the amino acid sequence QQTVVAPPL (SEQ ID NO: 403).

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes a sequence that is at least 90%, 91%, 92%, 93%, 94%, 95%, 96%, 97%, 98%, 99% or more identical to the amino acid sequence SYAMS (SEQ ID NO: 398); the VH CD2 sequence includes a sequence that is at least 90%, 91%, 92%, 93%, 94%, 95%, 96%, 97%, 98%, 99% or more identical to the amino acid sequence SIDPEGRQTYYADSVKG (SEQ ID NO: 399); the VH CDR3 sequence includes a sequence that is at least 90%, 91%, 92%, 93%, 94%, 95%, 96%, 97%, 98%, 99% or more identical to the amino acid sequence DIGGRSAFDY (SEQ ID NO: 400); the VL CDR1 sequence includes a sequence that is at least 90%, 91%, 92%, 93%, 94%, 95%, 96%, 97%, 98%, 99% or more identical to the amino acid sequence RASQSISSY (SEQ ID NO: 401); the VL CDR2 sequence includes a sequence that is at least 90%, 91%, 92%, 93%, 94%, 95%, 96%, 97%, 98%, 99% or more identical to the amino acid sequence AASSLQS (SEQ ID NO: 402); and the VL CDR3 sequence includes a sequence that is at least 90%, 91%, 92%, 93%, 94%, 95%, 96%, 97%, 98%, 99% or more identical to the amino acid sequence QQTVVAPPL (SEQ ID NO: 403).

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds Epidermal Growth Factor Receptor (EGFR) and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes at least the amino acid sequence NYGVH (SEQ ID NO: 404); a VH CD2 sequence that includes at least the amino acid sequence VIWSGGNTDYNTPFTS (SEQ ID NO: 405); a VH CDR3 sequence that includes at least the amino acid sequence ALTYYDYEFAY (SEQ ID NO: 406); and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes at least the amino acid sequence RASQSIGTNIH (SEQ ID NO: 407); a VL CDR2 sequence that includes at least the amino acid sequence KYASESIS (SEQ ID NO: 408); and a VL CDR3 sequence that includes at least the amino acid sequence QQNNNWPTT (SEQ ID NO: 409), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes a sequence that is at least 90%, 91%, 92%, 93%, 94%, 95%, 96%, 97%, 98%, 99% or more identical to the amino acid sequence NYGVH (SEQ ID NO: 404); a VH CD2 sequence that includes a sequence that is at least 90%, 91%, 92%, 93%, 94%, 95%, 96%, 97%, 98%, 99% or more identical to the amino acid sequence VIWSGGNTDYNTPFTS (SEQ ID NO: 405); a VH CDR3 sequence that includes a sequence that is at least 90%, 91%, 92%, 93%, 94%, 95%, 96%, 97%, 98%, 99% or more identical to the amino acid sequence ALTYYDYEFAY (SEQ ID NO: 406); and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes a sequence that is at least 90%, 91%, 92%, 93%, 94%, 95%, 96%, 97%, 98%, 99% or more identical to the amino acid sequence RASQSIGTNIH (SEQ ID NO: 407); a VL CDR2 sequence that includes a sequence that is at least 90%, 91%, 92%, 93%, 94%, 95%, 96%, 97%, 98%, 99% or more identical to the amino acid sequence KYASESIS (SEQ ID NO: 408); and a VL CDR3 sequence that includes a sequence that is at least 90%, 91%, 92%, 93%, 94%, 95%, 96%, 97%, 98%, 99% or more identical to the amino acid sequence QQNNNWPTT (SEQ ID NO: 409), and combinations thereof.

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes at least the amino acid sequence NYGVH (SEQ ID NO: 404); the VH CD2 sequence includes at least the amino acid sequence VIWSGGNTDYNTPFTS (SEQ ID NO: 405); the VH CDR3 sequence includes at least the amino acid sequence ALTYYDYEFAY (SEQ ID NO: 406); the VL CDR1 sequence includes at least the amino acid sequence RASQSIGTNIH (SEQ ID NO: 407); the VL CDR2 sequence includes at least the amino acid sequence KYASESIS (SEQ ID NO: 408); and the VL CDR3 sequence includes at least the amino acid sequence QQNNNWPTT (SEQ ID NO: 409).

In some embodiments, the activatable antibody and/or conjugated activatable antibody provided herein, including but not limited to a multispecific activatable antibody and/or conjugated multispecific activatable antibody of the disclosure, includes at least a first antibody or antigen binding fragment thereof (AB1) that specifically binds EGFR and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes a sequence that is at least 90%, 91%, 92%, 93%, 94%, 95%, 96%, 97%, 98%, 99% or more identical to the amino acid sequence NYGVH (SEQ ID NO: 404); the VH CD2 sequence includes a sequence that is at least 90%, 91%, 92%, 93%, 94%, 95%, 96%, 97%, 98%, 99% or more identical to the amino acid sequence VIWSGGNTDYNTPFTS (SEQ ID NO: 405); the VH CDR3 sequence includes a sequence that is at least 90%, 91%, 92%, 93%, 94%, 95%, 96%, 97%, 98%, 99% or more identical to the amino acid sequence ALTYYDYEFAY (SEQ ID NO: 406); the VL CDR1 sequence includes a sequence that is at least 90%, 91%, 92%, 93%, 94%, 95%, 96%, 97%, 98%, 99% or more identical to the amino acid sequence RASQSIGTNIH (SEQ ID NO: 407); the VL CDR2 sequence includes a sequence that is at least 90%, 91%, 92%, 93%, 94%, 95%, 96%, 97%, 98%, 99% or more identical to the amino acid sequence KYASESIS (SEQ ID NO: 408); and the VL CDR3 sequence includes a sequence that is at least 90%, 91%, 92%, 93%, 94%, 95%, 96%, 97%, 98%, 99% or more identical to the amino acid sequence QQNNNWPTT (SEQ ID NO: 409).

In some embodiments, the activatable antibody and/or conjugated activatable antibody provided herein, including but not limited to a multispecific activatable antibody and/or conjugated multispecific activatable antibody of the disclosure, comprises a CM1-CM2 substrate comprising an amino acid sequence selected from the group consisting of SEQ ID NOs: 1-17, 22, 469-471, 483-490, 515-522, 555, and 557, and an anti-Jagged antibody comprising an amino acid sequence of an anti-Jagged antibody disclosed herein. In some embodiments, the activatable antibody and/or conjugated activatable antibody provided herein, including but not limited to a multispecific activatable antibody and/or conjugated multispecific activatable antibody of the disclosure, comprises a CM1-CM2 substrate comprising an amino acid sequence selected from the group consisting of SEQ ID NOs: 1-17, 22, 469-471, 483-490, 515-522, 555, and 557, and an antibody having a light chain comprising amino acid sequence SEQ ID NO: 162 or SEQ ID NO: 164 and a heavy chain comprising amino acid sequence SEQ ID NO: 67 or SEQ ID NO: 163.

In some embodiments, the activatable antibody and/or conjugated activatable antibody provided herein, including but not limited to a multispecific activatable antibody and/or conjugated multispecific activatable antibody of the disclosure, includes at least a heavy chain amino acid sequence of SEQ ID NO: 67 and a light chain amino acid sequence selected from the group consisting of SEQ ID NOs: 420, 422, 424, 426, 428, 430, 432, 434, 436, 439, 477, 479, 507-514, 539-546, 561, and 562.

In some embodiments, the activatable antibody and/or conjugated activatable antibody provided herein, including but not limited to a multispecific activatable antibody and/or conjugated multispecific activatable antibody of the disclosure, comprises a CM1-CM2 substrate comprising an amino acid sequence selected from the group consisting of SEQ ID NOs: 1-17, 22, 469-471, 483-490, 515-522, 555, and 557, and an anti-EGFR antibody comprising an amino acid sequence of an anti-EGFR antibody disclosed herein. In some embodiments, the activatable antibody and/or conjugated activatable antibody provided herein, including but not limited to a multispecific activatable antibody and/or conjugated multispecific activatable antibody of the disclosure, comprises a CM1-CM2 substrate comprising an amino acid sequence selected from the group consisting of SEQ ID NOs: 1-17, 22, 469-471, 483-490, 515-522, 555, and 557, and an antibody having a light chain comprising amino acid sequence SEQ ID NO: 111 and a heavy chain comprising amino acid sequence SEQ ID NO: 108, SEQ ID NO: 109, or SEQ ID NO: 110.

In some embodiments, the activatable antibody and/or conjugated activatable antibody provided herein, including but not limited to a multispecific activatable antibody and/or conjugated multispecific activatable antibody of the disclosure, includes at least a heavy chain amino acid sequence of SEQ ID NO: 108 and a light chain amino acid sequence selected from the group consisting of SEQ ID NOs: 449, 451, 453, 455, 457, 459, 461, 463, 465, 467, 472, 474, 499-506, 531-538, 559, and 560.

In some embodiments, the activatable antibody and/or conjugated activatable antibody provided herein, including but not limited to a multispecific activatable antibody and/or conjugated multispecific activatable antibody of the disclosure, includes at least a heavy chain amino acid sequence that is at least 90%, 91%, 92%, 93%, 94%, 95%, 96%, 97%, 98%, 99% or more identical to the amino acid sequence of SEQ ID NO: 67 and a light chain amino acid sequence that is at least 90%, 91%, 92%, 93%, 94%, 95%, 96%, 97%, 98%, 99% or more identical to an amino acid sequence selected from the group consisting of SEQ ID NOs: 420, 422, 424, 426, 428, 430, 432, 434, 436, 439, 477, 479, 507-514, 539-546, 561, and 562.

In some embodiments, the activatable antibody and/or conjugated activatable antibody provided herein, including but not limited to a multispecific activatable antibody and/or conjugated multispecific activatable antibody of the disclosure, includes at least a heavy chain amino acid sequence that is at least 90%, 91%, 92%, 93%, 94%, 95%, 96%, 97%, 98%, 99% or more identical to the amino acid sequence of SEQ ID NO: 108 and a light chain amino acid sequence that is at least 90%, 91%, 92%, 93%, 94%, 95%, 96%, 97%, 98%, 99% or more identical to an amino acid sequence selected from the group consisting of SEQ ID NOs: 449, 451, 453, 455, 457, 459, 461, 463, 465, 467, 472, 474, 499-506, 531-538, 559, and 560.

In some embodiments, the activatable antibody also includes an agent conjugated to the AB. In some embodiments, the agent is a therapeutic agent. In some embodiments, the agent is an antineoplastic agent. In some embodiments, the agent is a toxin or a fragment thereof. In some embodiments, the agent is conjugated to the AB via a linker. In some embodiments, the linker is a cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is conjugated to the AB via a linker that includes at least one CM1-CM2 substrate sequence. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the agent is an anti-inflammatory agent.

In some embodiments, the activatable antibody also includes a detectable moiety. In some embodiments, the detectable moiety is a diagnostic agent.

In some embodiments, the conjugated antibody includes a detectable label. In some embodiments, the detectable label includes an imaging agent, a contrasting agent, an enzyme, a fluorescent label, a chromophore, a dye, one or more metal ions, or a ligand-based label. In some embodiments, the imaging agent comprises a radioisotope. In some embodiments, the radioisotope is indium or technetium. In some embodiments, the contrasting agent comprises iodine, gadolinium or iron oxide. In some embodiments, the enzyme comprises horseradish peroxidase, alkaline phosphatase, or β-galactosidase. In some embodiments, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments, the luminescent label comprises an N-methylacrydium derivative. In some embodiments, the label comprises an Alexa Fluor® label, such as Alex Fluor® 680 or Alexa Fluor® 750. In some embodiments, the ligand-based label comprises biotin, avidin, streptavidin or one or more haptens.

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer is joined directly to the MM of the activatable antibody in the structural arrangement from N-terminus to C-terminus of spacer-MM-CM1-CM2 substrate-AB. An example of a spacer joined directly to the N-terminus of MM of the activatable antibody is an amino acid sequence selected from the group consisting of QGQSGQ (SEQ ID NO: 410), GQSGQ (SEQ ID NO: 416), QSGQ (SEQ ID NO: 417), SGQ (SEQ ID NO: 418), GQ, and Q. In some embodiments, the spacer includes at least the amino acid sequence QGQSGQ (SEQ ID NO: 410). In some embodiments, the spacer includes at least the amino acid sequence GQSGQ (SEQ ID NO: 416). In some embodiments, the spacer includes at least the amino acid sequence QSGQ (SEQ ID NO: 417). In some embodiments, the spacer includes at least the amino acid sequence SGQ (SEQ ID NO: 418). In some embodiments, the spacer includes at least the amino acid sequence GQ. In some embodiments, the spacer includes at least the amino acid sequence Q.

In some embodiments, the AB of the activatable antibody naturally contains one or more disulfide bonds. In some embodiments, the AB can be engineered to include one or more disulfide bonds.

In some embodiments, the serum half-life of the activatable antibody is longer than that of the corresponding antibody; e.g., the pK of the activatable antibody is longer than that of the corresponding antibody. In some embodiments, the serum half-life of the activatable antibody is similar to that of the corresponding antibody. In some embodiments, the serum half-life of the activatable antibody is at least 15 days when administered to an organism. In some embodiments, the serum half-life of the activatable antibody is at least 12 days when administered to an organism. In some embodiments, the serum half-life of the activatable antibody is at least 11 days when administered to an organism. In some embodiments, the serum half-life of the activatable antibody is at least 10 days when administered to an organism. In some embodiments, the serum half-life of the activatable antibody is at least 9 days when administered to an organism. In some embodiments, the serum half-life of the activatable antibody is at least 8 days when administered to an organism. In some embodiments, the serum half-life of the activatable antibody is at least 7 days when administered to an organism. In some embodiments, the serum half-life of the activatable antibody is at least 6 days when administered to an organism. In some embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

The disclosure also provides compositions and methods that include an activatable antibody that includes an antibody or antibody fragment (AB) that specifically binds a given target, where the AB is coupled to a masking moiety (MM) that decreases the ability of the AB to bind its target. In some embodiments, the activatable antibody further includes a CM1-CM2 substrate that is a substrate for at least one MMP and at least one SP. The compositions and methods provided herein enable the attachment of one or more agents to one or more cysteine residues in the AB without compromising the activity (e.g., the masking, activating or binding activity) of the activatable antibody. In some embodiments, the compositions and methods provided herein enable the attachment of one or more agents to one or more cysteine residues in the AB without reducing or otherwise disturbing one or more disulfide bonds within the MM. The compositions and methods provided herein produce an activatable antibody that is conjugated to one or more agents, e.g., any of a variety of therapeutic, diagnostic and/or prophylactic agents, for example, in some embodiments, without any of the agent(s) being conjugated to the MM of the activatable antibody. The compositions and methods provided herein produce conjugated activatable antibodies in which the MM retains the ability to effectively and efficiently mask the AB of the activatable antibody in an uncleaved state. The compositions and methods provided herein produce conjugated activatable antibodies in which the activatable antibody is still activated, i.e., cleaved, in the presence of a MMP that can cleave the CM1-CM2 substrate.

The activatable antibodies have at least one point of conjugation for an agent, but in the methods and compositions provided herein less than all possible points of conjugation are available for conjugation to an agent. In some embodiments, the one or more points of conjugation are sulfur atoms involved in disulfide bonds. In some embodiments, the one or more points of conjugation are sulfur atoms involved in interchain disulfide bonds. In some embodiments, the one or more points of conjugation are sulfur atoms involved in interchain sulfide bonds, but not sulfur atoms involved in intrachain disulfide bonds. In some embodiments, the one or more points of conjugation are sulfur atoms of cysteine or other amino acid residues containing a sulfur atom. Such residues may occur naturally in the antibody structure or may be incorporated into the antibody by site-directed mutagenesis, chemical conversion, or mis-incorporation of non-natural amino acids.

Also provided are methods of preparing a conjugate of an activatable antibody having one or more interchain disulfide bonds in the AB and one or more intrachain disulfide bonds in the MM, and a drug reactive with free thiols is provided. The method generally includes partially reducing interchain disulfide bonds in the activatable antibody with a reducing agent, such as, for example, TCEP; and conjugating the drug reactive with free thiols to the partially reduced activatable antibody. As used herein, the term partial reduction refers to situations where an activatable antibody is contacted with a reducing agent and less than all disulfide bonds, e.g., less than all possible sites of conjugation are reduced. In some embodiments, less than 99%, 98%, 97%, 96%, 95%, 90%, 85%, 80%, 75%, 70%, 65%, 60%, 55%, 50%, 45%, 40%, 35%, 30%, 25%, 20%, 15%, 10% or less than 5% of all possible sites of conjugation are reduced.

In some embodiments, a method of reducing and conjugating an agent, e.g., a drug, to an activatable antibody resulting in selectivity in the placement of the agent is provided. The method generally includes partially reducing the activatable antibody with a reducing agent such that any conjugation sites in the masking moiety or other non-AB portion of the activatable antibody are not reduced, and conjugating the agent to interchain thiols in the AB. The conjugation site(s) are selected so as to allow desired placement of an agent to allow conjugation to occur at a desired site. The reducing agent is, for example, TCEP. The reduction reaction conditions such as, for example, the ratio of reducing agent to activatable antibody, the length of incubation, the temperature during the incubation, the pH of the reducing reaction solution, etc., are determined by identifying the conditions that produce a conjugated activatable antibody in which the MM retains the ability to effectively and efficiently mask the AB of the activatable antibody in an uncleaved state. The ratio of reduction agent to activatable antibody will vary depending on the activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

In some embodiments, a method of reducing interchain disulfide bonds in the AB of an activatable antibody and conjugating an agent, e.g., a thiol-containing agent such as a drug, to the resulting interchain thiols to selectively locate agent(s) on the AB is provided. The method generally includes partially reducing the AB with a reducing agent to form at least two interchain thiols without forming all possible interchain thiols in the activatable antibody; and conjugating the agent to the interchain thiols of the partially reduced AB. For example, the AB of the activatable antibody is partially reduced for about 1 hour at about 37° C. at a desired ratio of reducing agent:activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

The thiol-containing reagent can be, for example, cysteine or N-acetyl cysteine. The reducing agent can be, for example, TCEP. In some embodiments, the reduced activatable antibody can be purified prior to conjugation, using for example, column chromatography, dialysis, or diafiltration. In some embodiments, the reduced antibody is not purified after partial reduction and prior to conjugation.

The disclosure also provides partially reduced activatable antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds to the target, a masking moiety (MM) that inhibits the binding of the AB of the activatable antibody in an uncleaved state to the target, and a CM1-CM2 substrate coupled to the AB, wherein the CM1-CM2 substrate is a polypeptide that functions as a substrate for at least one MMP and one SP. In some embodiments, the MM is coupled to the AB via the CM1-CM2 substrate. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM1-CM2 substrate-AB or AB-CM1-CM2 substrate-MM. In some embodiments, the reducing agent is TCEP.

The disclosure also provides partially reduced activatable antibodies, including but not limited to multispecific activatable antibodies of the disclosure, in which at least one interchain disulfide bond in the activatable antibody has been reduced with a reducing agent without disturbing or otherwise compromising the activity and/or efficacy of the activatable antibody, wherein the activatable antibody includes an antibody or an antigen binding fragment thereof (AB) that specifically binds to a target, a masking moiety (MM) that inhibits the binding of the AB of the activatable antibody in an uncleaved state to the target, and a CM1-CM2 substrate coupled to the AB, and the CM1-CM2 substrate is a polypeptide that functions as a substrate for a protease. The activity and/or efficacy of the activatable antibody is, by way of nonlimiting example, masking activity, activation of the activatable antibody, and/or binding activity of the activated activatable antibody. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM1-CM2 substrate-AB or AB-CM1-CM2 substrate-MM. In some embodiments, the reducing agent is TCEP.

The disclosure also provides conjugated activatable antibodies that include an activatable antibody linked to monomethyl auristatin D (MMAD) payload, wherein the activatable antibody includes an antibody or an antigen binding fragment thereof (AB) that specifically binds to a target, a masking moiety (MM) that inhibits the binding of the AB of the activatable antibody in an uncleaved state to the target, and CM1-CM2 substrate coupled to the AB, and the CM1-CM2 substrate is a polypeptide that functions as a substrate for at least one MMP protease and at least one SP protease.

In some embodiments, the MMAD-conjugated activatable antibody can be conjugated using any of several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB.

In some embodiments, the MMAD payload is conjugated to the AB via a linker. In some embodiments, the MMAD payload is conjugated to a cysteine in the AB via a linker. In some embodiments, the MMAD payload is conjugated to a lysine in the AB via a linker. In some embodiments, the MMAD payload is conjugated to another residue of the AB via a linker, such as those residues disclosed herein. In some embodiments, the linker is a thiol-containing linker. In some embodiments, the linker is a cleavable linker. In some embodiments, the linker is a non-cleavable linker. In some embodiments, the linker is selected from the group consisting of the linkers shown in Tables 5 and 6. In some embodiments, the activatable antibody and the MMAD payload are linked via a maleimide caproyl-valine-citrulline linker. In some embodiments, the activatable antibody and the MMAD payload are linked via a maleimide PEG-valine-citrulline linker. In some embodiments, the activatable antibody and the MMAD payload are linked via a maleimide caproyl-valine-citrulline-para-aminobenzyloxycarbonyl linker. In some embodiments, the activatable antibody and the MMAD payload are linked via a maleimide PEG-valine-citrulline-para-aminobenzyloxycarbonyl linker. In some embodiments, the MMAD payload is conjugated to the AB using the partial reduction and conjugation technology disclosed herein.

The disclosure also provides polypeptides and other larger molecules that include one or more of the CM1-CM2 substrate sequences presented herein. By way of non-limiting example, the CM1-CM2 substrate sequences presented herein are useful in prodrug compositions and methods of use thereof. These CM1-CM2 substrate sequences presented herein are also useful in probes and other detection agents and methods of use thereof. For example, the CM1-CM2 substrate sequences presented herein can be used in conjunction with fluors and other quenchers to produce detection agents, such as imaging agents and/or other diagnostic agents. Those of ordinary skill in the art will appreciate that the CM1-CM2 substrate sequences presented herein are useful in any composition and/or method in the art that would use a substrate that is cleavable by at least one MMP and at least one SP.

The disclosure also provides an isolated nucleic acid molecule encoding an antibody and/or an activatable antibody described herein, as well as vectors that include these isolated nucleic acid sequences. The disclosure provides methods of producing an antibody and/or activatable antibody by culturing a cell under conditions that lead to expression of the antibody and/or activatable antibody, wherein the cell comprises such a vector.

The disclosure provides a method of manufacturing a conjugated antibody of the disclosure that bind a given target by (a) culturing a cell comprising a nucleic acid construct that encodes the antibody under conditions that lead to expression of the antibody, (i) wherein the antibody includes a CM1-CM2 substrate, and (ii) wherein the CM1-CM2 substrate is a polypeptide that functions as a substrate for a matrix metalloprotease and a serine protease; (b) recovering the antibody; and (c) conjugating the recovered antibody to one or more additional agents.

The disclosure also provides a method of manufacturing the activatable antibodies of the disclosure that bind in an activated state a given target by (a) culturing a cell comprising a nucleic acid construct that encodes the activatable antibody under conditions that lead to expression of the activatable antibody, wherein the activatable antibody comprises a masking moiety (MM), a CM1-CM2 substrate, and an antibody or an antigen binding fragment thereof (AB) that specifically binds the target, (i) wherein the CM1-CM2 substrate is a polypeptide that functions as a substrate for a MMP and a SP; and (ii) wherein the CM1-CM2 substrate is positioned in the activatable antibody such that, in an uncleaved state, the MM interferes with specific binding of the AB to the target and in a cleaved state the MM does not interfere or compete with specific binding of the AB to the target; and (b) recovering the activatable antibody.

The disclosure also provides a method of manufacturing the conjugated activatable antibodies of the disclosure that bind in an activated state a given target by (a) culturing a cell comprising a nucleic acid construct that encodes the activatable antibody under conditions that lead to expression of the activatable antibody, wherein the activatable antibody comprises a masking moiety (MM), a CM1-CM2 substrate, and an antibody or an antigen binding fragment thereof (AB) that specifically binds the target, (i) wherein the CM1-CM2 substrate is a polypeptide that functions as a substrate for a MMP and a SP; and (ii) wherein the CM1-CM2 substrate is positioned in the activatable antibody such that, in an uncleaved state, the MM interferes with specific binding of the AB to the target and in a cleaved state the MM does not interfere or compete with specific binding of the AB to the target; (b) recovering the activatable antibody; and (c) conjugating the recovered antibody to one or more additional agents.

The disclosure provides methods of preventing, delaying the progression of, treating, alleviating a symptom of, or otherwise ameliorating a target-related disease in a subject by administering a therapeutically effective amount of a conjugated antibody, an activatable antibody and/or a conjugated activatable antibody described herein to a subject in need thereof.

The disclosure provides methods of preventing, delaying the progression of, treating, alleviating a symptom of, or otherwise ameliorating inflammation and/or an inflammatory disorder in a subject by administering a therapeutically effective amount of a conjugated antibody, an activatable antibody and/or a conjugated activatable antibody described herein to a subject in need thereof. The disclosure also provides methods of preventing, delaying the progression of, treating, alleviating a symptom of, or otherwise ameliorating cancer in a subject by administering a therapeutically effective amount of a conjugated antibody, an activatable antibody and/or a conjugated activatable antibody described herein to a subject in need thereof. The disclosure also provides methods of preventing, delaying the progression of, treating, alleviating a symptom of, or otherwise ameliorating an autoimmune disease in a subject by administering a therapeutically effective amount a conjugated antibody, an activatable antibody and/or a conjugated activatable antibody described herein to a subject in need thereof.

A conjugated antibody, an activatable antibody and/or a conjugated activatable antibody used in any of the embodiments of these methods and uses can be administered at any stage of the disease. For example, such a conjugated antibody, activatable antibody and/or conjugated activatable antibody can be administered to a patient suffering cancer of any stage, from early to metastatic. The terms subject and patient are used interchangeably herein.

In some embodiments, the subject is a mammal, such as a human, non-human primate, companion animal (e.g., cat, dog, horse), farm animal, work animal, or zoo animal. In some embodiments, the subject is a rodent. In some embodiments, the subject is a human. In some embodiments, the subject is a companion animal. In some embodiments, the subject is an animal in the care of a veterinarian.

The conjugated antibody, activatable antibody and/or conjugated activatable antibody and therapeutic formulations thereof are administered to a subject suffering from or susceptible to a disease or disorder associated with aberrant target expression and/or activity. A subject suffering from or susceptible to a disease or disorder associated with aberrant target expression and/or activity is identified using any of a variety of methods known in the art. For example, subjects suffering from cancer or other neoplastic condition are identified using any of a variety of clinical and/or laboratory tests such as, physical examination and blood, urine and/or stool analysis to evaluate health status. For example, subjects suffering from inflammation and/or an inflammatory disorder are identified using any of a variety of clinical and/or laboratory tests such as physical examination and/or bodily fluid analysis, e.g., blood, urine and/or stool analysis, to evaluate health status.

Administration of a conjugated antibody, an activatable antibody and/or a conjugated activatable antibody to a patient suffering from a disease or disorder associated with aberrant target expression and/or activity is considered successful if any of a variety of laboratory or clinical objectives is achieved. For example, administration of a conjugated antibody, an activatable antibody and/or a conjugated activatable antibody to a patient suffering from a disease or disorder associated with aberrant target expression and/or activity is considered successful if one or more of the symptoms associated with the disease or disorder is alleviated, reduced, inhibited or does not progress to a further, i.e., worse, state. Administration of a conjugated antibody, an activatable antibody and/or a conjugated activatable antibody to a patient suffering from a disease or disorder associated with aberrant target expression and/or activity is considered successful if the disease or disorder enters remission or does not progress to a further, i.e., worse, state.

In some embodiments, the antibodies, conjugated antibodies, activatable antibodies, and/or conjugated activatable antibodies described herein are used in conjunction with one or more additional agents or a combination of additional agents. Suitable additional agents include current pharmaceutical and/or surgical therapies for an intended application, such as, for example, cancer. For example, the antibodies, conjugated antibodies, activatable antibodies, and/or conjugated activatable antibodies can be used in conjunction with an additional chemotherapeutic or anti-neoplastic agent.

In some embodiments, the additional agent(s) is a chemotherapeutic agent, such as a chemotherapeutic agent selected from the group consisting of docetaxel, paclitaxel, abraxane (i.e., albumin-conjugated paclitaxel), doxorubicin, oxaliplatin, carboplatin, cisplatin, irinotecan, and gemcitabine.

In some embodiments, the additional agent(s) is a checkpoint inhibitor, a kinase inhibitor, an agent targeting inhibitors in the tumor microenvironment, and/or a T cell or NK agonist. In some embodiments, the additional agent(s) is radiation therapy, alone or in combination with another additional agent(s) such as a chemotherapeutic or anti-neoplastic agent. In some embodiments, the additional agent(s) is a vaccine, an oncovirus, and/or a DC-activating agent such as, by way of non-limiting example, a toll-like receptor (TLR) agonist and/or α-CD40. In some embodiments, the additional agent(s) is a tumor-targeted antibody designed to kill the tumor via ADCC or via direct conjugation to a toxin (e.g., an antibody drug conjugate (ADC).

In some embodiments, the checkpoint inhibitor is an inhibitor of a target selected from the group consisting of CTLA-4, LAG-3, PD-1, PD-1, TIGIT, TIM-3, B7H4, BTLA, and Vista. In some embodiments, the kinase inhibitor is selected from the group consisting of B-RAFi, MEKi, and Btk inhibitors, such as ibrutinib. In some embodiments, the kinase inhibitor is crizotinib. In some embodiments, the tumor microenvironment inhibitor is selected from the group consisting of an IDO inhibitor, an α-CSF1R inhibitor, an α-CCR4 inhibitor, a TGF-beta, a myeloid-derived suppressor cell, or a T-regulatory cell. In some embodiments, the agonist is selected from the group consisting of Ox40, GITR, CD137, ICOS, CD27, and HVEM.

In some embodiments, the inhibitor is a CTLA-4 inhibitor. In some embodiments, the inhibitor is a LAG-3 inhibitor. In some embodiments, the inhibitor is a PD-1 inhibitor. In some embodiments, the inhibitor is a PD-1 inhibitor. In some embodiments, the inhibitor is a TIGIT inhibitor. In some embodiments, the inhibitor is a TIM-3 inhibitor. In some embodiments, the inhibitor is a B7H4 inhibitor. In some embodiments, the inhibitor is a Vista inhibitor. In some embodiments, the inhibitor is a B-RAFi inhibitor. In some embodiments, the inhibitor is a MEKi inhibitor. In some embodiments, the inhibitor is a Btk inhibitor. In some embodiments, the inhibitor is ibrutinib. In some embodiments, the inhibitor is crizotinib. In some embodiments, the inhibitor is an IDO inhibitor. In some embodiments, the inhibitor is an α-CSF1R inhibitor. In some embodiments, the inhibitor is an α-CCR4 inhibitor. In some embodiments, the inhibitor is a TGF-beta. In some embodiments, the inhibitor is a myeloid-derived suppressor cell. In some embodiments, the inhibitor is a T-regulatory cell.

In some embodiments, the agonist is Ox40. In some embodiments, the agonist is GITR. In some embodiments, the agonist is CD137. In some embodiments, the agonist is ICOS. In some embodiments, the agonist is CD27. In some embodiments, the agonist is HVEM.

In some embodiments, the antibody, conjugated antibody, activatable antibody, and/or conjugated activatable antibody is administered during and/or after treatment in combination with one or more additional agents such as, for example, a chemotherapeutic agent, an anti-inflammatory agent, and/or an immunosuppressive agent. In some embodiments, the antibody, conjugated antibody, activatable antibody, and/or conjugated activatable antibody and the additional agent are formulated into a single therapeutic composition, and the antibody, conjugated antibody, activatable antibody, and/or conjugated activatable antibody and additional agent are administered simultaneously. Alternatively, the antibody, conjugated antibody, activatable antibody, and/or conjugated activatable antibody and additional agent are separate from each other, e.g., each is formulated into a separate therapeutic composition, and the antibody, conjugated antibody, activatable antibody, and/or conjugated activatable antibody and the additional agent are administered simultaneously, or the antibody, conjugated antibody, activatable antibody, and/or conjugated activatable antibody and the additional agent are administered at different times during a treatment regimen. For example, the antibody, conjugated antibody, activatable antibody, and/or conjugated activatable antibody is administered prior to the administration of the additional agent, the antibody, conjugated antibody, activatable antibody, and/or conjugated activatable antibody is administered subsequent to the administration of the additional agent, or the antibody, conjugated antibody, activatable antibody, and/or conjugated activatable antibody and the additional agent are administered in an alternating fashion. As described herein, the antibody, conjugated antibody, activatable antibody, and/or conjugated activatable antibody and additional agent are administered in single doses or in multiple doses.

In some embodiments, the antibody, conjugated antibody, activatable antibody, and/or conjugated activatable antibody and the additional agent(s) are administered simultaneously. For example, the antibody, conjugated antibody, activatable antibody, and/or conjugated activatable antibody and the additional agent(s) can be formulated in a single composition or administered as two or more separate compositions. In some embodiments, the antibody, conjugated antibody, activatable antibody, and/or conjugated activatable antibody and the additional agent(s) are administered sequentially, or the antibody, conjugated antibody, activatable antibody, and/or conjugated activatable antibody and the additional agent are administered at different times during a treatment regimen.

In some embodiments, the conjugated antibody, activatable antibody and/or conjugated activatable antibody is administered during and/or after treatment in combination with one or more additional agents such as, by way of non-limiting example, an anti-inflammatory agent, an immunosuppressive agent, a chemotherapeutic agent, such as an alkylating agent, an anti-metabolite, an anti-microtubule agent, a topoisomerase inhibitor, a cytotoxic antibiotic, and/or any other nucleic acid damaging agent. In some embodiments, the additional agent is a taxane, such as paclitaxel (e.g., Abraxane®). In some embodiments, the additional agent is an anti-metabolite, such as gemcitabine. In some embodiments, the additional agent is an alkylating agent, such as platinum-based chemotherapy, such as carboplatin or cisplatin. In some embodiments, the additional agent is a targeted agent, such as a kinase inhibitor, e.g., sorafenib or erlotinib. In some embodiments, the additional agent is a targeted agent, such as another antibody, e.g., a monoclonal antibody (e.g., bevacizumab), a bispecific antibody, or a multispecific antibody. In some embodiments, the additional agent is a proteosome inhibitor, such as bortezomib or carfilzomib. In some embodiments, the additional agent is an immune modulating agent, such as lenolidominde or IL-2. In some embodiments, the additional agent is radiation. In some embodiments, the additional agent is an agent considered standard of care by those skilled in the art. In some embodiments, the additional agent is a chemotherapeutic agent well known to those skilled in the art.

In some embodiments, the additional agent is an antibody, another conjugated antibody, another activatable antibody and/or another conjugated activatable antibody. In some embodiments the additional agent is an antibody, another conjugated antibody, another activatable antibody and/or another conjugated activatable antibody against the same target as the first conjugated antibody, activatable antibody and/or a conjugated activatable antibody. In some embodiments the additional agent is an antibody, another conjugated antibody, another activatable antibody and/or another conjugated activatable antibody against a target different than the target of the first conjugated antibody, activatable antibody and/or a conjugated activatable antibody.

In some embodiments, the conjugated antibody, activatable antibody and/or conjugated activatable antibody and the additional agent(s) are administered simultaneously. For example, the conjugated antibody, activatable antibody and/or conjugated activatable antibody and the additional agent(s) can be formulated in a single composition or administered as two or more separate compositions. In some embodiments, the conjugated antibody, activatable antibody and/or conjugated activatable antibody and the additional agent(s) are administered sequentially, or the antibody and/or conjugated antibodies and the additional agent are administered at different times during a treatment regimen. For example, the antibody and/or conjugated antibodies is administered prior to the administration of the additional agent, the antibody and/or conjugated antibodies is administered subsequent to the administration of the additional agent, or the antibody and/or conjugated antibodies and the additional agent are administered in an alternating fashion. As described herein, the antibody and/or conjugated antibodies and additional agent are in single doses or in multiple doses.

The disclosure also provides methods and kits for using the conjugated antibodies, activatable antibodies and/or conjugated activatable antibodies in a variety of diagnostic and/or prophylactic indications.

Pharmaceutical compositions according to the disclosure can include an antibody, conjugated antibody, activatable antibody and/or a conjugated activatable antibody of the disclosure and a carrier. These pharmaceutical compositions can be included in kits, such as, for example, diagnostic kits.

BRIEF DESCRIPTION OF THE DRAWINGS

FIG. 8F is a graph that plots and compares the data presented in FIGS. 8A-8E in a single graph.

DETAILED DESCRIPTION OF THE INVENTION

Figure 1A:
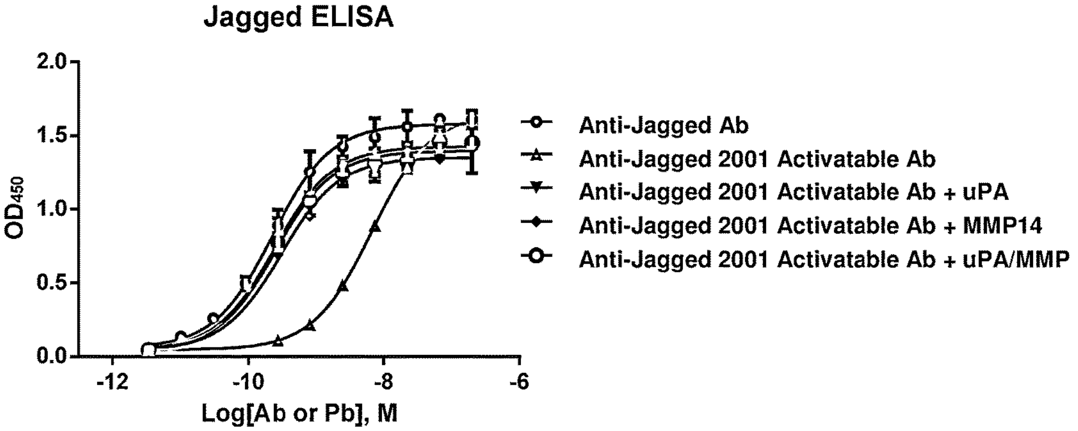
FIGS. 1A and 1B are a series of graphs depicting the results of human Jagged 1 binding ELISA assays that demonstrate the binding of the anti-Jagged antibody and the masked and activated activatable antibodies. Both the (A) 2001 and (B) 1001/LP'/0001 substrate-containing activatable antibodies were activated by uPA (a serine protease), MMP14 (an MMP), and uPA in combination with MMP14. The activated activatable antibodies showed binding equivalent to the anti-Jagged antibody.

The disclosure provides amino acid sequences that include at least a first cleavable moiety (CM1) that is a substrate for at least one matrix metalloprotease (MMP) and at least a second cleavable moiety (CM2) that is a substrate for at least one serine protease (SP). These CM1-CM2 substrates are useful in a variety of therapeutic, diagnostic and prophylactic indications. For example, these CM1-CM2 substrates are useful in activatable antibodies that include antibodies or antigen-binding fragments thereof (AB) that include at least one masking moiety (MM) linked to at least one antigen- or epitope-binding domain of the AB such that coupling of the MM reduces the ability of the AB to bind its target.

The working examples provided herein demonstrate that these CM1-CM2 substrates exhibit a number of desirable cleavage characteristics when exposed to at least one MMP protease and/or at least one SP protease under specified conditions.

The disclosure also provides antibodies that include one or more of these CM1-CM2 substrates. For example, these CM1-CM2 substrates are useful when conjugating antibodies to one or more additional agents to produce conjugated antibodies. These CM1-CM2 substrates are also useful in activatable antibodies and/or activatable antibody conjugates.

The conjugated antibodies, activatable antibodies, and/or conjugated activatable antibodies include an antibody or antigen-binding fragment thereof (AB) that specifically binds a target. Exemplary classes of targets of an AB include, but are not necessarily limited to, cell surface receptors and secreted binding proteins (e.g., growth factors), soluble enzymes, structural proteins (e.g. collagen, fibronectin) and the like. In some embodiments, conjugated antibodies and/or activatable antibodies have an AB that binds an extracellular target, usually an extracellular protein target. In some embodiments, conjugated antibodies and/or activatable antibodies are designed for cellular uptake and are switchable inside a cell.

As a non-limiting example, the AB is a binding partner for any target listed in Table 1.

TABLE 1

| Exemplary Targets |
| --- |
| 1-92-LFA-3 |
| Alpha-4 integrin |
| Alpha-V integrin |
| alpha4beta1 integrin |
| alpha4beta7 integrin |
| AGR2 |
| Anti-Lewis-Y |
| Apelin J receptor |
| APRIL |
| B7-H4 |
| BAFF |
| BTLA |
| C5 complement |
| C-242 |
| CA9 |
| CA19-9 (Lewis a) |
| Carbonic anhydrase 9 |
| CD2 |
| CD3 |
| CD6 |
| CD9 |
| CD11a |
| CD19 |
| CD20 |
| CD22 |
| CD24 |
| CD25 |
| CD27 |
| CD28 |

TABLE 1-continued

| Exemplary Targets |
|---|
| CD30 |
| CD33 |
| CD38 |
| CD40 |
| CD40L |
| CD41 |
| CD44 |
| CD44v6 |
| CD47 |
| CD51 |
| CD52 |
| CD56 |
| CD64 |
| CD70 |
| CD71 |
| CD74 |
| CD80 |
| CD81 |
| CD86 |
| CD95 |
| CD117 |
| CD125 |
| CD132 |
| (IL-2RG) |
| CD133 |
| CD137 |
| CD138 |
| CD166 |
| CD172A |
| CD248 |
| CDH6 |
| CEACAM5 (CEA) |
| CEACAM6 (NCA-90) |
| CLAUDIN-3 |
| CLAUDIN-4 |
| cMet |
| Collagen |
| Cripto |
| CSFR |
| CSFR-1 |
| CTLA-4 |
| CTGF |
| CXCL10 |
| CXCL13 |
| CXCR1 |
| CXCR2 |
| CXCR4 |
| CYR61 |
| DL44 |
| DLK1 |
| DLL4 |
| DPP-4 |
| DSG1 |
| EGFR |
| EGFRviii |
| Endothelin B receptor (ETBR) |
| ENPP3 |
| EpCAM |
| EPHA2 |
| EPHB 2 |
| ERBB3 |
| F protein of RSV |
| FAP |
| FGF-2 |
| FGF8 |
| FGFR1 |
| FGFR2 |
| FGFR3 |
| FGFR4 |
| Folate receptor |
| GAL3ST1 |
| G-CSF |
| G-CSFR |
| GD2 |
| GITR |
| GLUT1 |
| GLUT4 |
| GM-CSF |

TABLE 1-continued

| Exemplary Targets |
|---|
| GM-CSFR |
| GP IIb/IIIa receptors |
| Gp130 |
| GPNMB |
| GRP78 |
| HER2/neu |
| HGF |
| hGH |
| HVEM |
| Hyaluronidase |
| ICOS |
| IFNalpha |
| IFNbeta |
| IFNgamma |
| IgE |
| IgE Receptor (FceRI) |
| IGF |
| IGF1R |
| IL1B |
| IL1R |
| IL2 |
| IL11 |
| IL12 |
| IL12p40 |
| IL-12R, IL-12Rbeta1 |
| IL13 |
| IL13R |
| IL15 |
| IL17 |
| IL18 |
| IL21 |
| IL23 |
| IL23R |
| IL27/IL27R(wsx1) |
| IL29 |
| IL-31R |
| IL31/IL31R |
| IL2R |
| IL4 |
| IL4R |
| IL6, IL6R |
| Insulin Receptor |
| Jagged Ligands |
| Jagged 1 |
| Jagged 2 |
| LAG-3 |
| LIF-R |
| Lewis X |
| LIGHT |
| LRP4 |
| LRRC26 |
| MCSP |
| Mesothelin |
| MRP4 |
| MUC1 |
| Mucin-16 (MUC16, CA-125) |
| Na/K ATPase |
| Neutrophil elastase |
| NGF |
| Nicastrin |
| Notch Receptors |
| Notch 1 |
| Notch 2 |
| Notch 3 |
| Notch 4 |
| NOV |
| OSM-R |
| OX-40 |
| PAR2 |
| PDGF-AA |
| PDGF-BB |
| PDGFRalpha |
| PDGFRbeta |
| PD-1 |
| PD-L1 |
| PD-L2 |
| Phosphatidyl-serine |
| P1GF |

TABLE 1-continued

| Exemplary Targets |
|---|
| PSCA |
| PSMA |
| RAAG12 |
| RAGE |
| SLC44A4 |
| Sphingosine 1 Phosphate |
| STEAP1 |
| STEAP2 |
| TAG-72 |
| TAPA1 |
| TGFbeta |
| TIGIT |
| TIM-3 |
| TLR2 |
| TLR4 |
| TLR6 |
| TLR7 |
| TLR8 |
| TLR9 |
| TMEM31 |
| TNFalpha |
| TNFR |
| TNFRS 12 A |
| TRAIL-R1 |
| TRAIL-R2 |
| Transferrin |
| Transferrin receptor |
| TRK-A |
| TRK-B |
| uPAR |
| VAP1 |
| VCAM-1 |
| VEGF |
| VEGF-A |
| VEGF-B |
| VEGF-C |
| VEGF-D |
| VEGFR1 |
| VEGFR2 |
| VEGFR3 |
| VISTA |
| WISP-1 |
| WISP-2 |
| WISP-3 |

As a non-limiting example, the AB is or is derived from an antibody listed in Table 2.

TABLE 2

| Exemplary sources for Abs | |
|---|---|
| Antibody Trade Name (antibody name) | Target |
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |
| Humira ™ (adalimumab) | TNFα |
| Tysabri ™ (natalizumab) | Integrinα4 |
| Simulect ™ (basiliximab) | IL2R |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| Ocrelizumab | CD20 |
| Arzerra ™ (ofatumumab) | CD20 |
| Gazyva ™ (Obinutuzumab) | CD20 |
| Zenapax ™ (daclizumab) | CD25 |
| Adcetris ™ (brentuximab vedotin) | CD30 |
| Myelotarg ™ (gemtuzumab) | CD33 |
| Mylotarg ™ (gemtuzumab ozogamicin) | CD33 |
| Campath ™ (alemtuzumab) | CD52 |
| ReoPro ™ (abiciximab) | Glycoprotein receptor IIb/IIIa |

TABLE 2-continued

| Exemplary sources for Abs | |
|---|---|
| Antibody Trade Name (antibody name) | Target |
| Xolair ™ (omalizumab) | IgE |
| Herceptin ™ (trastuzumab) | Her2 |
| Kadcyla ™ (trastuzumab emtansine) | Her2 |
| Synagis ™ (palivizumab) | F protein of RSV |
| (ipilimumab) | CTLA-4 |
| (tremelimumab) | CTLA-4 |
| Hu5c8 | CD40L |
| (pertuzumab) | Her2-neu |
| (ertumaxomab) | CD3/Her2-neu |
| Orencia ™ (abatacept) | CTLA-4 |
| (tanezumab) | NGF |
| (bavituximab) | Phosphatidylserine |
| (zalutumumab) | EGFR |
| (mapatumumab) | EGFR |
| (matuzumab) | EGFR |
| (nimotuzumab) | EGFR |
| ICR62 | EGFR |
| mAb 528 | EGFR |
| CH806 | EGFR |
| MDX-447 | EGFR/CD64 |
| (edrecolomab) | EpCAM |
| RAV12 | RAAG12 |
| huJ591 | PSMA |
| Enbrel ™ (etanercept) | TNF-R |
| Amevive ™ (alefacept) | 1-92-LFA-3 |
| Antril ™, Kineret ™ (ankinra) | IL-1Ra |
| GC1008 | TGFbeta |
| | Notch, e.g., Notch 1 |
| | Jagged 1 or Jagged 2 |
| (adecatumumab) | EpCAM |
| (figitumumab) | IGF1R |
| (tocilizumab) | IL-6 receptor |
| Stelara ™ (ustekinumab) | IL-12/IL-23 |
| Prolia ™ (denosumab) | RANKL |

Exemplary conjugated antibodies, activatable antibodies and/or conjugated activatable antibodies of the disclosure include, for example, antibodies that bind interleukin 6 receptor (IL-6R) and that include a heavy chain and a light chain that are, or are derived from, the antibody referred to herein as the"Av1" antibody, which binds interleukin-6 receptor (IL-6R). The amino acid sequences for the Av1 heavy chain and the Av1 light chain are shown below in SEQ ID NO: 100 and SEQ ID NO: 101, respectively.

Av1 Antibody Heavy Chain Amino Acid Sequence:

```
                                    (SEQ ID NO: 100)
QVQLQESGPGLVRPSQTLSLTCTVSGYSITSDHAWSWVRQPPGRGLEWIG

YISYSGITTYNPSLKSRVTISRDNSKNTLYLQMNSLRAEDTAVYYCARSL

ARTTAMDYWGQGSLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK
```

Av1 Antibody Light Chain Amino Acid Sequence:

(SEQ ID NO: 101)
DIQMTQSPSSLSASVGDRVTITCRASQDISSYLNWYQQKPGKAPKLLIYY
TSRLHSGVPSRFSGSGSGTDFTFTISSLQPEDIATYYCQQGNTLPYTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

Exemplary activatable antibodies and/or conjugated activatable antibodies of the disclosure include, for example, antibodies that bind interleukin 6 receptor (IL-6R) and that include a heavy chain and a light chain that are, or are derived from, the Av1 antibody and a masking moiety. Exemplary activatable antibodies and/or conjugated activatable antibodies of the disclosure include an amino acid sequence attached to the N-terminus of the AV1 light chain. These N-terminal amino acid sequences include, for example, YGSCSWNYVHIFMDC (SEQ ID NO: 102); QGDFDIPFPAHWVPIT (SEQ ID NO: 103); MGVPAGCVWNYAHIFMDC (SEQ ID NO: 104); QGQSGQYGSCSWNYVHIFMDC (SEQ ID NO: 105); QGQSGQGDFDIPFPAHWVPIT (SEQ ID NO: 106); or QGQSGQMGVPAGCVWNYAHIFMDC (SEQ ID NO: 107). It is also to be appreciated that such amino acid sequences can be attached to the N-terminus of the AV1 heavy chain or to the C-terminus of the AV1 heavy or light chain.

Exemplary activatable antibodies of the disclosure include, for example, antibodies that bind Epidermal Growth Factor Receptor (EGFR) and that include a heavy chain and a light chain that are, or are derived from, an antibody selected from the group consisting of the antibody referred to herein as the"c225v5" antibody (also referred to herein as the C225v5 antibody), the antibody referred to herein as the"c225v4" antibody (also referred to herein as the C225v4 antibody), and the antibody referred to herein as the"c225v6" antibody (also referred to herein as the C225v6 antibody), each of which binds EGFR. The c225v5 antibody, the c225v4 antibody, and the c225v6 antibody share the same light chain sequence, referred to herein as "c225 light chain." The amino acid sequences for the c225v5 heavy chain, the c225v4 antibody, the c225v6 antibody, and the c225 light chain are shown below.

C225v5 Antibody Heavy Chain Amino Acid Sequence:

(SEQ ID NO: 108)
QVQLKQSGPGLVQPSQSLSITCTVSGFSLTNYGVHWVRQSPGKGLEWLGV
IWSGGNTDYNTPFTSRLSINKDNSKSQVFFKMNSLQSQDTAIYYCARALT
YYDYEFAYWGQGTLVTVSAASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK

C225v4 Antibody Heavy Chain Amino Acid Sequence:

(SEQ ID NO: 109)
QVQLKQSGPGLVQPSQSLSITCTVSGFSLTNYGVHWVRQSPGKGLEWLGV
IWSGGNTDYNTPFTSRLSINKDNSKSQVFFKMNSLQSNDTAIYYCARALT
YYDYEFAYWGQGTLVTVSAASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK

C225v6 Antibody Heavy Chain Amino Acid Sequence:

(SEQ ID NO: 110)
QVQLKQSGPGLVQPSQSLSITCTVSGFSLTNYGVHWVRQSPGKGLEWLGV
IWSGGNTDYNTPFTSRLSINKDNSKSQVFFKMNSLQSQDTAIYYCARALT
YYDYEFAYWGQGTLVTVSAASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYAS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGK

C225 Antibody Light Chain Amino Acid Sequence:

(SEQ ID NO: 111)
QILLTQSPVILSVSPGERVSFSCRASQSIGTNIHWYQQRTNGSPRLLIKY
ASESISGIPSRFSGSGSGTDFTLSINSVESEDIADYYCQQNNNWPTTFGA
GTKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

Exemplary conjugated antibodies and/or activatable antibodies of the disclosure include, for example, antibodies that bind a Jagged target, e.g., Jagged-1, Jagged-2 and/or both Jagged-1 and Jagged-2, and that include a combination of a variable heavy chain region and a variable light chain region that are, or are derived from, the variable heavy chain and variable light chain sequences shown below.

Variable Light Chain Amino Sequence Lc4
(SEQ ID NO: 112)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc4
(SEQ ID NO: 113)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc5
(SEQ ID NO: 114)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc5
(SEQ ID NO: 115)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPYHGQFDYWGQGTLVTVSS

Variable Light Chain Amino Sequence Lc7
(SEQ ID NO: 116)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc7
(SEQ ID NO: 117)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc8
(SEQ ID NO: 118)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc8
(SEQ ID NO: 119)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKHIGRTNPFDYWGQGTLVTVSS

Variable Light Chain Amino Sequence Lc13
(SEQ ID NO: 120)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc13
(SEQ ID NO: 121)
EVQLLESGGGLVQPGGSLRLSCAASGFTFSSYAMSWVRQAPGKGLEWVSSIEQMGWQTEYADSV

KGRFTISRDNSKNTLYLQMNSLRAEDTAVYYCAKSAAAFDYWGQGTLVTVSS

Variable Light Chain Amino Sequence Lc16
(SEQ ID NO: 122)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc16
(SEQ ID NO: 123)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPYYGQFDYWGQGTLVTVSS

Variable Light Chain Amino Sequence Lc19
(SEQ ID NO: 124)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

-continued

Variable Heavy Chain Amino Sequence Hc19
(SEQ ID NO: 125)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc21
(SEQ ID NO: 126)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc21
(SEQ ID NO: 127)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc24
(SEQ ID NO: 128)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc24
(SEQ ID NO: 129)
EVQLLESGGGLVQPGGSLRLSCAASGFTFSSYAMSWVRQAPGKGLEWVSSIEEMGWQTLYADSV

KGRFTISRDNSKNTLYLQMNSLRAEDTAVYYCAKSAAAFDYWGQGTLVTVSS

Variable Light Chain Amino Sequence Lc26
(SEQ ID NO: 130)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc26
(SEQ ID NO: 131)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc27
(SEQ ID NO: 132)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc27
(SEQ ID NO: 133)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFYGQFDYWGQGTLVTVSS

Variable Light Chain Amino Sequence Lc28
(SEQ ID NO: 134)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc28
(SEQ ID NO: 135)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc30
(SEQ ID NO: 136)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc30
(SEQ ID NO: 137)
EVQLLESGGGLVQPGGSLRLSCAASGFTFSSYAMSWVRQAPGKGLEWVSSIEEMGWQTLYADSV

KGRFTISRDNSKNTLYLQMNSLRAEDTAVYYAKSAAAFDYWGQGTLVTVSS

-continued

Variable Light Chain Amino Sequence Lc31

(SEQ ID NO: 138)

DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc31

(SEQ ID NO: 139)

EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc32

(SEQ ID NO: 140)

DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc32

(SEQ ID NO: 141)

EVQLLESGGGLVQPGGSLRLSCAASGFTFSSYAMSWVRQAPGKGLEWVSSIDPEGWQTYYADSV

KGRFTISRDNSKNTLYLQMNSLRAEDTAVYYCAKSAAAFDYWGQGTLVTVSS

Variable Light Chain Amino Sequence Lc37

(SEQ ID NO: 142)

DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc37

(SEQ ID NO: 143)

EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPHNGQFDYWGQGTLVTVSS

Variable Light Chain Amino Sequence Lc39

(SEQ ID NO: 144)

DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc39

(SEQ ID NO: 145)

EVQLLESGGGLVQPGGSLRLSCAASGFTFSSYAMSWVRQAPGKGLEWVSSIEQMGWQTEYADSV

KGRFTISRDNSKNTLYLQMNSLRAEDTAVYYCAKSAAAFDYWGQGTLVTVSS

Variable Light Chain Amino Sequence Lc40

(SEQ ID NO: 146)

DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Heavy Chain Amino Sequence Hc40

(SEQ ID NO: 147)

EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc47

(SEQ ID NO: 148)

DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc47

(SEQ ID NO: 149)

EVQLLESGGGLVQPGGSLRLSCAASGFTFSSYAMSWVRQAPGKGLEWVSSIDEMGWQTEYADSV

KGRFTISRDNSKNTLYLQMNSLRAEDTAVYYCAKSAAAFDYWGQGTLVTVSS

Variable 4B2 Light Chain (SEQ ID NO: 150)

DIQMTQSPSSLSASVGDRVTITCRASQSISSYLNWYQQKPGKAPKLLIYAASSLQSGVPSRFSG

SGSGTDFTLTISSLQPEDFATYYCQQTLDAPPQFGQGTKVEIKR

-continued

Variable 4B2 Heavy Chain
(SEQ ID NO: 151)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable 4D11 Light Chain
(SEQ ID NO: 152)
DIQMTQSPSSLSASVGDRVTITCRASQSISSYLNWYQQKPGKAPKLLIYAASSLQSGVPSRFSG

SGSGTDFTLTISSLQPEDFATYYCQQTVVAPPLFGQGTKVEIKR

Variable 4D11 Heavy Chain
(SEQ ID NO: 153)
EVQLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSS

Variable 4E7 Light Chain
(SEQ ID NO: 154)
DIQMTQSPSSLSASVGDRVTITCRASQSISSYLNWYQQKPGKAPKLLIYAASSLQSGVPSRFSG

SGSGTDFTLTISSLQPEDFATYYCQQSLVAPLTFGQGTKVEIKR

Variable 4E7 Heavy Chain
(SEQ ID NO: 155)
EVQLLESGGGLVQPGGSLRLSCAASGFTFSSYAMSWVRQAPGKGLEWVSSIEEMGWQTKYADSV

KGRFTISRDNSKNTLYLQMNSLRAEDTAVYYCAKSAAAFDYWGQGTLVTVSS

Variable 4E11 Light Chain
(SEQ ID NO: 156)
DIQMTQSPSSLSASVGDRVTITCRASQSISSYLNWYQQKPGKAPKLLIYAASSLQSGVPSRFSG

SGSGTDFTLTISSLQPEDFATYYCQQALDAPLMFGQGTKVEIKR

Variable 4E11 Heavy Chain
(SEQ ID NO: 157)
EVQLLESGGGLVQPGGSLRLSCAASGFTFSSYAMSWVRQAPGKGLEWVSSIEPMGQLTEYADSV

KGRFTISRDNSKNTLYLQMNSLRAEDTAVYYCAKDIGGRSAFDYWGQGTLVTVSS

Variable 6B7 Light Chain
(SEQ ID NO: 158)
DIQMTQSPSSLSASVGDRVTITCRASQSISSYLNWYQQKPGKAPKLLIYAASSLQSGVPSRFSG

SGSGTDFTLTISSLQPEDFATYYCQQALVAPLTFGQGTKVEIKR

Variable 6B7 Heavy Chain
(SEQ ID NO: 159)
EVQLLESGGGLVQPGGSLRLSCAASGFTFSSYAMSWVRQAPGKGLEWVSSIDEMGWQTYYADSV

KGRFTISRDNSKNTLYLQMNSLRAEDTAVYYCAKSAAAFDYWGQGTLVTVSS

Variable 6F8 Light Chain
(SEQ ID NO: 160)
DIQMTQSPSSLSASVGDRVTITCRASQSISSYLNWYQQKPGKAPKLLIYAASSLQSGVPSRFSG

SGSGTDFTLTISSLQPEDFATYYCQQALVAPLTFGQGTKVEIKR

Variable 6F8 Heavy Chain
(SEQ ID NO: 161)
EVQLLESGGGLVQPGGSLRLSCAASGFTFSSYAMSWVRQAPGKGLEWVSSIDEMGWQTYYADSV

KGRFTISRDNSKNTLYLQMNSLRAEDTAVYYCAKSAAAFDYWGQGTLVTVSS

Exemplary conjugated antibodies, activatable antibodies and/or conjugated activatable antibodies of the disclosure include, for example, antibodies that bind a Jagged target, e.g., Jagged-1, Jagged-2 and/or both Jagged-1 and Jagged-2, and that include a combination of a heavy chain region and a light chain region that are, or are derived from, the heavy chain and light chain sequences shown below.

4D11 Light Chain sequence:

(SEQ ID NO: 162)

DIQMTQSPSSLSASVGDRVTITCRASQSISSYLNWYQQKPGKAPKLLIYAASSLQSGVPSRFSG

SGSGTDFTLTISSLQPEDFATYYCQQTVVAPPLFGQGTKVEIKRTVAAPSVFIFPPSDEQLKSG

TASVVCLLNNFYPREAKVQWKVDNALQSGNSQESVTEQDSKDSTYSLSSTLTLSKADYEKHKVY

ACEVTHQGLSSPVTKSFNRGEC

4D11 Heavy Chain sequence:

(SEQ ID NO: 67)

EVQLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSSASTKGPSVF

PLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEALHNHYTQKSLSLSPG

K

4D11v2 Heavy Chain sequence (SEQ ID NO: 163)

EVHLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSSASTKGPSVF

PLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEALHNHYTQKSLSLSPG

K

4D11v2 Light Chain Sequence (SEQ ID NO: 164)

DIQMTQSPSSLSASVGDRVTITCRASQSISSYLNWYQQKPGKAPKLLIYAASSLQSGVPSRFSG

SGSGTDFTLTISSLQPEDFATYYCQQTVVAPPLFGQGTKVEIKRTVAAPSVFIFPPSDEQLKSG

TASVVCLLNNFYPREAKVQWKVDNALQSGNSQESVTEQDSKDSTYSLSSTLTLXKADYEKHKVY

ACEVTHQGLSSPVTKSFNRGEC

The activatable antibodies and activatable antibody compositions provided herein contain at least an antibody or antibody fragment thereof (collectively referred to as AB throughout the disclosure) that specifically binds a target, e.g., a human target, wherein the AB is modified by a masking moiety (MM).

In some embodiments, the masking moiety is selected for use with a specific antibody or antibody fragment. For example, suitable masking moieties for use with antibodies that bind EGFR include MMs that include the sequence CISPRG (SEQ ID NO: 165). By way of non-limiting examples, the MM can include a sequence such as CISPRGC (SEQ ID NO: 166); CISPRGCG (SEQ ID NO: 167); CISPRGCPDGPYVMY (SEQ ID NO: 168); CISPRGCPDGPYVM (SEQ ID NO: 169), CISPRGCEPGTYVPT (SEQ ID NO: 170) and CISPRGCPGQIWHPP (SEQ ID NO: 171). Other suitable masking moieties include any of the EGFR-specific masks disclosed in PCT Publication No. WO 2010/081173, such as, by way of non-limiting example, GSHCLIPINMGAPSC (SEQ ID NO: 172); CISPRGCGGSSASQSGQGSHCLIPINMGAPSC (SEQ ID NO: 173); CNHHYFYTCGCISPRGCPG (SEQ ID NO: 174); ADHVFWGSYGCISPRGCPG (SEQ ID NO: 175); CHHVYWGHCGCISPRGCPG (SEQ ID NO: 176); CPHFTTTSCGCISPRGCPG (SEQ ID NO: 177); CNHHYHYYCGCISPRGCPG (SEQ ID NO: 178); CPHVSFGSCGCISPRGCPG (SEQ ID NO: 179); CPYYTLSYCGCISPRGCPG (SEQ ID NO: 180); CNHVYFGTCGCISPRGCPG (SEQ ID NO: 181); CNHFTLTTCGCISPRGCPG (SEQ ID NO: 182); CHHFTLTTCGCISPRGCPG (SEQ ID NO: 183); YNPCATPMCCISPRGCPG (SEQ ID NO: 184); CNHHYFYTCGCISPRGCG (SEQ ID NO: 185); CNHHYHYYCGCISPRGCG (SEQ ID NO: 186); CNHVYFGTCGCISPRGCG (SEQ ID NO: 187); CHHVYWGHCGCISPRGCG (SEQ ID NO: 188); CPHFTTTSCGCISPRGCG (SEQ ID NO: 189); CNHFTLTTCGCISPRGCG (SEQ ID NO: 190); CHHFTLTTCGCISPRGCG (SEQ ID NO: 191); CPYYTLSYCGCISPRGCG (SEQ ID NO: 192);

CPHVSFGSCGCISPRGCG (SEQ ID NO: 193); ADHVFWGSYGCISPRGCG (SEQ ID NO: 194); YNPCATPMCCISPRGCG (SEQ ID NO: 195); CHHVYWGHCGCISPRGCG (SEQ ID NO: 196); C(N/P)H(H/V/F)(Y/T)(F/W/T/L)(Y/G/T/S)(T/S/Y/H)CGCISPRGCG (SEQ ID NO: 197); CISPRGCGQPIPSVK (SEQ ID NO: 198); CISPRGCTQPYHVSR (SEQ ID NO: 199); and/or CISPRGCNAVSGLGS (SEQ ID NO: 200).

Suitable masking moieties for use with antibodies that bind a Jagged target, e.g., Jagged 1 and/or Jagged 2, include, by way of non-limiting example, masking moieties that include a sequence such as QGQSGQCNIWLVGGDCRGWQG (SEQ ID NO: 201); QGQSGQGQQQWCNIWINGGDCRGWNG (SEQ ID NO: 202); PWCMQRQDFLRCPQP (SEQ ID NO: 203); QLGLPAYMCTFECLR (SEQ ID NO: 204); CNLWVSGGDCGGLQG (SEQ ID NO: 205); SCSLWTSGSCLPHSP (SEQ ID NO: 206); YCLQLPHYMQAMCGR (SEQ ID NO: 207); CFLYSCTDVSYWNNT (SEQ ID NO: 208); PWCMQRQDYLRCPQP (SEQ ID NO: 209); CNLWISGGDCRGLAG (SEQ ID NO: 210); CNLWVSGGDCRGVQG (SEQ ID NO: 211); CNLWVSGGDCRGLRG (SEQ ID NO: 212); CNLWISGGDCRGLPG (SEQ ID NO: 213); CNLWVSGGDCRDAPW (SEQ ID NO: 214); CNLWVSGGDCRDLLG (SEQ ID NO: 215); CNLWVSGGDCRGLQG (SEQ ID NO: 216); CNLWLHGGDCRGWQG (SEQ ID NO: 217); CNIWLVGGDCRGWQG (SEQ ID NO: 218); CTTWFCGGDCGVMRG (SEQ ID NO: 219); CNIWGPSVDCGALLG (SEQ ID NO: 220); CNIWVNGGDCRSFEG (SEQ ID NO: 221); YCLNLPRYMQDMCWA (SEQ ID NO: 222); YCLALPHYMQADCAR (SEQ ID NO: 223); CFLYSCGDVSYWGSA (SEQ ID NO: 224); CYLYSCTDSAFWNNR (SEQ ID NO: 225); CYLYSCNDVSYWSNT (SEQ ID NO: 226); CFLYSCTDVSYW (SEQ ID NO: 227); CFLYSCTDVAYWNSA (SEQ ID NO: 228); CFLYSCTDVSYWGDT (SEQ ID NO: 229); CFLYSCTDVSYWGNS (SEQ ID NO: 230); CFLYSCTDVAYWNNT (SEQ ID NO: 231); CFLYSCGDVSYWGNPGLS (SEQ ID NO: 232); CFLYSCTDVAYWSGL (SEQ ID NO: 233); CYLYSCTDGSYWNST (SEQ ID NO: 234); CFLYSCSDVSYWGNI (SEQ ID NO: 235); CFLYSCTDVAYW (SEQ ID NO: 236); CFLYSCTDVSYWGST (SEQ ID NO: 237); CFLYSCTDVAYWGDT (SEQ ID NO: 238); GCNIWLNGGDCRGWVDPLQG (SEQ ID NO: 239); GCNIWLVGGDCRGWIGDTNG (SEQ ID NO: 240); GCNIWLVGGDCRGWIEDSNG (SEQ ID NO: 241); GCNIWANGGDCRGWIDNIDG (SEQ ID NO: 242); GCNIWLVGGDCRGWLGEAVG (SEQ ID NO: 243); GCNIWLVGGDCRGWLEEAVG (SEQ ID NO: 244); GGPALCNIWLNGGDCRGWSG (SEQ ID NO: 245); GAPVFCNIWLNGGDCRGWMG (SEQ ID NO: 246); GQQQWCNIWINGGDCRGWNG (SEQ ID NO: 247); GKSEFCNIWLNGGDCRGWIG (SEQ ID NO: 248); GTPGGCNIWANGGDCRGWEG (SEQ ID NO: 249); GASQYCNLWINGGDCRGWRG (SEQ ID NO: 250); GCNIWLVGGDCRPWVEGG (SEQ ID NO: 251); GCNIWAVGGDCRPFVDGG (SEQ ID NO: 252); GCNIWLNGGDCRAWVDTG (SEQ ID NO: 253); GCNIWIVGGDCRPFINDG (SEQ ID NO: 254); GCNIWLNGGDCRPVVFGG (SEQ ID NO: 255); GCNIWLSGGDCRMFMNEG (SEQ ID NO: 256); GCNIWVNGGDCRSFVYSG (SEQ ID NO: 257); GCNIWLNGGDCRGWEASG (SEQ ID NO: 258); GCNIWAHGGDCRGFIEPG (SEQ ID NO: 259); GCNIWLNGGDCRTFVASG (SEQ ID NO: 260); GCNIWAHGGDCRGFIEPG (SEQ ID NO: 261); GFLENCNIWLNGGDCRTG (SEQ ID NO: 262); GIYENCNIWLNGGDCRMG (SEQ ID NO: 263); and/or GIPDNCNIWINGGDCRYG (SEQ ID NO: 264).

Suitable masking moieties for use with antibodies that bind an interleukin 6 target, e.g., interleukin 6 receptor (IL-6R), include, by way of non-limiting example, masking moieties that include a sequence such as QGQSGQYGSCSWNYVHIFMDC (SEQ ID NO: 265); QGQSGQGDFDIPFPAHWVPIT (SEQ ID NO: 266); QGQSGQMGVPAGCVWNYAHIFMDC (SEQ ID NO: 267); YRSCNWNYVSIFLDC (SEQ ID NO: 268); PGAFDIPFPAHWVPNT (SEQ ID NO: 269); ESSCVWNYVHIYMDC (SEQ ID NO: 270); YPGCKWNYDRIFLDC (SEQ ID NO: 271); YRTCSWNYVGIFLDC (SEQ ID NO: 272); YGSCSWNYVHIFMDC (SEQ ID NO: 273); YGSCSWNYVHIFLDC (SEQ ID NO: 274); YGSCNWNYVHIFLDC (SEQ ID NO: 275); YTSCNWNYVHIFMDC (SEQ ID NO: 276); YPGCKWNYDRIFLDC (SEQ ID NO: 277); WRSCNWNYAHIFLDC (SEQ ID NO: 278); WSNCHWNYVHIFLDC (SEQ ID NO: 279); DRSCTWNYVRISYDC (SEQ ID NO: 280); SGSCKWDYVHIFLDC (SEQ ID NO: 281); SRSCIWNYAHIHLDC (SEQ ID NO: 282); SMSCYWQYERIFLDC (SEQ ID NO: 283); YRSCNWNYVSIFLDC (SEQ ID NO: 284); SGSCKWDYVHIFLDC (SEQ ID NO: 285); YKSCHWDYVHIFLDC (SEQ ID NO: 286); YGSCTWNYVHIFMEC (SEQ ID NO: 287); FSSCNWNYVHIFLDC (SEQ ID NO: 288); WRSCNWNYAHIFLDC (SEQ ID NO: 289); YGSCQWNYVHIFLDC (SEQ ID NO: 290); YRSCNWNYVHIFLDC (SEQ ID NO: 291); NMSCHWDYVHIFLDC (SEQ ID NO: 292); FGPCTWNYARISWDC (SEQ ID NO: 293); XXsCXWXYvhIfXdC (SEQ ID NO: 294); MGVPAGCVWNYAHIFMDC (SEQ ID NO: 295); RDTGGQCRWDYVHIFMDC (SEQ ID NO: 296); AGVPAGCTWNYVHIFMEC (SEQ ID NO: 297); VGVPNGCVWNYAHIFMEC (SEQ ID NO: 298); DGGPAGCSWNYVHIFMEC (SEQ ID NO: 299); AVGPAGCWWNYVHIFMEC (SEQ ID NO: 300); CTWNYVHIFMDCGEGEGP (SEQ ID NO: 301); GGVPEGCTWNYAHIFMEC (SEQ ID NO: 302); AEVPAGCWWNYVHIFMEC (SEQ ID NO: 303); AGVPAGCTWNYVHIFMEC (SEQ ID NO: 304); SGASGGCKWNYVHIFMDC (SEQ ID NO: 305); TPGCRWNYVHIFMECEAL (SEQ ID NO: 306); VGVPNGCVWNYAHIFMEC (SEQ ID NO: 307); PGAFDIPFPAHWVPNT (SEQ ID NO: 308); RGACDIPFPAHWIPNT (SEQ ID NO: 309); QGDFDIPFPAHWVPIT (SEQ ID NO: 310); XGafDIPFPAHWvPnT (SEQ ID NO: 311); RGDGNDSDIPFPAHWVPRT (SEQ ID NO: 312); SGVGRDRDIPFPAHWVPRT (SEQ ID NO: 313); WAGGNDCDIPFPAHWIPNT (SEQ ID NO: 314); WGDGMDVDIPFPAHWVPVT (SEQ ID NO: 315); AGSGNDSDIPFPAHWVPRT (SEQ ID NO: 316); ESRSGYADIPFPAHWVPRT (SEQ ID NO: 317); and/or RECGRCGDIPFPAHWVPRT (SEQ ID NO: 318).

When the AB is modified with a MM and is in the presence of the target, specific binding of the AB to its target is reduced or inhibited, as compared to the specific binding of the AB not modified with an MM or the specific binding of the parental AB to the target.

The $K_d$ of the AB modified with a MM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000, 000, 100-1,000, 100-10,000, 100-100,000, 100-1,000,000, 100-10,000,000, 1,000-10,000, 1,000-100,000, 1,000-1,000, 000, 1000-10,000,000, 10,000-100,000, 10,000-1,000,000, 10,000-10,000,000, 100,000-1,000,000, or 100,000-10,000, 000 times greater than the $K_d$ of the AB not modified with an MM or of the parental AB towards the target. Conversely, the binding affinity of the AB modified with a MM towards the target is at least 2, 3, 4, 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1, 000,000, or 100,000-10,000,000 times lower than the binding affinity of the AB not modified with an MM or of the parental AB towards the target.

The dissociation constant ($K_d$) of the MM towards the AB is generally greater than the $K_d$ of the AB towards the target. The $K_d$ of the MM towards the AB can be at least 5, 10, 25, 50, 100, 250, 500, 1,000, 2,500, 5,000, 10,000, 100,000, 1,000,000 or even 10,000,000 times greater than the $K_d$ of the AB towards the target. Conversely, the binding affinity of the MM towards the AB is generally lower than the binding affinity of the AB towards the target. The binding affinity of MM towards the AB can be at least 5, 10, 25, 50, 100, 250, 500, 1,000, 2,500, 5,000, 10,000, 100,000, 1,000,000 or even 10,000,000 times lower than the binding affinity of the AB towards the target.

When the AB is modified with a MM and is in the presence of the target specific binding of the AB to its target is reduced or inhibited, as compared to the specific binding of the AB not modified with an MM or the specific binding of the parental AB to the target. When compared to the binding of the AB not modified with an MM or the binding of the parental AB to the target the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or more when measured in vivo or in an in vitro assay.

The MM inhibits the binding of the AB to the target. The MM binds the antigen binding domain of the AB and inhibits binding of the AB to the target. The MM can sterically inhibit the binding of the AB to the target. The MM can allosterically inhibit the binding of the AB to its target. In these embodiments when the AB is modified or coupled to a MM and in the presence of target there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the parental AB, or the AB not coupled to an MM to the target, for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

When an AB is coupled to or modified by a MM, the MM 'masks' or reduces or otherwise inhibits the specific binding of the AB to the target. When an AB is coupled to or modified by a MM, such coupling or modification can effect a structural change that reduces or inhibits the ability of the AB to specifically bind its target.

An AB coupled to or modified with an MM can be represented by the following formulae (in order from an amino (N) terminal region to carboxyl (C) terminal region:

(MM)-(AB)

(AB)-(MM)

(MM)-L-(AB)

(AB)-L-(MM)

where MM is a masking moiety, the AB is an antibody or antibody fragment thereof, and the L is a linker. In many embodiments, it may be desirable to insert one or more linkers, e.g., flexible linkers, into the composition so as to provide for flexibility.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 25% identical to any natural binding partner of the AB. In some embodiments, the MM is no more than 50% identical to any natural binding partner of the AB. In some embodiments, the MM is no more than 20% identical to any natural binding partner of the AB. In some embodiments, the MM is no more than 10% identical to any natural binding partner of the AB.

In some embodiments, the activatable antibodies include an AB that is modified by an MM and also includes at least one cleavable moiety (CM1) that is a substrate for at least one matrix metalloprotease (MMP) and at least a second cleavable moiety (CM2) that is a subject for at least one serine protease (SP). Such activatable antibodies exhibit activatable/switchable binding, to the AB's target. Activatable antibodies generally include an antibody or antibody fragment (AB), modified by or coupled to a masking moiety (MM) and a CM1-CM2 substrate.

The elements of the activatable antibodies are arranged so that the MM and CM1-CM2 substrate are positioned such that in a cleaved (or relatively active) state and in the presence of a target, the AB binds a target while in an uncleaved (or relatively inactive) state in the presence of the target, specific binding of the AB to its target is reduced or inhibited. The specific binding of the AB to its target can be reduced due to the inhibition or masking of the AB's ability to specifically bind its target by the MM.

The $K_d$ of the AB modified with a MM and a CM1-CM2 substrate towards the target is at least 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10, 000,000, 10,000-100,000, 10,000-1,000,000, 10,000-10, 000,000, 100,000-1,000,000, or 100,000-10,000,000 times greater than the $K_d$ of the AB not modified with an MM and a CM1-CM2 substrate or of the parental AB towards the target. Conversely, the binding affinity of the AB modified with a MM and a CM1-CM2 substrate towards the target is at least 2, 3, 4, 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM and a CM1-CM2 substrate or of the parental AB towards the target.

When the AB is modified with a MM and a CM1-CM2 substrate and is in the presence of the target but not in the presence of a modifying agent (for example a MMP and a SP), specific binding of the AB to its target is reduced or inhibited, as compared to the specific binding of the AB not modified with an MM and a CM1-CM2 substrate or of the parental AB to the target. When compared to the binding of the parental AB or the binding of an AB not modified with an MM and a CM1-CM2 substrate to its target, the AB's ability to bind the target when modified with an MM and a CM1-CM2 substrate can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

As used herein, the term cleaved state refers to the condition of the activatable antibodies following modification, i.e., cleavage, of the CM1-CM2 substrate by at least one matrix metalloprotease and/or at least one serine protease. The term uncleaved state or fully uncleaved, as used herein, refers to the condition of the activatable antibodies in the absence of cleavage of the CM1-CM2 substrate by a MMP and/or a SP. As discussed above, the term "activatable antibodies" is used herein to refer to an activatable antibody in both its uncleaved (native) state, as well as in its cleaved state. An activatable antibody in its cleaved state is also referred to herein as an activated antibody and/or activated activatable antibody. It will be apparent to the ordinarily skilled artisan that in some embodiments, a cleaved activatable antibody may lack an MM due to cleavage of the CM1-CM2 substrate by protease, resulting in release of at least the MM.

By activatable or switchable is meant that the activatable antibody exhibits a first level of binding to a target when in a inhibited, masked or uncleaved state (i.e., a first conformation), and a second level of binding to the target in the uninhibited, unmasked and/or cleaved state (i.e., a second conformation), where the second level of target binding is greater than the first level of binding. In general, the access of target to the AB of the activatable antibody is greater in the presence of a cleaving agent capable of cleaving the CM1-CM2 substrate than in the absence of such a cleaving agent. Thus, when the activatable antibody is in the uncleaved state, the AB is inhibited from target binding and can be masked from target binding (i.e., the first conformation is such the AB cannot bind the target), and in the cleaved state the AB is not inhibited or is unmasked to target binding.

The CM1-CM2 substrate and AB of the activatable antibodies are selected so that the AB represents a binding moiety for a given target, and the CM1-CM2 substrate represents a substrate for a MMP and a SP, where the MMP and/or the SP are co-localized with the target at a treatment site or diagnostic site in a subject. The activatable antibodies disclosed herein find particular use where, for example, a MMP and a SP, each capable of cleaving a site in the CM1-CM2 substrate, are present at relatively higher levels in target-containing tissue of a treatment site or diagnostic site than in tissue of non-treatment sites (for example in healthy tissue).

In some embodiments, activatable antibodies provide for reduced toxicity and/or adverse side effects that could otherwise result from binding of the AB at non-treatment sites if the AB were not masked or otherwise inhibited from binding to the target.

In general, an activatable antibody can be designed by selecting an AB of interest and constructing the remainder of the activatable antibody so that, when conformationally constrained, the MM provides for masking of the AB or reduction of binding of the AB to its target. Structural design criteria can be to be taken into account to provide for this functional feature.

Activatable antibodies exhibiting a switchable phenotype of a desired dynamic range for target binding in an inhibited versus an uninhibited conformation are provided. Dynamic range generally refers to a ratio of (a) a maximum detected level of a parameter under a first set of conditions to (b) a minimum detected value of that parameter under a second set of conditions. For example, in the context of an activatable antibody, the dynamic range refers to the ratio of (a) a maximum detected level of target protein binding to an activatable antibody in the presence of a MMP and a SP that are capable of cleaving the CM1-CM2 substrate of the activatable antibodies to (b) a minimum detected level of target protein binding to an activatable antibody in the absence of the protease. The dynamic range of an activatable antibody can be calculated as the ratio of the dissociation constant of an activatable antibody cleaving agent (e.g., enzyme) treatment to the dissociation constant of the activatable antibodies cleaving agent treatment. The greater the dynamic range of an activatable antibody, the better the switchable phenotype of the activatable antibody. Activatable antibodies having relatively higher dynamic range values (e.g., greater than 1) exhibit more desirable switching phenotypes such that target protein binding by the activatable antibodies occurs to a greater extent (e.g., predominantly occurs) in the presence of a cleaving agent (e.g., enzyme) capable of cleaving the CM1-CM2 substrate of the activatable antibodies than in the absence of a cleaving agent.

Activatable antibodies can be provided in a variety of structural configurations. Exemplary formulae for activatable antibodies are provided below. It is specifically contemplated that the N- to C-terminal order of the AB, MM and CM1-CM2 substrate may be reversed within an activatable antibody. It is also specifically contemplated that the CM and MM may overlap in amino acid sequence, e.g., such that the CM1-CM2 substrate is at least partially contained within the MM.

For example, activatable antibodies can be represented by the following formula (in order from an amino (N) terminal region to carboxyl (C) terminal region:

(MM)-(CM1-CM2 substrate)-(AB)

(AB)-(CM1-CM2 substrate)-(MM)

where MM is a masking moiety, the CM1-CM2 substrate is a cleavable moiety, and AB is an antibody or fragment thereof. As noted above, the term "CM1-CM2 substrate" is not intended to convey any requirement regarding the orientation or other structural arrangement of the first cleavable moiety (CM1) that is a substrate for at least one matrix metalloprotease (MMP) and at least a second cleavable moiety (CM2) that is a substrate for at least one serine protease (SP). Thus, the term "CM1-CM2 substrates" encompasses CM1-CM2 substrates having the structural arrangement from N-terminus to C-terminus as follows: CM1-CM2 or CM2-CM1. The term "CM1-CM2 substrates" also encompasses substrates where at least a portion of the CM1 sequence overlaps with at least a portion of the CM2 sequence. It should also be noted that although MM and CM1-CM2 substrate are indicated as distinct components in the formulae above, in all exemplary embodiments (including formulae) disclosed herein it is contemplated that the amino acid sequences of the MM and the CM1-CM2 substrate could overlap, e.g., such that the CM1-CM2 substrate is completely or partially contained within the MM. In addition, the formulae above provide for additional amino acid sequences that may be positioned N-terminal or C-terminal to the activatable antibodies elements.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 50% identical to any natural binding partner of the AB. In some embodiments, the MM is no more than 25% identical to any natural binding partner of the AB. In some embodiments, the MM is no more than 20% identical to any natural binding partner of the AB. In some embodiments, the MM is no more than 10% identical to any natural binding partner of the AB.

In many embodiments, it may be desirable to insert one or more linkers, e.g., flexible linkers, into the activatable antibody construct so as to provide for flexibility at one or more of the MM-CM1-CM2 substrate junction, the CM1-CM2 substrate-AB junction, or both. For example, the AB, MM, and/or CM1-CM2 substrate may not contain a sufficient number of residues (e.g., Gly, Ser, Asp, Asn, especially Gly and Ser, particularly Gly) to provide the desired flexibility. As such, the switchable phenotype of such activatable antibody constructs may benefit from introduction of one or more amino acids to provide for a flexible linker. In addition, as described below, where the activatable antibody is provided as a conformationally constrained construct, a flexible linker can be operably inserted to facilitate formation and maintenance of a cyclic structure in the uncleaved activatable antibody.

For example, in certain embodiments, an activatable antibody comprises one of the following formulae (where the formula below represent an amino acid sequence in either N- to C-terminal direction or C- to N-terminal direction):

(MM)-L1-(CM1-CM2 substrate)-(AB)

(MM)-(CM1-CM2 substrate)-L2-(AB)

(MM)-L1-(CM1-CM2 substrate)-L2-(AB)

wherein MM, CM1-CM2 substrate, and AB are as defined above; wherein L1 and L2 are each independently and optionally present or absent, are the same or different flexible linkers that include at least 1 flexible amino acid (e.g., Gly). In addition, the formulae above provide for additional amino acid sequences that may be positioned N-terminal or C-terminal to the activatable antibodies elements. Examples include, but are not limited to, targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HAS)).

The CM1-CM2 substrate is specifically cleaved by at least one MMP at a rate of about $0.001\text{-}1500\times10^4\ M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500\times10^4\ M^{-1}S^{-1}$ and is specifically cleaved by at least one SP at a rate of about $0.001\text{-}1500\times10^4\ M^{-1}S^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or $1500\times10^4\ M^{-1}S^{-1}$.

For specific cleavage by an enzyme, contact between the enzyme and CM1-CM2 substrate is made. When the activatable antibody comprising an AB coupled to a MM and a CM1-CM2 substrate is in the presence of target and sufficient enzyme activity, the CM1-CM2 substrate can be cleaved. Sufficient enzyme activity can refer to the ability of the enzyme to make contact with the CM1-CM2 substrate and effect cleavage. It can readily be envisioned that an enzyme may be in the vicinity of the CM1-CM2 substrate but unable to cleave because of other cellular factors or protein modification of the enzyme.

Linkers suitable for use in compositions described herein are generally ones that provide flexibility of the modified AB or the activatable antibodies to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, or 20 amino acids in length.

Exemplary flexible linkers include glycine polymers $(G)_n$, glycine-serine polymers (including, for example, $(GS)_n$, $(GSGGS)_n$ (SEQ ID NO: 381) and $(GGGS)_n$ (SEQ ID NO: 382), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 383), Gly-Gly-Ser-Gly-Gly (SEQ ID NO: 384, Gly-Ser-Gly-Ser-Gly (SEQ ID NO: 385), Gly-Ser-Gly-Gly-Gly (SEQ ID NO: 386), Gly-Gly-Gly-Ser-Gly (SEQ ID NO: 387), Gly-Ser-Ser-Ser-Gly (SEQ ID NO: 388), and the like. The ordinarily skilled artisan will recognize that design of an activatable antibodies can include linkers that are all or partially flexible, such that the linker can include a flexible linker as well as one or more portions that confer less flexible structure to provide for a desired activatable antibodies structure.

In some embodiments, the activatable antibodies described herein also include an agent conjugated to the activatable antibody. In some embodiments, the conjugated agent is a therapeutic agent, such as an anti-inflammatory and/or an antineoplastic agent. In such embodiments, the agent is conjugated to a carbohydrate moiety of the activatable antibody, for example, in some embodiments, where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate).

In some embodiments, the agent is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

The disclosure also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, dolastatins and derivatives thereof (e.g. auristatin E, AFP, MMAF, MMAE, MMAD, DMAF, DMAE). For example, the agent is monomethyl auristatin E (MMAE) or monomethyl auristatin D (MMAD). In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the agent is linked to the AB using a maleimide caproyl-valine-citrulline linker or a maleimide PEG-valine-citrulline linker. In some embodiments, the agent is linked to the AB using a maleimide caproyl-valine-citrulline linker. In some embodiments, the agent is linked to the AB using a maleimide PEG-valine-citrulline linker In some embodiments, the agent is monomethyl auristatin D (MMAD) linked to the AB using a maleimide PEG-valine-citrulline-para-aminobenzyloxycarbonyl linker, and this linker payload construct is referred to herein as "vc-MMAD." In some embodiments, the agent is monomethyl auristatin E (MMAE) linked to the AB using a maleimide PEG-valine-citrulline-para-aminobenzyloxycarbonyl linker, and this linker payload construct is referred to herein as "vc-MMAE." The structures of vc-MMAD and vc-MMAE are shown below:

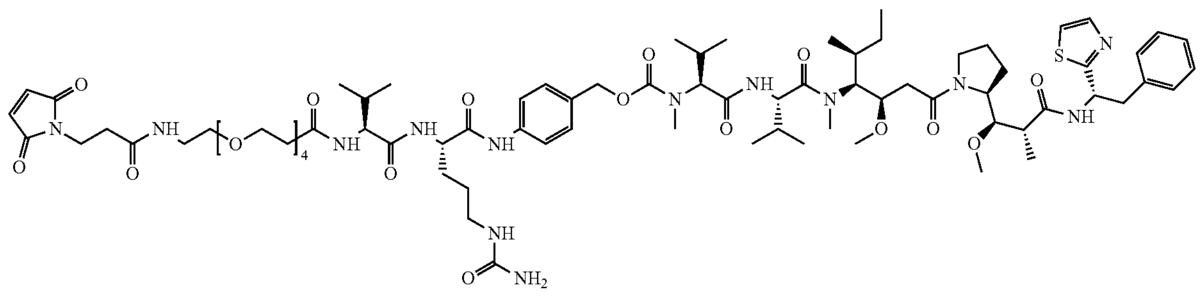

vc-MMAE:

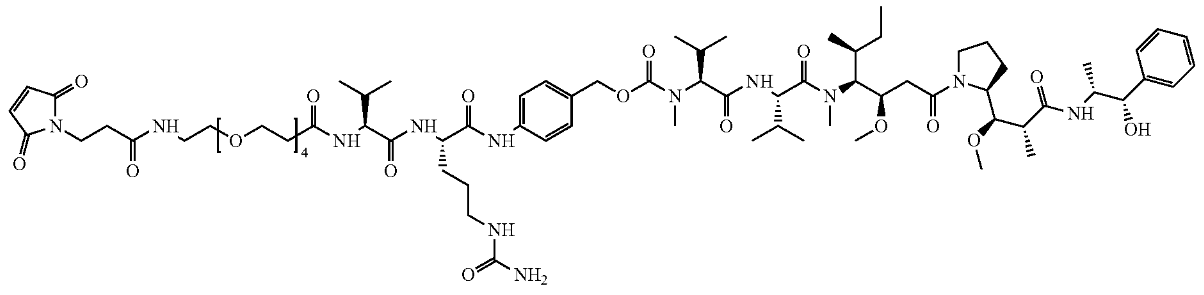

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I $^{131}$In $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutarelde-hyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Table 3 lists some of the exemplary pharmaceutical agents that may be employed in the herein described disclosure but in no way is meant to be an exhaustive list.

TABLE 3

| Exemplary Pharmaceutical Agents for Conjugation |
|---|
| CYTOTOXIC AGENTS |
| Auristatins |
| Auristatin E |
| Monomethyl auristatin D (MMAD) |
| Monomethyl auristatin E (MMAE) |
| Desmethyl auristatin E (DMAE) |
| Auristatin F |
| Monomethyl auristatin F (MMAF) |
| Desmethyl auristatin F (DMAF) |
| Auristatin derivatives, e.g., amides thereof |
| Auristatin tyramine |
| Auristatin quinoline |
| Dolastatins |
| Dolastatin derivatives |
| Dolastatin 16 DmJ |
| Dolastatin 16 Dpv |
| Maytansinoids, e.g. DM-1; DM-4 |
| Maytansinoid derivatives |
| Duocarmycin |
| Duocarmycin derivatives |
| Alpha-amanitin |
| Anthracyclines |
| Doxorubicin |
| Daunorubicin |
| Bryostatins |
| Camptothecin |
| Camptothecin derivatives |
| 7-substituted Camptothecin |
| 10, 11-Difluoromethylenedioxycamptothecin |
| Combretastatins |
| Debromoaplysiatoxin |
| Kahalalide-F |
| Discodermolide |
| Ecteinascidins |

TABLE 3-continued

| Exemplary Pharmaceutical Agents for Conjugation |
|---|
| ANTIVIRALS |
| Acyclovir |
| Vira A |
| Symmetrel |
| ANTIFUNGALS |
| Nystatin |
| ADDITIONAL ANTI-NEOPLASTICS |
| Adriamycin |
| Cerubidine |
| Bleomycin |
| Alkeran |
| Velban |
| Oncovin |
| Fluorouracil |
| Methotrexate |
| Thiotepa |
| Bisantrene |
| Novantrone |
| Thioguanine |
| Procarabizine |
| Cytarabine |
| ANTI-BACTERIALS |
| Aminoglycosides |
| Streptomycin |
| Neomycin |
| Kanamycin |
| Amikacin |
| Gentamicin |
| Tobramycin |
| Streptomycin B |
| Spectinomycin |
| Ampicillin |
| Sulfanilamide |
| Polymyxin |
| Chloramphenicol |
| Turbostatin |
| Phenstatins |
| Hydroxyphenstatin |
| Spongistatin 5 |
| Spongistatin 7 |
| Halistatin 1 |
| Halistatin 2 |
| Halistatin 3 |
| Modified Bryostatins |
| Halocomstatins |
| Pyrrolobenzimidazoles (PBI) |
| Cibrostatin6 |
| Doxaliform |
| Anthracycline analogues |
| Cemadotin analogue (CemCH2-SH) |
| Pseudomonas toxin A (PE38) variant |
| Pseudomonas toxin A (ZZ-PE38) variant |
| ZJ-101 |
| OSW-1 |
| 4-Nitrobenzyloxycarbonyl Derivatives of O6-Benzylguanine |
| Topoisomerase inhibitors |
| Hemiasterlin |
| Cephalotaxine |
| Homoharringtonine |
| Pyrrolobenzodiazepine (PBD) |
| Pyrrolobenzodiazepine (PBD) dimers |
| Functionalized pyrrolobenzodiazepines |
| Functionalized pyrrolobenzodiazepine dimers |
| Calicheamicins |
| Podophyllotoxins |
| Taxanes |
| Vinca alkaloids |

TABLE 3-continued

| Exemplary Pharmaceutical Agents for Conjugation |
| --- |
| CONJUGATABLE DETECTION REAGENTS |
| Fluorescein and derivatives thereof |
| Fluorescein isothiocyanate (FITC) |
| RADIOPHARMACEUTICALS |
| $^{125}I$ |
| $^{131}I$ |
| $^{89}Zr$ |
| $^{111}In$ |
| $^{123}I$ |
| $^{131}In$ |
| $^{99}mTc$ |
| $^{201}Tl$ |
| $^{133}Xe$ |
| $^{11}C$ |
| $^{62}Cu$ |
| $^{18}F$ |
| $^{68}Ga$ |
| $^{13}N$ |
| $^{15}O$ |
| $^{38}K$ |
| $^{82}Rb$ |
| $^{99}mTc$ (Technetium) |
| HEAVY METALS |
| Barium |
| Gold |
| Platinum |
| ANTI-MYCOPLASMALS |
| Tylosine |
| Spectinomycin |

Those of ordinary skill in the art will recognize that a large variety of possible moieties can be coupled to the resultant antibodies of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. In some embodiments, the binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present disclosure, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

In some embodiments, in addition to the compositions and methods provided herein, the conjugated activatable antibody can also be modified for site-specific conjugation through modified amino acid sequences inserted or otherwise included in the activatable antibody sequence. These modified amino acid sequences are designed to allow for controlled placement and/or dosage of the conjugated agent within a conjugated activatable antibody. For example, the activatable antibody can be engineered to include cysteine substitutions at positions on light and heavy chains that provide reactive thiol groups and do not negatively impact protein folding and assembly, nor alter antigen binding. In some embodiments, the activatable antibody can be engineered to include or otherwise introduce one or more non-natural amino acid residues within the activatable antibody to provide suitable sites for conjugation. In some embodiments, the activatable antibody can be engineered to include or otherwise introduce enzymatically activatable peptide sequences within the activatable antibody sequence.

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. In some embodiments, suitable linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC. Additional linkers include, but are not limited to, SMCC, sulfo-SMCC, SPDB, or sulfo-SPDB.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In some embodiments, the linkers are cleavable. In some embodiments, the linkers are non-cleavable. In some embodiments, two or more linkers are present. The two or more linkers are all the same, i.e., cleavable or non-cleavable, or the two or more linkers are different, i.e., at least one cleavable and at least one non-cleavable.

The present disclosure utilizes several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB. According to the disclosure, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present disclosure, suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097-3110).

According to the present disclosure, suitable linkers for attachment to neither oxidized nor reduced Abs include those having certain functional groups capable of reaction with the primary amino groups present in unmodified lysine residues in the Ab. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

According to the present disclosure, suitable linkers for attachment to neither oxidized nor reduced Abs include those having certain functional groups capable of reaction with the carboxylic acid groups present in aspartate or glutamate residues in the Ab, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In some embodiments, the AB is first attached to the MM, CM1-CM2 substrate and associated linkers and then attached to the linker for conjugation purposes.

Branched Linkers: In specific embodiments, branched linkers that have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

In some embodiments, higher specific activity (or higher ratio of agents to AB) can be achieved by attachment of a single site linker at a plurality of sites on the AB. This plurality of sites may be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

Cleavable Linkers: Peptide linkers that are susceptible to cleavage by enzymes of the complement system, such as but not limited to urokinase, tissue plasminogen activator, trypsin, plasmin, or another enzyme having proteolytic activity may be used in one embodiment of the present disclosure. According to one method of the present disclosure, an agent is attached via a linker susceptible to cleavage by complement. The antibody is selected from a class that can activate complement. The antibody-agent conjugate, thus, activates the complement cascade and releases the agent at the target site. According to another method of the present disclosure, an agent is attached via a linker susceptible to cleavage by enzymes having a proteolytic activity such as a urokinase, a tissue plasminogen activator, plasmin, or trypsin. These cleavable linkers are useful in conjugated activatable antibodies that include an extracellular toxin, e.g., by way of non-limiting example, any of the extracellular toxins shown in Table 3.

Non-limiting examples of cleavable linker sequences are provided in Table 4.

TABLE 4

Exemplary Linker Sequences for Conjugation

| Types of Cleavable Sequences | Amino Acid Sequence |
|---|---|
| Plasmin cleavable sequences | |
| Pro-urokinase | PRFKIIGG (SEQ ID NO: 319) |
| | PRFRIIGG (SEQ ID NO: 320) |
| TGFβ | SSRHRRALD (SEQ ID NO: 321) |
| Plasminogen | RKSSIIIRMRDVVL (SEQ ID NO: 322) |
| Staphylokinase | SSSFDKGKYKKGDDA (SEQ ID NO: 323) |
| | SSSFDKGKYKRGDDA (SEQ ID NO: 324) |
| Factor Xa cleavable sequences | |
| | IEGR (SEQ ID NO: 325) |
| | IDGR (SEQ ID NO: 326) |
| | GGSIDGR (SEQ ID NO: 327) |

TABLE 4-continued

| Exemplary Linker Sequences for Conjugation | |
|---|---|
| Types of Cleavable Sequences | Amino Acid Sequence |
| MMP cleavable sequences | |
| Gelatinase A | PLGLWA (SEQ ID NO: 328) |
| Collagenase cleavable sequences | |
| Calf skin collagen (α1(I) chain) | GPQGIAGQ (SEQ ID NO: 329) |
| Calf skin collagen (α2(I) chain) | GPQGLLGA (SEQ ID NO: 330) |
| Bovine cartilage collagen (α1(II) chain) | GIAGQ (SEQ ID NO: 331) |
| Human liver collagen (α1(III) chain) | GPLGIAGI (SEQ ID NO: 332) |
| Human $\alpha_2$M | GPEGLRVG (SEQ ID NO: 333) |
| Human PZP | YGAGLGVV (SEQ ID NO: 334) |
| | AGLGVVER (SEQ ID NO: 335) |
| | AGLGISST (SEQ ID NO: 336) |
| Rat $\alpha_1$M | EPQALAMS (SEQ ID NO: 337) |
| | QALAMSAI (SEQ ID NO: 338) |
| Rat $\alpha_2$M | AAYHLVSQ (SEQ ID NO: 339) |
| | MDAFLESS (SEQ ID NO: 340) |
| Rat $\alpha_1I_3$(2J) | ESLPVVAV (SEQ ID NO: 341) |
| Rat $\alpha_1I_3$(27J) | SAPAVESE (SEQ ID NO: 342) |
| Human fibroblast collagenase | DVAQFVLT (SEQ ID NO: 343) |
| (autolytic cleavages) | VAQFVLTE (SEQ ID NO: 344) |
| | AQFVLTEG (SEQ ID NO: 345) |
| | PVQPIGPQ (SEQ ID NO: 346) |

In addition, agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In certain specific embodiments, the reducing agent that would modify a CM1-CM2 substrate would also modify the linker of the conjugated activatable antibody.

Spacers and Cleavable Elements: In some embodiments, it may be necessary to construct the linker in such a way as to optimize the spacing between the agent and the AB of the activatable antibody. This may be accomplished by use of a linker of the general structure:

$$W—(CH_2)n\text{-}Q$$

wherein

W is either —NH—$CH_2$— or —$CH_2$—;

Q is an amino acid, peptide; and n is an integer from 0 to 20.

In some embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

Serum Complement and Selection of Linkers: According to one method of the present disclosure, when release of an agent is desired, an AB that is an antibody of a class that can activate complement is used. The resulting conjugate retains both the ability to bind antigen and activate the complement cascade. Thus, according to this embodiment of the present disclosure, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB that is capable of activating complement.

Linkers (or spacer elements of linkers) may be of any desired length, one end of which can be covalently attached to specific sites on the AB of the activatable antibody. The other end of the linker or spacer element may be attached to an amino acid or peptide linker.

Thus when these conjugates bind to antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 3.

Linkers for Release without Complement Activation: In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers: In some embodiments, the activatable antibody may be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome may be used, for example: bis-sialyl ether. Other suitable linkers include cathepsin-labile substrates, particularly those that show optimal function at an acidic pH.

Exemplary hetero-bifunctional cross-linkers are referenced in Table 5.

TABLE 5

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
|---|---|---|---|
| SMPT | Primary amines<br>Sulfhydryls | Greater stability | 11.2 Å |
| SPDP | Primary amines<br>Sulfhydryls | Thiolation<br>Cleavable cross-linking | 6.8 Å |
| LC-SPDP | Primary amines<br>Sulfhydryls | Extended spacer arm | 15.6 Å |
| Sulfo-LC-SPDP | Primary amines<br>Sulfhydryls | Extender spacer arm<br>Water-soluble | 15.6 Å |
| SMCC | Primary amines<br>Sulfhydryls | Stable maleimide reactive group<br>Enzyme-antibody conjugation<br>Hapten-carrier protein conjugation | 11.6 Å |
| Sulfo-SMCC | Primary amines<br>Sulfhydryls | Stable maleimide reactive group<br>Water-soluble<br>Enzyme-antibody conjugation | 11.6 Å |
| MBS | Primary amines<br>Sulfhydryls | Enzyme-antibody conjugation<br>Hapten-carrier protein conjugation | 9.9 Å |
| Sulfo-MBS | Primary amines<br>Sulfhydryls | Water-soluble | 9.9 Å |
| SIAB | Primary amines<br>Sulfhydryls | Enzyme-antibody conjugation | 10.6 Å |
| Sulfo-SIAB | Primary amines<br>Sulfhydryls | Water-soluble | 10.6 Å |
| SMPB | Primary amines<br>Sulfhydryls | Extended spacer arm<br>Enzyme-antibody conjugation | 14.5 Å |
| Sulfo-SMPB | Primary amines<br>Sulfhydryls | Extended spacer arm<br>Water-soluble | 14.5 Å |
| EDE/Sulfo-NHS | Primary amines<br>Carboxyl groups | Hapten-Carrier conjugation | 0 |
| ABH | Carbohydrates<br>Nonselective | Reacts with sugar groups | 11.9 Å |

Non-Cleavable Linkers or Direct Attachment: In some embodiments of the disclosure, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds that may be modified to include functional groups that can subsequently be utilized in attachment to ABs by the methods described herein. A-general formula for such an organic linker could be $$W—(CH_2)n\text{-}Q$$

wherein

W is either $—NH—CH_2—$ or $—CH_2—$;

Q is an amino acid, peptide; and n is an integer from 0 to 20.

Non-Cleavable Conjugates: In some embodiments, a compound may be attached to ABs that do not activate complement. When using ABs that are incapable of complement activation, this attachment may be accomplished using linkers that are susceptible to cleavage by activated complement or using linkers that are not susceptible to cleavage by activated complement.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin et al., J. Biol. Chem., 257: 286-288 (1982) via a disulfide-interchange reaction.

Definitions

Unless otherwise defined, scientific and technical terms used in connection with the present disclosure shall have the meanings that are commonly understood by those of ordinary skill in the art. The term "a" entity or "an" entity refers to one or more of that entity. For example, a compound refers to one or more compounds. As such, the terms "a", "an", "one or more" and "at least one" can be used interchangeably. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, domain antibody, single chain, Fab, and F(ab')2 fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, a scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 μM; in some embodiments, ≤100 nM and in some embodiments, ≤10 nM.

As used herein, the terms "specific binding," "immunological binding," and "immunological binding properties" refer to the non-covalent interactions of the type that occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to the target, when the binding constant ($K_d$) is ≤1 μM, in some embodiments ≤100 nM, in some embodiments ≤10 nM, and in some embodiments ≤100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide that it is not linked to in nature, or (3) does not occur in nature as part of a larger sequence. Polynucleotides in accordance with the disclosure include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length and in some embodiments, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the disclosure are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Gren, Eds., Sinauer Associates, Sunderland? Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, 6-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, in some embodiments, at least 90 percent sequence identity, in some embodiments, at least 95 percent sequence identity, and in some embodiments, at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present disclosure, providing that the variations in the amino acid sequence maintain at least 75%, in some embodiments, at least 80%, 90%, 95%, and in some embodiments, 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Suitable amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Suitable amino acid substitutions are those that: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, in some embodiments, at least 14 amino acids long, in some embodiments, at least 20 amino acids long, usually at least 50 amino acids long, and in some embodiments, at least 70 amino acids long. The term "analog" as used herein refers to polypeptides that are comprised of a segment of at least 25 amino acids that has substantial identity to a portion of a deduced amino acid sequence and that has specific binding to the target, under suitable binding conditions. Typically, polypeptide analogs comprise a conservative amino acid substitution (or addition or deletion) with respect to the naturally-occurring sequence. Analogs typically are at least 20 amino acids long, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{13}C$, $^{15}N$, $^{35}S$, $^{90}Y$, $^{99}Tc$, $^{111}In$, $^{125}I$, $^{131}I$) fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and in some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

Activatable antibodies of the disclosure specifically bind a given target, e.g., a human target protein. Also included in the disclosure are activatable antibodies that bind to the same epitope as the activatable antibodies described herein.

Those skilled in the art will recognize that it is possible to determine, without undue experimentation, if a monoclonal antibody (e.g., a murine monoclonal or humanized antibody) has the same specificity as a monoclonal antibody used in the methods described herein by ascertaining whether the former prevents the latter from binding to the target. If the monoclonal antibody being tested competes with the monoclonal antibody of the disclosure, as shown by a decrease in binding by the monoclonal antibody of the disclosure, then the two monoclonal antibodies bind to the same, or a closely related, epitope. A method for determining whether a monoclonal antibody has the specificity of a monoclonal antibody of the disclosure is to pre-incubate the monoclonal antibody of the disclosure with the target and then add the monoclonal antibody being tested to determine if the monoclonal antibody being tested is inhibited in its ability to bind the target. If the monoclonal antibody being tested is inhibited then, in all likelihood, it has the same, or functionally equivalent, epitopic specificity as the monoclonal antibody of the disclosure.

Multispecific Activatable Antibodies

The disclosure also provides multispecific activatable antibodies. The multispecific activatable antibodies provided herein are multispecific antibodies that recognize two or more different antigens or epitopes and that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a CM1-CM2 substrate that functions as a substrate for at least one MMP protease and at least one SP. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

In some embodiments, the multispecific activatable antibodies are designed to engage immune effector cells, also referred to herein as immune-effector cell engaging multispecific activatable antibodies. In some embodiments, the multispecific activatable antibodies are designed to engage leukocytes, also referred to herein as leukocyte engaging multispecific activatable antibodies. In some embodiments, the multispecific activatable antibodies are designed to engage T cells, also referred to herein as T-cell engaging multispecific activatable antibodies. In some embodiments, the multispecific activatable antibodies engage a surface antigen on a leukocyte, such as on a T cell, on a natural killer (NK) cell, on a myeloid mononuclear cell, on a macrophage, and/or on another immune effector cell. In some embodiments, the immune effector cell is a leukocyte. In some embodiments, the immune effector cell is a T cell. In some embodiments, the immune effector cell is a NK cell. In some embodiments, the immune effector cell is a mononuclear cell, such as a myeloid mononuclear cell. In some embodiments, the multispecific activatable antibodies are designed to bind or otherwise interact with more than one target and/or more than one epitope, also referred to herein as multi-antigen targeting activatable antibodies. As used herein, the terms "target" and "antigen" are used interchangeably.

In some embodiments, immune effector cell engaging multispecific activatable antibodies of the disclosure include a targeting antibody or antigen-binding fragment thereof and an immune effector cell engaging antibody or antigen-binding portion thereof, where at least one of the targeting antibody or antigen-binding fragment thereof and/or the immune effector cell engaging antibody or antigen-binding portion thereof is masked. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the non-immune effector cell engaging antibody is a cancer targeting antibody. In some embodiments the non-immune cell effector antibody is an IgG. In some embodiments the immune effector cell engaging antibody is a scFv. In some embodiments the targeting antibody (e.g., non-immune cell effector antibody) is an IgG and the immune effector cell engaging antibody is a scFv. In some embodiments, the immune effector cell is a leukocyte. In some embodiments, the immune effector cell is a T cell. In some embodiments, the immune effector cell is a NK cell. In some embodiments, the immune effector cell is a myeloid mononuclear cell.

In some embodiments, T-cell engaging multispecific activatable antibodies of the disclosure include a targeting antibody or antigen-binding fragment thereof and a T-cell engaging antibody or antigen-binding portion thereof, where at least one of the targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibodies include a cancer targeting antibody or antigen-binding fragment thereof and a T-cell engaging antibody or antigen-binding portion thereof, where at least one of the cancer targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibodies include a cancer targeting IgG antibody or antigen-binding fragment thereof and a T-cell engaging scFv, where at least one of the cancer targeting IgG antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments of an immune effector cell engaging multispecific activatable antibody, one antigen is typically an antigen present on the surface of a tumor cell or other cell type associated with disease, such as, but not limited to, any target listed in Table 1, such as, but not limited to, EGFR, erbB2, EpCAM, Jagged, PD-L1, B7H3, or CD71 (transferrin receptor), and another antigen is typically a stimulatory or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA. In some embodiments, the antigen is a stimulatory receptor present on the surface of a T cell or NK cell; examples of such stimulatory receptors include, but are not limited to, CD3, CD27, CD28, CD137 (also referred to as 4-1BB), GITR, HVEM, ICOS, NKG2D, and OX40. In some embodiments, the antigen is an inhibitory receptor present on the surface of a T-cell; examples of such inhibitory receptors include, but are not limited to, BTLA, CTLA-4, LAG3, PD-1, TIGIT, TIM3, and NK-expressed KIRs. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PD-L1, PD-L2, or TNFSF9.

One embodiment of the disclosure is a multispecific activatable antibody that is activatable in a cancer microenvironment and that includes an antibody, for example a IgG or scFv, directed to a tumor target and an agonist antibody, for example an IgG or scFv, directed to a co-stimulatory receptor expressed on the surface of an activated T cell or NK cell, wherein at least one of the cancer target antibody and/or agonist antibody is masked. Examples of co-stimulatory receptors include, but are not limited to, CD27, CD137, GITR, HVEM, NKG2D, and OX40. In this embodiment, the multispecific activatable antibody, once activated by tumor-associated proteases, would effectively crosslink and activate the T cell or NK cell expressed co-stimulatory receptors in a tumor-dependent manner to enhance the activity of T cells that are responding to any tumor antigen via their endogenous T cell antigen or NK-activating receptors. The activation-dependent nature of these T cell or NK cell costimulatory receptors would focus the activity of the activated multispecific activatable antibody to tumor-specific T cells, without activating all T cells independent of their antigen specificity. In one embodiment, at least the co-stimulatory receptor antibody of the multispecific activatable antibody is masked to prevent activation of auto-reactive T cells that may be present in tissues that also express the antigen recognized by the tumor target-directed antibody in the multispecific activatable antibody, but whose activity is restricted by lack of co-receptor engagement.

One embodiment of the disclosure is a multispecific activatable antibody that is activatable in a disease characterized by T cell overstimulation, such as, but not limited to, an autoimmune disease or inflammatory disease microenvironment. Such a multispecific activatable antibody includes an antibody, for example a IgG or scFv, directed to a target comprising a surface antigen expressed in a tissue targeted by a T cell in autoimmune or inflammatory disease and an antibody, for example a IgG or scFv, directed to an inhibitory receptor expressed on the surface of a T cell or NK cell, wherein at least one of the disease tissue target antibody and/or T cell inhibitory receptor antibody is masked. Examples of inhibitory receptors include, but are not limited to, BTLA, CTLA-4, LAGS, PD-1, TIGIT, TIM3, and NK-expressed KIRs. Examples of a tissue antigen targeted by T cells in autoimmune disease include, but are not limited to, a surface antigen expressed on myelin or nerve cells in multiple sclerosis or a surface antigen expressed on pancreatic islet cells in Type 1 diabetes. In this embodiment, the multispecific activatable antibody when localized in the tissue under autoimmune attack or inflammation is activated and co-engages the T cell or NK cell inhibitory receptor to suppress the activity of autoreactive T cells responding to any disease tissue-targeted antigens via their endogenous TCR or activating receptors. In one embodiment, at least one or multiple antibodies are masked to prevent suppression of T cell responses in non-disease tissues where the target antigen may also be expressed.

In some embodiments, the T-cell engaging multispecific activatable antibody includes an anti-CD3 epsilon (CD3ε, also referred to herein as CD3e and CD3) scFv and a targeting antibody or antigen-binding fragment thereof, where at least one of the anti-CD3ε scFv and/or the targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an anti-CD3ε scFv and a cancer targeting antibody or antigen-binding fragment thereof, where at least one of the anti-CD3ε scFv and/or the cancer targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CD3ε scFv and a cancer targeting IgG antibody or antigen-binding fragment thereof, where at least one of the anti-CD3ε scFv and/or the cancer targeting IgG antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody IgG or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CD3 epsilon (CD3ε) scFv that is derived from OKT3, where at least one of the targeting antibody or antigen-binding fragment thereof and/ or the OKT3 scFv or OKT3-derived scFv is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an OKT3 scFv or OKT3-derived scFv and a cancer targeting antibody or antigen-binding fragment thereof, where at least one of the OKT3 scFv or OKT3-derived scFv and/or the cancer targeting antibody or antigen-binding portion thereof is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an OKT3 scFv or OKT3-derived scFv and a cancer targeting IgG antibody or antigen-binding fragment thereof, where at least one of the OKT3 scFv or OKT3-derived scFv and/or the cancer targeting IgG antibody or antigen-binding portion thereof is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody IgG or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CTLA-4 scFv, where at least one of the targeting antibody or antigen-binding fragment thereof and/or the anti-CTLA-4 scFv is masked. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an anti-CTLA-4 scFv and a targeting IgG antibody or antigen-binding fragment thereof, where at least one of the anti-CTLA-4 scFv and/or the targeting IgG antibody or antigen-binding portion thereof is masked. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4. In some embodiments, the targeting IgG antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4, and the targeting antibody IgG or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the multi-antigen targeting antibodies and/or multi-antigen targeting activatable antibodies include at least a first antibody or antigen-binding fragment thereof that binds a first target and/or first epitope and a second antibody or antigen-binding fragment thereof that binds a second target and/or a second epitope. In some embodiments, the multi-antigen targeting antibodies and/or multi-antigen targeting activatable antibodies bind two or more different targets. In some embodiments, the multi-antigen targeting antibodies and/or multi-antigen targeting activatable antibodies bind two or more different epitopes on the same target. In some embodiments, the multi-antigen targeting antibodies and/or multi-antigen targeting activatable antibodies bind a combination of two or more different targets and two or more different epitopes on the same target.

In some embodiments, a multispecific activatable antibody comprising an IgG has the IgG variable domains masked. In some embodiments, a multispecific activatable antibody comprising a scFv has the scFv domains masked. In some embodiments, a multispecific activatable antibody has both IgG variable domains and scFv domains, where at least one of the IgG variable domains is coupled to a masking moiety. In some embodiments, a multispecific activatable antibody has both IgG variable domains and scFv domains, where at least one of the scFv domains is coupled to a masking moiety. In some embodiments, a multispecific activatable antibody has both IgG variable domains and scFv domains, where at least one of the IgG variable domains is coupled to a masking moiety and at least one of the scFv domains is coupled to a masking moiety. In some embodiments, a multispecific activatable antibody has both IgG variable domains and scFv domains, where each of the IgG variable domains and the scFv domains is coupled to its own masking moiety. In some embodiments, one antibody domain of a multispecific activatable antibody has specificity for a target antigen and another antibody domain has specificity for a T-cell surface antigen. In some embodiments, one antibody domain of a multispecific activatable antibody has specificity for a target antigen and another antibody domain has specificity for another target antigen. In some embodiments, one antibody domain of a multispecific activatable antibody has specificity for an epitope of a target antigen and another antibody domain has specificity for another epitope of the target antigen.

In a multispecific activatable antibody, a scFv can be fused to the carboxyl terminus of the heavy chain of an IgG activatable antibody, to the carboxyl terminus of the light chain of an IgG activatable antibody, or to the carboxyl termini of both the heavy and light chains of an IgG activatable antibody. In a multispecific activatable antibody, a scFv can be fused to the amino terminus of the heavy chain of an IgG activatable antibody, to the amino terminus of the light chain of an IgG activatable antibody, or to the amino termini of both the heavy and light chains of an IgG activatable antibody. In a multispecific activatable antibody, a scFv can be fused to any combination of one or more carboxyl termini and one or more amino termini of an IgG activatable antibody. In some embodiments, a masking moiety (MM) linked to a CM1-CM2 substrate is attached to and masks an antigen binding domain of the IgG. In some embodiments, a masking moiety (MM) linked to a CM1-CM2 substrate is attached to and masks an antigen binding domain of at least one scFv. In some embodiments, a masking moiety (MM) linked to a CM1-CM2 substrate is attached to and masks an antigen binding domain of an IgG and a masking moiety (MM) linked to a CM1-CM2 substrate is attached to and masks an antigen binding domain of at least one scFv.

The disclosure provides examples of multispecific activatable antibody structures that include, but are not limited to, the following: $(VL-CL)_2$:(VH-CH1-CH2-CH3-L4-VH*-L3-VL*-L2-CM1-CM2 substrate-L1-$MM)_2$; $(VL-CL)_2$:(VH-CH1-CH2-CH3-L4-VL*-L3-VH*-L2-CM1-CM2 substrate-L1-$MM)_2$; (MM-L1-CM1-CM2 substrate-L2-VL-$CL)_2$:(VH-CH1-CH2-CH3-L4-VH*-L3-$VL^*)_2$; (MM-L1-CM1-CM2 substrate-L2-VL-$CL)_2$:(VH-CH1-CH2-CH3-L4-VL*-L3-$VH^*)_2$; $(VL-CL)_2$:(MM-L1-CM1-CM2 substrate-L2-VL*-L3-VH*-L4-VH-CH1-CH2-$CH3)_2$; $(VL-CL)_2$:(MM-L1-CM1-CM2 substrate-L2-VH*-L3-VL*-L4-VH-CH1-CH2-$CH3)_2$; (MM-L1-CM1-CM2 substrate-L2-VL-$CL)_2$:(VL*-L3-VH*-L4-VH-CH1-CH2-$CH3)_2$; (MM-L1-CM1-CM2 substrate-L2-VL-$CL)_2$:(VH*-L3-VL*-L4-VH-CH1-CH2-$CH3)_2$; (VL-CL-L4-VH*-L3-VL*-L2-CM1-CM2 substrate-L1-$MM)_2$:(VH-CH1-CH2-$CH3)_2$; (VL-CL-L4-VL*-L3-VH*-L2-CM1-CM2 substrate-L1-$MM)_2$:(VH-CH1-CH2-$CH3)_2$; (MM-L1-CM1-CM2 substrate-L2-VL*-L3-VH*-L4-VL-$CL)_2$:(VH-CH1-CH2-$CH3)_2$; (MM-L1-CM1-CM2 substrate-L2-VH*-L3-VL*-L4-VL-$CL)_2$:(VH-CH1-CH2-$CH3)_2$; (VL-CL-L4-VH*-L3-VL*-L2-CM1-CM2 substrate-L1-$MM)_2$: (MM-L1-CM1-CM2 substrate-L2-VL*-L3-VH*-L4-VH-CH1-CH2-$CH3)_2$; (VL-CL-L4-VH*-L3-VL*-L2-CM1-CM2 substrate-L1-$MM)_2$: (MM-L1-CM1-CM2 substrate-L2-VH*-L3-VL*-L4-VH-CH1-CH2-$CH3)_2$; (VL-CL-L4-VL*-L3-VH*-L2-CM1-CM2 substrate-L1-$MM)_2$: (MM-L1-CM1-CM2 substrate-L2-VL*-L3-VH*-L4-VH-CH1-CH2-$CH3)_2$; (VL-CL-L4-VL*-L3-VH*-L2-CM1-CM2 substrate-L1-$MM)_2$: (MM-L1-CM1-CM2 substrate-L2-VH*-L3-VL*-L4-VH-CH1-CH2-$CH3)_2$; (VL-CL-L4-VH*-L3-$VL^*)_2$: (MM-L1-CM1-CM2 substrate-L2-VL*-L3-VH*-L4-VH-CH1-CH2-$CH3)_2$; (VL-CL-L4-VH*-L3-$VL^*)_2$: (MM-L1-CM1-CM2 substrate-L2-VH*-L3-VL*-L4-VH-CH1-CH2-$CH3)_2$; (VL-CL-L4-VL*-L3-$VH^*)_2$: (MM-L1-CM1-CM2 substrate-L2-VL*-L3-VH*-L4-VH-CH1-CH2-$CH3)_2$; (VL-CL-L4-VL*-L3-$VH^*)_2$: (MM-L1-CM1-CM2 substrate-L2-VH*-L3-VL*-L4-VH-CH1-CH2-$CH3)_2$; (VL-CL-L4-VH*-L3-VL*-L2-CM1-CM2 substrate-L1-$MM)_2$: (VL*-L3-VH*-L4-VH-CH1-CH2-$CH3)_2$; (VL-CL-L4-VH*-L3-VL*-L2-CM1-CM2 substrate-L1-$MM)_2$: (VH*-L3-VL*-L4-VH-CH1-CH2-$CH3)_2$; (VL-CL-L4-VL*-L3-VH*-L2-CM1-CM2 substrate-L1-$MM)_2$: (VL*-L3-VH*-L4-VH-CH1-CH2-$CH3)_2$; or (VL-CL-L4-VL*-L3-VH*-L2-CM1-CM2 substrate-L1-$MM)_2$: (VH*-L3-VL*-L4-VH-CH1-CH2-$CH3)_2$, wherein: VL and VH represent the light and heavy variable domains of the first specificity, contained in the IgG; VL* and VH* represent the variable domains of the second specificity, contained in the scFv; L1 is a linker peptide connecting the masking moiety (MM) and the CM1-CM2 substrate; L2 is a linker peptide connecting the CM1-CM2 substrate, and the antibody; L3 is a linker peptide connecting the variable domains of the scFv; L4 is a linker peptide connecting the antibody of the first specificity to the antibody of the second specificity; CL is the light-chain constant domain; and CH1, CH2, CH3 are the heavy chain constant domains. The first and second specificities may be toward any antigen or epitope.

In some embodiments of a T-cell engaging multispecific activatable antibody, one antigen is typically an antigen present on the surface of a tumor cell or other cell type associated with disease, such as, but not limited to, any target listed in Table 1, such as, but not limited to, EGFR, erbB2, EpCAM, Jagged, PD-L1, B7H3, or CD71 (transferrin receptor), and another antigen is typically a stimulatory (also referred to herein as activating) or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137 (also referred to as TNFRSF9), CTLA-4, GITR, HVEM, ICOS, LAGS, NKG2D, OX40, PD-1, TIGIT, TIM3, or VISTA. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PD-L1, PD-L2, or TNFSF9. In some embodiments of a multi-antigen targeting activatable antibody, one antigen is selected from the group of targets listed in Table 1, and another antigen is selected from the group of targets listed in Table 1.

In some embodiments, the targeting antibody is an anti-EGFR antibody. In some embodiments, the targeting antibody is C225v5, which is specific for binding to EGFR. In some embodiments, the targeting antibody is C225, which is specific for binding to EGFR. In some embodiments, the targeting antibody is C225v4, which is specific for binding to EGFR. In some embodiments, the targeting antibody is C225v6, which is specific for binding to EGFR. In some embodiments, the targeting antibody is an anti-Jagged antibody. In some embodiments, the targeting antibody is 4D11, which is specific for binding to human and mouse Jagged 1 and Jagged 2. In some embodiments, the targeting antibody is 4D11v2, which is specific for binding to human and mouse Jagged 1 and Jagged 2.

In some embodiments, the targeting antibody can be in the form an activatable antibody. In some embodiments, the scFv(s) can be in the form of a Pro-scFv (see, e.g., WO 2009/025846, WO 2010/081173).

In some embodiments, the scFv is specific for binding CD3, and is or is derived from an antibody or fragment thereof that binds CD3, e.g., CH2527, FN18, H2C, OKT3, 2C11, UCHT1, or V9. In some embodiments, the scFv is specific for binding CTLA-4 (also referred to herein as CTLA and CTLA4).

In some embodiments, the anti-CTLA-4 scFv includes the amino acid sequence:

(SEQ ID NO: 347)
GGGSGGGGSGSGGGSGGGGSGGGEIVLTQSPGTLSLSPGERATLSCRAS
QSVSSSYLAWYQQKPGQAPRLLIYGASSRATGIPDRFSGSGSGTDFTLT
ISRLEPEDFAVYYCQQYGSSPLTFGGGTKVEIKRSGGSTITSYNVYYTK
LSSSGTQVQLVQTGGGVVQPGRSLRLSCAASGSTFSSYAMSWVRQAPGK
GLEWVSAISGSGGSTYYADSVKGRFTISRDNSKNTLYLQMNSLRAEDTA
VYYCATNSLYWYFDLWGRGTLVTVSSAS

In some embodiments, the anti-CTLA-4 scFv includes the amino acid sequence that is at least 90%, 91%, 92%, 93%, 94%, 95%, 96%, 97%, 98%, 99% or more identical to the amino acid sequence of SEQ ID NO: 347.

In some embodiments, the anti-CD3c scFv includes the amino acid sequence:

(SEQ ID NO: 349)
GGGSGGGGSGSGGGSGGGGSGGGQVQLQQSGAELARPGASVKMSCKASG
YTFTRYTMHWVKQRPGQGLEWIGYINPSRGYTNYNQKFKDKATLTTDKS
SSTAYMQLSSLTSEDSAVYYCARYYDDHYCLDYWGQGTTLTVSSGGGGS
GGGGSGGGGSQIVLTQSPAIMSASPGEKVTMTCSASSSVSYMNWYQQKS
GTSPKRWIYDTSKLASGVPAHFRGSGSGTSYSLTISGMEAEDAATYYCQ
QWSSNPFTFGSGTKLEINR

In some embodiments, the anti-CD3c scFv includes the amino acid sequence that is at least 90%, 91%, 92%, 93%, 94%, 95%, 96%, 97%, 98%, 99% or more identical to the amino acid sequence of SEQ ID NO: 349.

In some embodiments, the scFv is specific for binding one or more T-cells, one or more NK-cells and/or one or more macrophages. In some embodiments, the scFv is specific for binding a target selected from the group consisting of B7-H4, BTLA, CD3, CD4, CD8, CD16a, CD25, CD27, CD28, CD32, CD56, CD137, CTLA-4, GITR, HVEM, ICOS, LAGS, NKG2D, OX40, PD-1, TIGIT, TIM3, or VISTA.

In some embodiments, the multispecific activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the multispecific activatable antibody via a linker. In some embodiments, the agent is conjugated to the AB via a cleavable linker. In some embodiments, the agent is conjugated to the AB via a linker that includes at least one CM1-CM2 substrate sequence. In some embodiments, the linker is a non-cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is an agent selected from the group listed in Table 4. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some embodiments, the multispecific activatable antibody also includes a detectable moiety. In some embodiments, the detectable moiety is a diagnostic agent.

In some embodiments, the multispecific activatable antibody naturally contains one or more disulfide bonds. In some embodiments, the multispecific activatable antibody can be engineered to include one or more disulfide bonds.

The disclosure also provides an isolated nucleic acid molecule encoding a multispecific activatable antibody described herein, as well as vectors that include these isolated nucleic acid sequences. The disclosure provides methods of producing a multispecific activatable antibody by culturing a cell under conditions that lead to expression of the activatable antibody, wherein the cell comprises such a nucleic acid molecule. In some embodiments, the cell comprises such a vector.

The disclosure also provides a method of manufacturing multispecific activatable antibodies of the disclosure by (a) culturing a cell comprising a nucleic acid construct that encodes the multispecific activatable antibody under conditions that lead to expression of the multispecific activatable, and (b) recovering the multispecific activatable antibody.

The disclosure also provides multispecific activatable antibodies and/or multispecific activatable antibody compositions that include at least a first antibody or antigen-binding fragment thereof (AB1) that specifically binds a first target or first epitope and a second antibody or antigen-biding fragment thereof (AB2) that binds a second target or a second epitope, where at least AB1 is coupled or otherwise attached to a masking moiety (MM1), such that coupling of the MM1 reduces the ability of AB1 to bind its target. In some embodiments, the MM1 is coupled to AB1 via a CM1-CM2 substrate for an MMP and a SP, where at least one of the MMP and the SP is co-localized with the target of AB1 at a treatment site or a diagnostic site in a subject. The multispecific activatable antibodies provided herein are stable in circulation, activated at intended sites of therapy and/or diagnosis but not in normal, i.e., healthy tissue, and, when activated, exhibit binding to the target of AB1 that is at least comparable to the corresponding, unmodified multispecific antibody.

In some embodiments, the multispecific activatable antibody comprises a linking peptide between the MM1 and the CM1-CM2 substrate.

In some embodiments, the multispecific activatable antibody comprises a linking peptide between the CM1-CM2 substrate and the AB1.

In some embodiments, the activatable antibody comprises a first linking peptide (LP1) and a second linking peptide (LP2), and at least a portion of the multispecific activatable antibody has the structural arrangement from N-terminus to C-terminus as follows in the uncleaved state: MM1-LP1-CM1-CM2 substrate-LP2-AB1 or AB1-LP2-CM1-CM2 substrate-LP1-MM1. In some embodiments, the two linking peptides need not be identical to each other.

In some embodiments, at least one of LP1 or LP2 includes an amino acid sequence selected from the group consisting of $(GS)_n$, $(GGS)_n$, $(GSGGS)_n$ (SEQ ID NO: 381) and $(GGGS)_n$ (SEQ ID NO: 382), where n is an integer of at least one. In some embodiments, at least one of LP1 or LP2 includes an amino acid sequence selected from the group consisting of GGSG (SEQ ID NO: 383), GGSGG (SEQ ID NO: 384), GSGSG (SEQ ID NO: 385), GSGGG (SEQ ID NO: 386), GGGSG (SEQ ID NO: 387), and GSSSG (SEQ ID NO: 388).

In some embodiments, the activatable antibody includes a linking peptide (LP') between CM1 and CM2.

In some embodiments, the activatable antibody comprises a first linking peptide (LP1), a second linking peptide (LP2), and a linking peptide (LP') between CM1 and CM2, and at least a portion of the multispecific activatable antibody has the structural arrangement from N-terminus to C-terminus as follows in the uncleaved state: MM1-LP1-CM1-CM2 substrate-LP2-AB1 or AB1-LP2-CM1-CM2 substrate-LP1-MM1. In some embodiments, linking peptides need not be identical to each other.

In some embodiments, LP' is GG. In some embodiments, LP' is GGSGGS (SEQ ID NO: 350).

In some embodiments, the multispecific activatable antibody includes at least a first antibody or antigen-binding fragment thereof (AB1) that specifically binds a first target or first epitope and a second antibody or antigen-binding fragment thereof (AB2) that specifically binds a second target or second epitope. In some embodiments, each of the AB in the multispecific activatable antibody is independently selected from the group consisting of a monoclonal antibody, domain antibody, single chain, Fab fragment, a $F(ab')_2$ fragment, a scFv, a scAb, a dAb, a single domain heavy chain antibody, and a single domain light chain antibody. In some embodiments, each of the AB in the multispecific activatable antibody is a rodent (e.g., mouse or rat), chimeric, humanized or fully human monoclonal antibody.

In some embodiments, each of the AB in the multispecific activatable antibody has a dissociation constant of about 100 nM or less for binding to its corresponding target or epitope.

In some embodiments, MM1 has a dissociation constant for binding to its corresponding AB that is greater than the dissociation constant of the AB to its corresponding target or epitope.

In some embodiments, MM1 has a dissociation constant for binding to its corresponding AB that is no more than the dissociation constant of the AB to its corresponding target or epitope.

In some embodiments, MM1 does not interfere or compete with its corresponding AB for binding to the corresponding target or epitope when the multispecific activatable antibody is in a cleaved state.

In some embodiments, MM1 is a polypeptide of about 2 to 40 amino acids in length. In some embodiments, each of the MM in the multispecific activatable antibody is a polypeptide of no more than 40 amino acids in length.

In some embodiments, MM1 has a polypeptide sequence that is different from that of target of the corresponding AB.

In some embodiments, MM1 has a polypeptide sequence that is no more than 50% identical to any natural binding partner of the corresponding AB. In some embodiments, MM1 has a polypeptide sequence that is no more than 25% identical to any natural binding partner of the corresponding AB. In some embodiments, MM1 has a polypeptide sequence that is no more than 10% identical to any natural binding partner of the corresponding AB.

In some embodiments, the coupling of MM1 reduces the ability of the corresponding AB to bind its target or epitope such that the dissociation constant ($K_d$) of the AB when coupled to the MM1 towards its corresponding target or epitope is at least 20 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 40 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 100 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 1000 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 10,000 times greater than the $K_d$ of the AB when not coupled to the MM1 towards its corresponding target or epitope.

In some embodiments, MM1 is an amino acid sequence selected from a MM disclosed herein.

In some embodiments, the multispecific activatable antibody includes at least a second masking moiety (MM2) that inhibits the binding of the AB2 to its target when the multispecific activatable antibody is in an uncleaved state, and an additional cleavable moiety (CM') coupled to the AB2, wherein the CM' is either a CM1-CM2 substrate or a polypeptide that functions as a substrate for a second protease. In some embodiments, CM' is a polypeptide of no more than 15 amino acids long. In some embodiments, CM' is a CM1-CM2 substrate, wherein each of CM1 and CM2 in the CM1-CM2 substrate is independently no more than 15 amino acids long.

In some embodiments, the MMP protease, the SP protease, and/or the second protease is co-localized with the second target or epitope in a tissue, and wherein the MMP protease, the SP protease, and/or the second protease cleaves the CM' in the multispecific activatable antibody when the multispecific activatable antibody is exposed to the MMP protease, the SP protease, and/or the second protease. In some embodiments, the MMP protease, the SP protease, and/or the second protease are co-localized with the first target or epitope and the second target or epitope in a tissue. In some embodiments, the MMP protease, the SP protease, and/or the second protease are the same MMP protease and the same SP protease. In some embodiments, the MMP protease, the SP protease, and/or the second protease are not the same MMP protease and not the same SP protease. In some embodiments, the CM1-CM2 substrate and CM' are different substrates for the same MMP protease and same SP protease. In some embodiments, the protease that cleaves CM' is selected from the group consisting of those shown in Table 6.

In some embodiments, each of the MM in the multispecific activatable antibody, e.g., MM1 and at least MM2, has a dissociation constant for binding to its corresponding AB that is greater than the dissociation constant of the AB to its corresponding target or epitope.

In some embodiments, each of the MM in the multispecific activatable antibody has a dissociation constant for binding to its corresponding AB that is no more than the dissociation constant of the AB to its corresponding target or epitope.

In some embodiments, each of the MM in the multispecific activatable antibody does not interfere or compete with its corresponding AB for binding to the corresponding target or epitope when the multispecific activatable antibody is in a cleaved state.

In some embodiments, each of the MM in the multispecific activatable antibody is a polypeptide of about 2 to 40 amino acids in length. In some embodiments, each of the MM in the multispecific activatable antibody is a polypeptide of no more than 40 amino acids in length.

In some embodiments, each of the MM in the multispecific activatable antibody has a polypeptide sequence that is different from that of target of the corresponding AB.

In some embodiments, each of the MM in the multispecific activatable antibody has a polypeptide sequence that is no more than 50% identical to any natural binding partner of the corresponding AB. In some embodiments, each of the MM in the multispecific activatable antibody has a polypeptide sequence that is no more than 25% identical to any natural binding partner of the corresponding AB. In some embodiments, each of the MM in the multispecific activatable antibody has a polypeptide sequence that is no more than 10% identical to any natural binding partner of the corresponding AB.

In some embodiments, the coupling of each of the MM reduces the ability of the corresponding AB to bind its target or epitope such that the dissociation constant ($K_d$) of the AB when coupled to the MM towards its corresponding target or epitope is at least 20 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 40 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 100 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 1000 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 10,000 times greater than the $K_d$ of the AB when not coupled to the MM towards its corresponding target or epitope.

In some embodiments, each of the MM is an amino acid sequence selected from a MM disclosed herein.

In some embodiments, the protease that cleaves the CM1-CM2 substrate sequence is co-localized with the target of the AB1 in the multispecific activatable antibody in a tissue, and the MMP protease and/or SP protease, i.e., at least one of the MMP protease and the SP protease, cleave the CM1-CM2 substrate in the multispecific activatable antibody when the multispecific activatable antibody is exposed to the proteases.

In some embodiments, the multispecific activatable antibody includes more than one CM1-CM2 substrate sequence, and the MMP protease and/or the SP protease that cleaves at least one CM1-CM2 substrate sequence is co-localized with the target of at least one of the AB regions in the multispecific activatable antibody in a tissue, and the MMP protease and/or SP protease cleaves the CM1-CM2 substrate in the multispecific activatable antibody when the multispecific activatable antibody is exposed to the proteases.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least twofold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least threefold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least fourfold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least fivefold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least tenfold greater than the dissociation constant of an unmodified AB binding to its target, and whereas in the cleaved state, the AB binds its target.

In some embodiments, each CM1-CM2 substrate, is positioned in the multispecific activatable antibody such that in the uncleaved state, binding of the multispecific activatable antibody to a target of one of the AB regions is reduced to occur with a dissociation constant that is at least 20-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 40-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 50-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 100-fold greater than the dissociation constant of an unmodified AB binding to its target, and whereas in the cleaved state, the AB binds its target.

In some embodiments, each CM1-CM2 substrate is positioned in the multispecific activatable antibody such that in the uncleaved state, binding of the multispecific activatable antibody to a target of one of the AB regions is reduced to occur with a dissociation constant that is at least 200-fold greater than the dissociation constant of an unmodified AB binding to its target, and whereas in the cleaved state, the AB binds its target.

The disclosure also provides compositions and methods that include a multispecific activatable antibody that includes at least a first antibody or antibody fragment (AB1) that specifically binds a target and a second antibody or antibody fragment (AB2), where at least the first AB in the multispecific activatable antibody is coupled to a masking moiety (MM1) that decreases the ability of AB1 to bind its target. In some embodiments, each AB is coupled to a MM that decreases the ability of its corresponding AB to each target. For example, in bispecific activatable antibody embodiments, AB1 is coupled to a first masking moiety (MM1) that decreases the ability of AB1 to bind its target, and AB2 is coupled to a second masking moiety (MM2) that decreases the ability of AB2 to bind its target. In some embodiments, the multispecific activatable antibody comprises more than two AB regions; in such embodiments, AB1 is coupled to a first masking moiety (MM1) that decreases the ability of AB1 to bind its target, AB2 is coupled to a second masking moiety (MM2) that decreases the ability of AB2 to bind its target, AB3 is coupled to a third masking moiety (MM3) that decreases the ability of AB3 to bind its target, and so on for each AB in the multispecific activatable antibody.

In some embodiments, the multispecific activatable antibody further includes at least one CM1-CM2 substrate that is a substrate for a MMP protease and a SP protease, where the CM1-CM2 substrate links a MM to an AB. For example, in some embodiments, the multispecific activatable antibody includes at least a first antibody or antibody fragment (AB1) that specifically binds a target and a second antibody or antibody fragment (AB2), where at least the first AB in the multispecific activatable antibody is coupled via a first CM1-CM2 substrate to a masking moiety (MM1) that decreases the ability of AB1 to bind its target. In some bispecific activatable antibody embodiments, AB1 is coupled via the first CM1-CM2 substrate to MM1, and AB2 is coupled via a second CM1-CM2 substrate to a second masking moiety (MM2) that decreases the ability of AB2 to bind its target. In some embodiments, the multispecific activatable antibody comprises more than two AB regions; in some of these embodiments, AB1 is coupled via the first CM1-CM2 substrate to MM1, AB2 is coupled via the second CM1-CM2 substrate to MM2, and AB3 is coupled via a third CM1-CM2 substrate to a third masking moiety (MM3) that decreases the ability of AB3 to bind its target, and so on for each AB in the multispecific activatable antibody.

Activatable Antibodies Having Non-Binding Steric Moieties or Binding Partners for Non-Binding Steric Moieties The disclosure also provides activatable antibodies that include non-binding steric moieties (NB) or binding partners (BP) for non-binding steric moieties, where the BP recruits or otherwise attracts the NB to the activatable antibody. The activatable antibodies provided herein include, for example, an activatable antibody that includes a non-binding steric moiety (NB), a CM1-CM2 substrate and antibody or antibody fragment (AB) that binds a target; an activatable antibody that includes a binding partner for a non-binding steric moiety (BP), a CM1-CM2 substrate and an AB; and an activatable antibody that includes a BP to which an NB has been recruited, a CM1-CM2 substrate and an AB that binds the target. Activatable antibodies in which the NB is covalently linked to the CM1-CM2 substrate and AB of the activatable antibody or is associated by interaction with a BP that is covalently linked to the CM1-CM2 substrate and AB of the activatable antibody are referred to herein as "NB-containing activatable antibodies." By activatable or switchable is meant that the activatable antibody exhibits a first level of binding to a target when the activatable antibody is in an inhibited, masked or uncleaved state (i.e., a first conformation), and a second level of binding to the target when the activatable antibody is in an uninhibited, unmasked and/or cleaved state (i.e., a second conformation, i.e., activated antibody), where the second level of target binding is greater than the first level of target binding. The activatable antibody compositions can exhibit increased bioavailability and more favorable biodistribution compared to conventional antibody therapeutics.

In some embodiments, activatable antibodies provide for reduced toxicity and/or adverse side effects that could otherwise result from binding of the at non-treatment sites and/or non-diagnostic sites if the AB were not masked or otherwise inhibited from binding to such a site.

In one embodiment, the activatable antibody includes a non-binding steric moiety (NB); a CM1-CM2 substrate; and an antibody or antibody fragment (AB) that binds specifically to the target, wherein the NB is a polypeptide that does not bind specifically to the AB; the CM1-CM2 substrate is a polypeptide that includes a substrate (S) for an enzyme; the CM1-CM2 substrate is positioned such that in an uncleaved state, the NB interferes with binding of the AB to the target and in a cleaved state, the NB does not interfere with binding of the AB to the target; and the NB does not inhibit cleavage of the CM1-CM2 substrate by the enzyme. As used herein and throughout, the term polypeptide refers to any polypeptide that includes at least two amino acid residues, including larger polypeptides, full-length proteins and fragments thereof, and the term polypeptide is not limited to single-chain polypeptides and can include multi-unit, e.g., multi-chain, polypeptides. In cases where the polypeptide is of a shorter length, for example, less than 50 amino acids total, the terms peptide and polypeptide are used interchangeably herein, and in cases where the polypeptide is of a longer length, e.g., 50 amino acids or greater, the terms polypeptide and protein are used interchangeably herein.

In one embodiment, the activatable antibody includes a non-binding steric moiety (NB); a CM1-CM2 substrate; and an antibody or antibody fragment (AB) that binds specifically to the target, wherein (i) the NB includes a polypeptide that does not bind specifically to the AB; (ii) CM1-CM2 substrate is a polypeptide of up to 50 amino acids in length that includes a substrate (S) for an enzyme; (iii) the CM1-CM2 substrate is positioned such that in an uncleaved state, the NB interferes with binding of the AB to the target and in a cleaved state, the NB does not interfere with binding of the AB to the target; and (iv) the NB does not inhibit cleavage of the CM1-CM2 substrate by the enzyme. For example, each of the CM1 substrate sequence and the CM2 substrate sequence in the CM1-CM2 substrate independent has a length of up to 15 amino acids.

In one embodiment, the activatable antibody includes a non-binding steric moiety (NB); a CM1-CM2 substrate; and an antibody or antibody fragment (AB) that binds specifically to the target, wherein (i) the NB includes a polypeptide that does not bind specifically to the AB; (ii) the CM1-CM2 substrate is a polypeptide that includes a substrate (S) for an enzyme; (iii) the CM1-CM2 substrate is positioned such that in an uncleaved state, the NB interferes with binding of the AB to the target and in a cleaved state, the NB does not interfere with binding of the AB to the target; (iv) the NB does not inhibit cleavage of the CM1-CM2 substrate by the enzyme; and (v) the activatable antibody has the structural arrangement from N-terminus to C-terminus as follows in the uncleaved state: NB-CM1-CM2 substrate-AB or AB-CM1-CM2 substrate-NB.

In one embodiment, the activatable antibody includes a non-binding steric moiety (NB); a CM1-CM2 substrate; and an antibody or antibody fragment (AB) that binds specifically to the target, wherein (i) the NB includes a polypeptide that does not bind specifically to the AB; (ii) the CM1-CM2 substrate is a polypeptide that includes a substrate (S) for an enzyme; (iii) the CM1-CM2 substrate is positioned such that in an uncleaved state, the NB interferes with binding of the AB to the target and in a cleaved state, the NB does not interfere with binding of the AB to the target, and wherein the NB in the uncleaved activatable antibody reduces the ability of the AB to bind the target by at least 50%, for example, by at least 60%, by at least 70%, by at least 75%, by at least 80%, by at least 85%, by at least 90%, by at least 95%, by at least 96%, by at least 97%, by at least 98%, by at least 99%, by at least 100% as compared to the ability of the cleaved AB to bind the target; and (iv) the NB does not inhibit cleavage of the CM1-CM2 substrate by the enzyme. The reduction in the ability of the AB to bind the target is determined, e.g., using an assay as described herein or an in vitro target displacement assay such as, for example, the assay described in PCT Publication Nos. WO 2009/025846 and WO 2010/081173.

In one embodiment, the activatable antibody includes a binding partner (BP) for a non-binding steric moiety (NB); a CM1-CM2 substrate; and an antibody or antibody fragment (AB) that binds specifically to the target, wherein the BP is a polypeptide that binds to the NB when exposed thereto; the NB does not bind specifically to the AB; the CM1-CM2 substrate is a polypeptide that includes a substrate (S) for an enzyme; the CM1-CM2 substrate is positioned such that in an uncleaved state in the presence of the NB, the NB interferes with binding of the AB to the target and in a cleaved state, the NB does not interfere with binding of the AB to the target and the BP does not interfere with binding of the AB to the target; and the NB and the BP do not inhibit cleavage of the CM1-CM2 substrate by the enzyme. In some examples of this embodiment, the BP of the activatable antibody is optionally bound to the NB. In one embodiment, the NB is recruited by the BP of the activatable antibody in vivo.

In some examples of any of these activatable antibody embodiments, the activatable antibody is formulated as a composition. In some of these embodiments, the composition also includes the NB, where the NB is co-formulated with the activatable antibody that includes the BP, the CM1-CM2 substrate, and the AB. In some examples of this embodiment, the BP is selected from the group consisting of an albumin binding peptide, a fibrinogen binding peptide, a fibronectin binding peptide, a hemoglobin binding peptide, a transferrin binding peptide, an immunoglobulin domain binding peptide, and other serum protein binding peptides.

In some examples of any of these activatable antibody embodiments, the NB is a soluble, globular protein. In some examples of any of these activatable antibody embodiments, the NB is a protein that circulates in the bloodstream. In some examples of any of these activatable antibody embodiments, the NB is selected from the group consisting of albumin, fibrinogen, fibronectin, hemoglobin, transferrin, an immunoglobulin domain, and other serum proteins.

In some examples of any of these activatable antibody embodiments, the CM1-CM2 substrate is a polypeptide that includes a substrate (S) for a protease. In some examples of any of these activatable antibody embodiments, the protease is co-localized with the in a tissue, and the protease cleaves the CM1-CM2 substrate in the activatable antibody when the activatable antibody is exposed to the protease. In some examples of any of these activatable antibody embodiments, the CM1-CM2 substrate is a polypeptide of up to 50 amino acids in length. In some examples of any of these activatable antibody embodiments, the CM1-CM2 substrate is a polypeptide that includes a substrate (S) having a length of up to 15 amino acids, e.g., 3 amino acids long, 4 amino acids long, 5 amino acids long, 6 amino acids long, 7 amino acids long, 8 amino acids long, 9 amino acids long, 10 amino acids long, 11 amino acids long, 12 amino acids long, 13 amino acids long, 14 amino acids long, or 15 amino acids long.

In some examples of any of these activatable antibody embodiments, the activatable antibody has the structural arrangement from N-terminus to C-terminus as follows in the uncleaved state: NB-CM1-CM2 substrate-AB, AB-CM1-CM2 substrate-NB, BP-CM1-CM2 substrate-AB or AB-CM1-CM2 substrate-BP. In embodiments where the activatable antibody includes a BP and the activatable antibody is in the presence of the corresponding NB, the activatable antibody has a structural arrangement from N-terminus to C-terminus as follows in the uncleaved state: NB:BP-CM1-CM2-AB, NB:BP-CM2-CM1-AB, AB-CM1-CM2-BP:NB or AB-CM2-CM1-BP:NB, where ":" represents an interaction, e.g., binding, between the NB and BP.

In some examples of any of these activatable antibody embodiments, the activatable antibody includes an antibody or antigen-binding fragment thereof that specifically binds a given target and is a monoclonal antibody, domain antibody, single chain, Fab fragment, a $F(ab')_2$ fragment, a scFv, a scab, a dAb, a single domain heavy chain antibody, or a single domain light chain antibody. In some embodiments, such an antibody or immunologically active fragment thereof that binds the target a mouse, other rodent, chimeric, humanized or fully human monoclonal antibody.

In some examples of any of these activatable antibody embodiments, the activatable antibody includes a combination of a variable heavy chain region comprising an amino acid sequence presented herein and a variable light chain region comprising an amino acid sequence presented herein. In some embodiments, the activatable antibody includes a combination of a variable heavy chain region comprising an amino acid sequence that is at least 90%, 91%, 92%, 93%, 94%, 95%, 96%, 97%, 98%, 99% or more identical to an amino acid sequence presented herein, and a variable light chain region comprising an amino acid sequence that is at least 90%, 91%, 92%, 93%, 94%, 95%, 96%, 97%, 98%, 99% or more identical to an amino acid sequence presented herein.

In some examples of any of these activatable antibody embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the AB via a linker. In some embodiments, the linker is a cleavable linker. In some embodiments, the agent is conjugated to the AB via a noncleavable linker. In some embodiments, the agent is an agent selected from the group listed in Table 3. In some embodiments, the agent is a microtubule inhibitor. In some embodiments, the agent is a nucleic acid damaging agent, such as a DNA alkylator or DNA intercalator, or other DNA damaging agent. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some examples of any of these activatable antibody embodiments, the activatable antibody also includes a detectable moiety. In some embodiments, the detectable moiety is a diagnostic agent.

In some examples of any of these activatable antibody embodiments, the activatable antibody also includes a spacer. In some examples of any of these activatable antibody embodiments, the activatable antibody also includes a signal peptide. In some embodiments, the signal peptide is conjugated to the activatable antibody via a spacer. In some examples of any of these activatable antibody embodiments, the spacer is joined directly to the MM of the activatable antibody.

In some embodiments, the serum half-life of the activatable antibody is longer than that of the corresponding antibody; e.g., the pK of the activatable antibody is longer than that of the corresponding antibody. In some embodiments, the serum half-life of the activatable antibody is similar to that of the corresponding antibody. In some embodiments, the serum half-life of the activatable antibody is at least 15 days when administered to an organism. In some embodiments, the serum half-life of the activatable antibody is at least 12 days when administered to an organism. In some embodiments, the serum half-life of the activatable antibody is at least 11 days when administered to an organism. In some embodiments, the serum half-life of the activatable antibody is at least 10 days when administered to an organism. In some embodiments, the serum half-life of the activatable antibody is at least 9 days when administered to an organism. In some embodiments, the serum half-life of the activatable antibody is at least 8 days when administered to an organism. In some embodiments, the serum half-life of the activatable antibody is at least 7 days when administered to an organism. In some embodiments, the serum half-life of the activatable antibody is at least 6 days when administered to an organism. In some examples of any of these activatable antibody embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

The disclosure also provides an isolated nucleic acid molecule encoding any of these activatable antibodies, as well as vectors that include these isolated nucleic acid sequences. The disclosure provides methods of producing an activatable antibody by culturing a cell under conditions that lead to expression of the activatable antibody, wherein the cell comprises such a nucleic acid sequence. In some embodiments, the cell comprises such a vector.

The dissociation constant ($K_d$) of the NB-containing activatable antibody toward the target is greater than the $K_d$ of the AB towards the target when it is not associated with the NB or NB:BP. The dissociation constant ($K_d$) of the NB-containing activatable antibody toward the target is greater than the $K_d$ of the parental AB towards the target. For example, the $K_d$ of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB when it is not associated with the NB or NB:BP or the $K_d$ of the parental AB towards the target. Conversely, the binding affinity of the NB-containing activatable antibody towards the target is lower than the binding affinity of the AB when it is not associated with the NB or NB:BP or lower than the binding affinity of the parental AB towards the target. For example, the binding affinity of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB when it is not associated with the NB or NB:BP or lower than the binding affinity of the parental AB towards the target.

When the NB-containing activatable antibody is in the presence of the target, specific binding of the AB to the target is reduced or inhibited, as compared to the specific binding of the AB when it is not associated with the NB or NB:BP. When the NB-containing activatable antibody is in the presence of the target, specific binding of the AB to the target is reduced or inhibited, as compared to the specific binding of the parental AB to the target. When compared to the binding of the AB not associated with an NB or NB:BP or the binding of the parental AB to the target, the ability of the NB-containing activatable antibody to bind the target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

When the NB-containing activatable antibody is in the presence of the target but not in the presence of a modifying agent (for example a protease or other enzyme), specific binding of the AB to the target is reduced or inhibited, as compared to the specific binding of the AB when it is not associated with the NB or NB:BP. When the NB-containing activatable antibody is in the presence of the target but not in the presence of a modifying agent (for example a protease, other enzyme, reduction agent, or light), specific binding of the AB to the target is reduced or inhibited, as compared to the specific binding of the parental AB to the target. When compared to the binding of the AB not associated with an NB or NB:BP or the binding of the parental AB to the target, the ability of the NB-containing activatable antibody to bind the target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

In some examples of any of these activatable antibody embodiments, the activatable antibody includes an agent conjugated to the AB to produce an activatable antibody conjugate. In some embodiments of the activatable antibody conjugate, the agent is a therapeutic agent. In some embodiments, the agent is a diagnostic agent. In some embodiments, the agent is a detectable marker. In some embodiments of the activatable antibody conjugate, the agent is an antineoplastic agent. In some embodiments of the activatable antibody conjugate, the agent is a toxin or fragment thereof. In some embodiments of the activatable antibody conjugate, the agent is conjugated to the AB via a linker. In some embodiments of the activatable antibody conjugate, the linker is a cleavable linker. In some embodiments, the agent is conjugated to the AB via a noncleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine. In some embodiments, the agent is a pyrrolobenzodiazepine dimer.

In some examples of any of these activatable antibody embodiments, the activatable antibodies are dual-target binding activatable antibodies. Such dual target binding activatable antibodies contain two Abs that may bind the same or different targets. In specific embodiments, dual-targeting activatable antibodies contain bispecific antibodies or antibody fragments.

Dual target binding activatable antibodies are designed so as to have a CM1-CM2 substrate cleavable by a cleaving agent that is co-localized in a target tissue with one or both of the targets capable of binding to the ABs of the activatable antibodies. Dual target binding activatable antibodies with more than one AB to the same or different targets can be designed so as to have more than one CM1-CM2 substrate, wherein the first CM1-CM2 substrate is cleavable by a cleaving agent in a first target tissue and wherein the second CM1-CM2 substrate is cleavable by a cleaving agent in a second target tissue, with one or more of the targets binding to the ABs of the activatable antibodies. In one embodiment, the first and second target tissues are spatially separated, for example, at different sites in the organism. In one embodiment, the first and second target tissues are the same tissue temporally separated, for example the same tissue at two different points in time, for example the first time point is when the tissue is an early stage tumor, and the second time point is when the tissue is a late stage tumor.

The disclosure also provides nucleic acid molecules encoding the activatable antibodies described herein. The disclosure also provides vectors that include these nucleic acids. The activatable antibodies described herein are produced by culturing a cell under conditions that lead to expression of the activatable antibody, wherein the cell includes these nucleic acid molecules or vectors.

The disclosure also provides methods of manufacturing activatable antibodies. In one embodiment, the method includes the steps of (a) culturing a cell that includes a nucleic acid construct that encodes the activatable antibody under conditions that lead to expression of the activatable antibody, wherein the activatable antibody includes (i) a non-binding steric moiety (NB); (ii) a CM1-CM2 substrate; and (iii) an antibody or an antigen binding fragment thereof (AB) that specifically binds a target, wherein (1) the NB does not bind specifically to the AB; (2) the CM1-CM2 substrate is a polypeptide that includes a substrate (S) for an enzyme; (3) the CM1-CM2 substrate is positioned such that in an uncleaved state, the NB interferes with binding of the AB to the target and in a cleaved state, the NB does not interfere with binding of the AB to the target; and (4) the NB does not inhibit cleavage of the CM1-CM2 substrate by the enzyme; and (b) recovering the activatable antibody.

In some embodiments, the method includes the steps of (a) culturing a cell that includes a nucleic acid construct that encodes the activatable antibody under conditions that lead to expression of the activatable antibody, wherein the activatable antibody includes (i) a binding partner (BP) for a non-binding steric moiety (NB); (ii) a CM1-CM2 substrate; and (iii) an antibody or an antigen binding fragment thereof (AB) that specifically binds a target, wherein (1) the NB does not bind specifically to the AB; (2) the CM1-CM2 substrate is a polypeptide that includes a substrate (S) for an enzyme; (3) the CM1-CM2 substrate is positioned such that in an uncleaved state in the presence of the NB, the NB interferes with binding of the AB to the target and in a cleaved state, the NB does not interfere with binding of the AB to the target and the BP does not interfere with binding of the AB to the target; and (4) the NB and the BP do not inhibit cleavage of the CM1-CM2 substrate by the enzyme; and (b) recovering the activatable antibody. In some examples of this embodiment, the BP of the activatable antibody is bound to the NB.

Use of Activatable Antibodies And Conjugated Activatable Antibodies

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci.89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the disclosure, which include a conjugated antibody, an activatable antibody and/or a conjugated activatable antibody, are used to prevent, treat or otherwise ameliorate a disease or disorder associated with aberrant target expression and/or activity. For example, therapeutic formulations of the disclosure, which include a conjugated antibody, an activatable antibody and/or a conjugated activatable antibody, are used to treat or otherwise ameliorate inflammation, an inflammatory disorder, an autoimmune disease and/or a cancer or other neoplastic condition. In some embodiments, the cancer is a solid tumor or a hematologic malignancy where the target is expressed. In some embodiments, the cancer is a solid tumor where the target is expressed. In some embodiments, the cancer is a hematologic malignancy where the target is expressed. In some embodiments, the target is expressed on parenchyma (e.g., in cancer, the portion of an organ or tissue that often carries out function(s) of the organ or tissue). In some embodiments, the target is expressed on a cell, tissue, or organ. In some embodiments, the target is expressed on stroma (i.e., the connective supportive framework of a cell, tissue, or organ). In some embodiments, the target is expressed on an osteoblast. In some embodiments, the target is expressed on the endothelium (vasculature). In some embodiments, the target is expressed on a cancer stem cell. In some embodiments, the agent to which the activatable antibody is conjugated is a microtubule inhibitor. In some embodiments, the agent to which the activatable antibody is conjugated is a nucleic acid damaging agent.

Efficaciousness of prevention, amelioration or treatment is determined in association with any known method for diagnosing or treating the disease or disorder associated with target expression and/or activity, such as, for example, aberrant target expression and/or activity. Prolonging the survival of a subject or otherwise delaying the progression of the disease or disorder associated with target expression and/or activity, e.g., aberrant target expression and/or activity, in a subject indicates that the conjugated antibody, activatable antibody and/or conjugated activatable antibody confers a clinical benefit.

A conjugated antibody, an activatable antibody and/or a conjugated activatable antibody can be administered in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

In some embodiments where antibody fragments are used, the smallest fragment that specifically binds to the binding domain of the target protein is selected. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compounds as necessary for the particular indication being treated, for example, in some embodiments, those with complementary activities that do not adversely affect each other. In some embodiments, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and $\gamma$ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

In some embodiments, the conjugated antibody, activatable antibody and/or conjugated activatable antibody contains a detectable label. An intact antibody, or a fragment thereof (e.g., Fab, scFv, or $F(ab)_2$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the disclosure can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELIS As), Western blots, immunoprecipitations, immunochemical staining, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

The conjugated antibodies, activatable antibodies and/or conjugated activatable antibodies of the disclosure are also useful in a variety of diagnostic and prophylactic formulations. In one embodiment, a conjugated antibody, an activatable antibody and/or a conjugated activatable antibody is administered to patients that are at risk of developing one or more of the aforementioned disorders. A patient's or organ's predisposition to one or more of the aforementioned disorders can be determined using genotypic, serological or biochemical markers.

In some embodiments, a conjugated antibody, an activatable antibody and/or a conjugated activatable antibody is administered to human individuals diagnosed with a clinical indication associated with one or more of the aforementioned disorders. Upon diagnosis, a conjugated antibody, an activatable antibody and/or a conjugated activatable antibody is administered to mitigate or reverse the effects of the clinical indication.

A conjugated antibody, an activatable antibody and/or a conjugated activatable antibody of the disclosure is also useful in the detection of a target in patient samples and accordingly are useful as diagnostics. For example, the antibodies and/or activatable antibodies, and conjugated versions thereof, of the disclosure are used in in vitro assays, e.g., ELISA, to detect target levels in a patient sample.

In one embodiment, a conjugated antibody, an activatable antibody and/or a conjugated activatable antibody of the disclosure is immobilized on a solid support (e.g., the well(s) of a microtiter plate). The immobilized conjugated antibody, activatable antibody and/or conjugated activatable antibody serves as a capture antibody for any target that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies of the disclosure, and conjugated versions thereof, in an in vitro diagnostic assay, it is possible to stage a disease in a subject based on expression levels of the target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

A conjugated antibody, an activatable antibody and/or a conjugated activatable antibody can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies having an enzymatically cleavable CM1-CM2 substrate can be used to detect the presence or absence of an enzyme that is capable of cleaving the CM1-CM2 substrate. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM1-CM2 substrate) but also that the tissue expresses target to which the activated antibody binds.

For example, the CM1-CM2 substrate can be selected to be substrate for a matrix metalloprotease (MMP) and a serine protease (SP) found at the site of a tumor, at the site of a viral or bacterial infection at a biologically confined site (e.g., such as in an abscess, in an organ, and the like), and the like. The AB can be one that binds a target antigen. Using methods as disclosed herein, or when appropriate, methods familiar to one skilled in the art, a detectable label (e.g., a fluorescent label or radioactive label or radiotracer) can be conjugated to an AB or other region of an antibody and/or activatable antibody. Suitable detectable labels are discussed in the context of the above screening methods and additional specific examples are provided below. Using an AB specific to a protein or peptide of the disease state, along with an MMP whose activity is elevated in the disease tissue of interest, activatable antibodies will exhibit an increased rate of binding to disease tissue relative to tissues where the CM1-CM2 substrate specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM1-CM2 substrate is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM1-CM2 substrate susceptible to cleavage by an enzyme, the activatable antibodies can be used to detect (either qualitatively or quantitatively) the presence of an enzyme in the sample. In another example, where the activatable antibodies contain a CM1-CM2 substrate susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. a fluorophore, Fluorescein Isothiocyanate (FITC), Rhodamine Isothiocyanate (TRITC), an Alexa Fluor® label), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a matrix metalloprotease (MMP) and one serine protease (SP) that are specific for the CM1-CM2 substrate of the activatable antibody. In some embodiments, the presence of the MMP can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a MMP and a SP specific for the CM1-CM2 substrate of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a MMP and a SP that is specific for the CM1-CM2 substrate of the activatable antibody.

These techniques are also useful in kits and/or as reagents for the detection, identification or characterization of protease activity in a variety of cells, tissues, and organisms based on the protease-specific CM1-CM2 substrate in the activatable antibody.

The disclosure provides methods of using the antibodies and/or activatable antibodies in a variety of diagnostic and/or prophylactic indications. For example, the disclosure provides methods of detecting presence or absence of a cleaving agent and a target of interest in a subject or a sample by (i) contacting a subject or sample with an activatable antibody, wherein the activatable antibody comprises a masking moiety (MM), a CM1-CM2 substrate that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent and the target are present in the subject or sample and wherein no detectable level of activated activatable antibody in the subject or sample indicates that the cleaving agent, the target or both the cleaving agent and the target are absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody in the presence of a target of interest, e.g., the target, wherein the activatable antibody comprises a masking moiety (MM), a CM1-CM2 substrate that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody comprises a masking moiety (MM), a CM1-CM2 substrate that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody, wherein the activatable antibody comprises a masking moiety (MM), a CM1-CM2 substrate that is cleaved by the cleaving agent, an antigen binding domain (AB) that specifically binds the target, and a detectable label, wherein the activatable antibody in an uncleaved, non-activated state comprises a structural arrangement from N-terminus to C-terminus as follows: MM-CM1-CM2 substrate-AB or AB-CM1-CM2 substrate-MM; wherein the MM is a peptide that inhibits binding of the AB to the target, and wherein the MM does not have an amino acid sequence of a naturally occurring binding partner of the AB and is not a modified form of a natural binding partner of the AB; wherein, in an uncleaved, non-activated state, the MM interferes with specific binding of the AB to the target, and in a cleaved, activated state the MM does not interfere or compete with specific binding of the AB to the target; and wherein the detectable label is positioned on a portion of the activatable antibody that is released following cleavage of the CM1-CM2 substrate; and (ii) measuring a level of detectable label in the subject or sample, wherein a detectable level of the detectable label in the subject or sample indicates that the cleaving agent is absent and/or not sufficiently present in the subject or sample and wherein no detectable level of the detectable label in the subject or sample indicates that the cleaving agent is present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody (e.g., an activatable antibody to which a therapeutic agent is conjugated) described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent and the target are present in the subject or biological sample and wherein no detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample.

The disclosure also provides methods of detecting presence or absence of a cleaving agent in a subject or a sample by (i) contacting a subject or biological sample with an activatable antibody in the presence of the target, and (ii) measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments, all antigen binding sites are masked. In some embodiments, the measuring step includes use of a secondary reagent comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample with an activatable antibody in the presence of the target, and measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments, all antigen binding sites are masked. In some embodiments, the measuring step includes use of a secondary reagent comprising a detectable label.

The disclosure also provides kits for use in methods of detecting presence or absence of a cleaving agent in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM1-CM2 substrate, wherein a detectable level of activated activatable antibody in the subject or biological sample indicates that the cleaving agent is absent and/or not sufficiently present in the subject or biological sample such that the target binding and/or protease cleavage of the activatable antibody cannot be detected in the subject or biological sample, and wherein no detectable level of activated activatable antibody in the subject or biological sample indicates that the cleaving agent is present in the subject or biological sample at a detectable level.

The disclosure provides methods of detecting presence or absence of a cleaving agent and the target in a subject or a sample by (i) contacting a subject or biological sample with an activatable antibody, wherein the activatable antibody includes a detectable label that is positioned on a portion of the activatable antibody that is released following cleavage of the CM1-CM2 substrate and (ii) measuring a level of activated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

The disclosure also provides methods of detecting presence or absence of a cleaving agent in a subject or a sample by (i) contacting a subject or biological sample with an activatable antibody, wherein the activatable antibody includes a detectable label that is positioned on a portion of the activatable antibody that is released following cleavage of the CM1-CM2 substrate; and (ii) measuring a level of detectable label in the subject or biological sample, wherein a detectable level of the detectable label in the subject or biological sample indicates that the cleaving agent is absent and/or not sufficiently present in the subject or biological sample at a detectable level, such that protease cleavage of the activatable antibody cannot be detected in the subject or biological sample, and wherein a reduced detectable level of the detectable label in the subject or biological sample indicates that the cleaving agent is present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a CM1-CM2 substrate that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM1-CM2 substrate-AB or AB-CM1-CM2 substrate-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent of interest in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM1-CM2 substrate, wherein a detectable level of the detectable label in the subject or biological sample indicates that the cleaving agent, the target, or both the cleaving agent and the target are absent and/or not sufficiently present in the subject or biological sample, such that the target binding and/or protease cleavage of the activatable antibody cannot be detected in the subject or biological sample, and wherein a reduced detectable level of the detectable label in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

In some embodiments of these methods and kits, the activatable antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods and kits, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments, in situ imaging is used to identify or otherwise refine a patient population suitable for treatment with an activatable antibody of the disclosure. For example, patients that test positive for both the target (e.g., the target) and a protease that cleaves the substrate in the CM1-CM2 substrate of the activatable antibody being tested (e.g., accumulate activated antibodies at the disease site) are identified as suitable candidates for treatment with such an activatable antibody comprising such a CM1-CM2 substrate. Likewise, patients that test negative for either or both of the target (e.g., the target) and the protease that cleaves the substrate in the CM1-CM2 substrate in the activatable antibody being tested using these methods might be identified as suitable candidates for another form of therapy. In some embodiments, such patients that test negative with respect to a first activatable antibody can be tested with other activatable antibodies comprising different CM1-CM2 substrates until a suitable activatable antibody for treatment is identified (e.g., an activatable antibody comprising a CM1-CM2 substrate that is cleaved by the patient at the site of disease). In some embodiments, the patient is then administered a therapeutically effective amount of the conjugated activatable antibody for which the patient tested positive.

In some embodiments, in vivo imaging is used to identify or otherwise refine a patient population suitable for treatment with an activatable antibody of the disclosure. For example, patients that test positive for both the target (e.g., the target) and a protease that cleaves the substrate in the CM1-CM2 substrate of the activatable antibody being tested (e.g., accumulate activated antibodies at the disease site) are identified as suitable candidates for treatment with such an activatable antibody comprising such a CM1-CM2 substrate. Likewise, patients that test negative might be identified as suitable candidates for another form of therapy. In some embodiments, such patients that test negative with respect to a first activatable antibody can be tested with other activatable antibodies comprising different CM1-CM2 substrates until a suitable activatable antibody for treatment is identified (e.g., an activatable antibody comprising a CM1-CM2 substrate that is cleaved by the patient at the site of disease). In some embodiments, the patient is then administered a therapeutically effective amount of the conjugated activatable antibody for which the patient tested positive.

In some embodiments of the methods and kits, the method or kit is used to identify or otherwise refine a patient population suitable for treatment with an activatable antibody of the disclosure. For example, patients that test positive for both the target (e.g., the target) and a protease that cleaves the substrate in the CM1-CM2 substrate of the activatable antibody being tested in these methods are identified as suitable candidates for treatment with such an activatable antibody comprising such a CM1-CM2 substrate. Likewise, patients that test negative for both of the targets (e.g., the target) and the protease that cleaves the substrate in the CM1-CM2 substrate in the activatable antibody being tested using these methods might be identified as suitable candidates for another form of therapy. In some embodiments, such patients can be tested with other activatable antibodies until a suitable activatable antibody for treatment is identified (e.g., an activatable antibody comprising a CM1-CM2 substrate that is cleaved by the patient at the site of disease). In some embodiments, patients that test negative for either of the target (e.g., the target) are identified as suitable candidates for treatment with such an activatable antibody comprising such a CM1-CM2 substrate. In some embodiments, patients that test negative for either of the target (e.g., the target) are identified as not being suitable candidates for treatment with such an activatable antibody comprising such a CM1-CM2 substrate. In some embodiments, such patients can be tested with other activatable antibodies until a suitable activatable antibody for treatment is identified (e.g., an activatable antibody comprising a CM1-CM2 substrate that is cleaved by the patient at the site of disease). In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

In some embodiments, a method or kit is used to identify or otherwise refine a patient population suitable for treatment with an anti-the target activatable antibody and/or conjugated activatable antibody (e.g., activatable antibody to which a therapeutic agent is conjugated) of the disclosure, followed by treatment by administering that activatable antibody and/or conjugated activatable antibody to a subject in need thereof. For example, patients that test positive for both the targets (e.g., the target) and a protease that cleaves the CM1-CM2 substrate of the activatable antibody and/or conjugated activatable antibody being tested in these methods are identified as suitable candidates for treatment with such antibody and/or such a conjugated activatable antibody comprising such a CM1-CM2 substrate, and the patient is then administered a therapeutically effective amount of the activatable antibody and/or conjugated activatable antibody that was tested. Likewise, patients that test negative for either or both of the target (e.g., the target) and the protease that cleaves the substrate in the CM1-CM2 substrate in the activatable antibody being tested using these methods might be identified as suitable candidates for another form of therapy. In some embodiments, such patients can be tested with other antibody and/or conjugated activatable antibody until a suitable antibody and/or conjugated activatable antibody for treatment is identified (e.g., an activatable antibody and/or conjugated activatable antibody comprising a CM1-CM2 substrate that is cleaved by the patient at the site of disease). In some embodiments, the patient is then administered a therapeutically effective amount of the activatable antibody and/or conjugated for which the patient tested positive.

In some embodiments of these methods and kits, the MM is a peptide having a length from about 4 to 40 amino acids. In some embodiments of these methods and kits, the activatable antibody comprises a linker peptide, wherein the linker peptide is positioned between the MM and the CM1-CM2 substrate. In some embodiments of these methods and kits, the activatable antibody comprises a linker peptide, where the linker peptide is positioned between the AB and the CM1-CM2 substrate. In some embodiments of these methods and kits, the activatable antibody comprises a first linker peptide (L1) and a second linker peptide (L2), wherein the first linker peptide is positioned between the MM and the CM1-CM2 substrate and the second linker peptide is positioned between the AB and the CM1-CM2 substrate. In some embodiments of these methods and kits, each of L1 and L2 is a peptide of about 1 to 20 amino acids in length, and wherein each of L1 and L2 need not be the same linker. In some embodiments of these methods and kits, one or both of L1 and L2 comprises a glycine-serine polymer. In some embodiments of these methods and kits, at least one of L1 and L2 comprises an amino acid sequence selected from the group consisting of $(GS)_n$, $(GSGGS)_n$ (SEQ ID NO: 381) and $(GGGS)_n$ (SEQ ID NO: 382), where n is an integer of at least one. In some embodiments of these methods and kits, at least one of L1 and L2 comprises an amino acid sequence having the formula $(GGS)_n$, where n is an integer of at least one. In some embodiments of these methods and kits, at least one of L1 and L2 comprises an amino acid sequence selected from the group consisting of Gly-Gly-Ser-Gly (SEQ ID NO: 383), Gly-Gly-Ser-Gly-Gly (SEQ ID NO: 384), Gly-Ser-Gly-Ser-Gly (SEQ ID NO: 385), Gly-Ser-Gly-Gly-Gly (SEQ ID NO: 386), Gly-Gly-Gly-Ser-Gly (SEQ ID NO: 387), and Gly-Ser-Ser-Ser-Gly (SEQ ID NO: 388).

In some embodiments of these methods and kits, the AB comprises an antibody or antibody fragment sequence selected from the cross-reactive antibody sequences presented herein. In some embodiments of these methods and kits, the AB comprises a Fab fragment, a scFv or a single chain antibody (scAb).

In some embodiments of these methods and kits, the cleaving agent is a protease that is co-localized in the subject or sample with the target and the CM1-CM2 substrate is a polypeptide that functions as a substrate for the protease, wherein the protease cleaves the CM1-CM2 substrate in the activatable antibody when the activatable antibody is exposed to the protease. In some embodiments of these methods and kits, each of the CM1 substrate sequence and the CM2 substrate sequence in the CM1-CM2 substrate is independently a polypeptide of up to 15 amino acids in length. In some embodiments of these methods and kits, the CM1-CM2 substrate is coupled to the N-terminus of the AB. In some embodiments of these methods and kits, the CM1-CM2 substrate is coupled to the C-terminus of the AB. In some embodiments of these methods and kits, the CM1-CM2 substrate is coupled to the N-terminus of a VL chain of the AB.

The activatable antibodies and/or conjugated activatable antibodies of the disclosure are used in diagnostic and prophylactic formulations. In one embodiment, an activatable antibody is administered to patients that are at risk of developing one or more of the aforementioned inflammation, inflammatory disorders, cancer or other disorders.

A patient's or organ's predisposition to one or more of the aforementioned disorders can be determined using genotypic, serological or biochemical markers.

In some embodiments, an activatable antibody and/or conjugated activatable antibodies is administered to human individuals diagnosed with a clinical indication associated with one or more of the aforementioned disorders. Upon diagnosis, an activatable antibody and/or conjugated activatable antibodies is administered to mitigate or reverse the effects of the clinical indication.

Activatable antibodies and/or conjugated activatable antibodies of the disclosure are also useful in the detection of the target in patient samples and accordingly are useful as diagnostics. For example, the activatable antibodies and/or conjugated activatable antibodies of the disclosure are used in in vitro assays, e.g., ELISA, to detect target levels in a patient sample.

In one embodiment, an activatable antibody of the disclosure is immobilized on a solid support (e.g., the well(s) of a microtiter plate). The immobilized activatable antibody serves as a capture antibody for any target that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies of the disclosure in an in vitro diagnostic assay, it is possible to stage a disease in a subject based on expression levels of the Target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Activatable antibodies and/or conjugated activatable antibodies can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies having an enzymatically cleavable CM1-CM2 substrate can be used to detect the presence or absence of an enzyme that is capable of cleaving the CM1-CM2 substrate. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM1-CM2 substrate) but also that the tissue expresses target to which the activated antibody binds.

For example, the CM1-CM2 substrate can be selected to be a protease substrate for a protease found at the site of a tumor, at the site of a viral or bacterial infection at a biologically confined site (e.g., such as in an abscess, in an organ, and the like), and the like. The AB can be one that binds a target antigen. Using methods familiar to one skilled in the art, a detectable label (e.g., a fluorescent label or radioactive label or radiotracer) can be conjugated to an AB or other region of an activatable antibody. Suitable detectable labels are discussed in the context of the above screening methods and additional specific examples are provided below. Using an AB specific to a protein or peptide of the disease state, along with a protease whose activity is elevated in the disease tissue of interest, activatable antibodies will exhibit an increased rate of binding to disease tissue relative to tissues where the CM1-CM2 substrate specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM1-CM2 substrate is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM1-CM2 substrate susceptible to cleavage by an enzyme, the activatable antibodies can be used to detect (either qualitatively or quantitatively) the presence of an enzyme in the sample. In another example, where the activatable antibodies contain a CM1-CM2 substrate susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. Fluorescein Isothiocyanate (FITC), Rhodamine Isothiocyanate (TRITC), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a protease that is specific for the CM1-CM2 substrate of the activatable antibody. In some embodiments, the presence of the protease can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM1-CM2 substrate of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a protease that is specific for the CM1-CM2 substrate of the activatable antibody.

These techniques are also useful in kits and/or as reagents for the detection, identification or characterization of protease activity in a variety of cells, tissues, and organisms based on the protease-specific CM1-CM2 substrate in the activatable antibody.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments, in situ imaging is used to identify or otherwise refine a patient population suitable for treatment with an activatable antibody of the disclosure. For example, patients that test positive for both the target and a protease that cleaves the substrate in the cleavable moiety (CM1-CM2 substrate) of the activatable antibody being tested (e.g., accumulate activated antibodies at the disease site) are identified as suitable candidates for treatment with such an activatable antibody comprising such a CM1-CM2 substrate. Likewise, patients that test negative for either or both of the target and the protease that cleaves the substrate in the CM1-CM2 substrate in the activatable antibody being tested using these methods are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM1-CM2 substrate that is cleaved by the patient at the site of disease).

In some embodiments, in vivo imaging is used to identify or otherwise refine a patient population suitable for treatment with an activatable antibody of the disclosure. For example, patients that test positive for both the target and a protease that cleaves the substrate in the cleavable moiety (CM1-CM2 substrate) of the activatable antibody being tested (e.g., accumulate activated antibodies at the disease site) are identified as suitable candidates for treatment with such an activatable antibody comprising such a CM1-CM2 substrate. Likewise, patients that test negative are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM1-CM2 substrate that is cleaved by the patient at the site of disease).

Pharmaceutical Compositions

The conjugated antibodies, activatable antibodies and/or conjugated activatable antibodies of the disclosure (also referred to herein as "active compounds"), and derivatives, fragments, analogs and homologs thereof, can be incorporated into pharmaceutical compositions suitable for administration. Such compositions typically comprise the conjugated antibody, activatable antibody and/or conjugated activatable antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL' (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1. Matrix Metalloprotease (MMP) and Serine Protease (SP) Cleavable Anti-Jagged Activatable Antibodies This Example demonstrates the generation and evaluation of activatable antibodies that bind a Jagged target, e.g., Jagged 1 and/or Jagged 2, where the activatable antibodies are activated in the presence of at least one matrix metalloprotease (MMP) and at least one serine protease.

The studies described herein used the following substrate sequences, where LP' is a linking peptide between CM1 and CM2. For the CM1-CM2 substrate 1001/L1Y/0001, LP' is GGSGGS (SEQ ID NO: 350), and for all other CM1-CM2 in the Table below, LP' is GG:

| CM1-CM2 Substrate | AA sequence | SEQ ID NO: |
|---|---|---|
| 2001 | ISSGLLSGRSDNH | 1 |
| 1001/LP'/0001 | ISSGLLSSGGSGGSLSGRSDNH | 2 |
| 1004/LP'/0003 | AVGLLAPPGGTSTSGRSANPRG | 3 |
| 0003/LP'/1004 | TSTSGRSANPRGGGAVGLLAPP | 4 |
| 1003/LP'/0003 | VHMPLGFLGPGGTSTSGRSANPRG | 5 |
| 0003/LP'/1003 | TSTSGRSANPRGGGVHMPLGFLGP | 6 |
| 1004/LP'/0001 | AVGLLAPPGGLSGRSDNH | 7 |
| 0001/LP'/1004 | LSGRSDNHGGAVGLLAPP | 8 |
| 1003/LP'/0001 | VHMPLGFLGPGGLSGRSDNH | 9 |
| 0001/LP'/1003 | LSGRSDNHGGVHMPLGFLGP | 10 |

Construction of the Anti-Jagged activatable antibody light chains was performed as follows.

The CM1-CM2 substrates were incorporated into the Jagged activatable antibody vector (described in PCT Publication No. WO2013/192550) as follows. Using standard molecular biology techniques, the forward (F) primers encoding the CM1-CM2 substrates (see Table A) and the reverse (R) primer CX1198 were used to amplify the substrate and VL domain of the Jagged activatable antibody and were subsequently cloned into the activatable antibody vector using the XhoI and BsiWI restriction sites. The resulting vectors encoded the following anti-Jagged activatable antibody light chains.

TABLE A

| Primers used to construct the CM1-CM2 expression vectors | | |
|---|---|---|
| CX1198 | Light chain R | Gtgcagccaccgtacgtttgatttccaccttggtccc (SEQ ID NO: 37) |
| CX2066 | 2001 F | CaggggggctcgagcGGCGGCTCTATCTCTTCCGGACTGCTGTCCGGCAGATCCGACAATCACGGCGGAGGCTCTGacatccagatgacccagtctc (SEQ ID NO: 38) |
| CX2067 | 1001/LP'/0001 F | CaggggggctcgagcGGCGGCTCTATCTCTTCTGGCCTGCTGTCTAGCGGCGGCTCCGGCGGATCTCTGTCTGGCAGATCTGACAACCACGGCGGAGGCTCCGacatccagatgacccagtctc (SEQ ID NO: 39) |
| CX2190 | 1004/LP'/0003 F | CaggggggctcgagcGGAGGATCTGCTGTGGGACTGCTGGCTCCTCCTGGCGGCACATCTACCTCTGGCAGATCCGCCAACCCTCGGGGCGGAGGATCTGacatccagatgacccagtctc (SEQ ID NO: 40) |

TABLE A-continued

| Primers used to construct the CM1-CM2 expression vectors | | |
|---|---|---|
| CX2191 | 0003/LP'/1004 F | CagggggctcgagcGGCGGCTCCACATCTACCTCTGGCAGATCCGCCAACCCCAGAGGTGGCGGAGCTGTGGGACTGCTGGCTCCACCAGGCGGATCTGacatccagatgacccagtctc (SEQ ID NO: 41) |
| CX2192 | 1003/LP'/0003 F | CagggggctcgagcGGCGGCTCTGTGCATATGCCCCTGGGCTTTCTGGGCCCTGGCGGCACATCTACCTCTGGCAGATCCGCCAACCCTCGGGGCGGAGGATCTGacatccagatgacccagtctc (SEQ ID NO: 42) |
| CX2193 | 0003/LP'/1003 F | CagggggctcgagcGGCGGCTCCACATCTACCTCTGGCAGATCCGCCAACCCCAGAGGCGGCGGAGTGCATATGCCTCTGGGCTTTCTGGGACCTGGCGGCTCTGacatccagatgacccag/tctc (SEQ ID NO: 43) |
| CX2242 | 1004/LP'/0001 F | CagggggctcgagcGGAGGATCTGCTGTGGGACTGCTGGCTCCTCCTGGTGGCCTGTCTGGCAGATCTGATAACCACGGCGGCTCCGacatccagatgacccagtctc (SEQ ID NO: 44) |
| CX2243 | 0001/LP'/1004 F | CagggggctcgagcGGAGGCTCTGGCCTGTCTGGCAGATCCGATAACCATGGCGGCGCTGTGGGACTGCTGGCTCCTCCTGGTGGATCTGacatccagatgacccagtctc (SEQ ID NO: 45) |
| CX2244 | 1003/LP'/0001 F | CagggggctcgagcGGCGGCTCTGTGCATATGCCCCTGGGCTTTCTGGGACCTGGCGGCCTGTCTGGCAGATCCGATAATCACGGCGGCTCCGacatccagatgacccagtctc (SEQ ID NO: 46) |
| CX2245 | 0001/LP'/1003 F | CagggggctcgagcGGAGGCTCTGGCCTGTCTGGCAGATCTGATAACCACGGCGGCGTGCACATGCCCCTGGGCTTTCTGGGACCTGGCGGATCTGacatccagatgacccagtctc (SEQ ID NO: 47) |

Anti-Jagged 2001 activatable antibody Lc with spacer sequence
Nucleotide sequence (SEQ ID NO: 48)

Caaggccagtctggccagtgcaatatttggctcgtaggtggtgattgcaggggctggcaggggg gctcgagcggcggctctatctcttccggactgctgtccggcagatccgacaatcacggcggagg ctctgacatccagatgacccagtctccatcctccctgtctgcatctgtaggagacagagtcacc atcacttgccgggcaagtcagagcattagcagctatttaaattggtatcagcagaaaccaggga aagcccctaagctcctgatctatgcggcatccagtttgcaaagtggggtcccatcaaggttcag tggcagtggatctgggacagatttcactctcaccatcagcagtctgcaacctgaagattttgca acttactactgtcaacagacggttgtggcgcctccgttattcggccaagggaccaaggtggaaa tcaaacgtacggtggctgcaccatctgtcttcatcttcccgccatctgatgagcagttgaaatc tggaactgcctctgttgtgtgcctgctgaataacttctatcccagagaggccaaagtacagtgg aaggtggataacgccctccaatcgggtaactcccaggagagtgtcacagagcaggacagcaagg acagcacctacagcctcagcagcaccctgacgctgagcaaagcagactacgagaaacacaaagt ctacgcctgcgaagtcacccatcagggcctgagctcgcccgtcacaaagagcttcaacagggga gagtgt Amino Acid sequence (SEQ ID NO: 49)

QGQSGQCNIWLVGGDCRGWQGGSSGGSISSGLLSGRSDNHGGGSDIQMTQSPSSLSASVGDRVT

ITCRASQSISSYLNWYQQKPGKAPKLLIYAASSLQSGVPSRFSGSGSGTDFTLTISSLQPEDFA

-continued

TYYCQQTVVAPPLFGQGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQGLSSPVTKSFNRG

EC

Anti-Jagged 2001 activatable antibody Lc
Nucleotide sequence (SEQ ID NO: 419)

Tgcaatatttggctcgtaggtggtgattgcaggggctggcagggggggctcgagcggcggctcta tctcttccggactgctgtccggcagatccgacaatcacggcggaggctctgacatccagatgac ccagtctccatcctccctgtctgcatctgtaggagacagagtcaccatcacttgccgggcaagt cagagcattagcagctatttaaattggtatcagcagaaaccagggaaagcccctaagctcctga tctatgcggcatccagtttgcaaagtggggtcccatcaaggttcagtggcagtggatctgggac agatttcactctcaccatcagcagtctgcaacctgaagattttgcaacttactactgtcaacag acggttgtggcgcctccgttattcggccaagggaccaaggtggaaatcaaacgtacggtggctg caccatctgtcttcatcttcccgccatctgatgagcagttgaaatctggaactgcctctgttgt gtgcctgctgaataacttctatcccagagaggccaaagtacagtggaaggtggataacgccctc caatcgggtaactcccaggagagtgtcacagagcaggacagcaaggacagcacctacagcctca gcagcaccctgacgctgagcaaagcagactacgagaaacacaaagtctacgcctgcgaagtcac ccatcagggcctgagctcgcccgtcacaaagagcttcaacaggggagagtgt Amino Acid sequence (SEQ ID NO: 420)

CNIWLVGGDCRGWQGGSSGGSISSGLLSGRSDNHGGGSDIQMTQSPSSLSASVGDRVTITCRAS

QSISSYLNWYQQKPGKAPKLLIYAASSLQSGVPSRFSGSGSGTDFTLTISSLQPEDFATYYCQQ

TVVAPPLFGQGTKVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

Anti-Jagged activatable antibody 1001/LP'/0001 Lc with spacer sequence
Nucleotide sequence (SEQ ID NO: 50)

Caaggccagtctggccagtgcaatatttggctcgtaggtggtgattgcaggggctggcaggggg gctcgagcggcggctctatctcttctggcctgctgtctagcggcggctccggcggatctctgtc tggcagatctgacaaccacggcggaggctccgacatccagatgacccagtctccatcctccctg tctgcatctgtaggagacagagtcaccatcacttgccgggcaagtcagagcattagcagctatt taaattggtatcagcagaaaccagggaaagcccctaagctcctgatctatgcggcatccagttt gcaaagtggggtcccatcaaggttcagtggcagtggatctgggacagatttcactctcaccatc agcagtctgcaacctgaagattttgcaacttactactgtcaacagacggttgtggcgcctccgt tattcggccaagggaccaaggtggaaatcaaacgtacggtggctgcaccatctgtcttcatctt cccgccatctgatgagcagttgaaatctggaactgcctctgttgtgtgcctgctgaataacttc tatcccagagaggccaaagtacagtggaaggtggataacgccctccaatcgggtaactcccagg agagtgtcacagagcaggacagcaaggacagcacctacagcctcagcagcaccctgacgctgag caaagcagactacgagaaacacaaagtctacgcctgcgaagtcacccatcagggcctgagctcg cccgtcacaaagagcttcaacaggggagagtgt Amino Acid sequence (SEQ ID NO: 51)

QGQSGQCNIWLVGGDCRGWQGGSSGGSISSGLLSSGGSGGSLSGRSDNHGGGSDIQMTQSPSSL

SASVGDRVTITCRASQSISSYLNWYQQKPGKAPKLLIYAASSLQSGVPSRFSGSGSGTDFTLTI

SSLQPEDFATYYCQQTVVAPPLFGQGTKVEIKRTVAAPSVFIFPPSDEQLKSGTASVVCLLNNF

-continued

YPREAKVQWKVDNALQSGNSQESVTEQDSKDSTYSLSSTLTLSKADYEKHKVYACEVTHQGLSS

PVTKSFNRGEC

Anti-Jagged activatable antibody 1001/LP'/0001 Lc
Nucleotide sequence (SEQ ID NO: 421)

Tgcaatatttggctcgtaggtggtgattgcaggggctggcagggggctcgagcggcggctcta tctcttctggcctgctgtctagcggcggctccggcggatctctgtctggcagatctgacaacca cggcggaggctccgacatccagatgacccagtctccatcctccctgtctgcatctgtaggagac agagtcaccatcacttgccgggcaagtcagagcattagcagctatttaaattggtatcagcaga aaccagggaaagcccctaagctcctgatctatgcggcatccagtttgcaaagtggggtcccatc aaggttcagtggcagtggatctgggacagatttcactctcaccatcagcagtctgcaacctgaa gattttgcaacttactactgtcaacagacggttgtggcgcctccgttattcggccaagggacca aggtggaaatcaaacgtacggtggctgcaccatctgtcttcatcttcccgccatctgatgagca gttgaaatctggaactgcctctgttgtgtgcctgctgaataacttctatcccagagaggccaaa gtacagtggaaggtggataacgccctccaatcgggtaactcccaggagagtgtcacagagcagg acagcaaggacagcacctacagcctcagcagcaccctgacgctgagcaaagcagactacgagaa acacaaagtctacgcctgcgaagtcacccatcagggcctgagctcgcccgtcacaaagagcttc aacaggggagagtgt Amino Acid sequence (SEQ ID NO: 422)

CNIWLVGGDCRGWQGGSSGGSISSGLLSSGGSGGSLSGRSDNHGGGSDIQMTQSPSSLSASVGD

RVTITCRASQSISSYLNWYQQKPGKAPKLLIYAASSLQSGVPSRFSGSGSGTDFTLTISSLQPE

DFATYYCQQTVVAPPLFGQGTKVEIKRTVAAPSVFIFPPSDEQLKSGTASVVCLLNNFYPREAK

VQWKVDNALQSGNSQESVTEQDSKDSTYSLSSTLTLSKADYEKHKVYACEVTHQGLSSPVTKSF

NRGEC

Anti-Jagged 1004/LP'/0003 activatable antibody Lc with spacer sequence
Nucleotide sequence (SEQ ID NO: 52)

Caaggccagtctggccagtgcaatatttggctcgtaggtggtgattgcaggggctggcaggggg gctcgagcggaggatctgctgtgggactgctggctcctcctggcggcacatctacctctggcag atccgccaaccctcggggcggaggatctgacatccagatgacccagtctccatcctccctgtct gcatctgtaggagacagagtcaccatcacttgccgggcaagtcagagcattagcagctatttaa attggtatcagcagaaaccagggaaagcccctaagctcctgatctatgcggcatccagtttgca aagtggggtcccatcaaggttcagtggcagtggatctgggacagatttcactctcaccatcagc agtctgcaacctgaagattttgcaacttactactgtcaacagacggttgtggcgcctccgttat tcggccaagggaccaaggtggaaatcaaacgtacggtggctgcaccatctgtcttcatcttccc gccatctgatgagcagttgaaatctggaactgcctctgttgtgtgcctgctgaataacttctat cccagagaggccaaagtacagtggaaggtggataacgccctccaatcgggtaactcccaggaga gtgtcacagagcaggacagcaaggacagcacctacagcctcagcagcaccctgacgctgagcaa agcagactacgagaaacacaaagtctacgcctgcgaagtcacccatcagggcctgagctcgccc gtcacaaagagcttcaacaggggagagtgt Amino Acid sequence (SEQ ID NO: 53)

QGQSGQCNIWLVGGDCRGWQGGSSGGSAVGLLAPPGGTSTSGRSANPRGGGSDIQMTQSPSSLS

ASVGDRVTITCRASQSISSYLNWYQQKPGKAPKLLIYAASSLQSGVPSRFSGSGSGTDFTLTIS

-continued

SLQPEDFATYYCQQTVVAPPLFGQGTKVEIKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSP

VTKSFNRGEC

Anti-Jagged 1004/LP'/0003 activatable antibody Lc
Nucleotide sequence (SEQ ID NO: 423)

Tgcaatatttggctcgtaggtggtgattgcaggggctggcagggggctcgagcggaggatctg ctgtgggactgctggctcctcctggcggcacatctacctctggcagatccgccaaccctcgggg cggaggatctgacatccagatgacccagtctccatcctccctgtctgcatctgtaggagacaga gtcaccatcacttgccgggcaagtcagagcattagcagctatttaaattggtatcagcagaaac cagggaaagcccctaagctcctgatctatgcggcatccagtttgcaaagtggggtcccatcaag gttcagtggcagtggatctgggacagatttcactctcaccatcagcagtctgcaacctgaagat tttgcaacttactactgtcaacagacggttgtggcgcctccgttattcggccaagggaccaagg tggaaatcaaacgtacggtggctgcaccatctgtcttcatcttcccgccatctgatgagcagtt gaaatctggaactgcctctgttgtgtgcctgctgaataacttctatcccagagaggccaaagta cagtggaaggtggataacgccctccaatcgggtaactcccaggagagtgtcacagagcaggaca gcaaggacagcacctacagcctcagcagcaccctgacgctgagcaaagcagactacgagaaaca caaagtctacgcctgcgaagtcacccatcagggcctgagctcgcccgtcacaaagagcttcaac aggggagagtgt Amino Acid sequence (SEQ ID NO: 424)

CNIWLVGGDCRGWQGGSSGGSAVGLLAPPGGTSTSGRSANPRGGGSDIQMTQSPSSLSASVGDR

VTITCRASQSISSYLNWYQQKPGKAPKLLIYAASSLQSGVPSRFSGSGSGTDFTLTISSLQPED

FATYYCQQTVVAPPLFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEVTHQGLSSPVTKSFN

RGEC

Anti-Jagged 0003/LP'/1004 activatable antibody Lc with spacer
sequence
Nucleotide sequence (SEQ ID NO: 54)

Caaggccagtctggccagtgcaatatttggctcgtaggtggtgattgcaggggctggcaggggg gctcgagcggcggctccacatctacctctggcagatccgccaaccccagaggtggcggagctgt gggactgctggctccaccaggcggatctgacatccagatgacccagtctccatcctccctgtct gcatctgtaggagacagagtcaccatcacttgccgggcaagtcagagcattagcagctatttaa attggtatcagcagaaaccagggaaagcccctaagctcctgatctatgcggcatccagtttgca aagtggggtcccatcaaggttcagtggcagtggatctgggacagatttcactctcaccatcagc agtctgcaacctgaagattttgcaacttactactgtcaacagacggttgtggcgcctccgttat tcggccaagggaccaaggtggaaatcaaacgtacggtggctgcaccatctgtcttcatcttccc gccatctgatgagcagttgaaatctggaactgcctctgttgtgtgcctgctgaataacttctat cccagagaggccaaagtacagtggaaggtggataacgccctccaatcgggtaactcccaggaga gtgtcacagagcaggacagcaaggacagcacctacagcctcagcagcaccctgacgctgagcaa agcagactacgagaaacacaaagtctacgcctgcgaagtcacccatcagggcctgagctcgccc gtcacaaagagcttcaacaggggagagtgt -continued Amino Acid sequence (SEQ ID NO: 55)

QGQSGQCNIWLVGGDCRGWQGGSSGGSTSTSGRSANPRGGGAVGLLAPPGGSDIQMTQSPSSLS

ASVGDRVTITCRASQSISSYLNWYQQKPGKAPKLLIYAASSLQSGVPSRFSGSGSGTDFTLTIS

SLQPEDFATYYCQQTVVAPPLFGQGTKVEIKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSP

VTKSFNRGEC

Anti-Jagged 0003/LP'/1004 activatable antibody Lc
Nucleotide sequence (SEQ ID NO: 425)

Tgcaatatttggctcgtaggtggtgattgcaggggctggcagggggctcgagcggcggctcca catctacctctggcagatccgccaaccccagaggtggcggagctgtgggactgctggctccacc aggcggatctgacatccagatgacccagtctccatcctccctgtctgcatctgtaggagacaga gtcaccatcacttgccgggcaagtcagagcattagcagctatttaaattggtatcagcagaaac cagggaaagcccctaagctcctgatctatgcggcatccagtttgcaaagtggggtcccatcaag gttcagtggcagtggatctgggacagatttcactctcaccatcagcagtctgcaacctgaagat tttgcaacttactactgtcaacagacggttgtggcgcctccgttattcggccaagggaccaagg tggaaatcaaacgtacggtggctgcaccatctgtcttcatcttcccgccatctgatgagcagtt gaaatctggaactgcctctgttgtgtgcctgctgaataacttctatcccagagaggccaaagta cagtggaaggtggataacgccctccaatcgggtaactcccaggagagtgtcacagagcaggaca gcaaggacagcacctacagcctcagcagcaccctgacgctgagcaaagcagactacgagaaaca caaagtctacgcctgcgaagtcacccatcagggcctgagctcgcccgtcacaaagagcttcaac aggggagagtgt Amino Acid sequence (SEQ ID NO: 426)

CNIWLVGGDCRGWQGGSSGGSTSTSGRSANPRGGGAVGLLAPPGGSDIQMTQSPSSLSASVGDR

VTITCRASQSISSYLNWYQQKPGKAPKLLIYAASSLQSGVPSRFSGSGSGTDFTLTISSLQPED

FATYYCQQTVVAPPLFGQGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEVTHQGLSSPVTKSFN

RGEC

Anti-Jagged 1003/LP'/0003 activatable antibody Lc with spacer
sequence
Nucleotide sequence (SEQ ID NO: 56)

Caaggccagtctggccagtgcaatatttggctcgtaggtggtgattgcaggggctggcaggggg gctcgagcggcggctctgtgcatatgcccctgggctttctgggccctggcggcacatctacctc tggcagatccgccaaccctcggggcggaggatctgacatccagatgacccagtctccatcctcc ctgtctgcatctgtaggagacagagtcaccatcacttgccgggcaagtcagagcattagcagct atttaaattggtatcagcagaaaccagggaaagcccctaagctcctgatctatgcggcatccag tttgcaaagtggggtcccatcaaggttcagtggcagtggatctgggacagatttcactctcacc atcagcagtctgcaacctgaagattttgcaacttactactgtcaacagacggttgtggcgcctc cgttattcggccaagggaccaaggtggaaatcaaacgtacggtggctgcaccatctgtcttcat cttcccgccatctgatgagcagttgaaatctggaactgcctctgttgtgtgcctgctgaataac ttctatcccagagaggccaaagtacagtggaaggtggataacgccctccaatcgggtaactccc -continued aggagagtgtcacagagcaggacagcaaggacagcacctacagcctcagcagcaccctgacgct gagcaaagcagactacgagaaacacaaagtctacgcctgcgaagtcacccatcagggcctgagc tcgcccgtcacaaagagcttcaacaggggagagtgt Amino Acid sequence
(SEQ ID NO: 57)
QGQSGQCNIWLVGGDCRGWQGGSSGGSVHMPLGFLGPGGTSTSGRSANPRGGGSDIQMTQSPSS

LSASVGDRVTITCRASQSISSYLNWYQQKPGKAPKLLIYAASSLQSGVPSRFSGSGSGTDFTLT

ISSLQPEDFATYYCQQTVVAPPLFGQGTKVEIKRTVAAPSVFIFPPSDEQLKSGTASVVCLLNN

FYPREAKVQWKVDNALQSGNSQESVTEQDSKDSTYSLSSTLTLSKADYEKHKVYACEVTHQGLS

SPVTKSFNRGEC

Anti-Jagged 1003/LP'/0003 activatable antibody Lc
Nucleotide sequence
(SEQ ID NO: 427)
Tgcaatatttggctcgtaggtggtgattgcaggggctggcagggggctcgagcggcggctctg tgcatatgcccctgggctttctgggccctggcggcacatctacctctggcagatccgccaaccc tcggggcggaggatctgacatccagatgacccagtctccatcctccctgtctgcatctgtagga gacagagtcaccatcacttgccgggcaagtcagagcattagcagctatttaaattggtatcagc agaaaccagggaaagcccctaagctcctgatctatgcggcatccagtttgcaaagtggggtccc atcaaggttcagtggcagtggatctgggacagatttcactctcaccatcagcagtctgcaacct gaagattttgcaacttactactgtcaacagacggttgtggcgcctccgttattcggccaaggga ccaaggtggaaatcaaacgtacggtggctgcaccatctgtcttcatcttcccgccatctgatga gcagttgaaatctggaactgcctctgttgtgtgcctgctgaataacttctatcccagagaggcc aaagtacagtggaaggtggataacgccctccaatcgggtaactcccaggagagtgtcacagagc aggacagcaaggacagcacctacagcctcagcagcaccctgacgctgagcaaagcagactacga gaaacacaaagtctacgcctgcgaagtcacccatcagggcctgagctcgcccgtcacaaagagc ttcaacaggggagagtgt Amino Acid sequence
(SEQ ID NO: 428)
CNIWLVGGDCRGWQGGSSGGSVHMPLGFLGPGGTSTSGRSANPRGGGSDIQMTQSPSSLSASVG

DRVTITCRASQSISSYLNWYQQKPGKAPKLLIYAASSLQSGVPSRFSGSGSGTDFTLTISSLQP

EDFATYYCQQTVVAPPLFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVYACEVTHQGLSSPVTKS

FNRGEC

Anti-Jagged 0003/LP'/1003 activatable antibody Lc with spacer
sequence
Nucleotide sequence
(SEQ ID NO: 58)
Caaggccagtctggccagtgcaatatttggctcgtaggtggtgattgcaggggctggcaggggg gctcgagcggcggctccacatctacctctggcagatccgccaaccccagaggcggcggagtgca tatgcctctgggctttctgggacctggcggctctgacatccagatgacccagtctccatcctcc ctgtctgcatctgtaggagacagagtcaccatcacttgccgggcaagtcagagcattagcagct atttaaattggtatcagcagaaaccagggaaagcccctaagctcctgatctatgcggcatccag tttgcaaagtggggtcccatcaaggttcagtggcagtggatctgggacagatttcactctcacc atcagcagtctgcaacctgaagattttgcaacttactactgtcaacagacggttgtggcgcctc cgttattcggccaagggaccaaggtggaaatcaaacgtacggtggctgcaccatctgtcttcat cttcccgccatctgatgagcagttgaaatctggaactgcctctgttgtgtgcctgctgaataac -continued ttctatcccagagaggccaaagtacagtggaaggtggataacgccctccaatcgggtaactccc aggagagtgtcacagagcaggacagcaaggacagcacctacagcctcagcagcaccctgacgct gagcaaagcagactacgagaaacacaaagtctacgcctgcgaagtcacccatcagggcctgagc tcgcccgtcacaaagagcttcaacaggggagagtgt Amino Acid sequence (SEQ ID NO: 59)

QGQSGQCNIWLVGGDCRGWQGGSSGGSTSTSGRSANPRGGGVHMPLGFLGPGGSDIQMTQSPSS

LSASVGDRVTITCRASQSISSYLNWYQQKPGKAPKLLIYAASSLQSGVPSRFSGSGSGTDFTLT

ISSLQPEDFATYYCQQTVVAPPLFGQGTKVEIKRTVAAPSVFIFPPSDEQLKSGTASVVCLLNN

FYPREAKVQWKVDNALQSGNSQESVTEQDSKDSTYSLSSTLTLSKADYEKHKVYACEVTHQGLS

SPVTKSFNRGEC

Anti-Jagged 0003/LP'/1003 activatable antibody Lc
Nucleotide sequence (SEQ ID NO: 429)

Tgcaatatttggctcgtaggtggtgattgcaggggctggcagggggggctcgagcggcggctcca catctacctctggcagatccgccaaccccagaggcggcggagtgcatatgcctctgggctttct gggacctggcggctctgacatccagatgacccagtctccatcctccctgtctgcatctgtagga gacagagtcaccatcacttgccgggcaagtcagagcattagcagctatttaaattggtatcagc agaaaccagggaaagcccctaagctcctgatctatgcggcatccagtttgcaaagtggggtccc atcaaggttcagtggcagtggatctgggacagatttcactctcaccatcagcagtctgcaacct gaagattttgcaacttactactgtcaacagacggttgtggcgcctccgttattcggccaaggga ccaaggtggaaatcaaacgtacggtggctgcaccatctgtcttcatcttcccgccatctgatga gcagttgaaatctggaactgcctctgttgtgtgcctgctgaataacttctatcccagagaggcc aaagtacagtggaaggtggataacgccctccaatcgggtaactcccaggagagtgtcacagagc aggacagcaaggacagcacctacagcctcagcagcaccctgacgctgagcaaagcagactacga gaaacacaaagtctacgcctgcgaagtcacccatcagggcctgagctcgcccgtcacaaagagc ttcaacaggggagagtgt Amino Acid sequence (SEQ ID NO: 430)

CNIWLVGGDCRGWQGGSSGGSTSTSGRSANPRGGGVHMPLGFLGPGGSDIQMTQSPSSLSASVG

DRVTITCRASQSISSYLNWYQQKPGKAPKLLIYAASSLQSGVPSRFSGSGSGTDFTLTISSLQP

EDFATYYCQQTVVAPPLFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVYACEVTHQGLSSPVTKS

FNRGEC

Anti-Jagged 1004/LP'/0001 activatable antibody Lc with spacer
sequence
Nucleotide sequence (SEQ ID NO: 60)

Caaggccagtctggccagtgcaatatttggctcgtaggtggtgattgcaggggctggcaggggg gctcgagcggaggatctgctgtgggactgctggctcctcctggtggcctgtctggcagatctga taaccacggcggctccgacatccagatgacccagtctccatcctccctgtctgcatctgtagga gacagagtcaccatcacttgccgggcaagtcagagcattagcagctatttaaattggtatcagc agaaaccagggaaagcccctaagctcctgatctatgcggcatccagtttgcaaagtggggtccc atcaaggttcagtggcagtggatctgggacagatttcactctcaccatcagcagtctgcaacct gaagattttgcaacttactactgtcaacagacggttgtggcgcctccgttattcggccaaggga ccaaggtggaaatcaaacgtacggtggctgcaccatctgtcttcatcttcccgccatctgatga -continued gcagttgaaatctggaactgcctctgttgtgtgcctgctgaataacttctatcccagagaggcc aaagtacagtggaaggtggataacgccctccaatcgggtaactcccaggagagtgtcacagagc aggacagcaaggacagcacctacagcctcagcagcaccctgacgctgagcaaagcagactacga gaaacacaaagtctacgcctgcgaagtcacccatcagggcctgagctcgcccgtcacaaagagc ttcaacaggggagagtgt Amino Acid sequence (SEQ ID NO: 61)

QGQSGQCNIWLVGGDCRGWQGGSSGGSAVGLLAPPGGLSGRSDNHGGSDIQMTQSPSSLSASVG

DRVTITCRASQSISSYLNWYQQKPGKAPKLLIYAASSLQSGVPSRFSGSGSGTDFTLTISSLQP

EDFATYYCQQTVVAPPLFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVYACEVTHQGLSSPVTKS

FNRGEC

Anti-Jagged 1004/LP'/0001 activatable antibody Lc
Nucleotide sequence (SEQ ID NO: 431)

Tgcaatatttggctcgtaggtggtgattgcaggggctggcagggggggctcgagcggaggatctg ctgtgggactgctggctcctcctggtggcctgtctggcagatctgataaccacggcggctccga catccagatgacccagtctccatcctccctgtctgcatctgtaggagacagagtcaccatcact tgccgggcaagtcagagcattagcagctatttaaattggtatcagcagaaaccagggaaagccc ctaagctcctgatctatgcggcatccagtttgcaaagtggggtcccatcaaggttcagtggcag tggatctgggacagatttcactctcaccatcagcagtctgcaacctgaagattttgcaacttac tactgtcaacagacggttgtggcgcctccgttattcggccaagggaccaaggtggaaatcaaac gtacggtggctgcaccatctgtcttcatcttcccgccatctgatgagcagttgaaatctggaac tgcctctgttgtgtgcctgctgaataacttctatcccagagaggccaaagtacagtggaaggtg gataacgccctccaatcgggtaactcccaggagagtgtcacagagcaggacagcaaggacagca cctacagcctcagcagcaccctgacgctgagcaaagcagactacgagaaacacaaagtctacgc ctgcgaagtcacccatcagggcctgagctcgcccgtcacaaagagcttcaacaggggagagtgt Amino Acid sequence (SEQ ID NO: 432)

CNIWLVGGDCRGWQGGSSGGSAVGLLAPPGGLSGRSDNHGGSDIQMTQSPSSLSASVGDRVTIT

CRASQSISSYLNWYQQKPGKAPKLLIYAASSLQSGVPSRFSGSGSGTDFTLTISSLQPEDFATY

YCQQTVVAPPLFGQGTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTKSFNRGEC

Anti-Jagged 0001/LP'/1004 activatable antibody Lc with spacer
sequence
Nucleotide sequence (SEQ ID NO: 62)

Caaggccagtctggccagtgcaatatttggctcgtaggtggtgattgcaggggctggcaggggg gctcgagcggaggctctggcctgtctggcagatccgataaccatggcggcgctgtgggactgct ggctcctcctggtggatctgacatccagatgacccagtctccatcctccctgtctgcatctgta ggagacagagtcaccatcacttgccgggcaagtcagagcattagcagctatttaaattggtatc agcagaaaccagggaaagcccctaagctcctgatctatgcggcatccagtttgcaaagtggggt cccatcaaggttcagtggcagtggatctgggacagatttcactctcaccatcagcagtctgcaa cctgaagattttgcaacttactactgtcaacagacggttgtggcgcctccgttattcggccaag ggaccaaggtggaaatcaaacgtacggtggctgcaccatctgtcttcatcttcccgccatctga tgagcagttgaaatctggaactgcctctgttgtgtgcctgctgaataacttctatcccagagag -continued gccaaagtacagtggaaggtggataacgccctccaatcgggtaactcccaggagagtgtcacag agcaggacagcaaggacagcacctacagcctcagcagcaccctgacgctgagcaaagcagacta cgagaaacacaaagtctacgcctgcgaagtcacccatcagggcctgagctcgcccgtcacaaag agcttcaacaggggagagtgt Amino Acid sequence (SEQ ID NO: 63)

QGQSGQCNIWLVGGDCRGWQGGSSGGSGLSGRSDNHGGAVGLLAPPGGSDIQMTQSPSSLSASV

GDRVTITCRASQSISSYLNWYQQKPGKAPKLLIYAASSLQSGVPSRFSGSGSGTDFTLTISSLQ

PEDFATYYCQQTVVAPPLFGQGTKVEIKRTVAAPSVFIFPPSDEQLKSGTASVVCLLNNFYPRE

AKVQWKVDNALQSGNSQESVTEQDSKDSTYSLSSTLTLSKADYEKHKVYACEVTHQGLSSPVTK

SFNRGEC

Anti-Jagged 0001/LP'/1004 activatable antibody Lc
Nucleotide sequence (SEQ ID NO: 433)

Tgcaatatttggctcgtaggtggtgattgcaggggctggcagggggggctcgagcggaggctctg gcctgtctggcagatccgataaccatggcggcgctgtgggactgctggctcctcctggtggatc tgacatccagatgacccagtctccatcctccctgtctgcatctgtaggagacagagtcaccatc acttgccgggcaagtcagagcattagcagctatttaaattggtatcagcagaaaccagggaaag cccctaagctcctgatctatgcggcatccagtttgcaaagtggggtcccatcaaggttcagtgg cagtggatctgggacagatttcactctcaccatcagcagtctgcaacctgaagattttgcaact tactactgtcaacagacggttgtggcgcctccgttattcggccaagggaccaaggtggaaatca aacgtacggtggctgcaccatctgtcttcatcttcccgccatctgatgagcagttgaaatctgg aactgcctctgttgtgtgcctgctgaataacttctatcccagagaggccaaagtacagtggaag gtggataacgccctccaatcgggtaactcccaggagagtgtcacagagcaggacagcaaggaca gcacctacagcctcagcagcaccctgacgctgagcaaagcagactacgagaaacacaaagtcta cgcctgcgaagtcacccatcagggcctgagctcgcccgtcacaaagagcttcaacaggggagag tgt Amino Acid sequence (SEQ ID NO: 434)

CNIWLVGGDCRGWQGGSSGGSGLSGRSDNHGGAVGLLAPPGGSDIQMTQSPSSLSASVGDRVTI

TCRASQSISSYLNWYQQKPGKAPKLLIYAASSLQSGVPSRFSGSGSGTDFTLTISSLQPEDFAT

YYCQQTVVAPPLFGQGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQGLSSPVTKSFNRGE

C

Anti-Jagged 1003/LP'/0001 activatable antibody Lc with spacer
sequence
Nucleotide sequence (SEQ ID NO: 64)

Caaggccagtctggccagtgcaatatttggctcgtaggtggtgattgcaggggctggcaggggg gctcgagcggcggctctgtgcatatgcccctgggctttctgggacctggcggcctgtctggcag atccgataatcacggcggctccgacatccagatgacccagtctccatcctccctgtctgcatct gtaggagacagagtcaccatcacttgccgggcaagtcagagcattagcagctatttaaattggt atcagcagaaaccagggaaagcccctaagctcctgatctatgcggcatccagtttgcaaagtgg ggtcccatcaaggttcagtggcagtggatctgggacagatttcactctcaccatcagcagtctg caacctgaagattttgcaacttactactgtcaacagacggttgtggcgcctccgttattcggcc aagggaccaaggtggaaatcaaacgtacggtggctgcaccatctgtcttcatcttcccgccatc -continued tgatgagcagttgaaatctggaactgcctctgttgtgtgcctgctgaataacttctatcccaga gaggccaaagtacagtggaaggtggataacgccctccaatcgggtaactcccaggagagtgtca cagagcaggacagcaaggacagcacctacagcctcagcagcaccctgacgctgagcaaagcaga ctacgagaaacacaaagtctacgcctgcgaagtcacccatcagggcctgagctcgcccgtcaca aagagcttcaacaggggagagtgt Amino Acid sequence (SEQ ID NO: 65)

QGQSGQCNIWLVGGDCRGWQGGSSGGSVHMPLGFLGPGGLSGRSDNHGGSDIQMTQSPSSLSAS

VGDRVTITCRASQSISSYLNWYQQKPGKAPKLLIYAASSLQSGVPSRFSGSGSGTDFTLTISSL

QPEDFATYYCQQTVVAPPLFGQGTKVEIKRTVAAPSVFIFPPSDEQLKSGTASVVCLLNNFYPR

EAKVQWKVDNALQSGNSQESVTEQDSKDSTYSLSSTLTLSKADYEKHKVYACEVTHQGLSSPVT

KSFNRGEC

Anti-Jagged 1003/LP'/0001 activatable antibody Lc
Nucleotide sequence (SEQ ID NO: 435)

Tgcaatatttggctcgtaggtggtgattgcaggggctggcagggggggctcgagcggcggctctg tgcatatgcccctgggctttctgggacctggcggcctgtctggcagatccgataatcacggcgg ctccgacatccagatgacccagtctccatcctccctgtctgcatctgtaggagacagagtcacc atcacttgccgggcaagtcagagcattagcagctatttaaattggtatcagcagaaaccaggga aagcccctaagctcctgatctatgcggcatccagtttgcaaagtggggtcccatcaaggttcag tggcagtggatctgggacagatttcactctcaccatcagcagtctgcaacctgaagattttgca acttactactgtcaacagacggttgtggcgcctccgttattcggccaagggaccaaggtggaaa tcaaacgtacggtggctgcaccatctgtcttcatcttcccgccatctgatgagcagttgaaatc tggaactgcctctgttgtgtgcctgctgaataacttctatcccagagaggccaaagtacagtgg aaggtggataacgccctccaatcgggtaactcccaggagagtgtcacagagcaggacagcaagg acagcacctacagcctcagcagcaccctgacgctgagcaaagcagactacgagaaacacaaagt ctacgcctgcgaagtcacccatcagggcctgagctcgcccgtcacaaagagcttcaacagggga gagtgt Amino Acid sequence (SEQ ID NO: 436)

CNIWLVGGDCRGWQGGSSGGSVHMPLGFLGPGGLSGRSDNHGGSDIQMTQSPSSLSASVGDRVT

ITCRASQSISSYLNWYQQKPGKAPKLLIYAASSLQSGVPSRFSGSGSGTDFTLTISSLQPEDFA

TYYCQQTVVAPPLFGQGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQGLSSPVTKSFNRG

EC

Anti-Jagged 0001/LP'/1003 activatable antibody Lc with spacer
sequence
Nucleotide sequence (SEQ ID NO: 66)

Caaggccagtctggccagtgcaatatttggctcgtaggtggtgattgcaggggctggcaggggg gctcgagcggaggctctggcctgtctggcagatctgataaccacggcggcgtgcacatgcccct gggctttctgggacctggcggatctgacatccagatgacccagtctccatcctccctgtctgca tctgtaggagacagagtcaccatcacttgccgggcaagtcagagcattagcagctatttaaatt ggtatcagcagaaaccagggaaagcccctaagctcctgatctatgcggcatccagtttgcaaag tggggtcccatcaaggttcagtggcagtggatctgggacagatttcactctcaccatcagcagt ctgcaacctgaagattttgcaacttactactgtcaacagacggttgtggcgcctccgttattcg -continued gccaagggaccaaggtggaaatcaaacgtacggtggctgcaccatctgtcttcatcttcccgcc atctgatgagcagttgaaatctggaactgcctctgttgtgtgcctgctgaataacttctatccc agagaggccaaagtacagtggaaggtggataacgccctccaatcgggtaactcccaggagagtg tcacagagcaggacagcaaggacagcacctacagcctcagcagcaccctgacgctgagcaaagc agactacgagaaacacaaagtctacgcctgcgaagtcacccatcagggcctgagctcgcccgtc acaaagagcttcaacaggggagagtgt Amino Acid sequence (SEQ ID NO: 437)

QGQSGQCNIWLVGGDCRGWQGGSSGGSGLSGRSDNHGGVHMPLGFLGPGGSDIQMTQSPSSLSA

SVGDRVTITCRASQSISSYLNWYQQKPGKAPKLLIYAASSLQSGVPSRFSGSGSGTDFTLTISS

LQPEDFATYYCQQTVVAPPLFGQGTKVEIKRTVAAPSVFIFPPSDEQLKSGTASVVCLLNNFYP

REAKVQWKVDNALQSGNSQESVTEQDSKDSTYSLSSTLTLSKADYEKHKVYACEVTHQGLSSPV

TKSFNRGEC

Anti-Jagged 0001/LP'/1003 activatable antibody Lc
Nucleotide sequence (SEQ ID NO: 438)

Tgcaatatttggctcgtaggtggtgattgcaggggctggcagggggggctcgagcggaggctctg gcctgtctggcagatctgataaccacggcggcgtgcacatgcccctgggctttctgggacctgg cggatctgacatccagatgacccagtctccatcctccctgtctgcatctgtaggagacagagtc accatcacttgccgggcaagtcagagcattagcagctatttaaattggtatcagcagaaaccag ggaaagcccctaagctcctgatctatgcggcatccagtttgcaaagtggggtcccatcaaggtt cagtggcagtggatctgggacagatttcactctcaccatcagcagtctgcaacctgaagatttt gcaacttactactgtcaacagacggttgtggcgcctccgttattcggccaagggaccaaggtgg aaatcaaacgtacggtggctgcaccatctgtcttcatcttcccgccatctgatgagcagttgaa atctggaactgcctctgttgtgtgcctgctgaataacttctatcccagagaggccaaagtacag tggaaggtggataacgccctccaatcgggtaactcccaggagagtgtcacagagcaggacagca aggacagcacctacagcctcagcagcaccctgacgctgagcaaagcagactacgagaaacacaa agtctacgcctgcgaagtcacccatcagggcctgagctcgcccgtcacaaagagcttcaacagg ggagagtgt Amino Acid sequence (SEQ ID NO: 439)

CNIWLVGGDCRGWQGGSSGGSGLSGRSDNHGGVHMPLGFLGPGGSDIQMTQSPSSLSASVGDRV

TITCRASQSISSYLNWYQQKPGKAPKLLIYAASSLQSGVPSRFSGSGSGTDFTLTISSLQPEDF

ATYYCQQTVVAPPLFGQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEVTHQGLSSPVTKSFNR

GEC

Anti-Jagged activatable antibody Hc (SEQ ID NO: 67)

EVQLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSSASTKGPSVF

PLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

-continued

YKCKVSNKALPAPIEKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEALHNHYTQKSLSLSPG

K

Anti-Jagged CM1-CM2 Activatable antibody in vitro binding and activation was evaluated as follows.

Anti-Jagged activatable antibodies were expressed from transiently transfected HEK-293 cells and purified from the culture supernatant by Protein A chromatography. To verify that the anti-Jagged CM1-CM2 activatable antibodies could be activated by both MMPs and serine proteases, the purified activatable antibodies were digested with uPA and/or MMP14 and subsequently evaluated for their ability to bind to human Jagged 1-Fc by ELISA. ELISA plates (Greiner Bio-One #655061) were coated with human Jag1-Fc (R&D #1277-JG-050) in Hank's Balanced Salt Solution pH 7.4 (HBSS) (Teknova #H8057) at 1 microgram/ml overnight at 4° C.; as used herein, microgram(s) is also represented by ug and µg. Plates were blocked with 2% Nonfat dry milk (NFDM) in HBSS for 1 hour at room temperature (RT). The block was removed and anti-Jagged antibody 4D11, an anti-Jagged CM1-CM2 activatable antibody, or a digested activatable antibody was added to the indicated concentration in 2% NFDM/HBSS and incubated at RT for 1 hours. The ELISA plate was washed 3 times with excess HBSS, 0.05% TWEEN (HBSS-T) before adding the mouse anti-human IgG, F'Ab(2) specific, HRP conjugated (Jackson ImmunoResearch #209-035-097) diluted to 1:30,000 in 2% NFDM/HBSS. The ELISA plate was subsequently washed 3× with HBSS-T and developed using 1-Step TMB Substrate (Pierce/Thermo Fisher #NC0140927). The plates were read at $OD_{450}$ and plotted using Prism software.

Figure 1B:
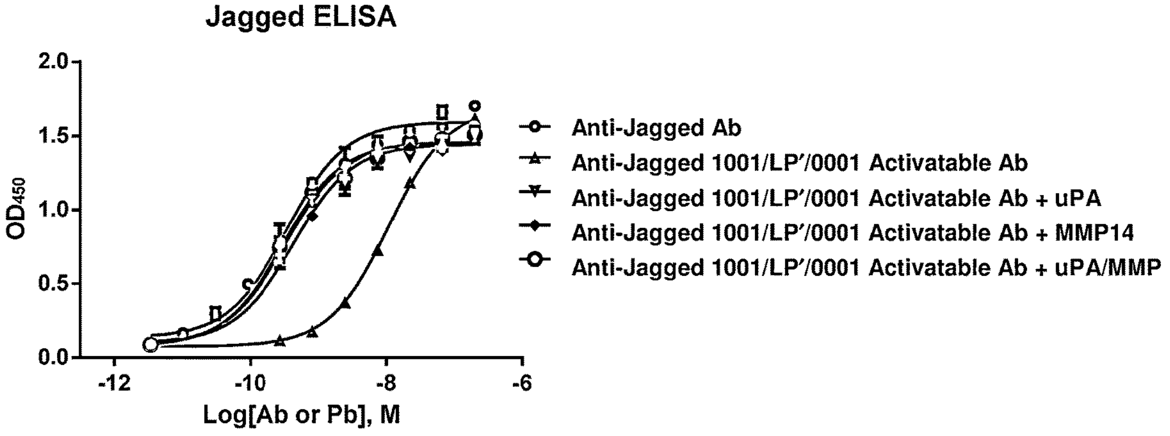

FIG. 1 demonstrates the anti-Jagged CM1-CM2 activatable antibodies (a) were effectively masked prior to cleavage by uPA or MMP14 and (b) showed binding equivalent to the antibody when cleaved by uPA or MMP14 or a combination of uPA and MMP14.

Anti-Jagged activatable antibody containing CM1-CM2 Substrate pharmacokinetics were evaluated in non-tumor bearing nude mice as follows.

As a surrogate for the stability of the mask and substrate, the pharmacokinetics of the anti-Jagged activatable antibodies containing the CM1-CM2 substrates 2001 and 1001/L1Y/0001 were compared to that of the anti-Jagged antibody in non-tumor bearing mice. The mouse/human cross-reactive anti-Jagged antibody shows rapid clearance in mice due to the binding of Jagged ½ in normal tissues. If the anti-Jagged CM1-CM2 Activatable antibody remains masked (stable) in circulation, then the activatable antibody should avoid target-mediated clearance and show prolonged serum half-life.

The plasma pharmacokinetics of the anti-Jagged antibody and activatable antibodies were evaluated as follows. As shown in Table B, each group consisted of 2 cohorts of 5 mice. Mice were given a single intravenous dose of 5 mg/kg of the indicated compound. Lithium heparinized plasma was collected from cohort 1 at 24 hours, 96 hours, and 10 days post dose while plasma was collected from cohort 2 at 48 hours, 7 days, and 14 days by the retro-orbital route with isoflurane anesthesia. Total plasma human IgG levels were detected using a human IgG sandwich ELISA. Briefly, ELISA plates (Costar 3590 Fisher Scientific Cat. #07-200-35) were coated with AffiniPure Goat Anti-Human IgG F(ab')2 Fragment Specific, (Jackson ImmunoResearch Cat. #109-006-097) in phosphate buffered saline (PBS) at 1 ug/ml overnight at 4° C. Plates were blocked with Super-block (ScyTek Laboratories Cat. #AAA500) for 1 hour at room temperature (RT). The block was removed and an appropriate dilution of standard (test article) and test samples (plasma samples) were added to the plate and incubated at RT for 1 hour. The ELISA plate was washed 3 times with excess PBS, 0.05% TWEEN (PBS-T) before adding the AffiniPure Goat Anti-Human IgG $F_{(ab')2}$ Fragment Specific Horseradish Peroxidase (HRP) (Jackson ImmunoResearch Cat. #109-035-097) diluted to 1:25,000. The ELISA plate was subsequently washed 3× with PBS-T and developed using 1-Step TMB Substrate (Pierce/Thermo Fisher #NC0140927) following the manufacturers protocol. Serum human IgG levels were calculated by comparing the test sample values to the standard curve. Pharmacokinetic parameters were calculated using a noncompartmental analysis with sparse sampling (Phoenix WinNonlin v6.3).

Figure 2:
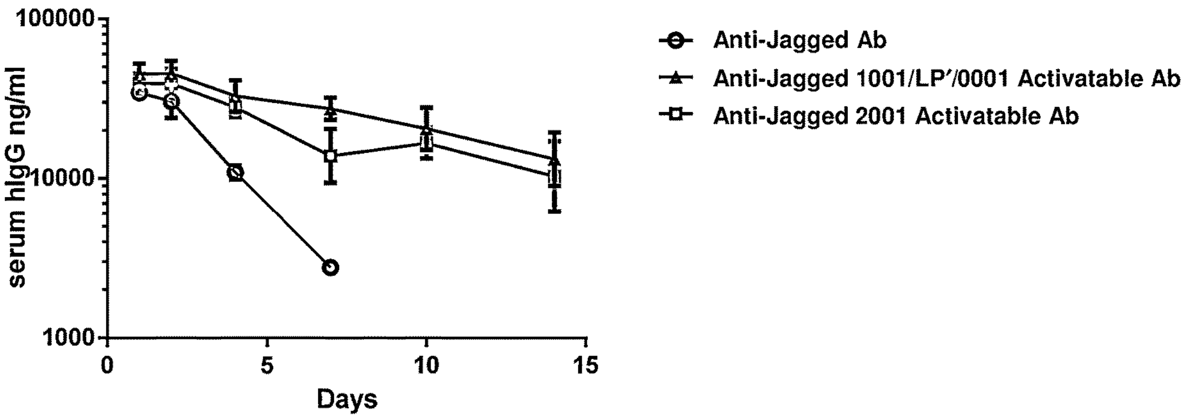
FIG. 2 is a graph depicting human IgG serum concentrations for anti-Jagged antibody and the 1001/LP'/0001 and 2001 activatable antibodies following a single 5 mg/kg intravenous dose. The anti-Jagged antibody is rapidly cleared due to target-mediated clearance. In contrast, the anti-Jagged activatable antibodies remain masked in circulation.

As shown in FIG. 2, the anti-Jagged antibody was rapidly cleared and was below the detection limit of the assay by day 10. In contrast, the anti-Jagged CM1-CM2 activatable antibodies 1001/LP'/0001 and 2001 showed significantly extended half-life indicating that the activatable antibodies remained stable and well masked in circulation.

TABLE B

Groups and dosing for the pharmacokinetic analysis of the anti-Jagged CM1-CM2 Activatable antibodies 2001 and 1001/LP'/0001.

| Group | N | Treatment | Dose (mg/kg) | Dose volume (mL/kg) | Schedule | Route |
|---|---|---|---|---|---|---|
| 1 | 2 × 5 | Anti-Jagged | 5 | 10 | Single | IP |
| 2 | 2 × 5 | Anti-Jagged Activatable antibody 2001 | 5 | 10 | Single | IP |
| 3 | 2 × 5 | Anti-Jagged Activatable antibody 1001/LP'/0001 | 5 | 10 | Single | IP |

In vivo evaluation of the safety and efficacy of an anti-Jagged CM1-CM2 substrate containing activatable antibody drug conjugate was performed as follows.

The efficacy of the anti-Jagged CM1-CM2 substrate containing 2001 activatable antibody drug conjugate, which comprised the anti-Jagged 2001 activatable antibody conjugated to maytansinoid DM4 (see, e.g., U.S. Pat. No. 7,276,497) via a SPDB linker, was evaluated in the human breast cancer cell line HCC1806 xenograft tumor model. HCC1806 cells were harvested during log phase growth and resuspended in 50% Matrigel (BD Biosciences) in PBS at a concentration of $5\times10^7$ cells/ml. Mice were injected subcutaneously in the right flank with $5\times10^6$ cells and allowed to grow to a mean volume of 100-150 $mm^3$. Mice were randomized and dosed as indicated in Table C. Tumor volume and body weight were measured twice weekly for the duration of the study, and measures of efficacy and safety, respectively were obtained.

Figure 3:
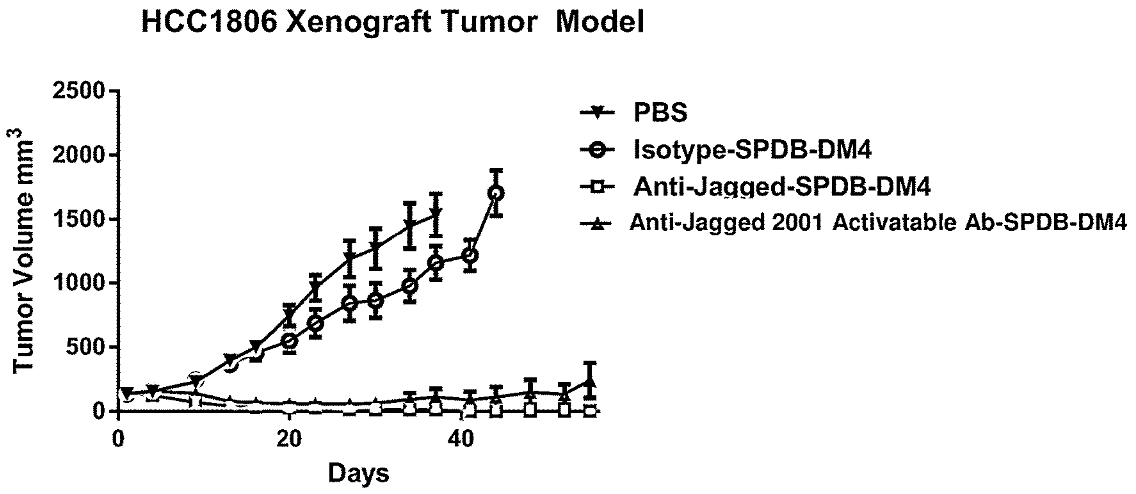
FIG. 3 is a graph depicting HCC1806 tumor volume (group mean±SEM n=8) plotted vs time post initial dose. Groups were dosed on day 1 and day 8 of the study. The anti-Jagged-SPDB-DM4 antibody and anti-Jagged 2001 activatable antibody-SPDB-DM4 groups both showed tumor regression while the isotype-SPDB-DM4 group did not show tumor growth inhibition.
Figure 4:
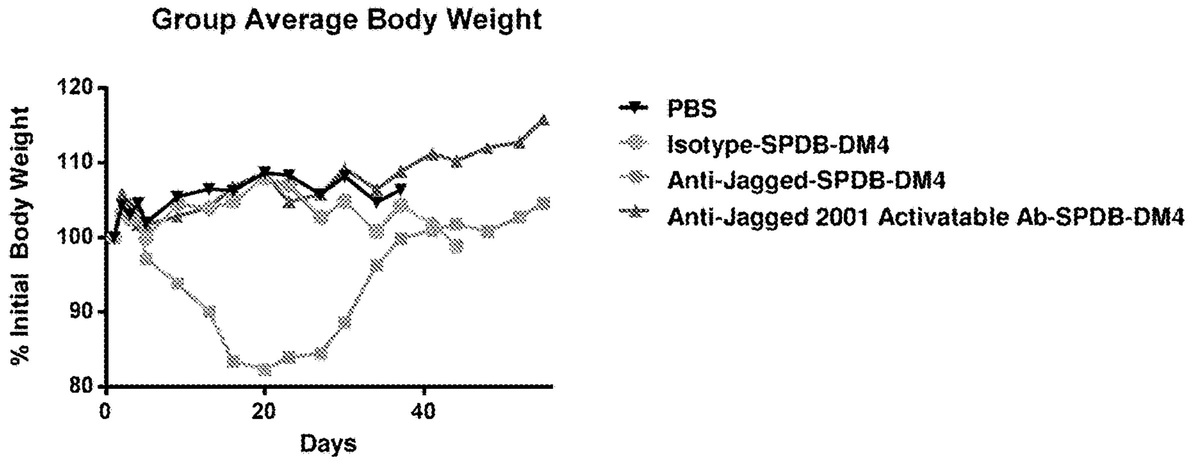
FIG. 4 is a graph depicting percent initial body weight (group mean n=8) plotted vs time post initial dose. Groups were dosed on day 1 and day 8 of the study. Animals in the anti-Jagged-SPDB-DM4 ADC treated group showed significant body weight loss, whereas the PBS, Isotype-SPDB-DM4 ADC, and anti-Jagged 2001 activatable antibody-SPDB-DM4 treated animals showed no significant weight loss.
Figure 5:
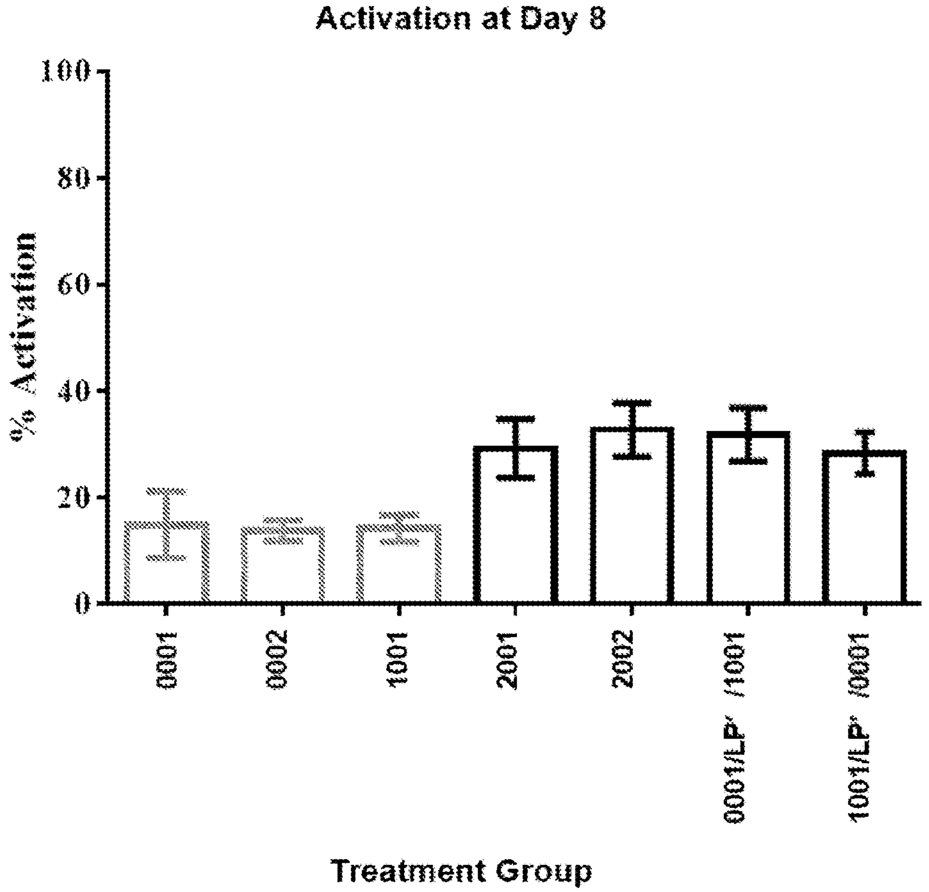
FIG. 5 is a graph depicting in vivo activation of EGFR activatable antibodies measured in plasma 8 days post-dose of 12.5 mg/kg of such EGFR activatable antibodies in H292 xenograft tumor-bearing mice.

FIG. 3 shows the group mean tumor volume±the standard error of the mean (SEM) for the PBS, Isotype-SPDB-DM4, anti-Jagged-SPDB-DM4 drug conjugate (ADC), and anti-Jagged 2001 activatable antibody drug conjugate treated animals. Neither control group (PBS nor Isotype-SPDB-DM4) showed tumor growth inhibition while both the anti-Jagged ADC and anti-Jagged 2001 activatable antibody drug conjugate groups showed tumor regression. The animals treated with the anti-Jagged ADC showed significant side effects as measured by weight loss, as shown in FIG. 4. However, animals treated with anti-Jagged 2001 activatable antibody drug conjugate showed no weight loss (also shown in FIG. 4) demonstrating that the anti-Jagged CM1-CM2 activatable antibody drug conjugate's activity was localized to the tumor.

TABLE C

Groups and dose schedule for the HCC1806 study

| Group | Count | Treatment | Dose (mg/kg) | Schedule | Route |
|---|---|---|---|---|---|
| 1 | 8 | PBS | 10 | q7d × 2 | IV |
| 3 | 8 | Isotype-SPDB-DM4 | 10 | q7d × 2 | IV |

TABLE C-continued

Groups and dose schedule for the HCC1806 study

| Group | Count | Treatment | Dose (mg/kg) | Schedule | Route |
|---|---|---|---|---|---|
| 4 | 8 | Anti-Jagged-SPDB-DM4 | 10 | q7d × 2 | IV |
| 5 | 8 | Anti-Jagged 2001 activatable antibody-SPDB-DM4 | 10 | q7d × 2 | IV |

Example 2. Matrix Metalloprotease (MMP) and Serine Protease (SP) Cleavable Anti-EGFR Activatable Antibodies This Example demonstrates the generation and evaluation of activatable antibodies that bind Epidermal Growth Factor Receptor (EGFR), where the activatable antibodies are activated in the presence of at least one matrix metalloprotease (MMP) and at least one serine protease.

The activatable anti-EGFR antibodies used in this Example were generated using a method similar to the methods used in Example 1 to generate activatable anti-Jagged antibodies.

The studies described herein used the following substrate sequences, where LP' is a linking peptide between CM1 and CM2. For all CM1-CM2 substrates in the Table below, LP' is GGSGGS (SEQ ID NO: 350):

| CM1-CM2 Substrate | Amino Acid Sequence | Nucleotide Sequence |
|---|---|---|
| 0001 | LSGRSDNH (SEQ ID NO: 18) | TTAAGCGGGCGGTCGGACAACCAC (SEQ ID NO: 23) |
| 0002 | LSGRSGNH (SEQ ID NO: 19) | CTTAGCGGGCGGAGCGGCAACCAC (SEQ ID NO: 24) |
| 1001 | ISSGLLSS (SEQ ID NO: 20) | ATCTCCTCCGGGCTACTGAGTTCT (SEQ ID NO: 25) |
| 1002 | QNQALRMA (SEQ ID NO: 21) | CAGAACCAGGCGCTCAGAATGGCA (SEQ ID NO: 26) |
| 2001 | ISSGLLSGRSDNH (SEQ ID NO: 1) | ATATCATCCGGCCTCCTTAGCGGC CGTTCCGACAATCAC (SEQ ID NO: 27) |
| 2002 | ISSGLLSGRSGNH (SEQ ID NO: 22) | ATAAGTTCTGGGCTCCTGTCGGGC CGGAGTGGAAATCAC (SEQ ID NO: 28) |
| 0001/LP'/1001 | LSGRSDNHGGSGGSISSGLLSS (SEQ ID NO: 11) | CTGAGCGGGCGGTCCGATAATCAT GGTGGTTCAGGAGGGAGTATTTCT TCCGGCTTACTGAGTAGC (SEQ ID NO: 29) |
| 1001/LP'/0001 | ISSGLLSSGGSGGSLSGRSDNH (SEQ ID NO: 2) | ATCTCCTCTGGGTTGCTTTCTTCA GGAGGTTCAGGGGGGAGCCTGAGC GGACGCTCCGACAACCAT (SEQ ID NO: 30) |
| 0002/LP'/1001 | LSGRSGNHGGSGGSISSGLLSS (SEQ ID NO: 12) | CTCTCAGGAAGATCCGGAAATCAT GGGGGGTCTGGGGGGAGTATCTCA TCAGGTCTGCTGAGCAGC (SEQ ID NO: 31) |
| 1001/LP'/0002 | ISSGLLSSGGSGGSLSGRSGNH (SEQ ID NO: 13) | ATCTCAAGTGGGCTGTTAAGTTCC GGCGGCAGTGGAGGGTCCCTAAGC GGCCGCAGCGGGAATCAC (SEQ ID NO: 32) |

-continued

| CM1-CM2 Substrate | Amino Acid Sequence | Nucleotide Sequence |
|---|---|---|
| 0001/LP'/1002 | LSGRSDNHGGSGGSQNQALRMA (SEQ ID NO: 14) | CTCTCTGGCCGCTCCGATAATCAT GGTGGATCCGGTGGCTCTCAGAAC CAGGCACTACGGATGGCA (SEQ ID NO: 33) |
| 1002/LP'/0001 | QNQALRMAGGSGGSLSGRSDNH (SEQ ID NO: 15) | CAGAACCAGGCGCTCAGGATGGCA GGGGGGAGTGGCGGAAGCCTTTCT GGTCGATCCGATAATCAC (SEQ ID NO: 34) |
| 0002/LP'/1002 | LSGRSGNHGGSGGSQNQALRMA (SEQ ID NO: 16) | CTTAGCGGACGCTCTGGCAACCAC GGAGGATCTGGAGGAAGTCAGAAC CAGGCCTTGCGCATGGCC (SEQ ID NO: 35) |
| 1002/LP'/0002 | QNQALRMAGGSGGSLSGRSGNH (SEQ ID NO: 17) | CAAAACCAGGCTCTGCGCATGGCT GGGGGGTCTGGTGGGAGCCTGAGC GGGCGGTCAGGAAACCAC (SEQ ID NO: 36) |

Anti-EGFR Heavy Chain (Hc):
Nucleotide sequence:

(SEQ ID NO: 68)

CAGGTACAGCTGAAACAGTCTGGACCCGGGCTTGTACAGCCTAGTCAGTCACTGTCTATCACCT

GTACCGTCTCAGGTTTTAGCCTGACAAATTACGGTGTGCATTGGGTACGCCAGTCTCCCGGTAA

GGGGCTGGAGTGGCTCGGCGTGATCTGGTCCGGGGGGAACACAGATTATAATACTCCTTTCACA

TCTAGACTGTCCATCAACAAAGACAACTCCAAATCGCAGGTTTTTTTCAAGATGAATTCCCTGC

AATCACAGGACACTGCCATCTATTATTGCGCGAGGGCCCTGACTTATTATGACTATGAGTTCGC

TTATTGGGGCCAGGGGACGCTTGTGACCGTAAGCGCTGCTAGTACCAAGGGCCCCAGTGTGTTC

CCCCTTGCCCCCAGCAGTAAGTCCACCTCAGGTGGCACAGCTGCCCTTGGGTGCCTTGTGAAGG

ATTACTTCCCAGAACCAGTGACCGTGAGCTGGAATTCCGGAGCCCTTACCAGCGGTGTGCATAC

CTTTCCGGCCGTCCTGCAAAGCAGCGGACTTTACAGTCTGTCTAGCGTGGTCACCGTGCCCAGC

AGCAGCCTGGGTACACAGACGTATATTTGCAACGTTAATCACAAACCCTCAAACACAAAGGTGG

ACAAGAAAGTGGAGCCTAAATCATGTGATAAGACACATACATGCCCTCCCTGCCCTGCACCGGA

GCTCTTAGGTGGACCTTCAGTCTTTTTATTTCCACCTAAACCCAAAGATACACTTATGATCTCA

CGGACACCCGAGGTGACCTGCGTTGTCGTGGATGTCTCACACGAAGACCCTGAAGTGAAATTCA

ATTGGTATGTTGACGGTGTTGAGGTGCATAACGCAAAGACCAAGCCACGCGAGGAGCAGTATAA

TAGCACCTATAGGGTAGTCAGCGTACTGACTGTTCTGCATCAGGATTGGCTGAACGGTAAAGAG

TACAAATGCAAGGTCTCAAACAAGGCTCTCCCTGCCCCGATCGAGAAGACAATTTCTAAGGCCA

AAGGGCAGCCCCGGGAACCACAAGTCTATACCCTGCCACCCAGTCGGGATGAACTAACAAAAAA

TCAGGTGTCTCTAACCTGCCTGGTGAAGGGATTTTACCCTTCCGATATAGCTGTGGAGTGGGAG

TCTAATGGCCAACCAGAGAATAATTACAAGACTACCCCCCCCGTTCTTGACAGTGATGGCTCGT

TCTTCTTATACTCAAAATTAACAGTCGACAAATCCCGATGGCAACAGGGCAATGTGTTTAGCTG

TAGCGTGATGCATGAAGCCCTGCACAACCATTACACACAGAAGTCTCTGTCCTTGTCACCTGGC

AAG

Amino acid Sequence:

(SEQ ID NO: 69)

QVQLKQSGPGLVQPSQSLSITCTVSGFSLTNYGVHWVRQSPGKGLEWLGVIWSGGNTDYNTPFT

SRLSINKDNSKSQVFFKSLQSQDTAIYYCARALTYYDYEFAYWGQGTLVTVSAASTKGPSVFPL

-continued

APSSKSTSGGTAALGCLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVFLFPPKPKDTLMISRT

PEVTCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALHNHYTQKSLSLSPGK

Anti-EGFR Light Chain:
Nucleotide Sequence:

(SEQ ID NO: 70)

ACCCAAATCCTCCTGACCCAGTCCCCTGTTATCCTTTCTGTGTCGCCCGGGGAGCGCGTTAGCT

TTAGCTGCCGCGCCAGTCAGTCAATCGGAACAAACATCCATTGGTACCAGCAGCGTACGAACGG

CAGTCCAAGGCTGCTGATCAAATACGCAAGTGAATCTATATCGGGGATTCCGTCTCGGTTCAGC

GGATCCGGAAGCGGGACTGACTTTACGCTCTCCATAAATAGCGTCGAAAGTGAGGACATTGCAG

ACTATTACTGTCAGCAGAATAACAACTGGCCGACCACATTTGGGGCCGGAACCAAGTTGGAACT

GAAGCGCACTGTGGCAGCTCCTAGTGTTTTTATTTTCCCCCCTTCTGACGAGCAACTGAAAAGT

GGTACAGCTTCAGTAGTTTGTTTGCTCAATAATTTCTACCCACGGGAAGCAAAGGTGCAGTGGA

AAGTCGACAACGCATTACAGAGCGGCAACTCTCAAGAAAGCGTGACGGAGCAGGATAGCAAGGA

CTCAACATATTCCTTGTCTTCCACTCTCACTCTGTCAAAGGCTGATTATGAGAAGCATAAGGTG

TATGCGTGCGAAGTGACACACCAGGGATTATCAAGCCCAGTGACCAAGTCCTTTAACCGTGGCG

AATGC

Amino acid Sequence:

(SEQ ID NO: 111)

QILLTQSPVILSVSPGERVSFSCRASQSIGTNIHWYQQRTNGSPRLLIKYASESISGIPSRFSG

SGSGTDFTLSINSVESEDIADYYCQQNNNWPTTFGAGTKLELKRTVAAPSVFIFPPSDEQLKSG

TASVVCLLNNFYPREAKVQWKVDNALQSGNSQESVTEQDSKDSTYSLSSTLTLSKADYEKHKVY

ACEVTHQGLSSPVTKSFNRGEC

Anti-EGFR 0001 Activatable Antibody Light Chain with spacer sequence:
Nucleotide sequence:

(SEQ ID NO: 72)

CAGGGCCAGAGCGGCCAATGCATCTCCCCCCGCGGTTGTCCCGACGGGCCGTACGTGATGTACG

GCAGCTCCGGCGGCAGTGGGGGTAGCGGTGGGTCCGGGCTGAGTGGCCGGTCCGACAATCACGG

GAGCTCGGGAACACAGATTCTGCTGACGCAATCTCCCGTGATCCTCTCGGTCTCACCCGGCGAA

CGGGTCTCGTTCAGCTGCAGAGCGTCCCAATCAATCGGGACCAATATTCACTGGTACCAGCAAA

GGACTAATGGGTCTCCCCGGCTGCTGATAAAATACGCCTCCGAGTCTATCTCGGGCATCCCATC

CCGATTTAGTGGTAGCGGAAGCGGCACTGATTTCACCTTGTCTATTAACAGCGTAGAATCTGAG

GACATTGCAGACTATTACTGTCAGCAGAATAACAATTGGCCTACAACTTTCGGCGCCGGGACCA

AACTAGAGTTAAAGCGTACTGTGGCTGCCCCCAGCGTTTTTATTTTTCCGCCCAGCGACGAACA

GCTGAAGTCAGGCACAGCCTCTGTGGTGTGTCTCCTGAATAACTTCTACCCCAGAGAGGCCAAA

GTTCAGTGGAAAGTGGACAATGCCTTGCAGTCCGGAAACAGTCAAGAGTCCGTGACCGAGCAGG

ACAGTAAGGATAGCACGTATAGCCTCTCTAGTACTTTAACACTGTCCAAGGCCGACTACGAGAA

GCACAAGGTGTACGCATGCGAAGTGACCCATCAGGGGCTTTCCTCCCCCGTCACCAAGTCTTTC

AATCGCGGGGAGTGT

Amino acid Sequence:

(SEQ ID NO: 73)

QGQSGQCISPRGCPDGPYVMYGSSGGSGGSGGSGLSGRSDNHGSSGTQILLTQSPVILSVSPGE

RVSFSCRASQSIGTNIHWYQQRTNGSPRLLIKYASESISGIPSRFSGSGSGTDFTLSINSVESE

-continued

DIADYYCQQNNNWPTTFGAGTKLELKRTVAAPSVFIFPPSDEQLKSGTASVVCLLNNFYPREAK

VQWKVDNALQSGNSQESVTEQDSKDSTYSLSSTLTLSKADYEKHKVYACEVTHQGLSSPVTKSF

NRGEC

Anti-EGFR 0001 Activatable Antibody Light Chain:
Nucleotide sequence:

(SEQ ID NO: 440)

TGCATCTCCCCCCGCGGTTGTCCCGACGGGCCGTACGTGATGTACGGCAGCTCCGGCGGCAGTG

GGGGTAGCGGTGGGTCCGGGCTGAGTGGCCGGTCCGACAATCACGGGAGCTCGGGAACACAGAT

TCTGCTGACGCAATCTCCCGTGATCCTCTCGGTCTCACCCGGCGAACGGGTCTCGTTCAGCTGC

AGAGCGTCCCAATCAATCGGGACCAATATTCACTGGTACCAGCAAAGGACTAATGGGTCTCCCC

GGCTGCTGATAAAATACGCCTCCGAGTCTATCTCGGGCATCCCATCCCGATTTAGTGGTAGCGG

AAGCGGCACTGATTTCACCTTGTCTATTAACAGCGTAGAATCTGAGGACATTGCAGACTATTAC

TGTCAGCAGAATAACAATTGGCCTACAACTTTCGGCGCCGGGACCAAACTAGAGTTAAAGCGTA

CTGTGGCTGCCCCCAGCGTTTTTATTTTTCCGCCCAGCGACGAACAGCTGAAGTCAGGCACAGC

CTCTGTGGTGTGTCTCCTGAATAACTTCTACCCCAGAGAGGCCAAAGTTCAGTGGAAAGTGGAC

AATGCCTTGCAGTCCGGAAACAGTCAAGAGTCCGTGACCGAGCAGGACAGTAAGGATAGCACGT

ATAGCCTCTCTAGTACTTTAACACTGTCCAAGGCCGACTACGAGAAGCACAAGGTGTACGCATG

CGAAGTGACCCATCAGGGGCTTTCCTCCCCCGTCACCAAGTCTTTCAATCGCGGGGAGTGT

Amino acid Sequence:

(SEQ ID NO: 441)

CISPRGCPDGPYVMYGSSGGSGGSGGSGLSGRSDNHGSSGTQILLTQSPVILSVSPGERVSFSC

RASQSIGTNIHWYQQRTNGSPRLLIKYASESISGIPSRFSGSGSGTDFTLSINSVESEDIADYY

CQQNNNWPTTFGAGTKLELKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLSSPVTKSFNRGEC

Anti-EGFR 0002 Activatable Antibody Light Chain with spacer
sequence:
Nucleotide sequence:

(SEQ ID NO: 74)

CAAGGTCAGTCCGGACAGTGTATTTCCCCTAGAGGTTGCCCTGACGGGCCGTATGTCATGTACG

GTAGTTCTGGCGGTAGTGGCGGATCTGGCGGCAGTGGGCTGAGCGGACGTAGCGGGAATCACGG

CTCATCCGGGACGCAGATACTGCTGACCCAGTCCCCCGTGATCCTGTCCGTGTCACCGGGCGAA

AGGGTCAGTTTCTCTTGCCGAGCATCACAGTCCATAGGTACGAATATCCATTGGTACCAGCAGC

GGACCAATGGGAGCCCAAGACTGCTCATTAAGTACGCATCTGAGAGTATCTCAGGCATTCCAAG

CAGGTTTTCCGGCAGTGGGAGCGGCACTGACTTCACCCTCAGCATTAACAGCGTGGAAAGCGAA

GACATTGCAGATTACTACTGCCAACAGAACAATAACTGGCCTACTACATTCGGGGCAGGAACTA

AGTTGGAGCTCAAACGTACCGTCGCTGCTCCTAGCGTATTTATTTTCCCTCCTAGCGATGAACA

GTTGAAATCTGGTACCGCTAGTGTTGTGTGCTTACTGAACAACTTTTATCCCCGGGAGGCCAAG

GTACAATGGAAGGTGGACAATGCCCTCCAATCAGGGAACAGCCAGGAGTCTGTTACCGAGCAGG

ACTCCAAGGACAGCACCTACAGCCTGAGCTCTACCCTTACATTGAGCAAGGCTGATTATGAGAA

GCATAAGGTCTACGCTTGTGAGGTGACCCATCAGGGGCTCAGCAGCCCGGTGACAAAAAGCTTT

AACCGGGGGGAATGC

Amino acid Sequence:

(SEQ ID NO: 75)

QGQSGQCISPRGCPDGPYVMYGSSGGSGGSGGSGLSGRSGNHGSSGTQILLTQSPVILSVSPGE

RVSFSCRASQSIGTNIHWYQQRTNGSPRLLIKYASESISGIPSRFSGSGSGTDFTLSINSVESE

-continued

DIADYYCQQNNNWPTTFGAGTKLELKRTVAAPSVFIFPPSDEQLKSGTASVVCLLNNFYPREAK

VQWKVDNALQSGNSQESVTEQDSKDSTYSLSSTLTLSKADYEKHKVYACEVTHQGLSSPVTKSF

NRGEC

Anti-EGFR 0002 Activatable Antibody Light Chain:
Nucleotide sequence:

(SEQ ID NO: 442)

TGTATTTCCCCTAGAGGTTGCCCTGACGGGCCGTATGTCATGTACGGTAGTTCTGGCGGTAGTG

GCGGATCTGGCGGCAGTGGGCTGAGCGGACGTAGCGGGAATCACGGCTCATCCGGGACGCAGAT

ACTGCTGACCCAGTCCCCCGTGATCCTGTCCGTGTCACCGGGCGAAAGGGTCAGTTTCTCTTGC

CGAGCATCACAGTCCATAGGTACGAATATCCATTGGTACCAGCAGCGGACCAATGGGAGCCCAA

GACTGCTCATTAAGTACGCATCTGAGAGTATCTCAGGCATTCCAAGCAGGTTTTCCGGCAGTGG

GAGCGGCACTGACTTCACCCTCAGCATTAACAGCGTGGAAAGCGAAGACATTGCAGATTACTAC

TGCCAACAGAACAATAACTGGCCTACTACATTCGGGGCAGGAACTAAGTTGGAGCTCAAACGTA

CCGTCGCTGCTCCTAGCGTATTTATTTTCCCTCCTAGCGATGAACAGTTGAAATCTGGTACCGC

TAGTGTTGTGTGCTTACTGAACAACTTTTATCCCCGGGAGGCCAAGGTACAATGGAAGGTGGAC

AATGCCCTCCAATCAGGGAACAGCCAGGAGTCTGTTACCGAGCAGGACTCCAAGGACAGCACCT

ACAGCCTGAGCTCTACCCTTACATTGAGCAAGGCTGATTATGAGAAGCATAAGGTCTACGCTTG

TGAGGTGACCCATCAGGGGCTCAGCAGCCCGGTGACAAAAAGCTTTAACCGGGGGGAATGC

Amino acid Sequence:

(SEQ ID NO: 443)

CISPRGCPDGPYVMYGSSGGSGGSGGSGLSGRSGNHGSSGTQILLTQSPVILSVSPGERVSFSC

RASQSIGTNIHWYQQRTNGSPRLLIKYASESISGIPSRFSGSGSGTDFTLSINSVESEDIADYY

CQQNNNWPTTFGAGTKLELKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLSSPVTKSFNRGEC

Anti-EGFR 1001 Activatable Antibody Light Chain with spacer
sequence:
Nucleotide sequence:

(SEQ ID NO: 76)

CAGGGGCAGTCTGGGCAGTGTATTAGCCCCAGGGGGTGCCCCGACGGGCCTTACGTGATGTATG

GCAGCTCCGGTGGCAGCGGAGGCTCTGGCGGGAGTGGGATCAGTTCCGGCCTGCTGAGCTCCGG

GTCAAGCGGGACCCAGATCTTGCTCACCCAATCACCAGTGATCCTAAGCGTGAGCCCTGGCGAA

CGGGTCAGCTTCTCTTGCCGGGCATCTCAGAGTATTGGCACTAACATACACTGGTACCAGCAGC

GAACCAATGGGTCCCCCCGCCTTCTAATCAAATATGCTAGCGAATCCATTTCAGGAATTCCTAG

CCGATTTAGCGGCAGCGGATCAGGCACTGACTTCACTCTGTCAATCAACTCAGTTGAAAGCGAG

GACATTGCAGACTACTATTGCCAGCAGAATAATAATTGGCCCACTACATTTGGAGCTGGAACAA

AATTGGAGCTTAAGAGGACAGTGGCTGCGCCTAGTGTATTTATCTTTCCCCCCTCTGACGAACA

GTTGAAATCGGGAACCGCATCCGTCGTCTGTTTACTGAACAACTTCTATCCCAGAGAGGCCAAA

GTGCAGTGGAAAGTGGATAATGCTTTGCAGTCTGGCAACAGCCAGGAAAGCGTGACGGAGCAGG

ACTCAAAGGATAGTACATACTCCCTGTCCTCCACCCTGACTCTGAGTAAGGCCGACTACGAGAA

GCACAAGGTCTACGCCTGCGAAGTGACGCACCAAGGGCTATCGAGCCCGGTCACCAAGTCTTTC

AATCGTGGAGAATGC

Amino acid Sequence:

(SEQ ID NO: 77)

QGQSGQCISPRGCPDGPYVMYGSSGGSGGSGGSGISSGLLSSGSSGTQILLTQSPVILSVSPGE

RVSFSCRASQSIGTNIHWYQQRTNGSPRLLIKYASESISGIPSRFSGSGSGTDFTLSINSVESE

-continued

DIADYYCQQNNNWPTTFGAGTKLELKRTVAAPSVFIFPPSDEQLKSGTASVVCLLNNFYPREAK

VQWKVDNALQSGNSQESVTEQDSKDSTYSLSSTLTLSKADYEKHKVYACEVTHQGLSSPVTKSF

NRGEC

Anti-EGFR 1001 Activatable Antibody Light Chain:
Nucleotide sequence:

(SEQ ID NO: 444)

TGTATTAGCCCCAGGGGGTGCCCCGACGGGCCTTACGTGATGTATGGCAGCTCCGGTGGCAGCG

GAGGCTCTGGCGGGAGTGGGATCAGTTCCGGCCTGCTGAGCTCCGGGTCAAGCGGGACCCAGAT

CTTGCTCACCCAATCACCAGTGATCCTAAGCGTGAGCCCTGGCGAACGGGTCAGCTTCTCTTGC

CGGGCATCTCAGAGTATTGGCACTAACATACACTGGTACCAGCAGCGAACCAATGGGTCCCCCC

GCCTTCTAATCAAATATGCTAGCGAATCCATTTCAGGAATTCCTAGCCGATTTAGCGGCAGCGG

ATCAGGCACTGACTTCACTCTGTCAATCAACTCAGTTGAAAGCGAGGACATTGCAGACTACTAT

TGCCAGCAGAATAATAATTGGCCCACTACATTTGGAGCTGGAACAAAATTGGAGCTTAAGAGGA

CAGTGGCTGCGCCTAGTGTATTTATCTTTCCCCCCTCTGACGAACAGTTGAAATCGGGAACCGC

ATCCGTCGTCTGTTTACTGAACAACTTCTATCCCAGAGAGGCCAAAGTGCAGTGGAAAGTGGAT

AATGCTTTGCAGTCTGGCAACAGCCAGGAAAGCGTGACGGAGCAGGACTCAAAGGATAGTACAT

ACTCCCTGTCCTCCACCCTGACTCTGAGTAAGGCCGACTACGAGAAGCACAAGGTCTACGCCTG

CGAAGTGACGCACCAAGGGCTATCGAGCCCGGTCACCAAGTCTTTCAATCGTGGAGAATGC

Amino acid Sequence:

(SEQ ID NO: 445)

CISPRGCPDGPYVMYGSSGGSGGSGGSGISSGLLSSGSSGTQILLTQSPVILSVSPGERVSFSC

RASQSIGTNIHWYQQRTNGSPRLLIKYASESISGIPSRFSGSGSGTDFTLSINSVESEDIADYY

CQQNNNWPTTFGAGTKLELKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLSSPVTKSFNRGEC

Anti-EGFR 1002 Activatable Antibody Light Chain with spacer
sequence:
Nucleotide sequence:

(SEQ ID NO: 78)

CAGGGGCAATCAGGACAATGCATCAGCCCTAGGGGCTGCCCAGACGGCCCATATGTGATGTACG

GTAGCTCTGGGGGCTCAGGAGGCAGCGGGGGAAGCGGACAAAACCAGGCCTTACGAATGGCTGG

CAGCTCTGGCACCCAGATATTGCTGACGCAGAGTCCAGTTATCCTTAGTGTCAGCCCTGGTGAA

CGGGTTTCATTTAGTTGCCGTGCCTCCCAGTCTATTGGAACGAACATTCATTGGTACCAGCAAA

GGACCAACGGTTCACCCAGGTTGCTTATCAAGTATGCTTCAGAGTCAATCTCCGGGATTCCCTC

AAGGTTTTCAGGCTCTGGCTCAGGTACCGATTTTACGCTGAGCATCAACTCCGTGGAGAGTGAG

GACATTGCTGATTATTACTGTCAGCAGAATAACAATTGGCCGACAACTTTCGGCGCCGGCACAA

AGCTGGAACTTAAGCGTACTGTGGCTGCGCCATCTGTCTTCATTTTTCCGCCCTCGGACGAGCA

GTTGAAGTCAGGGACCGCCTCTGTCGTGTGCCTTCTCAATAACTTCTATCCCAGAGAGGCTAAA

GTCCAGTGGAAAGTTGATAATGCACTTCAGAGCGGGAATAGCCAGGAGAGCGTGACGGAACAGG

ACTCTAAGGACTCCACCTATTCTCTCTCATCCACCCTTACTCTCTCTAAAGCCGACTACGAAAA

GCATAAGGTTTATGCTTGCGAAGTCACTCATCAAGGGCTATCTAGTCCGGTCACTAAAAGCTTC

AACAGAGGTGAATGT

Amino acid Sequence:

(SEQ ID NO: 79)

QGQSGQCISPRGCPDGPYVMYGSSGGSGGSGGSGQNQALRMAGSSGTQILLTQSPVILSVSPGE

RVSFSCRASQSIGTNIHWYQQRTNGSPRLLIKYASESISGIPSRFSGSGSGTDFTLSINSVESE

DIADYYCQQNNNWPTTFGAGTKLELKRTVAAPSVFIFPPSDEQLKSGTASVVCLLNNFYPREAK

-continued

VQWKVDNALQSGNSQESVTEQDSKDSTYSLSSTLTLSKADYEKHKVYACEVTHQGLSSPVTKSF

NRGEC

Anti-EGFR 1002 Activatable Antibody Light Chain:
Nucleotide sequence:
(SEQ ID NO: 446)
TGCATCAGCCCTAGGGGCTGCCCAGACGGCCCATATGTGATGTACGGTAGCTCTGGGGGCTCAG

GAGGCAGCGGGGGAAGCGGACAAAACCAGGCCTTACGAATGGCTGGCAGCTCTGGCACCCAGAT

ATTGCTGACGCAGAGTCCAGTTATCCTTAGTGTCAGCCCTGGTGAACGGGTTTCATTTAGTTGC

CGTGCCTCCCAGTCTATTGGAACGAACATTCATTGGTACCAGCAAAGGACCAACGGTTCACCCA

GGTTGCTTATCAAGTATGCTTCAGAGTCAATCTCCGGGATTCCCTCAAGGTTTTCAGGCTCTGG

CTCAGGTACCGATTTTACGCTGAGCATCAACTCCGTGGAGAGTGAGGACATTGCTGATTATTAC

TGTCAGCAGAATAACAATTGGCCGACAACTTTCGGCGCCGGCACAAAGCTGGAACTTAAGCGTA

CTGTGGCTGCGCCATCTGTCTTCATTTTTCCGCCCTCGGACGAGCAGTTGAAGTCAGGGACCGC

CTCTGTCGTGTGCCTTCTCAATAACTTCTATCCCAGAGAGGCTAAAGTCCAGTGGAAAGTTGAT

AATGCACTTCAGAGCGGGAATAGCCAGGAGAGCGTGACGGAACAGGACTCTAAGGACTCCACCT

ATTCTCTCTCATCCACCCTTACTCTCTCTAAAGCCGACTACGAAAAGCATAAGGTTTATGCTTG

CGAAGTCACTCATCAAGGGCTATCTAGTCCGGTCACTAAAAGCTTCAACAGAGGTGAATGT

Amino acid Sequence:
(SEQ ID NO: 447)
CISPRGCPDGPYVMYGSSGGSGGSGGSGQNQALRMAGSSGTQILLTQSPVILSVSPGERVSFSC

RASQSIGTNIHWYQQRTNGSPRLLIKYASESISGIPSRFSGSGSGTDFTLSINSVESEDIADYY

CQQNNNWPTTFGAGTKLELKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLSSPVTKSFNRGEC

Anti-EGFR 2001 Activatable Antibody Light Chain with spacer
sequence:
Nucleotide sequence:
(SEQ ID NO: 80)
CAAGGCCAGTCTGGACAATGTATCAGCCCCCGTGGCTGTCCAGACGGTCCTTACGTTATGTATG

GATCTAGCGGGGGCTCTGGAGGGTCTGGCGGCTCTGGAATCTCTAGTGGACTTCTCTCCGGAAG

AAGCGATAATCATGGATCCAGCGGGACACAAATCCTGTTGACACAGTCCCCAGTGATCCTGTCA

GTCTCGCCCGGAGAAAGGGTGTCTTTCTCTTGTAGGGCTAGTCAGTCTATCGGAACTAACATCC

ATTGGTACCAGCAGCGGACAAATGGGAGCCCGAGGCTTCTGATCAAGTATGCTTCAGAGAGTAT

AAGCGGCATCCCCTCAAGATTTAGTGGCAGCGGGTCCGGGACAGATTTCACCTTGTCAATCAAT

TCTGTCGAATCCGAAGACATTGCAGACTACTATTGCCAGCAAAACAACAACTGGCCCACCACTT

TCGGTGCTGGAACCAAACTCGAGCTGAAACGCACTGTGGCAGCTCCTTCAGTGTTCATCTTCCC

ACCTAGCGACGAGCAGTTGAAATCGGGGACAGCCTCAGTGGTGTGTCTACTGAACAACTTTTAC

CCCCGGGAAGCCAAAGTGCAGTGGAAGGTCGACAATGCGCTGCAATCAGGGAACAGTCAGGAGT

CAGTTACAGAGCAGGACTCTAAGGACAGTACATATTCTTTGAGTTCCACCTTGACATTAAGCAA

GGCAGACTACGAGAAACACAAGGTGTACGCATGTGAAGTTACACACCAGGGCCTTTCCTCCCCA

GTTACGAAAAGCTTCAACAGAGGCGAATGC

Amino acid Sequence:
(SEQ ID NO: 81)
QGQSGQCISPRGCPDGPYVMYGSSGGSGGSGGSGISSGLLSGRSDNHGSSGTQILLTQSPVILS

VSPGERVSFSCRASQSIGTNIHWYQQRTNGSPRLLIKYASESISGIPSRFSGSGSGTDFTLSIN

-continued

SVESEDIADYYCQQNNNWPTTFGAGTKLELKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSP

VTKSFNRGEC

Anti-EGFR 2001 Activatable Antibody Light Chain:
Nucleotide sequence:

(SEQ ID NO: 448)

TGTATCAGCCCCCGTGGCTGTCCAGACGGTCCTTACGTTATGTATGGATCTAGCGGGGGCTCTG

GAGGGTCTGGCGGCTCTGGAATCTCTAGTGGACTTCTCTCCGGAAGAAGCGATAATCATGGATC

CAGCGGGACACAAATCCTGTTGACACAGTCCCCAGTGATCCTGTCAGTCTCGCCCGGAGAAAGG

GTGTCTTTCTCTTGTAGGGCTAGTCAGTCTATCGGAACTAACATCCATTGGTACCAGCAGCGGA

CAAATGGGAGCCCGAGGCTTCTGATCAAGTATGCTTCAGAGAGTATAAGCGGCATCCCCTCAAG

ATTTAGTGGCAGCGGGTCCGGGACAGATTTCACCTTGTCAATCAATTCTGTCGAATCCGAAGAC

ATTGCAGACTACTATTGCCAGCAAAACAACAACTGGCCCACCACTTTCGGTGCTGGAACCAAAC

TCGAGCTGAAACGCACTGTGGCAGCTCCTTCAGTGTTCATCTTCCCACCTAGCGACGAGCAGTT

GAAATCGGGGACAGCCTCAGTGGTGTGTCTACTGAACAACTTTTACCCCCGGGAAGCCAAAGTG

CAGTGGAAGGTCGACAATGCGCTGCAATCAGGGAACAGTCAGGAGTCAGTTACAGAGCAGGACT

CTAAGGACAGTACATATTCTTTGAGTTCCACCTTGACATTAAGCAAGGCAGACTACGAGAAACA

CAAGGTGTACGCATGTGAAGTTACACACCAGGGCCTTTCCTCCCCAGTTACGAAAAGCTTCAAC

AGAGGCGAATGC

Amino acid Sequence:

(SEQ ID NO: 449)

CISPRGCPDGPYVMYGSSGGSGGSGGSGISSGLLSGRSDNHGSSGTQILLTQSPVILSVSPGER

VSFSCRASQSIGTNIHWYQQRTNGSPRLLIKYASESISGIPSRFSGSGSGTDFTLSINSVESED

IADYYCQQNNNWPTTFGAGTKLELKRTVAAPSVFIFPPSDEQLKSGTASVVCLLNNFYPREAKV

QWKVDNALQSGNSQESVTEQDSKDSTYSLSSTLTLSKADYEKHKVYACEVTHQGLSSPVTKSFN

RGEC

Anti-EGFR 2002 Activatable Antibody Light Chain with spacer
sequence:
Nucleotide sequence:

(SEQ ID NO: 82)

CAAGGTCAGAGTGGCCAATGCATATCGCCCAGAGGATGTCCTGACGGACCCTACGTGATGTACG

GGAGTTCTGGGGGGAGTGGAGGCTCTGGCGGGTCAGGGATTAGTTCCGGCCTCTTGTCTGGACG

CTCCGGAAATCACGGATCATCTGGGACCCAGATCCTCCTGACCCAGTCTCCCGTCATTCTGTCT

GTTTCTCCAGGCGAGCGGGTTTCATTTAGCTGTAGGGCCAGTCAGAGCATTGGCACCAACATCC

ATTGGTACCAGCAGAGAACTAATGGCAGTCCCAGACTGCTCATTAAATATGCAAGCGAATCAAT

TTCCGGGATTCCTTCTCGCTTCTCGGGATCTGGATCTGGCACCGACTTCACGCTGTCCATCAAC

AGCGTGGAGAGTGAGGACATCGCCGATTACTACTGCCAGCAGAACAACAACTGGCCAACAACTT

TTGGCGCCGGGACCAAGCTTGAGTTAAAGAGAACCGTAGCTGCACCCTCTGTTTTCATTTTCCC

ACCCTCAGACGAGCAGCTTAAGTCAGGAACTGCCAGTGTGGTGTGCCTGCTGAACAACTTCTAC

CCGAGAGAGGCTAAAGTCCAGTGGAAGGTAGACAATGCCCTTCAGTCTGGCAACTCTCAGGAGA

GTGTCACAGAGCAGGATTCTAAGGACTCCACGTACAGTCTGAGTTCCACCCTCACCCTCAGTAA

GGCAGACTACGAGAAGCACAAAGTCTACGCATGTGAGGTTACTCACCAGGGGCTCAGCTCTCCC

GTGACGAAGTCATTTAACAGAGGTGAGTGC

-continued

Amino acid Sequence:

(SEQ ID NO: 83)

QGQSGQCISPRGCPDGPYVMYGSSGGSGGSGGSGISSGLLSGRSGNHGSSGTQILLTQSPVILS

VSPGERVSFSCRASQSIGTNIHWYQQRTNGSPRLLIKYASESISGIPSRFSGSGSGTDFTLSIN

SVESEDIADYYCQQNNNWPTTFGAGTKLELKRTVAAPSVFIFPPSDEQLKSGTASVVCLLNNFY

PREAKVQWKVDNALQSGNSQESVTEQDSKDSTYSLSSTLTLSKADYEKHKVYACEVTHQGLSSP

VTKSFNRGEC

Anti-EGFR 2002 Activatable Antibody Light Chain:
Nucleotide sequence:

(SEQ ID NO: 450)

TGCATATCGCCCAGAGGATGTCCTGACGGACCCTACGTGATGTACGGGAGTTCTGGGGGGAGTG

GAGGCTCTGGCGGGTCAGGGATTAGTTCCGGCCTCTTGTCTGGACGCTCCGGAAATCACGGATC

ATCTGGGACCCAGATCCTCCTGACCCAGTCTCCCGTCATTCTGTCTGTTTCTCCAGGCGAGCGG

GTTTCATTTAGCTGTAGGGCCAGTCAGAGCATTGGCACCAACATCCATTGGTACCAGCAGAGAA

CTAATGGCAGTCCCAGACTGCTCATTAAATATGCAAGCGAATCAATTTCCGGGATTCCTTCTCG

CTTCTCGGGATCTGGATCTGGCACCGACTTCACGCTGTCCATCAACAGCGTGGAGAGTGAGGAC

ATCGCCGATTACTACTGCCAGCAGAACAACAACTGGCCAACAACTTTTGGCGCCGGGACCAAGC

TTGAGTTAAAGAGAACCGTAGCTGCACCCTCTGTTTTCATTTTCCCACCCTCAGACGAGCAGCT

TAAGTCAGGAACTGCCAGTGTGGTGTGCCTGCTGAACAACTTCTACCCGAGAGAGGCTAAAGTC

CAGTGGAAGGTAGACAATGCCCTTCAGTCTGGCAACTCTCAGGAGAGTGTCACAGAGCAGGATT

CTAAGGACTCCACGTACAGTCTGAGTTCCACCCTCACCCTCAGTAAGGCAGACTACGAGAAGCA

CAAAGTCTACGCATGTGAGGTTACTCACCAGGGGCTCAGCTCTCCCGTGACGAAGTCATTTAAC

AGAGGTGAGTGC

Amino acid Sequence:

(SEQ ID NO: 451)

CISPRGCPDGPYVMYGSSGGSGGSGGSGISSGLLSGRSGNHGSSGTQILLTQSPVILSVSPGER

VSFSCRASQSIGTNIHWYQQRTNGSPRLLIKYASESISGIPSRFSGSGSGTDFTLSINSVESED

IADYYCQQNNNWPTTFGAGTKLELKRTVAAPSVFIFPPSDEQLKSGTASVVCLLNNFYPREAKV

QWKVDNALQSGNSQESVTEQDSKDSTYSLSSTLTLSKADYEKHKVYACEVTHQGLSSPVTKSFN

RGEC

Anti-EGFR 0001/LP'/1001 Activatable Antibody Light Chain with
spacer sequence:
Nucleotide sequence:

(SEQ ID NO: 84)

CAGGGACAGTCGGGACAGTGCATTTCTCCGAGAGGCTGCCCTGACGGCCCATACGTAATGTACG

GATCATCCGGTGGCAGTGGAGGGTCCGGGGGATCCGGTCTAAGCGGCAGAAGTGATAATCATGG

AGGCTCTGGCGGGAGCATCAGCTCCGGATTGCTTTCCAGCGGAAGTTCTGGCACTCAAATTCTG

CTGACACAAAGCCCTGTGATCTTGTCAGTCTCACCTGGCGAGCGGGTGAGCTTTTCATGCCGGG

CTTCCCAGAGCATCGGTACAAATATTCACTGGTATCAGCAGAGAACCAATGGCAGTCCGCGGTT

GCTGATTAAGTATGCGAGCGAGAGCATATCAGGCATACCAAGCAGATTTAGCGGGAGTGGCTCT

GGGACCGATTTTACACTCAGTATAAATTCAGTGGAGAGCGAGGATATAGCCGACTACTACTGCC

AGCAAAACAATAACTGGCCCACCACCTTCGGCGCAGGGACCAAGCTTGAACTGAAGCGTACAGT

TGCCGCCCCAAGCGTATTTATTTTCCCTCCAAGCGACGAACAGCTGAAAAGCGGTACCGCAAGC

GTTGTGTGCCTGCTGAATAACTTTTACCCAAGGGAAGCTAAGGTGCAGTGGAAGGTTGACAATG

-continued

CGCTGCAGTCAGGCAACTCCCAGGAATCGGTAACAGAGCAGGACTCCAAGGATTCAACTTATAG

TCTTAGTAGTACCCTTACTCTTTCCAAAGCTGATTATGAAAAACACAAAGTGTATGCATGCGAG

GTGACCCACCAAGGACTGTCATCTCCTGTCACCAAGTCCTTCAACCGGGGAGAGTGT

Substitute Specification-clean copy
Amino acid Sequence:
(SEQ ID NO: 85)
QGQSGQCISPRGCPDGPYVMYGSSGGSGGSGGSGLSGRSDNHGGSGGSISSGLLSSGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 0001/LP'/1001 Activatable Antibody Light Chain:
Nucleotide sequence:
(SEQ ID NO: 452)
TGCATTTCTCCGAGAGGCTGCCCTGACGGCCCATACGTAATGTACGGATCATCCGGTGGCAGTG

GAGGGTCCGGGGGATCCGGTCTAAGCGGCAGAAGTGATAATCATGGAGGCTCTGGCGGGAGCAT

CAGCTCCGGATTGCTTTCCAGCGGAAGTTCTGGCACTCAAATTCTGCTGACACAAAGCCCTGTG

ATCTTGTCAGTCTCACCTGGCGAGCGGGTGAGCTTTTCATGCCGGGCTTCCCAGAGCATCGGTA

CAAATATTCACTGGTATCAGCAGAGAACCAATGGCAGTCCGCGGTTGCTGATTAAGTATGCGAG

CGAGAGCATATCAGGCATACCAAGCAGATTTAGCGGGAGTGGCTCTGGGACCGATTTTACACTC

AGTATAAATTCAGTGGAGAGCGAGGATATAGCCGACTACTACTGCCAGCAAAACAATAACTGGC

CCACCACCTTCGGCGCAGGGACCAAGCTTGAACTGAAGCGTACAGTTGCCGCCCCAAGCGTATT

TATTTTCCCTCCAAGCGACGAACAGCTGAAAAGCGGTACCGCAAGCGTTGTGTGCCTGCTGAAT

AACTTTTACCCAAGGGAAGCTAAGGTGCAGTGGAAGGTTGACAATGCGCTGCAGTCAGGCAACT

CCCAGGAATCGGTAACAGAGCAGGACTCCAAGGATTCAACTTATAGTCTTAGTAGTACCCTTAC

TCTTTCCAAAGCTGATTATGAAAAACACAAAGTGTATGCATGCGAGGTGACCCACCAAGGACTG

TCATCTCCTGTCACCAAGTCCTTCAACCGGGGAGAGTGT

Amino acid Sequence:
(SEQ ID NO: 453)
CISPRGCPDGPYVMYGSSGGSGGSGGSGLSGRSDNHGGSGGSISSGLLSSGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

Anti-EGFR 1001/LP'/0001 Activatable Antibody Light Chain with
spacer sequence:
Nucleotide sequence:
(SEQ ID NO: 86)
CAAGGTCAGAGCGGCCAGTGCATTAGTCCTCGCGGTTGCCCTGATGGACCATACGTAATGTATG

GAAGCTCTGGTGGATCCGGGGGCTCTGGCGGATCAGGAATCTCCAGCGGGCTGCTCTCATCAGG

TGGCAGCGGGGGCTCATTAAGCGGCCGAAGTGACAATCACGGCTCGTCCGGTACACAGATTCTG

CTCACTCAGTCACCCGTTATACTGTCTGTGTCGCCTGGAGAGCGTGTCAGCTTTTCATGTAGAG

CCTCGCAGTCAATAGGCACGAATATACACTGGTACCAGCAGAGAACTAATGGAAGCCCAAGGTT

GCTCATCAAATACGCATCTGAGTCGATTAGCGGCATTCCGTCCAGGTTTAGTGGCAGTGGAAGC

GGCACCGATTTCACTTTGTCTATTAACTCTGTGGAAAGCGAGGACATCGCCGATTATTATTGTC

AGCAGAATAACAATTGGCCCACCACCTTCGGTGCCGGTACTAAGCTGGAGCTGAAACGTACAGT

-continued

TGCCGCTCCCTCTGTGTTTATTTTCCCTCCCTCGGATGAGCAACTCAAATCAGGGACAGCGAGT

GTCGTATGTCTCCTGAACAATTTTTACCCACGTGAAGCTAAAGTTCAGTGGAAGGTGGACAACG

CTCTGCAGTCCGGCAACAGTCAGGAAAGCGTAACTGAACAGGACTCAAAGGATAGCACTTACTC

CTTGAGCAGCACTCTCACTCTTTCCAAGGCTGATTATGAGAAGCACAAGGTGTACGCGTGTGAA

GTCACCCATCAGGGACTGTCAAGTCCGGTGACTAAATCATTTAACAGGGGCGAATGC

Amino acid Sequence:

(SEQ ID NO: 87)

QGQSGQCISPRGCPDGPYVMYGSSGGSGGSGGSGISSGLLSSGGSGGSLSGRSDNHGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 1001/LP'/0001 Activatable Antibody Light Chain:
Nucleotide sequence:

(SEQ ID NO: 454)

TGCATTAGTCCTCGCGGTTGCCCTGATGGACCATACGTAATGTATGGAAGCTCTGGTGGATCCG

GGGGCTCTGGCGGATCAGGAATCTCCAGCGGGCTGCTCTCATCAGGTGGCAGCGGGGGCTCATT

AAGCGGCCGAAGTGACAATCACGGCTCGTCCGGTACACAGATTCTGCTCACTCAGTCACCCGTT

ATACTGTCTGTGTCGCCTGGAGAGCGTGTCAGCTTTTCATGTAGAGCCTCGCAGTCAATAGGCA

CGAATATACACTGGTACCAGCAGAGAACTAATGGAAGCCCAAGGTTGCTCATCAAATACGCATC

TGAGTCGATTAGCGGCATTCCGTCCAGGTTTAGTGGCAGTGGAAGCGGCACCGATTTCACTTTG

TCTATTAACTCTGTGGAAAGCGAGGACATCGCCGATTATTATTGTCAGCAGAATAACAATTGGC

CCACCACCTTCGGTGCCGGTACTAAGCTGGAGCTGAAACGTACAGTTGCCGCTCCCTCTGTGTT

TATTTTCCCTCCCTCGGATGAGCAACTCAAATCAGGGACAGCGAGTGTCGTATGTCTCCTGAAC

AATTTTTACCCACGTGAAGCTAAAGTTCAGTGGAAGGTGGACAACGCTCTGCAGTCCGGCAACA

GTCAGGAAAGCGTAACTGAACAGGACTCAAAGGATAGCACTTACTCCTTGAGCAGCACTCTCAC

TCTTTCCAAGGCTGATTATGAGAAGCACAAGGTGTACGCGTGTGAAGTCACCCATCAGGGACTG

TCAAGTCCGGTGACTAAATCATTTAACAGGGGCGAATGC

Amino acid Sequence:

(SEQ ID NO: 455)

CISPRGCPDGPYVMYGSSGGSGGSGGSGISSGLLSSGGSGGSLSGRSDNHGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

Anti-EGFR 0002/LP'/1001 Activatable Antibody Light Chain with
spacer sequence:
Nucleotide sequence:

(SEQ ID NO: 88)

CAGGGCCAGAGTGGGCAGTGTATTTCCCCTCGCGGATGTCCCGACGGTCCATACGTAATGTATG

GGTCAAGCGGGGGATCAGGAGGAAGTGGAGGCTCCGGACTCAGCGGTCGCTCCGGCAATCACGG

GGGGTCTGGCGGATCAATAAGTTCGGGCCTCCTGAGCTCCGGTTCATCTGGCACTCAGATCCTG

CTCACGCAGTCGCCGGTAATACTGAGTGTCTCACCAGGCGAGCGTGTCAGCTTCAGCTGTCGCG

CCTCACAGTCAATCGGCACAAATATCCATTGGTACCAGCAAAGGACCAATGGCAGCCCTAGGCT

GCTGATAAAATACGCATCCGAGTCAATTTCAGGGATTCCATCGAGATTCTCGGGCAGCGGAAGT

GGGACCGACTTTACTCTCTCCATCAACAGCGTCGAGTCGGAGGACATCGCGGACTACTACTGCC

-continued

AGCAGAATAACAATTGGCCAACAACATTCGGCGCAGGAACAAAGCTAGAGCTCAAGAGGACAGT

GGCTGCACCCAGTGTATTCATCTTCCCACCTAGCGACGAGCAACTGAAGAGCGGGACGGCTTCC

GTCGTTTGTCTATTAAATAATTTCTATCCCCGTGAGGCTAAAGTTCAGTGGAAGGTTGATAATG

CGTTGCAGTCCGGCAACTCCCAGGAATCCGTCACAGAGCAGGATTCTAAGGATTCAACCTATAG

CTTAAGCTCTACACTTACGCTTTCTAAAGCCGATTATGAAAAACACAAGGTGTACGCTTGTGAG

GTTACCCACCAGGGCCTGAGCAGCCCCGTGACCAAGTCGTTCAACCGGGGCGAGTGT

Amino acid Sequence:

(SEQ ID NO: 89)

QGQSGQCISPRGCPDGPYVMYGSSGGSGGSGGSGLSGRSGNHGGSGGSISSGLLSSGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 0002/LP'/1001 Activatable Antibody Light Chain:
Nucleotide sequence:

(SEQ ID NO: 456)

TGTATTTCCCCTCGCGGATGTCCCGACGGTCCATACGTAATGTATGGGTCAAGCGGGGGATCAG

GAGGAAGTGGAGGCTCCGGACTCAGCGGTCGCTCCGGCAATCACGGGGGGTCTGGCGGATCAAT

AAGTTCGGGCCTCCTGAGCTCCGGTTCATCTGGCACTCAGATCCTGCTCACGCAGTCGCCGGTA

ATACTGAGTGTCTCACCAGGCGAGCGTGTCAGCTTCAGCTGTCGCGCCTCACAGTCAATCGGCA

CAAATATCCATTGGTACCAGCAAAGGACCAATGGCAGCCCTAGGCTGCTGATAAAATACGCATC

CGAGTCAATTTCAGGGATTCCATCGAGATTCTCGGGCAGCGGAAGTGGGACCGACTTTACTCTC

TCCATCAACAGCGTCGAGTCGGAGGACATCGCGGACTACTACTGCCAGCAGAATAACAATTGGC

CAACAACATTCGGCGCAGGAACAAAGCTAGAGCTCAAGAGGACAGTGGCTGCACCCAGTGTATT

CATCTTCCCACCTAGCGACGAGCAACTGAAGAGCGGGACGGCTTCCGTCGTTTGTCTATTAAAT

AATTTCTATCCCCGTGAGGCTAAAGTTCAGTGGAAGGTTGATAATGCGTTGCAGTCCGGCAACT

CCCAGGAATCCGTCACAGAGCAGGATTCTAAGGATTCAACCTATAGCTTAAGCTCTACACTTAC

GCTTTCTAAAGCCGATTATGAAAAACACAAGGTGTACGCTTGTGAGGTTACCCACCAGGGCCTG

AGCAGCCCCGTGACCAAGTCGTTCAACCGGGGCGAGTGT

Amino acid Sequence:

(SEQ ID NO: 457)

CISPRGCPDGPYVMYGSSGGSGGSGGSGLSGRSGNHGGSGGSISSGLLSSGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

Anti-EGFR 1001/LP'/0002 Activatable Antibody Light Chain with
spacer sequence:
Nucleotide sequence:

(SEQ ID NO: 90)

CAAGGACAGAGCGGACAGTGTATCTCACCTCGCGGCTGCCCCGACGGCCCTTACGTCATGTACG

GCTCCTCGGGTGGGTCCGGGGGAAGTGGCGGGTCTGGCATTAGTTCAGGGCTCTTATCTTCCGG

CGGAAGCGGGGGATCTCTTTCCGGGCGGAGTGGCAATCACGGCAGTAGCGGAACTCAGATCCTA

CTCACTCAGTCACCAGTGATCCTGTCTGTCAGTCCAGGGGAGAGAGTGTCTTTCAGTTGTAGAG

CTTCCCAGTCTATTGGGACAAACATTCACTGGTATCAACAGCGAACTAATGGATCGCCAAGACT

CCTGATTAAATATGCTTCTGAGAGCATCTCTGGAATTCCATCAAGATTCTCAGGGAGTGGTAGC

-continued

GGCACCGATTTTACGTTATCGATCAATTCCGTTGAGAGCGAAGATATCGCGGACTATTACTGTC

AGCAGAACAATAACTGGCCTACAACGTTCGGGGCAGGGACGAAATTGGAGCTGAAGCGGACCGT

CGCCGCGCCAAGCGTGTTCATCTTCCCCCCTAGCGACGAGCAATTGAAAAGCGGCACCGCAAGT

GTGGTTTGCCTGCTGAACAACTTTTATCCTCGCGAGGCGAAAGTGCAGTGGAAAGTCGACAATG

CACTCCAGTCAGGGAACAGCCAAGAGTCCGTTACTGAACAAGACTCTAAAGATAGTACTTATAG

CTTATCCAGCACACTGACGCTCAGTAAGGCCGATTATGAAAAACATAAGGTGTATGCGTGTGAG

GTTACCCATCAAGGATTGTCATCACCCGTCACCAAATCCTTTAACAGAGGAGAATGT

Amino acid Sequence:

(SEQ ID NO: 91)

QGQSGQCISPRGCPDGPYVMYGSSGGSGGSGGSGISSGLLSSGGSGGSLSGRSGNHGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 1001/LP'/0002 Activatable Antibody Light Chain:
Nucleotide sequence:

(SEQ ID NO: 458)

TGTATCTCACCTCGCGGCTGCCCCGACGGCCCTTACGTCATGTACGGCTCCTCGGGTGGGTCCG

GGGGAAGTGGCGGGTCTGGCATTAGTTCAGGGCTCTTATCTTCCGGCGGAAGCGGGGGATCTCT

TTCCGGGCGGAGTGGCAATCACGGCAGTAGCGGAACTCAGATCCTACTCACTCAGTCACCAGTG

ATCCTGTCTGTCAGTCCAGGGGAGAGAGTGTCTTTCAGTTGTAGAGCTTCCCAGTCTATTGGGA

CAAACATTCACTGGTATCAACAGCGAACTAATGGATCGCCAAGACTCCTGATTAAATATGCTTC

TGAGAGCATCTCTGGAATTCCATCAAGATTCTCAGGGAGTGGTAGCGGCACCGATTTTACGTTA

TCGATCAATTCCGTTGAGAGCGAAGATATCGCGGACTATTACTGTCAGCAGAACAATAACTGGC

CTACAACGTTCGGGGCAGGGACGAAATTGGAGCTGAAGCGGACCGTCGCCGCGCCAAGCGTGTT

CATCTTCCCCCCTAGCGACGAGCAATTGAAAAGCGGCACCGCAAGTGTGGTTTGCCTGCTGAAC

AACTTTTATCCTCGCGAGGCGAAAGTGCAGTGGAAAGTCGACAATGCACTCCAGTCAGGGAACA

GCCAAGAGTCCGTTACTGAACAAGACTCTAAAGATAGTACTTATAGCTTATCCAGCACACTGAC

GCTCAGTAAGGCCGATTATGAAAAACATAAGGTGTATGCGTGTGAGGTTACCCATCAAGGATTG

TCATCACCCGTCACCAAATCCTTTAACAGAGGAGAATGT

Amino acid Sequence:

(SEQ ID NO: 459)

CISPRGCPDGPYVMYGSSGGSGGSGGSGISSGLLSSGGSGGSLSGRSGNHGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

Anti-EGFR 0001/LP'/1002 Activatable Antibody Light Chain with
spacer sequence:
Nucleotide sequence:

(SEQ ID NO: 92)

CAGGGTCAAAGTGGACAGTGTATCTCGCCCCGCGGCTGCCCAGACGGCCCATATGTGATGTATG

GTTCTTCCGGTGGATCCGGCGGATCAGGTGGGTCTGGCCTCTCAGGTCGTTCCGACAACCACGG

CGGCTCAGGTGGGTCTCAGAATCAGGCACTGCGGATGGCCGGATCTTCTGGCACCCAGATATTG

CTCACACAGTCACCAGTTATTCTGTCCGTATCTCCAGGAGAACGGGTATCTTTCTCTTGTAGGG

CAAGCCAGTCCATCGGAACAAACATCCATTGGTACCAGCAGCGGACCAATGGCAGTCCACGGCT

-continued

TCTGATCAAGTATGCTAGTGAAAGCATTAGCGGGATTCCAAGCCGATTTTCTGGGTCGGGTAGT

GGAACCGACTTCACCCTGAGCATTAACTCTGTCGAATCCGAAGATATTGCTGACTATTACTGTC

AGCAGAACAACAATTGGCCGACTACGTTTGGCGCCGGAACCAAATTAGAACTTAAGAGAACCGT

GGCCGCTCCCTCTGTCTTCATTTTCCCGCCTTCCGACGAACAGCTGAAGAGCGGAACTGCCTCC

GTGGTGTGCCTGTTGAATAACTTTTATCCAAGGGAAGCAAAGGTGCAGTGGAAAGTGGACAATG

CTCTGCAGTCTGGCAATAGCCAGGAGTCCGTGACTGAACAGGACAGTAAAGACTCAACCTACTC

ACTGAGCAGTACTCTCACATTATCCAAAGCCGATTATGAAAAGCATAAGGTTTATGCATGCGAG

GTTACCCACCAGGGACTGAGCTCCCCCGTGACCAAAAGCTTCAATAGGGGTGAGTGC

Amino acid Sequence:

(SEQ ID NO: 93)

QGQSGQCISPRGCPDGPYVMYGSSGGSGGSGGSGLSGRSDNHGGSGGSQNQALRMAGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 0001/LP'/1002 Activatable Antibody Light Chain:
Nucleotide sequence:

(SEQ ID NO: 460)

TGTATCTCGCCCCGCGGCTGCCCAGACGGCCCATATGTGATGTATGGTTCTTCCGGTGGATCCG

GCGGATCAGGTGGGTCTGGCCTCTCAGGTCGTTCCGACAACCACGGCGGCTCAGGTGGGTCTCA

GAATCAGGCACTGCGGATGGCCGGATCTTCTGGCACCCAGATATTGCTCACACAGTCACCAGTT

ATTCTGTCCGTATCTCCAGGAGAACGGGTATCTTTCTCTTGTAGGGCAAGCCAGTCCATCGGAA

CAAACATCCATTGGTACCAGCAGCGGACCAATGGCAGTCCACGGCTTCTGATCAAGTATGCTAG

TGAAAGCATTAGCGGGATTCCAAGCCGATTTTCTGGGTCGGGTAGTGGAACCGACTTCACCCTG

AGCATTAACTCTGTCGAATCCGAAGATATTGCTGACTATTACTGTCAGCAGAACAACAATTGGC

CGACTACGTTTGGCGCCGGAACCAAATTAGAACTTAAGAGAACCGTGGCCGCTCCCTCTGTCTT

CATTTTCCCGCCTTCCGACGAACAGCTGAAGAGCGGAACTGCCTCCGTGGTGTGCCTGTTGAAT

AACTTTTATCCAAGGGAAGCAAAGGTGCAGTGGAAAGTGGACAATGCTCTGCAGTCTGGCAATA

GCCAGGAGTCCGTGACTGAACAGGACAGTAAAGACTCAACCTACTCACTGAGCAGTACTCTCAC

ATTATCCAAAGCCGATTATGAAAAGCATAAGGTTTATGCATGCGAGGTTACCCACCAGGGACTG

AGCTCCCCCGTGACCAAAAGCTTCAATAGGGGTGAGTGC

Amino acid Sequence:

(SEQ ID NO: 461)

CISPRGCPDGPYVMYGSSGGSGGSGGSGLSGRSDNHGGSGGSQNQALRMAGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

Anti-EGFR 1002/LP'/0001 Activatable Antibody Light Chain with
spacer sequence:
Nucleotide sequence:

(SEQ ID NO: 94)

CAGGGGCAGTCCGGACAATGCATCAGCCCCCGAGGCTGCCCTGATGGCCCCTACGTGATGTACG

GGTCCAGCGGTGGCAGCGGGGGCTCAGGGGGGAGCGGGCAGAATCAGGCCCTGAGAATGGCGGG

TGGATCCGGGGGGTCCCTTTCTGGCAGGTCCGATAACCACGGTTCTAGTGGAACACAGATTTTG

CTGACACAAAGTCCCGTCATCCTCTCTGTGTCTCCCGGTGAGCGGGTCAGTTTTTCCTGCCGAG

-continued

CGTCCCAGAGCATCGGGACAAATATCCATTGGTACCAGCAGAGAACGAACGGCTCTCCTAGACT

GCTCATCAAGTACGCCTCGGAAAGTATTTCCGGCATTCCCTCCCGTTTCAGCGGCTCCGGAAGT

GGTACAGATTTTACCCTGAGTATTAATTCCGTCGAATCTGAGGACATAGCCGACTACTATTGCC

AACAGAATAACAATTGGCCAACAACTTTTGGCGCCGGGACTAAGCTGGAGCTGAAACGGACCGT

CGCAGCACCAAGTGTTTTCATCTTCCCACCAAGTGACGAGCAGCTGAAATCCGGAACAGCGAGC

GTGGTGTGCCTACTCAATAACTTCTATCCACGCGAAGCCAAGGTGCAGTGGAAAGTGGACAACG

CTCTGCAGTCCGGCAATAGCCAGGAAAGCGTGACAGAGCAAGATTCTAAGGACAGTACGTATTC

ACTGTCCAGTACGCTCACCTTAAGCAAGGCTGACTACGAAAAACACAAGGTCTACGCCTGTGAG

GTCACACATCAGGGCCTCTCCAGTCCGGTTACAAAAAGTTTCAATCGCGGGGAATGT

Amino acid Sequence:

(SEQ ID NO: 95)

QGQSGQCISPRGCPDGPYVMYGSSGGSGGSGGSGQNQALRMAGGSGGSLSGRSDNHGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 1002/LP'/0001 Activatable Antibody Light Chain:
Nucleotide sequence:

(SEQ ID NO: 462)

TGCATCAGCCCCCGAGGCTGCCCTGATGGCCCCTACGTGATGTACGGGTCCAGCGGTGGCAGCG

GGGGCTCAGGGGGGAGCGGGCAGAATCAGGCCCTGAGAATGGCGGGTGGATCCGGGGGGTCCCT

TTCTGGCAGGTCCGATAACCACGGTTCTAGTGGAACACAGATTTTGCTGACACAAAGTCCCGTC

ATCCTCTCTGTGTCTCCCGGTGAGCGGGTCAGTTTTTCCTGCCGAGCGTCCCAGAGCATCGGGA

CAAATATCCATTGGTACCAGCAGAGAACGAACGGCTCTCCTAGACTGCTCATCAAGTACGCCTC

GGAAAGTATTTCCGGCATTCCCTCCCGTTTCAGCGGCTCCGGAAGTGGTACAGATTTTACCCTG

AGTATTAATTCCGTCGAATCTGAGGACATAGCCGACTACTATTGCCAACAGAATAACAATTGGC

CAACAACTTTTGGCGCCGGGACTAAGCTGGAGCTGAAACGGACCGTCGCAGCACCAAGTGTTTT

CATCTTCCCACCAAGTGACGAGCAGCTGAAATCCGGAACAGCGAGCGTGGTGTGCCTACTCAAT

AACTTCTATCCACGCGAAGCCAAGGTGCAGTGGAAAGTGGACAACGCTCTGCAGTCCGGCAATA

GCCAGGAAAGCGTGACAGAGCAAGATTCTAAGGACAGTACGTATTCACTGTCCAGTACGCTCAC

CTTAAGCAAGGCTGACTACGAAAAACACAAGGTCTACGCCTGTGAGGTCACACATCAGGGCCTC

TCCAGTCCGGTTACAAAAAGTTTCAATCGCGGGGAATGT

Amino acid Sequence:

(SEQ ID NO: 463)

CISPRGCPDGPYVMYGSSGGSGGSGGSGQNQALRMAGGSGGSLSGRSDNHGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

Anti-EGFR 0002/LP'/1002 Activatable Antibody Light Chain with
spacer sequence:
Nucleotide sequence:

(SEQ ID NO: 96)

CAAGGCCAATCCGGTCAGTGCATCAGTCCCAGAGGCTGCCCTGACGGGCCCTACGTGATGTATG

GTAGCTCAGGGGGCTCCGGCGGCTCCGGCGGAAGCGGACTTAGCGGCCGTAGCGGCAACCATGG

GGGTTCTGGAGGATCCCAGAATCAGGCTCTGCGCATGGCTGGAAGCAGCGGTACCCAGATCCTG

-continued

CTCACCCAATCACCCGTCATCTTGTCTGTGAGTCCTGGCGAAAGGGTGTCGTTCTCTTGTCGCG

CGTCCCAGTCCATTGGGACCAACATTCATTGGTACCAGCAGAGGACTAACGGGAGCCCCCGCCT

GCTGATCAAATACGCCAGTGAATCTATCTCTGGAATCCCATCACGATTTTCAGGGTCCGGTAGT

GGGACCGACTTCACTTTGAGTATTAACAGTGTGGAATCCGAGGACATAGCCGACTATTACTGTC

AGCAGAACAATAACTGGCCAACAACCTTTGGCGCCGGGACAAAGTTAGAGCTTAAGCGGACTGT

TGCAGCCCCCTCCGTTTTTATCTTCCCGCCCAGTGATGAACAGCTGAAAAGCGGTACCGCCTCC

GTAGTGTGCCTTCTCAATAATTTTTACCCCAGAGAAGCTAAAGTACAGTGGAAAGTCGACAACG

CCCTCCAGAGCGGCAACAGTCAGGAGTCCGTCACCGAGCAGGATTCTAAAGACTCAACATATAG

CCTTTCGTCCACCCTAACACTTTCAAAAGCAGACTATGAAAAACATAAGGTGTATGCCTGCGAG

GTCACACACCAGGGGCTCAGCTCTCCAGTTACTAAGTCATTCAACCGCGGAGAGTGT

Amino acid Sequence:

(SEQ ID NO: 97)

QGQSGQCISPRGCPDGPYVMYGSSGGSGGSGGSGLSGRSGNHGGSGGSQNQALRMAGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 0002/LP'/1002 Activatable Antibody Light Chain:
Nucleotide sequence:

(SEQ ID NO: 464)

TGCATCAGTCCCAGAGGCTGCCCTGACGGGCCCTACGTGATGTATGGTAGCTCAGGGGGCTCCG

GCGGCTCCGGCGGAAGCGGACTTAGCGGCCGTAGCGGCAACCATGGGGGTTCTGGAGGATCCCA

GAATCAGGCTCTGCGCATGGCTGGAAGCAGCGGTACCCAGATCCTGCTCACCCAATCACCCGTC

ATCTTGTCTGTGAGTCCTGGCGAAAGGGTGTCGTTCTCTTGTCGCGCGTCCCAGTCCATTGGGA

CCAACATTCATTGGTACCAGCAGAGGACTAACGGGAGCCCCCGCCTGCTGATCAAATACGCCAG

TGAATCTATCTCTGGAATCCCATCACGATTTTCAGGGTCCGGTAGTGGGACCGACTTCACTTTG

AGTATTAACAGTGTGGAATCCGAGGACATAGCCGACTATTACTGTCAGCAGAACAATAACTGGC

CAACAACCTTTGGCGCCGGGACAAAGTTAGAGCTTAAGCGGACTGTTGCAGCCCCCTCCGTTTT

TATCTTCCCGCCCAGTGATGAACAGCTGAAAAGCGGTACCGCCTCCGTAGTGTGCCTTCTCAAT

AATTTTTACCCCAGAGAAGCTAAAGTACAGTGGAAAGTCGACAACGCCCTCCAGAGCGGCAACA

GTCAGGAGTCCGTCACCGAGCAGGATTCTAAAGACTCAACATATAGCCTTTCGTCCACCCTAAC

ACTTTCAAAAGCAGACTATGAAAAACATAAGGTGTATGCCTGCGAGGTCACACACCAGGGGCTC

AGCTCTCCAGTTACTAAGTCATTCAACCGCGGAGAGTGT

Amino acid Sequence:

(SEQ ID NO: 465)

CISPRGCPDGPYVMYGSSGGSGGSGGSGLSGRSGNHGGSGGSQNQALRMAGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

Anti-EGFR 1002/LP'/0002 Activatable Antibody Light Chain with
spacer sequence:
Nucleotide sequence:

(SEQ ID NO: 98)

CAGGGCCAATCAGGTCAGTGCATTAGCCCCCGAGGGTGTCCCGATGGGCCCTACGTAATGTACG

GATCATCGGGCGGATCTGGGGGCTCCGGTGGCTCTGGTCAGAATCAAGCTCTGCGCATGGCCGG

-continued

AGGTAGCGGTGGAAGCCTGAGCGGCCGAAGTGGAAACCACGGCTCCTCTGGCACTCAGATTCTT

CTCACGCAGTCGCCCGTGATCTTGTCCGTGAGCCCAGGCGAGCGGGTGAGCTTCTCTTGCCGGG

CCAGCCAAAGTATAGGTACAAATATTCACTGGTACCAACAGCGAACCAACGGGTCGCCTAGGTT

GCTCATAAAGTACGCATCCGAGAGTATAAGCGGCATACCATCTAGGTTCTCAGGTAGCGGCAGC

GGGACCGATTTTACCCTCAGCATTAATTCGGTTGAATCTGAAGATATCGCCGATTATTATTGTC

AGCAGAATAACAATTGGCCTACTACTTTCGGCGCCGGAACAAAGCTGGAACTTAAGCGCACAGT

GGCCGCTCCTTCTGTCTTTATCTTCCCTCCATCTGACGAGCAATTAAAGAGTGGGACAGCCTCG

GTGGTGTGTTTGCTCAATAACTTCTATCCAAGGGAGGCAAAGGTGCAGTGGAAGGTCGATAACG

CTCTCCAGAGTGGGAATTCCCAGGAGTCCGTGACCGAGCAGGATTCTAAAGATAGCACATACTC

ACTGTCTTCCACCCTGACCCTGTCCAAGGCAGACTACGAGAAGCACAAAGTTTACGCCTGTGAA

GTGACACACCAGGGCCTCAGCTCTCCTGTCACAAAGAGTTTTAATCGGGGCGAGTGT

Amino acid Sequence:

(SEQ ID NO: 99)

QGQSGQCISPRGCPDGPYVMYGSSGGSGGSGGSGQNQALRMAGGSGGSLSGRSGNHGSSGTQIL

LTQSPVILSVSPGERVSFSCRASQSIGTNIHWYQQRTNGSPRLLIKYASESISGIPSRFSGSGS

GTDFTLSINSVESEDIADYYCQQNNNWPTTFGAGTKLELKRTVAAPSVFIFPPSDEQLKSGTAS

VVCLLNNFYPREAKVQWKVDNALQSGNSQESVTEQDSKDSTYSLSSTLTLSKADYEKHKVYACE

VTHQGLSSPVTKSFNRGEC

Anti-EGFR 1002/LP'/000 Activatable Antibody Light Chain:
Nucleotide sequence:

(SEQ ID NO: 466)

TGCATTAGCCCCCGAGGGTGTCCCGATGGGCCCTACGTAATGTACGGATCATCGGGCGGATCTG

GGGGCTCCGGTGGCTCTGGTCAGAATCAAGCTCTGCGCATGGCCGGAGGTAGCGGTGGAAGCCT

GAGCGGCCGAAGTGGAAACCACGGCTCCTCTGGCACTCAGATTCTTCTCACGCAGTCGCCCGTG

ATCTTGTCCGTGAGCCCAGGCGAGCGGGTGAGCTTCTCTTGCCGGGCCAGCCAAAGTATAGGTA

CAAATATTCACTGGTACCAACAGCGAACCAACGGGTCGCCTAGGTTGCTCATAAAGTACGCATC

CGAGAGTATAAGCGGCATACCATCTAGGTTCTCAGGTAGCGGCAGCGGGACCGATTTTACCCTC

AGCATTAATTCGGTTGAATCTGAAGATATCGCCGATTATTATTGTCAGCAGAATAACAATTGGC

CTACTACTTTCGGCGCCGGAACAAAGCTGGAACTTAAGCGCACAGTGGCCGCTCCTTCTGTCTT

TATCTTCCCTCCATCTGACGAGCAATTAAAGAGTGGGACAGCCTCGGTGGTGTGTTTGCTCAAT

AACTTCTATCCAAGGGAGGCAAAGGTGCAGTGGAAGGTCGATAACGCTCTCCAGAGTGGGAATT

CCCAGGAGTCCGTGACCGAGCAGGATTCTAAAGATAGCACATACTCACTGTCTTCCACCCTGAC

CCTGTCCAAGGCAGACTACGAGAAGCACAAAGTTTACGCCTGTGAAGTGACACACCAGGGCCTC

AGCTCTCCTGTCACAAAGAGTTTTAATCGGGGCGAGTGT

Amino acid Sequence:

(SEQ ID NO: 467)

CISPRGCPDGPYVMYGSSGGSGGSGGSGQNQALRMAGGSGGSLSGRSGNHGSSGTQILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC

The following materials were used in the studies described herein.

Reagents and Strains: Human u-PA (Research & Diagnostics Systems, Inc.) was used without modifications. Human matriptase (Research & Diagnostics Systems, Inc.) was used without modifications. Human MMP14 (Research & Diagnostics Systems, Inc.) was activated following the supplied protocol and used without modifications. MMP14 Buffer HCM (50 mM HEPES (pH 6.8), 10 mM $CaCl_2$, 0.5 mM $MgCl_2$) was used. u-PA and Matriptase Buffer TBST (50 mM Tris-HCl, 150 mM NaCl, 0.05% Tween20, pH 7.4) was used.

The following methods were used to evaluate in Vitro substrate activity in activatable antibodies.

Substrate Proteolysis: The ability of substrates in the activatable antibodies to be cleaved by u-PA, matriptase and/or MMP14 was determined as follows. Samples were incubated overnight for 16 to 24 hours at 37° C. in the presence or absence of protease in PBS pH 7.2. Protease digests were prepared to maintain an activatable antibody to protease ratio of 9-to-1. Proteolysis was confirmed by capillary electrophoresis, ELISA, or SDS-PAGE.

Substrate Cleavage Kinetics ($k_{cat}/K_m$): The ability of EGFR activatable antibodies containing substrates, 2001, 2002, 0001/LP'/1001 or 1001/L1Y/0001, to be cleaved by matriptase and/or MMP14 was determined as follows. Matriptase protease digests were performed in TBST, 50 mM Tris-HCl, 150 mM NaCl, 0.05% Tween20, pH 7.4. MMP14 protease digests were performed in HCM, 50 mM HEPES (pH 6.8), 10 mM $CaCl_2$, 0.5 mM $MgCl_2$. Varying concentrations of active site titrated matriptase or MMP14 were combined with a fixed activatable antibody concentration to maintain a substrate to protease ratio of at least 50. Samples comprising these substrates were incubated at 37° C. for up to 24 hr. To stop the reaction, 5 μl of the digest was added to 7 μl of HT Protein Express Sample Buffer (Caliper LifeSciences) containing 20 mM 2-Mercaptoethanol for 10 minutes at 95° C. After heat denaturation, 32 μl of $ddH_2O$ was added and samples analyzed on a LabChip GXII per manufacturer's instructions. The LabChip GXII software was used to quantify light chain peak area. Product conversion was calculated by plugging the light chain peak areas into the following equation: cleaved LC/(cleaved LC+uncleaved LC), LC=light chain peak area. $k_{cat}/K_m$ values were determined with the following equation $$\frac{k_{cat}}{K_m} = -\ln(1-C)/(t*p)$$

where C is product conversion, t is time (s), and p is protease concentration (M), which assumes that the substrate concentration is below the $K_m$ and in excess of the protease concentration.

The following methods can be used to evaluate the in vivo substrate stability of activatable antibodies described herein.

This section describes the experimental method for evaluating in vivo stability of substrates of the embodiments when they were incorporated into EGFR activatable antibodies and injected into mice.

Three nude mice (Crl:NU-Foxnlnu) received a single IP dose of each EGFR activatable antibodies containing 2001, 2002, 0001/LP'/1001, 1001/L1Y/0001, 1001/LP'/0002, 0001/LP'/1002, or 0002/LP'/1002 substrates at 12.5 mg/kg on Day 0. Mice were euthanized on day 4 (~96 hours post-dose) by $CO_2$ asphyxiation, and blood was collected immediately as plasma-EDTA and stored at −80° C.

The EGFR activatable antibodies were purified from plasma by anti-human IgG immunoprecipitation using magnetic beads. Eluted EGFR activatable antibodies were prepared for analysis by capillary electrophoresis as described in the $k_{cat}/K_m$ section. Briefly, 5 μl of eluted IgG was added to 7 μl Protein Express Sample Buffer with 2-mercaptoethanol. The method of quantification of circulating stability was identical to quantification of product conversion.

The following methods are used to evaluate in vivo efficacy of activatable antibodies.

This section describes the experimental method for evaluating that EGFR activatable antibodies comprising matriptase-cleavable substrates, MMP14-cleavable substrates, or substrates of the embodiments, i.e., substrates cleavable by matriptase and MMP14, are efficacious in vivo. Seven EGFR activatable antibodies comprising substrate sequences of 0001, 0002, 1001, 2001, 2002, 0001/LP'/1001 or 1001/LP'/0001, cleavable by either or both matriptase and/or MMP14 were administered at 12.5 mg/kg intraperitoneally (i.p.) to H292 xenograft tumor-bearing (lung cancer) mice on Day 0. Mice were retro-orbitally bled on day 8 (~192 hours post-dose). Blood was collected immediately as plasma-EDTA and stored at −80° C. EGFR activatable antibodies were purified from plasma by anti-human IgG immunoprecipitation using magnetic beads. Eluted EGFR activatable antibodies were prepared for analysis by capillary electrophoresis. Briefly, 5 μl of eluted IgG was added to 7 μl Protein Express Sample Buffer with 2-mercaptoethanol. Quantification of circulating stability was identical to quantification of product conversion.

At day 8, the three EGFR activatable antibodies containing matriptase-cleavable substrates or MMP14-cleavable substrates, 0001, 0002 or 1001, demonstrated mean percent (%) activation values ranging from 14% to 15% and the four EGFR activatable antibodies containing substrates, 2001, 2002, 0001/LP'/1001 or 1001/LP'/0001, of the embodiments, i.e., substrates cleavable by matriptase and MMP14, demonstrated mean % activation values of 28% to 33%. Mean % activation is calculated as ((product conversion sum of the test group)*100%)/(number of animals in the test group).

All seven EGFR activatable antibodies containing substrate sequences of 0001, 0002, 1001, 2001, 2002, 0001/LP'/1001 or 1001/LP'/0001 also comprised the masking moiety comprising the amino acid sequence CISPRGCPDGPYVMY (SEQ ID NO: 168) and anti-EGFR antibody C225v5 antibody comprising a light chain (SEQ ID NO: 111) and a heavy chain (SEQ ID NO: 108). The configuration of the light chain of the activatable antibody was masking moiety-substrate-light chain of C225v5.

At day 21, the three EGFR activatable antibodies containing matriptase-cleavable substrates or MMP14-cleavable substrates, 0001, 0002 or 1001, demonstrated tumor growth inhibition ranging from 41% to 57% as measured by mean percent (%) inhibition and the four EGFR activatable antibodies containing substrates, 2001, 2002, 0001/LP'/1001 or 1001/LP'/0001, of the embodiments, i.e., substrates cleavable by matriptase and MMP14, demonstrated tumor growth inhibition ranging from 77% to 80% as measured by mean % inhibition. Mean % inhibition is calculated as (mean(C)−mean(C0))−(mean(T)−mean(T0))/(mean(C)−mean (C0))*100%, wherein T is the current test group value, T0 is the current test group initial value, C is the control group value, and C0 is the control group initial value. The EGFR antibody cetuximab at day 21 demonstrated 86% inhibition in this study.

Example 3. In Situ Imaging of Anti-EGFR Activatable Antibodies

The present Example describes the use of in situ imaging of non-labeled anti-EGFR activatable antibodies. The cleavage and binding was detected using a secondary antibody that specifically binds to the AB portion of the activatable antibody.

Figure 6:
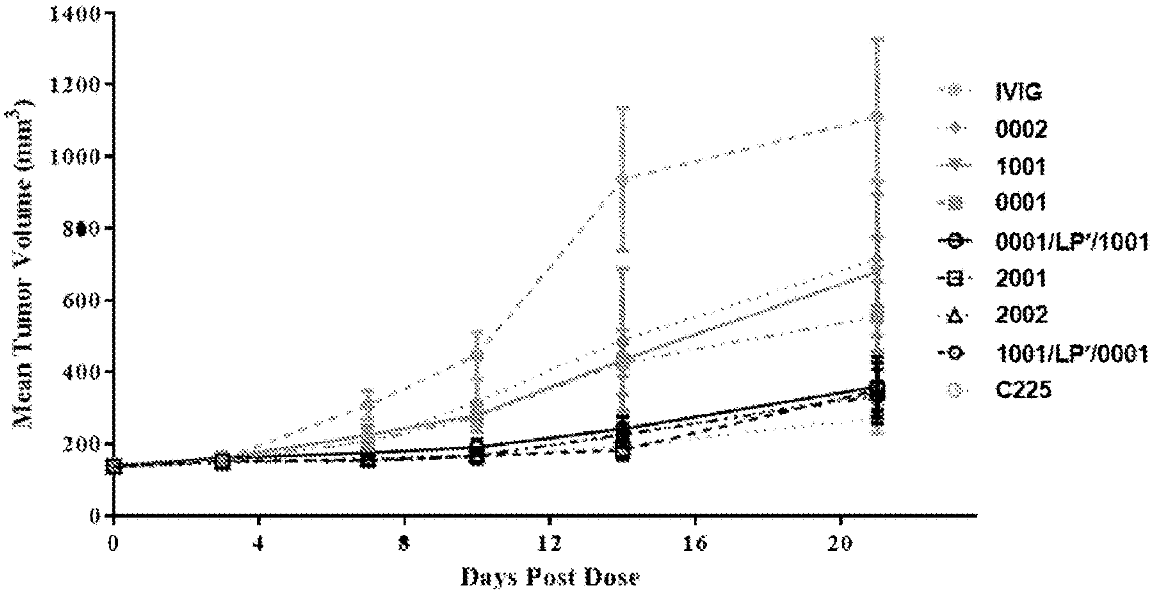
FIG. 6 is a graph depicting in vivo efficacy of EGFR activatable antibodies in H292 xenograft tumor-bearing mice.
Figure 7:
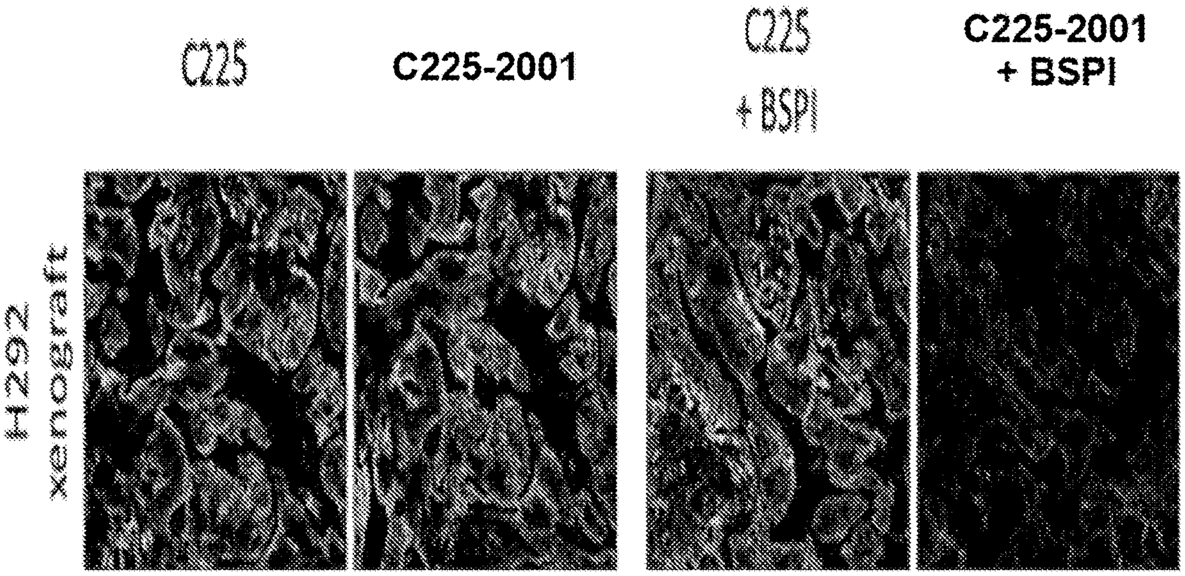
FIG. 7 is a graph depicting in situ evaluation of EGFR activatable antibody activation in a H292 xenograft tumor microenvironment.
Figures 8A, 8B, 8C, 8D, 8E:
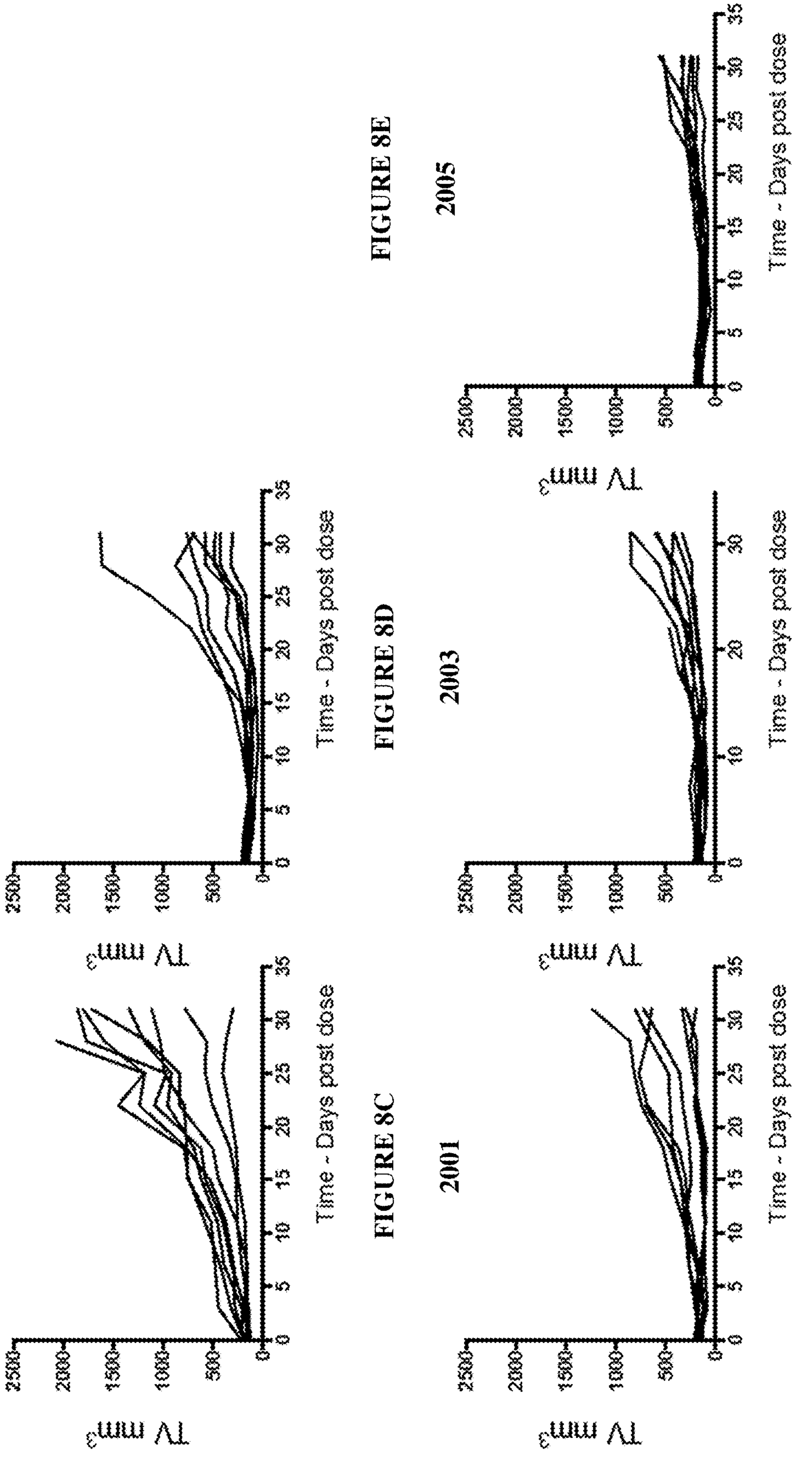
FIGS. 8A, 8B, 8C, 8D, 8E, and 8F are a series of graphs depicting the tumor volume of H292 xenograft tumors in nu/nu mice at various time points following administration with a control intravenous immunoglobulin (IVIG, FIG. 8A), the anti-EGFR antibody cetuximab (FIG. 8B), the anti-EGFR activatable antibody referred to herein as anti-EGFR 2001 activatable antibody, which includes the heavy chain sequence of SEQ ID NO: 108, and the light chain sequence of SEQ ID NO: 449 (FIG. 8C); the anti-EGFR activatable antibody referred to herein as anti-EGFR 2003 activatable antibody, which includes the heavy chain sequence of SEQ ID NO: 108, and the light chain sequence of SEQ ID NO: 472 (FIG. 8D); or the anti-EGFR activatable antibody referred to herein as anti-EGFR 2005 activatable antibody, which includes the heavy chain sequence of SEQ ID NO: 108, and the light chain sequence of SEQ ID NO: 474 (FIG. 8E). For the data shown in FIGS. 8C and 8D, each group lost one animal each due to body weight loss.
Figure 8F:
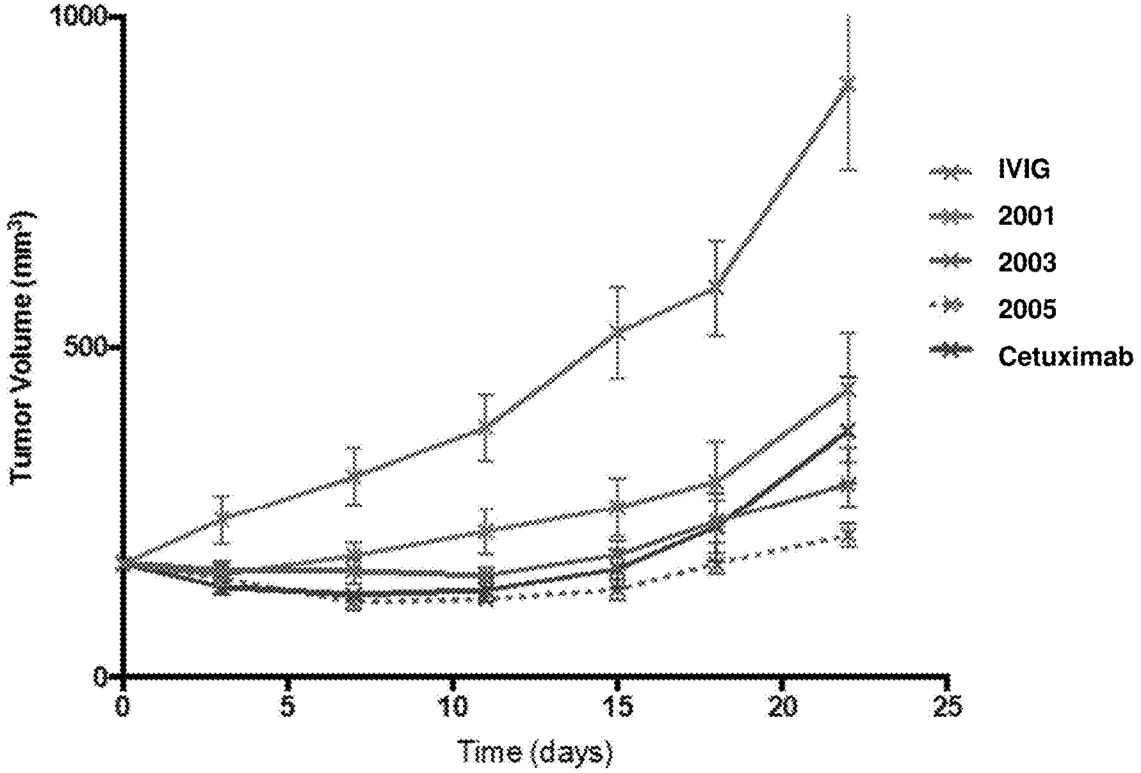

In situ imaging of the activation and binding of a non-labeled anti-EGFR activatable antibody 3954-2001-C225v5 on H292 lung cancer tumor tissue was conducted as follows: Frozen tissue sections were laid over glass slides. A solution containing non-labeled anti-EGFR activatable antibodies was applied on the tissue and incubated, e.g., for 1 hour at room temperature (about 22-24° C.) in an incubation buffer of 10 mM Hepes buffer pH 7.4, containing 150 mM NaCl, 10 μM $ZnCl_2$, 2 mM $CaCl_2$) and 0.005% Tween 20; activatable antibody at a concentration of about 1 μg/ml. The conditions of such an incubation can be adjusted to be conducive to the cleavage agent in the tissue section by, for example, varying the pH of the solution (e.g., within a range of about pH 7 to about pH 8.5), the temperature of the incubation (e.g., within a range of about 20° C. to about 40° C., e.g., room temperature or 37° C.), the incubation time (e.g., within a range of about 15 minutes to about 150 minutes, and/or the activatable antibody concentrations (e.g., within a range of about 0.05 μg/ml to about 10 μg/ml). The tissue was then extensively washed to remove non-bound material. The presence of activated antibody on the tissue was detected using a secondary anti-human IgG antibody labeled with AlexaFluor-647. The conditions of that detection can be adjusted to the detecting reagent and detection modality (e.g., fluorescently labeled). For example, when a fluorescent tag was used, the tissue was submitted to fluorescent microscopy. As shown in FIG. 6, anti-EGFR activatable antibody 3954-2001-C225v5 demonstrated staining with comparable intensity and pattern as parental anti-EGFR antibody. The fluorescent signal of anti-EGFR activatable antibody 3954-2001-C225v5 was significantly inhibited by pre-treatment of the tissue with a 1:100 dilution of broad spectrum inhibitor cocktail set III (539134, EMD Millipore, Billerica, Mass.) and 50 mM EDTA.

Example 4. Additional Matrix Metalloprotease (MMP) and Serine Protease (SP) Activatable Antibodies This Example demonstrates the generation and evaluation of additional substrate sequences that are activated in the presence of at least one matrix metalloprotease (MMP) and at least one serine protease.

The studies described herein used the following substrate sequences:

| CM1-CM2 Substrate | AA sequence | SEQ ID NO: |
|---|---|---|
| 2001 | ISSGLLSGRSDNH | 1 |
| 1004/LP'/0003 | AVGLLAPPGGTSTSGRSANPRG | 3 |

-continued

| CM1-CM2 Substrate | AA sequence | SEQ ID NO: |
|---|---|---|
| 1004/LP'/0001 | AVGLLAPPGGLSGRSDNH | 7 |
| 2003 | ISSGLLSGRSANPRG | 469 |
| 2004 | AVGLLAPPTSGRSANPRG | 470 |
| 2005 | AVGLLAPPSGRSANPRG | 471 |

The ability of substrates, 2001, 1004/LP'/0001, 1004/LP'/0003, 2003, 2004, or 2005 to be cleaved by human matriptase and/or human uPA was determined as described above in Example 2.

Substrate 2003 demonstrated approximately a 50-fold increase in the cleavage kinetics for matriptase as compared to substrate 2001, and substrate 2005 demonstrated approximately a 50-fold increase in the cleavage kinetics for matriptase as compared to substrate 1004/L1Y/0001.

Substrates 2003 and 2005 also demonstrated modest increases in the range of about 3- to 4-fold in uPA kinetics as compared to 2001 and 1004/LP'/0001, respectively. Substrates 2003 and 2005 were found to be cleaved in the presence of mouse uPA as well.

Substrates 2003, 2004, and 2005 were incorporated in the following activatable antibodies:

```
Anti-EGFR Heavy Chain:
Amino acid Sequence:
                                        (SEQ ID NO: 108)
QVQLKQSGPGLVQPSQSLSITCTVSGFSLTNYGVHWVRQSPGKGLEWLG

VIWSGGNTDYNTPFTSRLSINKDNSKSQVFFKMNSLQSQDTAIYYCARA

LTYYDYEFAYWGQGTLVTVSAASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK

Anti-EGFR Light Chain:
Amino acid Sequence:
                                        (SEQ ID NO: 111)
QILLTQSPVILSVSPGERVSFSCRASQSIGTNIHWYQQRTNGSPRLLIK

YASESISGIPSRFSGSGSGTDFTLSINSVESEDIADYYCQQNNNWPTTF

GAGTKLELKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Anti-EGFR 2003 Activatable Antibody Light Chain:
Amino acid Sequence:
                                        (SEQ ID NO: 472)
CISPRGCPDGPYVMYGSSGGSGGSGGSGISSGLLSGRSANPRGGSSGTQ

ILLTQSPVILSVSPGERVSFSCRASQSIGTNIHWYQQRTNGSPRLLIKY

ASESISGIPSRFSGSGSGTDFTLSINSVESEDIADYYCQQNNNWPTTFG
```

-continued

```
AGTKLELKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC
```

Anti-EGFR 2003 Activatable Antibody Light Chain with spacer sequence:
Amino acid Sequence:

(SEQ ID NO: 473)

```
QGQSGQCISPRGCPDGPYVMYGSSGGSGGSGGSGISSGLLSGRSANPRG

GSSGTQILLTQSPVILSVSPGERVSFSCRASQSIGTNIHWYQQRTNGSP

RLLIKYASESISGIPSRFSGSGSGTDFTLSINSVESEDIADYYCQQNNN

WPTTFGAGTKLELKRTVAAPSVFIFPPSDEQLKSGTASVVCLLNNFYPR

EAKVQWKVDNALQSGNSQESVTEQDSKDSTYSLSSTLTLSKADYEKHKV

YACEVTHQGLSSPVTKSFNRGEC
```

Anti-EGFR 2005 Activatable Antibody Light Chain:
Amino acid Sequence:

(SEQ ID NO: 474)

```
CISPRGCPDGPYVMYGSSGGSGGSGGSGAVGLLAPPSGRSANPRGGSSG

TQILLTQSPVILSVSPGERVSFSCRASQSIGTNIHWYQQRTNGSPRLLI

KYASESISGIPSRFSGSGSGTDFTLSINSVESEDIADYYCQQNNNWPTT

FGAGTKLELKRTVAAPSVFIFPPSDEQLKSGTASVVCLLNNFYPREAKV

QWKVDNALQSGNSQESVTEQDSKDSTYSLSSTLTLSKADYEKHKVYACE

VTHQGLSSPVTKSFNRGEC
```

Anti-EGFR 2005 Activatable Antibody Light Chain with spacer sequence:
Amino acid Sequence:

(SEQ ID NO: 475)

```
QGQSGQCISPRGCPDGPYVMYGSSGGSGGSGGSGAVGLLAPPSGRSANP

RGGSSGTQILLTQSPVILSVSPGERVSFSCRASQSIGTNIHWYQQRTNG

SPRLLIKYASESISGIPSRFSGSGSGTDFTLSINSVESEDIADYYCQQN

NNWPTTFGAGTKLELKRTVAAPSVFIFPPSDEQLKSGTASVVCLLNNFY

PREAKVQWKVDNALQSGNSQESVTEQDSKDSTYSLSSTLTLSKADYEKH

KVYACEVTHQGLSSPVTKSFNRGEC
```

The substrates used in all of the anti-EGFR activatable antibodies shown above were cleaved by human matriptase, by human uPA, by human matrix metalloprotease 14 (MMP14), and human matrix metalloprotease 9 (MMP9).

This section describes the evaluation of various anti-EGFR activatable antibodies shown above in a H292 tumor efficacy study using H292 xenograft tumors in nu/nu mice. The H292 tumor efficacy study is described in Example 2 and is also described in PCT Publication No. WO 2013/163631.

In this study, the mice were group and dosed as shown in the Table below using a control intravenous immunoglobulin (IVIG), the anti-EGFR antibody cetuximab, the anti-EGFR activatable antibody referred to herein as anti-EGFR 2001 activatable antibody, which includes the heavy chain sequence of SEQ ID NO: 108, and the light chain sequence of SEQ ID NO: 449; the anti-EGFR activatable antibody referred to herein as anti-EGFR 2003 activatable antibody, which includes the heavy chain sequence of SEQ ID NO: 108, and the light chain sequence of SEQ ID NO: 472; or the anti-EGFR activatable antibody referred to herein as anti-EGFR 2005 activatable antibody, which includes the heavy chain sequence of SEQ ID NO: 108, and the light chain sequence of SEQ ID NO: 474:

| Group | Count | Treatment | Dose (mg/kg) | Schedule |
|---|---|---|---|---|
| 1 | 8 | IVIG | 9 | Single Dose |
| 2 | 8 | Cetuximab | 9 | Single Dose |
| 3 | 8 | Anti-EGFR 2001 Activatable Antibody | 9 | Single Dose |
| 4 | 8 | Anti-EGFR 2003 Activatable Antibody | 9 | Single Dose |
| 5 | 8 | Anti-EGFR 2005 Activatable Antibody | 9 | Single Dose |

The efficacy of the substrates used in the anti-EGFR antibodies shown above was evaluated by measuring tumor volume (TV $mm^3$) at various time points post-administration. The results of this study are shown in FIGS. 8A-8F.

This section describes the evaluation of various anti-Jagged activatable antibodies in a toxicology study using methods similar to those described in Example 2 with regard to the data shown in FIG. 4.

In this study, toxicity was measured as a function of body weight (BW) loss in DBA/1 mice following administration with a control intravenous immunoglobulin (IVIG), a 20 mg/kg dose of the anti-Jagged antibody referred to herein as 4D11, which includes the heavy chain sequence of SEQ ID NO: 67 and the light chain sequence of SEQ ID NO: 162, a 10 mg/kg dose of the 4D11 antibody, a 5 mg/kg dose of the 4D11 antibody, the anti-Jagged activatable antibody referred to herein as anti-Jagged 2001 activatable antibody, which includes the heavy chain sequence of SEQ ID NO: 67, and the light chain sequence of SEQ ID NO: 420, the anti-Jagged activatable antibody referred to herein as anti-Jagged 1004/LP'/0001 activatable antibody, which includes the heavy chain sequence of SEQ ID NO: 67, and the light chain sequence of SEQ ID NO: 432, the anti-Jagged activatable antibody referred to herein as anti-Jagged 1004/LP'/0003 activatable antibody, which includes the heavy chain sequence of SEQ ID NO: 67, and the light chain sequence of SEQ ID NO: 424, the anti-Jagged activatable antibody referred to herein as anti-Jagged 2003 activatable antibody, which includes the heavy chain sequence of SEQ ID NO: 67, and the light chain sequence of SEQ ID NO: 477 shown below, and the anti-Jagged activatable antibody referred to herein as anti-Jagged 2005 activatable antibody, which includes the heavy chain sequence of SEQ ID NO: 67, and the light chain sequence of SEQ ID NO: 479 shown below.

Anti-Jagged 2003 activatable antibody Lc with spacer sequence
Amino Acid sequence (SEQ ID NO: 476)

```
QGQSGQCNIWLVGGDCRGWQGGSSGGSISSGLLSGRSANPRGGGSDIQMT

QSPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKVE

IKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPV

TKSFNRGEC
```

Anti-Jagged 2003 activatable antibody Lc
Amino Acid sequence (SEQ ID NO: 477)

```
CNIWLVGGDCRGWQGGSSGGSISSGLLSGRSANPRGGGSDIQMTQSPSSL

SASVGDRVTITCRASQSISSYLNWYQQKPGKAPKLLIYAASSLQSGVPSR
```

-continued

FSGSGSGTDFTLTISSLQPEDFATYYCQQTVVAPPLFGQGTKVEIKRTVA

APSVFIFPPSDEQLKSGTASVVCLLNNFYPREAKVQWKVDNALQSGNSQE

SVTEQDSKDSTYSLSSTLTLSKADYEKHKVYACEVTHQGLSSPVTKSFNR

GEC

Anti-Jagged 2005 activatable antibody Lc with spacer sequence
Amino Acid sequence
(SEQ ID NO: 478)

QGQSGQCNIWLVGGDCRGWQGGSSGGSAVGLLAPPSGRSANPRGGGSDIQ

MTQSPSSLSASVGDRVTITCRASQSISSYLNWYQQKPGKAPKLLIYAASS

LQSGVPSRFSGSGSGTDFTLTISSLQPEDFATYYCQQTVVAPPLFGQGTK

VEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSS

PVTKSFNRGEC

Anti-Jagged 2005 activatable antibody Lc
Amino Acid sequence
(SEQ ID NO: 479)

CNIWLVGGDCRGWQGGSSGGSAVGLLAPPSGRSANPRGGGSDIQMTQSPS

SLSASVGDRVTITCRASQSISSYLNWYQQKPGKAPKLLIYAASSLQSGVP

SRFSGSGSGTDFTLTISSLQPEDFATYYCQQTVVAPPLFGQGTKVEIKRT

VAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSF

NRGEC

In the study depicted in FIG. 9, the mice were group and dosed as shown in the Table below:

| Group | Count | Treatment | Dose (mg/kg) | Schedule | Route |
|---|---|---|---|---|---|
| 1 | 3 | IVIG | — | Single dose | IP |
| 2 | 3 | 4D11 | 20 mg/kg | Single dose | IP |

-continued

| Group | Count | Treatment | Dose (mg/kg) | Schedule | Route |
|---|---|---|---|---|---|
| 3 | 3 | 4D11 | 10 mg/kg | Single dose | IP |
| 4 | 3 | 4D11 | 5 mg/kg | Single dose | IP |
| 5 | 3 | Anti-Jagged 2001 Activatable Antibody | 20 mg/kg | Single dose | IP |
| 6 | 3 | Anti-Jagged 1004/LP'/0001 Activatable Antibody | 20 mg/kg | Single dose | IP |
| 7 | 3 | Anti-Jagged 2003 Activatable Antibody | 20 mg/kg | Single dose | IP |
| 8 | 3 | Anti-Jagged 2005 Activatable Antibody | 20 mg/kg | Single dose | IP |

Figure 9:
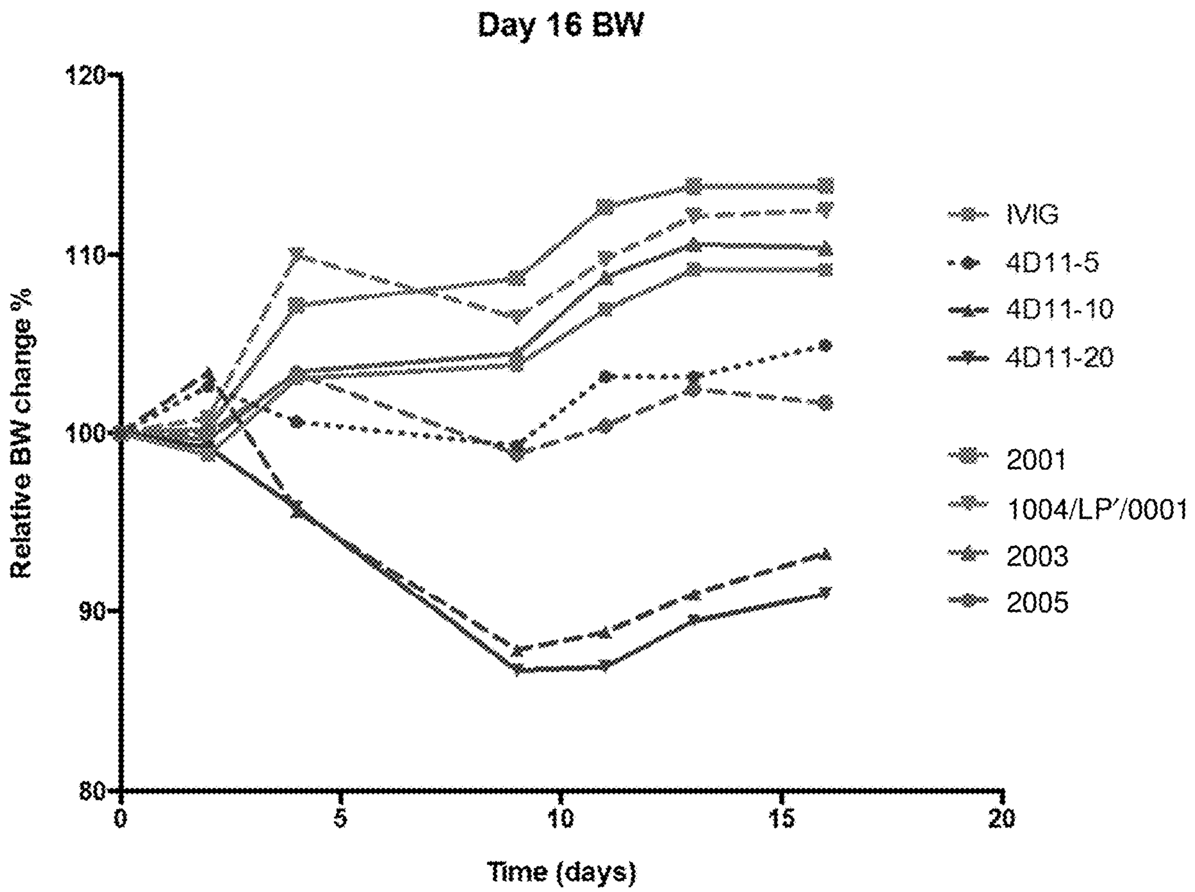
FIG. 9 is a graph depicting toxicity as measured by body weight (BW) loss following administration with an isotype control intravenous immunoglobulin (IVIG), a 20 mg/kg dose of the anti-Jagged antibody referred to herein as 4D11, which includes the heavy chain sequence of SEQ ID NO: 67 and the light chain sequence of SEQ ID NO: 162, a 10 mg/kg dose of the 4D11 antibody, a 5 mg/kg dose of the 4D11 antibody, the anti-Jagged activatable antibody referred to herein as anti-Jagged 2001 activatable antibody, which includes the heavy chain sequence of SEQ ID NO: 67, and the light chain sequence of SEQ ID NO: 420, the anti-Jagged activatable antibody referred to herein as anti-Jagged 1004/LP'/0001 activatable antibody, which includes the heavy chain sequence of SEQ ID NO: 67, and the light chain sequence of SEQ ID NO: 432, the anti-Jagged activatable antibody referred to herein as anti-Jagged 2003 activatable antibody, which includes the heavy chain sequence of SEQ ID NO: 67, and the light chain sequence of SEQ ID NO: 477, and the anti-Jagged activatable antibody referred to herein as anti-Jagged 2005 activatable antibody, which includes the heavy chain sequence of SEQ ID NO: 67, and the light chain sequence of SEQ ID NO: 479. The results are shown as relative body weight (BW) change percent (%) at various time points during the study.

The results are shown in FIG. 9 as relative body weight (BW) change percent (%) at various time points during the study.

Figure 10:
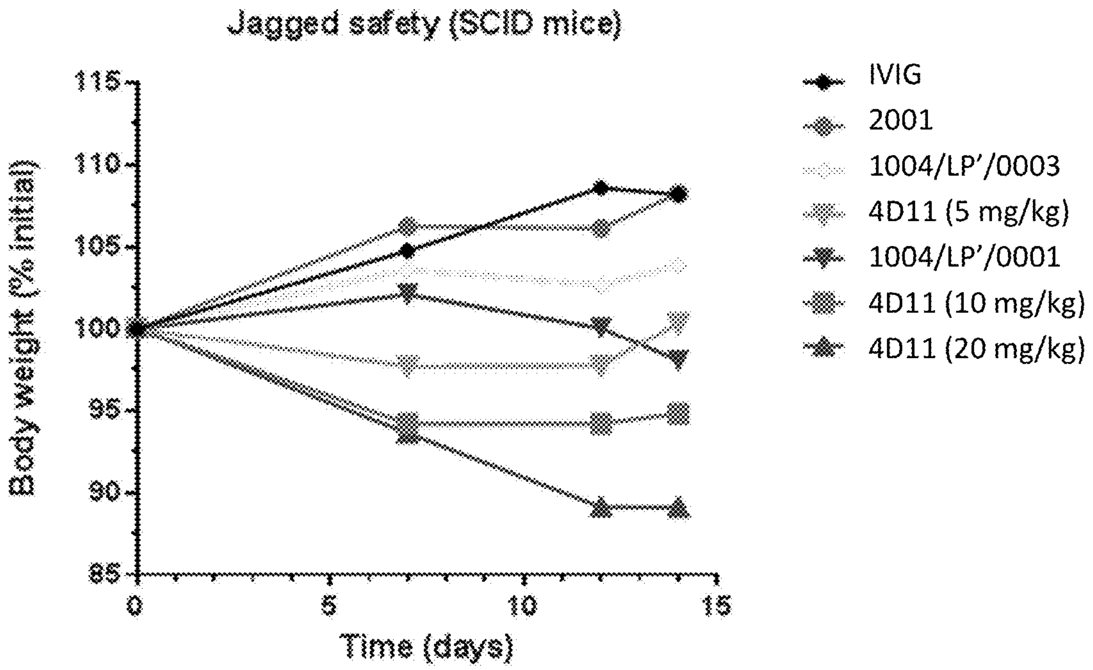
FIG. 10 is a graph depicting toxicity as measured by body weight (BW) loss following administration with an isotype control intravenous immunoglobulin (IVIG), a 20 mg/kg dose of the anti-Jagged antibody referred to herein as 4D11, which includes the heavy chain sequence of SEQ ID NO: 67 and the light chain sequence of SEQ ID NO: 162, a 10 mg/kg dose of the 4D11 antibody, a 5 mg/kg dose of the 4D11 antibody, the anti-Jagged activatable antibody referred to herein as anti-Jagged 2001 activatable antibody ("2001"), which includes the heavy chain sequence of SEQ ID NO: 67, and the light chain sequence of SEQ ID NO: 420, the anti-Jagged activatable antibody referred to herein as anti-Jagged 1004/LP'/0001 activatable antibody, which includes the heavy chain sequence of SEQ ID NO: 67, and the light chain sequence of SEQ ID NO: 432, and the anti-Jagged activatable antibody referred to herein as anti-Jagged 1004/LP'/0003 activatable antibody, which includes the heavy chain sequence of SEQ ID NO: 67, and the light chain sequence of SEQ ID NO: 424. The results are shown as relative body weight (BW) change percent (%) at various time points during the study.
Figure 11A:
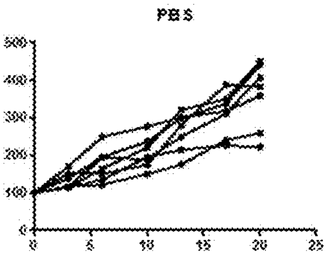
FIGS. 11A, 11B, 11C, 11D, 11E, 11F, 11G, and 11H and FIG. 12 are a series of graphs depicting the efficacy of various substrates of the disclosure when incorporated in activatable anti-EGFR antibodies of the disclosure. Efficacy of the substrates was evaluated by measuring tumor volume (TV $mm^3$) at various time points post-administration.
Figure 11B:
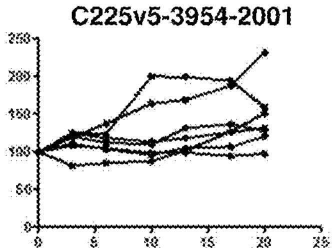
Figure 11C:
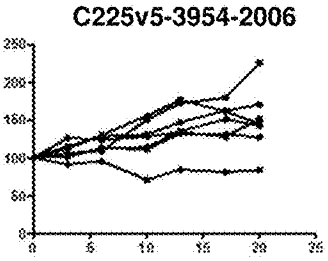
Figure 11D:
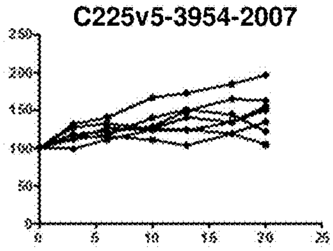
Figure 11E:
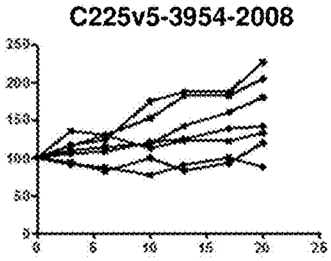
Figure 11F:
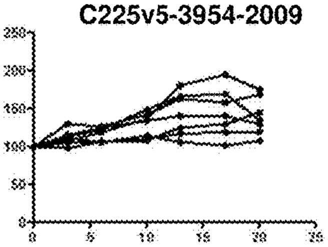
Figure 11G:
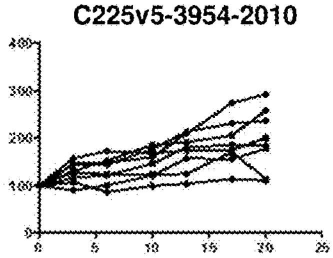
Figure 11H:
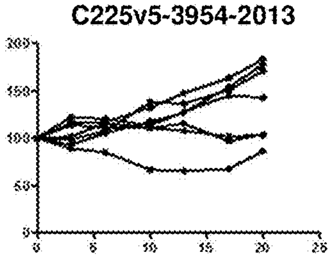
Figure 12:
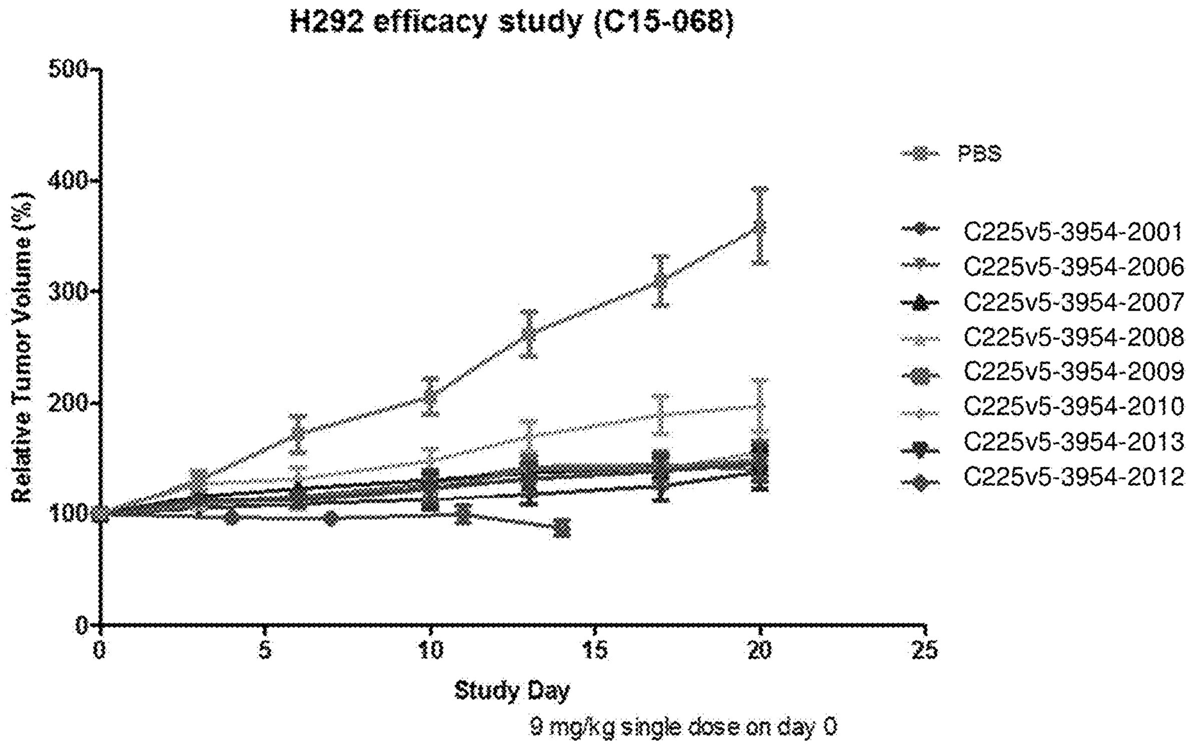

The results are shown in FIG. 10 as relative body weight (BW) change percent (%) at various time points during the study.

As shown in FIGS. 8A-8F, FIG. 9, and FIG. 10, activatable antibodies including the cleavable substrates of the disclosure are safe and efficacious. In particular, the 2003 substrate has demonstrated efficacy comparable to the 2001 substrate and safety comparable to IVIG, and the 2005 substrate has demonstrated efficacy comparable to parental and safety comparable to parental dosed 4-fold lower.

Example 5. Additional Matrix Metalloprotease (MMP) and Serine Protease (SP) Activatable Antibodies This Example demonstrates the generation and evaluation of additional substrate sequences that are activated in the presence of at least one matrix metalloprotease (MMP) and at least one serine protease.

The studies described herein used the following substrate sequences:

| CM1-CM2 Substrate | Amino Acid Sequence | Nucleotide Sequence |
|---|---|---|
| 2006 | ISSGLLSGRSDDH (SEQ ID NO: 483) | ATATCGAGTGGATTGCTGTCTGGCAGATCTGACGATCAC (SEQ ID NO: 491) |
| 2007 | ISSGLLSGRSDIH (SEQ ID NO: 484) | ATATCGAGTGGATTGCTGTCTGGCAGATCTGACATACAC (SEQ ID NO: 492) |
| 2008 | ISSGLLSGRSDQH (SEQ ID NO: 485) | ATATCGAGTGGATTGCTGTCTGGCAGATCTGACCAACAC (SEQ ID NO: 493) |
| 2009 | ISSGLLSGRSDTH (SEQ ID NO: 486) | ATATCGAGTGGATTGCTGTCTGGCAGATCTGACACTCAC (SEQ ID NO: 494) |
| 2010 | ISSGLLSGRSDYH (SEQ ID NO: 487) | ATATCGAGTGGATTGCTGTCTGGCAGATCTGACTATCAC (SEQ ID NO: 495) |
| 2011 | ISSGLLSGRSDNP (SEQ ID NO: 488) | ATTAGCTCAGGCCTTCTTAGCGGCCGCAGCGACAATCCC (SEQ ID NO: 496) |
| 2012 | ISSGLLSGRSANP (SEQ ID NO: 489) | ATATCGAGTGGATTGCTGTCTGGCAGATCTGCTAATCCC (SEQ ID NO: 497) |
| 2013 | ISSGLLSGRSANI (SEQ ID NO: 490) | ATATCGAGTGGATTGCTGTCTGGCAGATCTGCTAATATA (SEQ ID NO: 498) |
| 2014 | ISSGLLSGRSDNI (SEQ ID NO: 555) | ATATCGAGTGGATTGCTGTCTGGCAGATCTGACAATATA (SEQ ID NO: 556) |

-continued

| CM1-CM2 Substrate | Amino Acid Sequence | Nucleotide Sequence |
|---|---|---|
| 3006 | AVGLLAPPGGLSGRSDDH (SEQ ID NO: 515) | GCTGTGGGACTGCTGGCTCCTCCTGGTGGCCTGTCT GGCAGATCTGACGATCAC (SEQ ID NO: 523) |
| 3007 | AVGLLAPPGGLSGRSDIH (SEQ ID NO: 516) | GCTGTGGGACTGCTGGCTCCTCCTGGTGGCCTGTCT GGCAGATCTGACATACAC (SEQ ID NO: 524) |
| 3008 | AVGLLAPPGGLSGRSDQH (SEQ ID NO: 517) | GCTGTGGGACTGCTGGCTCCTCCTGGTGGCCTGTCT GGCAGATCTGACCAACAC (SEQ ID NO: 525) |
| 3009 | AVGLLAPPGGLSGRSDTH (SEQ ID NO: 518) | GCTGTGGGACTGCTGGCTCCTCCTGGTGGCCTGTCT GGCAGATCTGACACTCAC (SEQ ID NO: 526) |
| 3010 | AVGLLAPPGGLSGRSDYH (SEQ ID NO: 519) | GCTGTGGGACTGCTGGCTCCTCCTGGTGGCCTGTCT GGCAGATCTGACTATCAC (SEQ ID NO: 527) |
| 3011 | AVGLLAPPGGLSGRSDNP (SEQ ID NO: 520) | GCTGTGGGACTGCTGGCTCCTCCTGGTGGCCTGTCT GGCAGATCTGACAATCCC (SEQ ID NO: 528) |
| 3012 | AVGLLAPPGGLSGRSANP (SEQ ID NO: 521) | GCTGTGGGACTGCTGGCTCCTCCTGGTGGCCTGTCT GGCAGATCTGCTAATCCC (SEQ ID NO: 529) |
| 3013 | AVGLLAPPGGLSGRSANI (SEQ ID NO: 522) | GCTGTGGGACTGCTGGCTCCTCCTGGTGGCCTGTCT GGCAGATCTGCTAATATA (SEQ ID NO: 530) |
| 3014 | AVGLLAPPGGLSGRSDNI (SEQ ID NO: 557) | GCTGTGGGACTGCTGGCTCCTCCTGGTGGCCTGTCTGGCA GATCTGACAATATA (SEQ ID NO: 558) |

Those of ordinary skill in the art will appreciate that the nucleotide sequences presented herein are exemplary, and the skilled artisan can also use other codon combinations and/or degenerate nucleotide sequence(s) to express the same peptide sequence.

Substrates 2006-2014 and substrates 3006-3014 were incorporated in the following activatable antibodies:

Anti-EGFR Heavy Chain:
Amino acid Sequence:
(SEQ ID NO: 108)

QVQLKQSGPGLVQPSQSLSITCTVSGFSLTNYGVHWVRQSPGKGLEWLG

VIWSGGNTDYNTPFTSRLSINKDNSKSQVFFKMNSLQSQDTAIYYCARA

LTYYDYEFAYWGQGTLVTVSAASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK

Anti-EGFR Light Chain:
Amino acid Sequence:
(SEQ ID NO: 111)

QILLTQSPVILSVSPGERVSFSCRASQSIGTNIHWYQQRTNGSPRLLIK

YASESISGIPSRFSGSGSGTDFTLSINSVESEDIADYYCQQNNNWPTTF

GAGTKLELKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

-continued

Anti-EGFR 2006 Activatable Antibody Light Chain:
Amino acid Sequence:
(SEQ ID NO: 499)

CISPRGCPDGPYVMYGSSGGSGGSGGSGISSGLLSGRSDDHGSSGTQIL

LTQSPVILSVSPGERVSFSCRASQSIGTNIHWYQQRTNGSPRLLIKYAS

ESISGIPSRFSGSGSGTDFTLSINSVESEDIADYYCQQNNNWPTTFGAG

TKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQ

GLSSPVTKSFNRGEC

Anti-EGFR 2007 Activatable Antibody Light Chain:
Amino acid Sequence:
(SEQ ID NO: 500)

CISPRGCPDGPYVMYGSSGGSGGSGGSGISSGLLSGRSDIHGSSGTQIL

LTQSPVILSVSPGERVSFSCRASQSIGTNIHWYQQRTNGSPRLLIKYAS

ESISGIPSRFSGSGSGTDFTLSINSVESEDIADYYCQQNNNWPTTFGAG

TKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQ

GLSSPVTKSFNRGEC

Anti-EGFR 2008 Activatable Antibody Light Chain:
Amino acid Sequence:
(SEQ ID NO: 501)

CISPRGCPDGPYVMYGSSGGSGGSGGSGISSGLLSGRSDQHGSSGTQIL

LTQSPVILSVSPGERVSFSCRASQSIGTNIHWYQQRTNGSPRLLIKYAS

ESISGIPSRFSGSGSGTDFTLSINSVESEDIADYYCQQNNNWPTTFGAG

TKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQ

GLSSPVTKSFNRGEC

-continued

Anti-EGFR 2009 Activatable Antibody Light Chain:
Amino acid Sequence:
(SEQ ID NO: 502)
CISPRGCPDGPYVMYGSSGGSGGSGGSGISSGLLSGRSDTHGSSGTQIL
LTQSPVILSVSPGERVSFSCRASQSIGTNIHWYQQRTNGSPRLLIKYAS
ESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC Anti-EGFR 2010 Activatable Antibody Light Chain:
Amino acid Sequence:
(SEQ ID NO: 503)
CISPRGCPDGPYVMYGSSGGSGGSGGSGISSGLLSGRSDYHGSSGTQIL
LTQSPVILSVSPGERVSFSCRASQSIGTNIHWYQQRTNGSPRLLIKYAS
ESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC Anti-EGFR 2011 Activatable Antibody Light Chain:
Amino acid Sequence:
(SEQ ID NO: 504)
CISPRGCPDGPYVMYGSSGGSGGSGGSGISSGLLSGRSDNPGSSGTQIL
LTQSPVILSVSPGERVSFSCRASQSIGTNIHWYQQRTNGSPRLLIKYAS
ESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC Anti-EGFR 2012 Activatable Antibody Light Chain:
Amino acid Sequence:
(SEQ ID NO: 505)
CISPRGCPDGPYVMYGSSGGSGGSGGSGISSGLLSGRSANPGSSGTQIL
LTQSPVILSVSPGERVSFSCRASQSIGTNIHWYQQRTNGSPRLLIKYAS
ESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC Anti-EGFR 2013 Activatable Antibody Light Chain:
Amino acid Sequence:
(SEQ ID NO: 506)
CISPRGCPDGPYVMYGSSGGSGGSGGSGISSGLLSGRSANIGSSGTQIL
LTQSPVILSVSPGERVSFSCRASQSIGTNIHWYQQRTNGSPRLLIKYAS
ESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC Anti-EGFR 2014 Activatable Antibody Light Chain:
Amino acid Sequence:
(SEQ ID NO: 559)
CISPRGCPDGPYVMYGSSGGSGGSGGSGISSGLLSGRSDNIGSSGTQIL
LTQSPVILSVSPGERVSFSCRASQSIGTNIHWYQQRTNGSPRLLIKYAS -continued ESISGIPSRFSGSGSGTDFTLSINSVESEDIADYYCQQNNNWPTTFGAG
TKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQ
GLSSPVTKSFNRGEC Anti-EGFR 3006 Activatable Antibody Light Chain:
Amino acid Sequence:
(SEQ ID NO: 531)
CISPRGCPDGPYVMYGSSGGSGGSGGSGAVGLLAPPGGLSGRSDDHGSS
GTQILLTQSPVILSVSPGERVSFSCRASQSIGTNIHWYQQRTNGSPRLL
IKYASESISGIPSRFSGSGSGTDFTLSINSVESEDIADYYCQQNNNWPT
TFGAGTKLELKRTVAAPSVFIFPPSDEQLKSGTASVVCLLNNFYPREAK
VQWKVDNALQSGNSQESVTEQDSKDSTYSLSSTLTLSKADYEKHKVYAC
EVTHQGLSSPVTKSFNRGEC Anti-EGFR 3007 Activatable Antibody Light Chain:
Amino acid Sequence:
(SEQ ID NO: 532)
CISPRGCPDGPYVMYGSSGGSGGSGGSGAVGLLAPPGGLSGRSDIHGSS
GTQILLTQSPVILSVSPGERVSFSCRASQSIGTNIHWYQQRTNGSPRLL
IKYASESISGIPSRFSGSGSGTDFTLSINSVESEDIADYYCQQNNNWPT
TFGAGTKLELKRTVAAPSVFIFPPSDEQLKSGTASVVCLLNNFYPREAK
VQWKVDNALQSGNSQESVTEQDSKDSTYSLSSTLTLSKADYEKHKVYAC
EVTHQGLSSPVTKSFNRGEC Anti-EGFR 3008 Activatable Antibody Light Chain:
Amino acid Sequence:
(SEQ ID NO: 533)
CISPRGCPDGPYVMYGSSGGSGGSGGSGAVGLLAPPGGLSGRSDQHGSS
GTQILLTQSPVILSVSPGERVSFSCRASQSIGTNIHWYQQRTNGSPRLL
IKYASESISGIPSRFSGSGSGTDFTLSINSVESEDIADYYCQQNNNWPT
TFGAGTKLELKRTVAAPSVFIFPPSDEQLKSGTASVVCLLNNFYPREAK
VQWKVDNALQSGNSQESVTEQDSKDSTYSLSSTLTLSKADYEKHKVYAC
EVTHQGLSSPVTKSFNRGEC Anti-EGFR 3009 Activatable Antibody Light Chain:
Amino acid Sequence:
(SEQ ID NO: 534)
CISPRGCPDGPYVMYGSSGGSGGSGGSGAVGLLAPPGGLSGRSDTHGSS
GTQILLTQSPVILSVSPGERVSFSCRASQSIGTNIHWYQQRTNGSPRLL
IKYASESISGIPSRFSGSGSGTDFTLSINSVESEDIADYYCQQNNNWPT
TFGAGTKLELKRTVAAPSVFIFPPSDEQLKSGTASVVCLLNNFYPREAK
VQWKVDNALQSGNSQESVTEQDSKDSTYSLSSTLTLSKADYEKHKVYAC
EVTHQGLSSPVTKSFNRGEC Anti-EGFR 3010 Activatable Antibody Light Chain:
Amino acid Sequence:
(SEQ ID NO: 535)
CISPRGCPDGPYVMYGSSGGSGGSGGSGAVGLLAPPGGLSGRSDYHGSS
GTQILLTQSPVILSVSPGERVSFSCRASQSIGTNIHWYQQRTNGSPRLL
IKYASESISGIPSRFSGSGSGTDFTLSINSVESEDIADYYCQQNNNWPT
TFGAGTKLELKRTVAAPSVFIFPPSDEQLKSGTASVVCLLNNFYPREAK -continued

VQWKVDNALQSGNSQESVTEQDSKDSTYSLSSTLTLSKADYEKHKVYAC

EVTHQGLSSPVTKSFNRGEC

Anti-EGFR 3011 Activatable Antibody Light Chain: Amino acid Sequence:

(SEQ ID NO: 536)

CISPRGCPDGPYVMYGSSGGSGGSGGSGAVGLLAPPGGLSGRSDNPGSS

GTQILLTQSPVILSVSPGERVSFSCRASQSIGTNIHWYQQRTNGSPRLL

IKYASESISGIPSRFSGSGSGTDFTLSINSVESEDIADYYCQQNNNWPT

TFGAGTKLELKRTVAAPSVFIFPPSDEQLKSGTASVVCLLNNFYPREAK

VQWKVDNALQSGNSQESVTEQDSKDSTYSLSSTLTLSKADYEKHKVYAC

EVTHQGLSSPVTKSFNRGEC

Anti-EGFR 3012 Activatable Antibody Light Chain: Amino acid Sequence:

(SEQ ID NO: 537)

CISPRGCPDGPYVMYGSSGGSGGSGGSGAVGLLAPPGGLSGRSANPGSS

GTQILLTQSPVILSVSPGERVSFSCRASQSIGTNIHWYQQRTNGSPRLL

IKYASESISGIPSRFSGSGSGTDFTLSINSVESEDIADYYCQQNNNWPT

TFGAGTKLELKRTVAAPSVFIFPPSDEQLKSGTASVVCLLNNFYPREAK

VQWKVDNALQSGNSQESVTEQDSKDSTYSLSSTLTLSKADYEKHKVYAC

EVTHQGLSSPVTKSFNRGEC

Anti-EGFR 3013 Activatable Antibody Light Chain: Amino acid Sequence:

(SEQ ID NO: 538)

CISPRGCPDGPYVMYGSSGGSGGSGGSGAVGLLAPPGGLSGRSANIGSS

GTQILLTQSPVILSVSPGERVSFSCRASQSIGTNIHWYQQRTNGSPRLL

IKYASESISGIPSRFSGSGSGTDFTLSINSVESEDIADYYCQQNNNWPT

TFGAGTKLELKRTVAAPSVFIFPPSDEQLKSGTASVVCLLNNFYPREAK

VQWKVDNALQSGNSQESVTEQDSKDSTYSLSSTLTLSKADYEKHKVYAC

EVTHQGLSSPVTKSFNRGEC

Anti-EGFR 3014 Activatable Antibody Light Chain: Amino acid Sequence:

(SEQ ID NO: 560)

CISPRGCPDGPYVMYGSSGGSGGSGGSGAVGLLAPPGGLSGRSDNIGSS

GTQILLTQSPVILSVSPGERVSFSCRASQSIGTNIHWYQQRTNGSPRLL

IKYASESISGIPSRFSGSGSGTDFTLSINSVESEDIADYYCQQNNNWPT

TFGAGTKLELKRTVAAPSVFIFPPSDEQLKSGTASVVCLLNNFYPREAK

VQWKVDNALQSGNSQESVTEQDSKDSTYSLSSTLTLSKADYEKHKVYAC

EVTHQGLSSPVTKSFNRGEC

All eighteen EGFR activatable antibodies containing substrate sequences of substrate 2006 (SEQ ID NO: 483), substrate 2007 (SEQ ID NO: 484), substrate 2008 (SEQ ID NO: 485), substrate 2009 (SEQ ID NO: 486), substrate 2010 (SEQ ID NO: 487), substrate 2011 (SEQ ID NO: 488), substrate 2012 (SEQ ID NO: 489), substrate 2013 (SEQ ID NO: 490), 2014 (SEQ ID NO: 555), substrate 3006 (SEQ ID NO: 515), substrate 3007 (SEQ ID NO: 516), substrate 3008 (SEQ ID NO: 517), substrate 3009 (SEQ ID NO: 518), substrate 3010 (SEQ ID NO: 519), substrate 3011 (SEQ ID NO: 520), substrate 3012 (SEQ ID NO: 521), substrate 3013 (SEQ ID NO: 522), or substrate 3014 (SEQ ID NO: 557) also comprised the masking moiety comprising the amino acid sequence CISPRGCPDGPYVMY (SEQ ID NO: 168) and anti-EGFR antibody C225v5 antibody comprising a light chain (SEQ ID NO: 111) and a heavy chain (SEQ ID NO: 108). The configuration of the light chain of the activatable antibody was masking moiety-substrate-light chain of C225v5.

Cleavage of anti-EGFR activatable antibodies comprising substrates 2001, 2006-2010 and 2012 by human matriptase using techniques similar to those described herein exhibited a range of $k_{cat}/K_m$ values ranging from 6E+02 to 2E+04. Cleavage of anti-EGFR activatable antibodies comprising substrates 2001, 2006-2010, 2012 and 2013 by human matrix metalloprotease 14 (MMP14) using techniques similar to those described herein exhibited a range of $k_{cat}/K_m$ values ranging from 1E+04 to 5E+04. In vivo, these antibodies also exhibited comparable 4-day stability in both normal and tumor-bearing mice using techniques similar to those described herein.

This section describes the evaluation of various anti-EGFR activatable antibodies shown above in a H292 tumor efficacy study using H292 xenograft tumors in nu/nu mice. The H292 tumor efficacy study is described in Example 2 and is also described in PCT Publication No. WO 2013/163631, the contents of each of which are hereby incorporated by reference in their entireties.

In this study, the mice were group and dosed as shown in the Table below using a control PBS, activatable antibody, which includes the heavy chain sequence of SEQ ID NO: 108, and the light chain sequence of SEQ ID NO: 111; the anti-EGFR C225v5-3954-2001 activatable antibody, anti-EGFR C225v5-3954-2006 activatable antibody, anti-EGFR C225v5-3954-2007 activatable antibody, etc., as shown in the Table below:

| Group | Count | Treatment | Dose (mg/kg) | Schedule |
|---|---|---|---|---|
| 1 | 8 | IVIG | 9 | Single Dose |
| 2 | 8 | C225v5-3954-2001 | 9 | Single Dose |
| 3 | 8 | C225v5-3954-2007 | 9 | Single Dose |
| 4 | 8 | C225v5-3954-2006 | 9 | Single Dose |
| 5 | 8 | C225v5-3954-2008 | 9 | Single Dose |
| 6 | 8 | C225v5-3954-2009 | 9 | Single Dose |
| 7 | 8 | C225v5-3954-2010 | 9 | Single Dose |
| 8 | 8 | C225v5-3954-2012 | 9 | Single Dose |
| 9 | 8 | C225v5-3954-2013 | 9 | Single Dose |

The efficacy of the substrates used in the anti-EGFR antibodies shown above was evaluated by measuring tumor volume (TV $mm^3$) at various time points post-administration. The results of this study are shown in FIGS. 11A-11H and 12.

This section describes the evaluation of various anti-Jagged activatable antibodies in a toxicology study using methods similar to those described in Example 2 with regard to the data shown in FIG. 4.

In this study, 20 mg/kg dose of the anti-Jagged antibody referred to herein as 4D11, which includes the heavy chain sequence of SEQ ID NO: 67 and the light chain sequence of SEQ ID NO: 162, a 10 mg/kg dose of the 4D11 antibody, a 5 mg/kg dose of the 4D11 antibody, the anti-Jagged activatable antibody referred to herein as anti-Jagged 2006 activatable antibody, which includes the heavy chain sequence of SEQ ID NO: 67, and the light chain sequence of SEQ ID NO: 507-514 shown below.

Anti-Jagged 2006 activatable antibody Lc Amino Acid sequence (SEQ ID NO: 507)

CNIWLVGGDCRGWQGGSSGGSISSGLLSGRSDDHGGGSDIQMTQSPSSL
SASVGDRVTITCRASQSISSYLNWYQQKPGKAPKLLIYAASSLQSGVPS
RFSGSGSGTDFTLTISSLQPEDFATYYCQQTVVAPPLFGQGTKVEIKRT
VAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTK
SFNRGEC

Anti-Jagged 2007 activatable antibody Lc Amino Acid sequence (SEQ ID NO: 508)

CNIWLVGGDCRGWQGGSSGGSISSGLLSGRSDIHGGGSDIQMTQSPSSL
SASVGDRVTITCRASQSISSYLNWYQQKPGKAPKLLIYAASSLQSGVPS
RFSGSGSGTDFTLTISSLQPEDFATYYCQQTVVAPPLFGQGTKVEIKRT
VAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTK
SFNRGEC

Anti-Jagged 2008 activatable antibody Lc Amino Acid sequence (SEQ ID NO: 509)

CNIWLVGGDCRGWQGGSSGGSISSGLLSGRSDQHGGGSDIQMTQSPSSL
SASVGDRVTITCRASQSISSYLNWYQQKPGKAPKLLIYAASSLQSGVPS
RFSGSGSGTDFTLTISSLQPEDFATYYCQQTVVAPPLFGQGTKVEIKRT
VAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTK
SFNRGEC

Anti-Jagged 2009 activatable antibody Lc Amino Acid sequence (SEQ ID NO: 510)

CNIWLVGGDCRGWQGGSSGGSISSGLLSGRSDTHGGGSDIQMTQSPSSL
SASVGDRVTITCRASQSISSYLNWYQQKPGKAPKLLIYAASSLQSGVPS
RFSGSGSGTDFTLTISSLQPEDFATYYCQQTVVAPPLFGQGTKVEIKRT
VAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTK
SFNRGEC

Anti-Jagged 2010 activatable antibody Lc Amino Acid sequence (SEQ ID NO: 511)

CNIWLVGGDCRGWQGGSSGGSISSGLLSGRSDYHGGGSDIQMTQSPSSL
SASVGDRVTITCRASQSISSYLNWYQQKPGKAPKLLIYAASSLQSGVPS
RFSGSGSGTDFTLTISSLQPEDFATYYCQQTVVAPPLFGQGTKVEIKRT
VAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTK
SFNRGEC

Anti-Jagged 2011 activatable antibody Lc Amino Acid sequence (SEQ ID NO: 512)

CNIWLVGGDCRGWQGGSSGGSISSGLLSGRSDNPGGGSDIQMTQSPSSL
SASVGDRVTITCRASQSISSYLNWYQQKPGKAPKLLIYAASSLQSGVPS

-continued

RFSGSGSGTDFTLTISSLQPEDFATYYCQQTVVAPPLFGQGTKVEIKRT
VAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTK
SFNRGEC

Anti-Jagged 2012 activatable antibody Lc Amino Acid sequence (SEQ ID NO: 513)

CNIWLVGGDCRGWQGGSSGGSISSGLLSGRSANPGGGSDIQMTQSPSSL
SASVGDRVTITCRASQSISSYLNWYQQKPGKAPKLLIYAASSLQSGVPS
RFSGSGSGTDFTLTISSLQPEDFATYYCQQTVVAPPLFGQGTKVEIKRT
VAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTK
SFNRGEC

Anti-Jagged 2013 activatable antibody Lc Amino Acid sequence (SEQ ID NO: 514)

CNIWLVGGDCRGWQGGSSGGSISSGLLSGRSANIGGGSDIQMTQSPSSL
SASVGDRVTITCRASQSISSYLNWYQQKPGKAPKLLIYAASSLQSGVPS
RFSGSGSGTDFTLTISSLQPEDFATYYCQQTVVAPPLFGQGTKVEIKRT
VAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTK
SFNRGEC

Anti-Jagged 2014 activatable antibody Lc Amino Acid sequence (SEQ ID NO: 561)

CNIWLVGGDCRGWQGGSSGGSISSGLLSGRSDNIGGGSDIQMTQSPSSL
SASVGDRVTITCRASQSISSYLNWYQQKPGKAPKLLIYAASSLQSGVPS
RFSGSGSGTDFTLTISSLQPEDFATYYCQQTVVAPPLFGQGTKVEIKRT
VAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTK
SFNRGEC

Anti-Jagged 3006 activatable antibody Lc Amino Acid sequence (SEQ ID NO: 539)

CNIWLVGGDCRGWQGGSSGGSAVGLLAPPGGLSGRSDDHGGGSDIQMTQ
SPSSLSASVGDRVTITCRASQSISSYLNWYQQKPGKAPKLLIYAASSLQ
SGVPSRFSGSGSGTDFTLTISSLQPEDFATYYCQQTVVAPPLFGQGTKV
EIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLS
SPVTKSFNRGEC

Anti-Jagged 3007 activatable antibody Lc Amino Acid sequence (SEQ ID NO: 540)

CNIWLVGGDCRGWQGGSSGGSAVGLLAPPGGLSGRSDIHGGGSDIQMTQ
SPSSLSASVGDRVTITCRASQSISSYLNWYQQKPGKAPKLLIYAASSLQ
SGVPSRFSGSGSGTDFTLTISSLQPEDFATYYCQQTVVAPPLFGQGTKV

-continued

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

Anti-Jagged 3008 activatable antibody Lc
Amino Acid sequence (SEQ ID NO: 541)

CNIWLVGGDCRGWQGGSSGGSAVGLLAPPGGLSGRSDQHGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

Anti-Jagged 3009 activatable antibody Lc
Amino Acid sequence (SEQ ID NO: 542)

CNIWLVGGDCRGWQGGSSGGSAVGLLAPPGGLSGRSDTHGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

Anti-Jagged 3010 activatable antibody Lc
Amino Acid sequence (SEQ ID NO: 543)

CNIWLVGGDCRGWQGGSSGGSAVGLLAPPGGLSGRSDYHGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

Anti-Jagged 3011 activatable antibody Lc
Amino Acid sequence (SEQ ID NO: 544)

CNIWLVGGDCRGWQGGSSGGSAVGLLAPPGGLSGRSDNPGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

Anti-Jagged 3012 activatable antibody Lc
Amino Acid sequence (SEQ ID NO: 545)

CNIWLVGGDCRGWQGGSSGGSAVGLLAPPGGLSGRSANPGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

-continued

Anti-Jagged 3013 activatable antibody Lc
Amino Acid sequence (SEQ ID NO: 546)

CNIWLVGGDCRGWQGGSSGGSAVGLLAPPGGLSGRSANIGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

Anti-Jagged 3014 activatable antibody Lc
Amino Acid sequence (SEQ ID NO: 562)

CNIWLVGGDCRGWQGGSSGGSAVGLLAPPGGLSGRSDNIGGGSDIQMTQ

SPSSLSASVGDRVTITCRASQSISSYLNWYQQKPGKAPKLLIYAASSLQ

SGVPSRFSGSGSGTDFTLTISSLQPEDFATYYCQQTVVAPPLFGQGTKV

EIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLS

SPVTKSFNRGEC

All eighteen anti-Jagged activatable antibodies containing substrate sequences of substrate 2006 (SEQ ID NO: 483), substrate 2007 (SEQ ID NO: 484), substrate 2008 (SEQ ID NO: 485), substrate 2009 (SEQ ID NO: 486), substrate 2010 (SEQ ID NO: 487), substrate 2011 (SEQ ID NO: 488), substrate 2012 (SEQ ID NO: 489), substrate 2013 (SEQ ID NO: 490), 2014 (SEQ ID NO: 555); substrate 3006 (SEQ ID NO: 515); substrate 3007 (SEQ ID NO: 516); substrate 3008 (SEQ ID NO: 517); substrate 3009 (SEQ ID NO: 518); substrate 3010 (SEQ ID NO: 519); substrate 3011 (SEQ ID NO: 520); substrate 3012 (SEQ ID NO: 521); substrate 3013 (SEQ ID NO: 522); or substrate 3014 (SEQ ID NO: 557) also comprised the masking moiety comprising the amino acid sequence and anti-Jagged antibody 4D11 antibody comprising a light chain (SEQ ID NO: 162) and a heavy chain (SEQ ID NO: 67). The configuration of the light chain of the activatable antibody was masking moiety-substrate-light chain of 4D11.

In this study, the mice were group and dosed as shown in the Table below:

| Group | Count | Treatment | Dose (mg/kg) | Schedule |
|---|---|---|---|---|
| A | 3 | IVIG | 20 | Single Dose |
| B | 4 | 4D11 | 5 | Single Dose |
| C | 4 | 4D11 | 10 | Single Dose |
| D | 4 | 4D11 | 20 | Single Dose |
| E | 4 | 4D11-5342-2001 | 20 | Single Dose |
| F | 3 | 4D11-5342-2006 | 20 | Single Dose |
| G | 3 | 4D11-5342-2007 | 20 | Single Dose |
| H | 3 | 4D11-5342-2008 | 20 | Single Dose |
| I | 3 | 4D11-5342-2009 | 20 | Single Dose |
| J | 3 | 4D11-5342-2010 | 20 | Single Dose |
| K | 3 | 4D11-5342-2012 | 20 | Single Dose |
| L | 3 | 4D11-5342-2013 | 20 | Single Dose |

Figure 13:
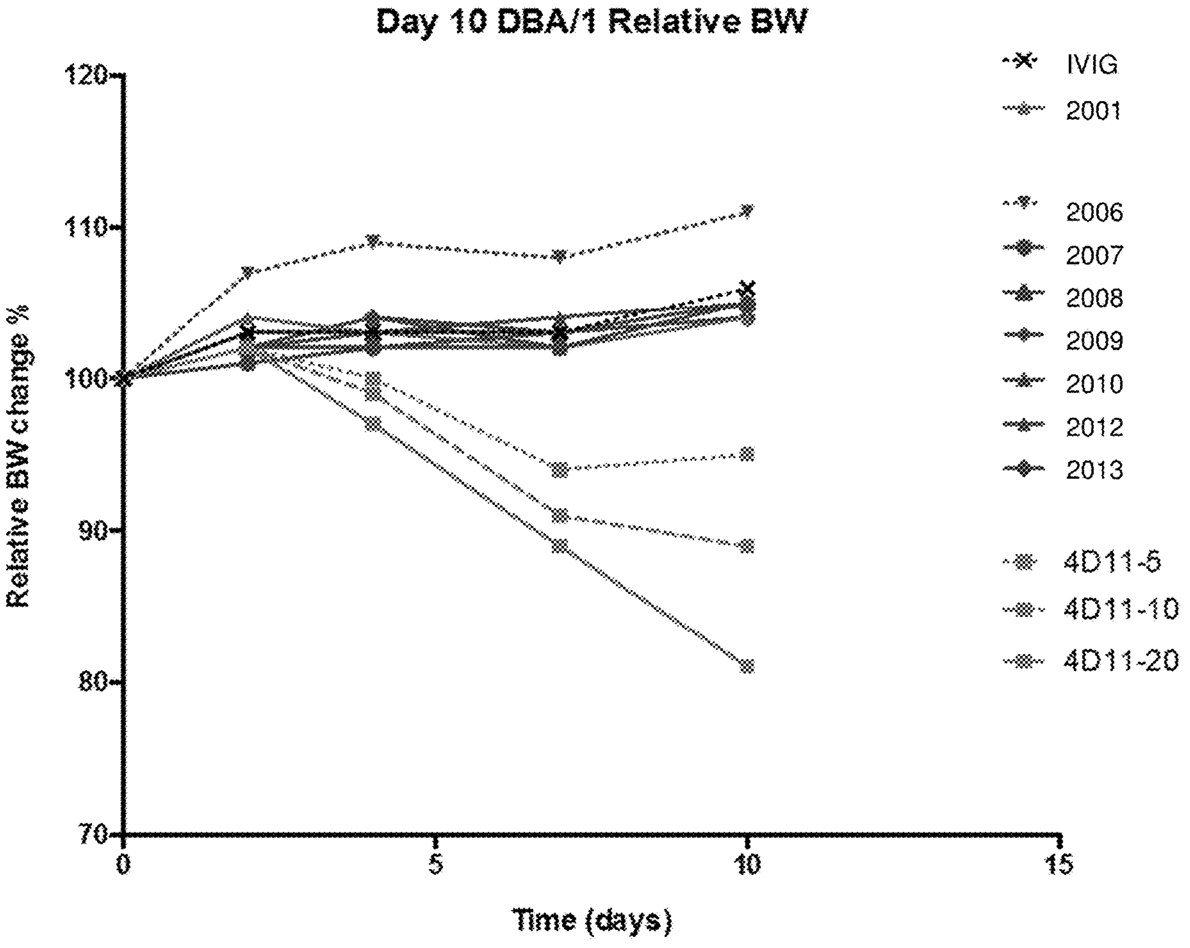
FIG. 13 is a graph depicting toxicity as measured as a function of body weight (BW) loss in DBA/1 mice following administration with a control intravenous immunoglobulin (IVIG), with anti-Jagged antibodies of the disclosure, and with activatable anti-Jagged antibodies of the disclosure that include various substrates of the disclosure.

The results are shown in FIG. 13 as relative body weight (BW) change percent (%) at various time points during the study.

As shown in FIGS. 11A-11H, FIG. 12, and FIG. 13, activatable antibodies including the cleavable substrates of the disclosure are safe and efficacious.

Figure 14:
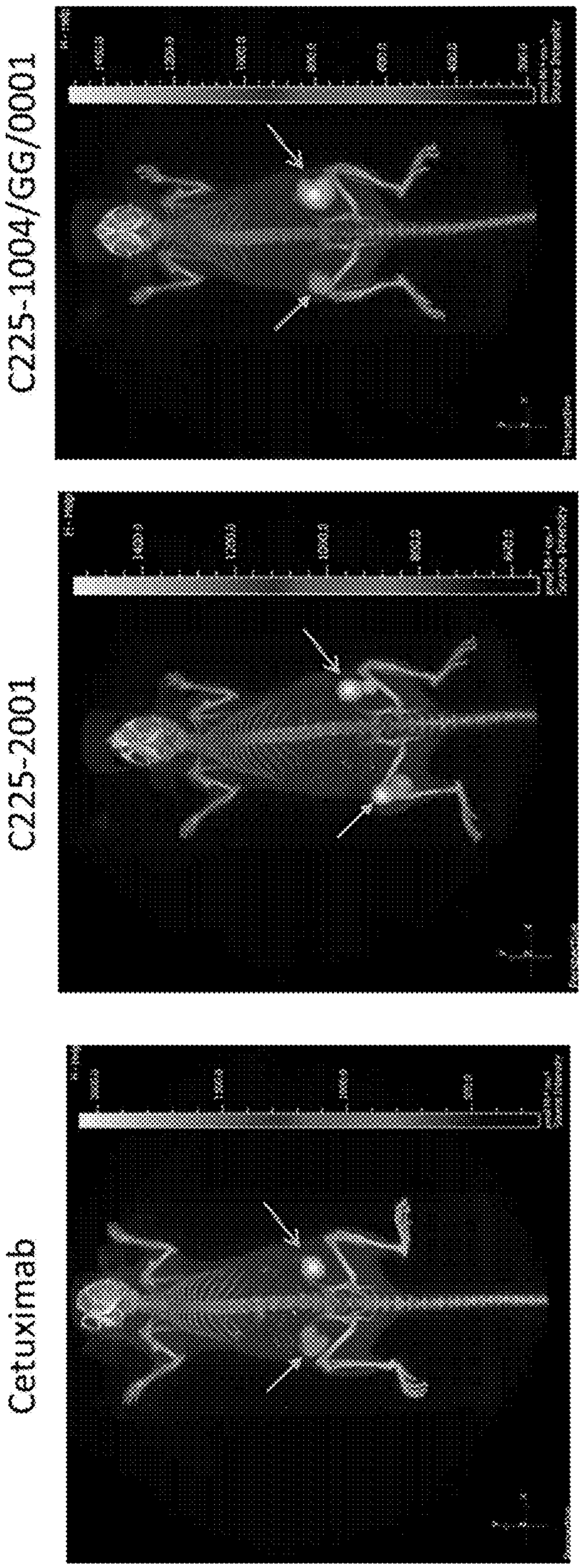
FIG. 14 is a graph depicting 3D reconstruction of FLIT-XT imaging data for cetuximab and two EGFR activatable antibodies containing tandem substrates in H292 (open arrows) and FaDu (filled arrows) co-implanted xenograft tumor model.

Example 6. In Vivo Imaging 7- to 9-week-old female athymic nu/nu (Charles River Laboratories) mice were inoculated subcutaneously with $5\times10^6$ NCI-H292 (left hind flank) and FaDu cells (right hind flank). The NCI-H292 cells (ATCC) and FaDu cells (ATCC) were suspended 1:1 with Matrigel in serum-free or without Matrigel in serum free medium, respectively. Clinical observations, body weights, and digital caliper tumor volume measurements were made two times weekly once tumors become measureable. Tumor volumes were calculated with the formula (ab^2)/2, where a is the longer and b is the smaller of two perpendicular diameters. H292 and FaDu xenograft tumor-bearing mice with tumor volumes of 250-500 mm3 were distributed by tumor size into 3 groups with n=3 per group. The animals were injected intraperitoneally with 15 mg/kg of AlexaFluor 750 (AF750)-conjugated cetuximab (Cetuximab-AF750) or activatable antibodies containing 2001 and 1004/LP'/0001 substrates (Pb2001-AF750 and Pb1004/LP'/0001-SF750). Computed tomography (CT) scans with subsequent fluorescent images were obtained with an IVIS Spectrum/CT imaging system (Caliper Life Sciences, PE). A series of fluorescent surface radiance images were acquired at multiple transillumination locations encompassing the region of interest at excitation and emission wavelengths of 745 nm and 800 nm, respectively (FIG. 14). Three-dimensional reconstruction of the optical and μCT images and their co-registration were performed with the Living Image software 4.2 (Caliper Life Sciences). Obtained imaging data demonstrate accumulation of activatable antibodies in both xenograft tumors with the fluorescent signal similar to cetuximab parental antibody.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

The invention claimed is:

1. An isolated polypeptide comprising a cleavable moiety (CM), wherein the CM comprises the amino acid sequence ISSGLLSGRSANPRG (SEQ ID NO: 469).

2. The isolated polypeptide of claim 1, further comprising an antibody or antigen binding fragment thereof (AB).

3. The isolated polypeptide of claim 2, wherein the antigen binding fragment thereof is selected from the group consisting of a Fab fragment, a $F(ab')_2$ fragment, a scFv, and a scAb.

4. A composition comprising the isolated polypeptide of claim 1 and a pharmaceutically acceptable carrier.

5. An isolated polypeptide comprising a cleavable moiety (CM), wherein the CM comprises the amino acid sequence AVGLLAPPGGTSTSGRSANPRG (SEQ ID NO: 3).

6. The isolated polypeptide of claim 5, further comprising an antibody or antigen binding fragment thereof (AB).

7. The isolated polypeptide of claim 6, wherein the antigen binding fragment thereof is selected from the group consisting of a Fab fragment, a F(ab')2 fragment, a scFv, and a scAb.

8. A composition comprising the isolated polypeptide of claim 5 and a pharmaceutically acceptable carrier.

* * * * *